(12) United States Patent
Imig et al.

(10) Patent No.: US 9,422,318 B2
(45) Date of Patent: Aug. 23, 2016

(54) EPOXYEICOSATRIENOIC ACID ANALOGS AND METHODS OF MAKING AND USING THE SAME

(71) Applicants: THE MEDICAL COLLEGE OF WISCONSIN, INC., Milwaukee, WI (US); THE BOARD OF REGENTS OF THE UNIVERSITY OF TEXAS SYSTEM, Austin, TX (US)

(72) Inventors: John David Imig, Pewaukee, WI (US); William B. Campbell, Whitefish Bay, WI (US); John Russell Falck, University Park, TX (US)

(73) Assignees: The Medical College of Wisconsin, Inc., Milwaukee, WI (US); The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 14/813,615

(22) Filed: Jul. 30, 2015

(65) Prior Publication Data
US 2015/0336916 A1    Nov. 26, 2015

Related U.S. Application Data

(62) Division of application No. 14/009,658, filed as application No. PCT/US2012/032090 on Apr. 4, 2012, now Pat. No. 9,127,027.

(60) Provisional application No. 61/608,361, filed on Mar. 8, 2012, provisional application No. 61/472,410, filed on Apr. 6, 2011.

(51) Int. Cl.
| | | |
|---|---|---|
| *A61K 31/41* | (2006.01) | |
| *C07F 9/40* | (2006.01) | |
| *C07C 233/46* | (2006.01) | |
| *C07C 233/56* | (2006.01) | |
| *C07C 275/20* | (2006.01) | |
| *C07C 309/15* | (2006.01) | |
| *C07C 311/18* | (2006.01) | |
| *C07C 311/51* | (2006.01) | |
| *C07C 317/28* | (2006.01) | |
| *C07C 323/44* | (2006.01) | |
| *C07D 249/12* | (2006.01) | |
| *C07D 257/04* | (2006.01) | |
| *C07D 271/06* | (2006.01) | |
| *C07D 277/34* | (2006.01) | |
| *C07D 277/82* | (2006.01) | |
| *C07D 291/04* | (2006.01) | |
| *C07C 233/47* | (2006.01) | |
| *C07C 237/22* | (2006.01) | |
| *C07C 311/19* | (2006.01) | |
| *C07D 271/07* | (2006.01) | |
| *C07D 277/593* | (2006.01) | |
| *C07D 285/08* | (2006.01) | |

(52) U.S. Cl.
CPC ............... *C07F 9/40* (2013.01); *C07C 233/46* (2013.01); *C07C 233/47* (2013.01); *C07C 233/56* (2013.01); *C07C 237/22* (2013.01); *C07C 275/20* (2013.01); *C07C 309/15* (2013.01); *C07C 311/18* (2013.01); *C07C 311/19* (2013.01); *C07C 311/51* (2013.01); *C07C 317/28* (2013.01); *C07C 323/44* (2013.01); *C07D 249/12* (2013.01); *C07D 257/04* (2013.01); *C07D 271/06* (2013.01); *C07D 271/07* (2013.01); *C07D 277/34* (2013.01); *C07D 277/593* (2013.01); *C07D 277/82* (2013.01); *C07D 285/08* (2013.01); *C07D 291/04* (2013.01)

(58) Field of Classification Search
USPC .................. 514/362, 365, 381; 548/125, 146
See application file for complete search history.

(56) References Cited

U.S. PATENT DOCUMENTS 9,127,027 B2 *   9/2015   Imig ..................... C07C 233/46

* cited by examiner

*Primary Examiner* — Rei-Tsang Shiao
(74) *Attorney, Agent, or Firm* — Boyle Fredrickson, S.C.

(57) ABSTRACT

Compounds and compositions comprising epoxyeicosatrienoic acid (EET) analogs that act as EET agonists and are useful as medications in the treatment of drug-induced nephrotoxicity, hypertension and other related conditions. Methods of making and using the compounds and compositions are further described.

7 Claims, 29 Drawing Sheets

SRD-I-71-9

JLJ-I-94-6

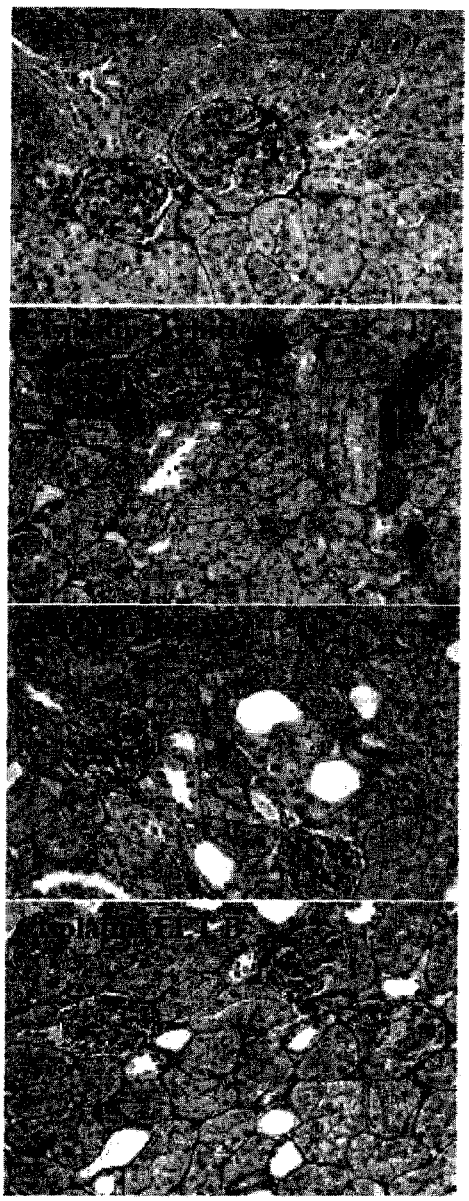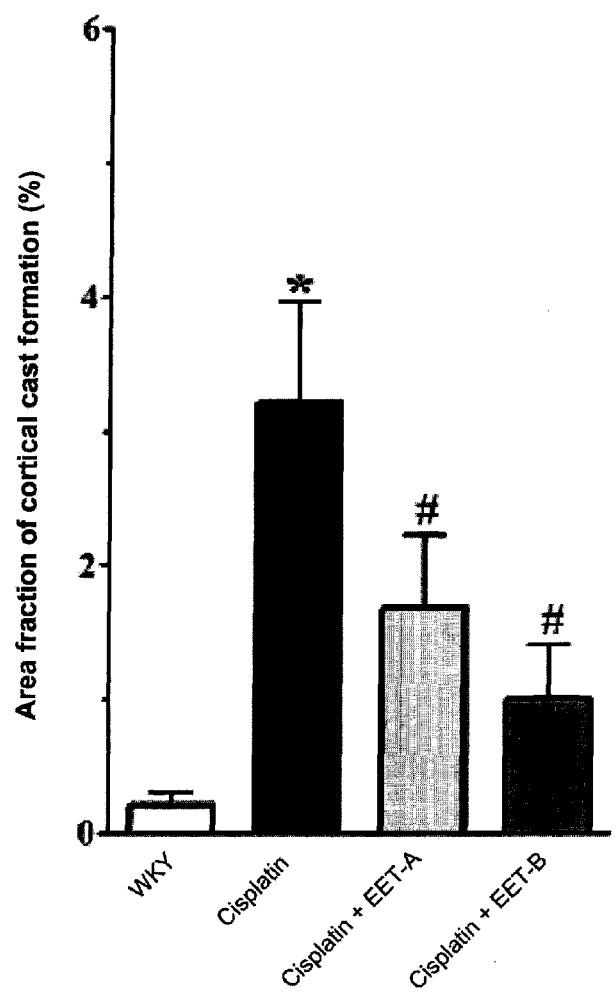
Figure 8A

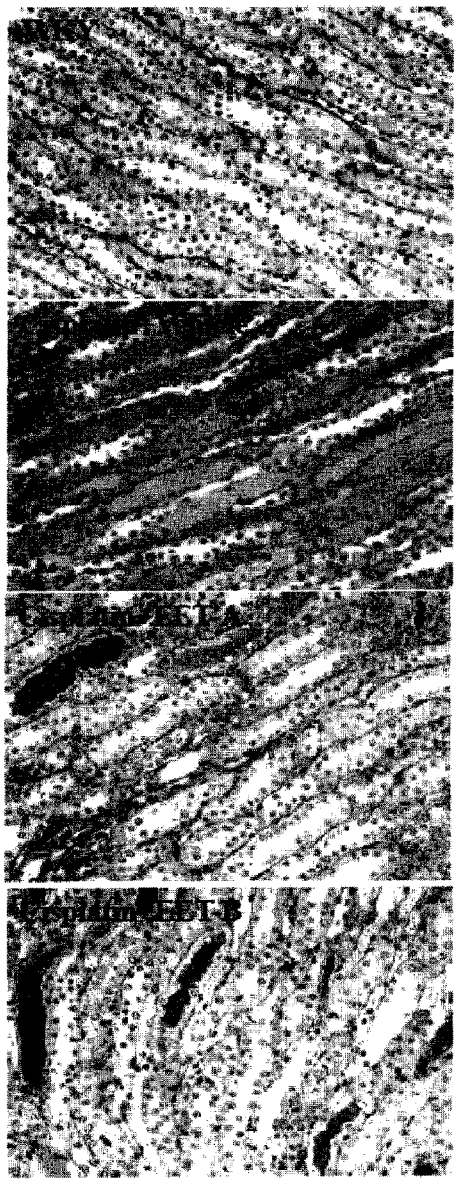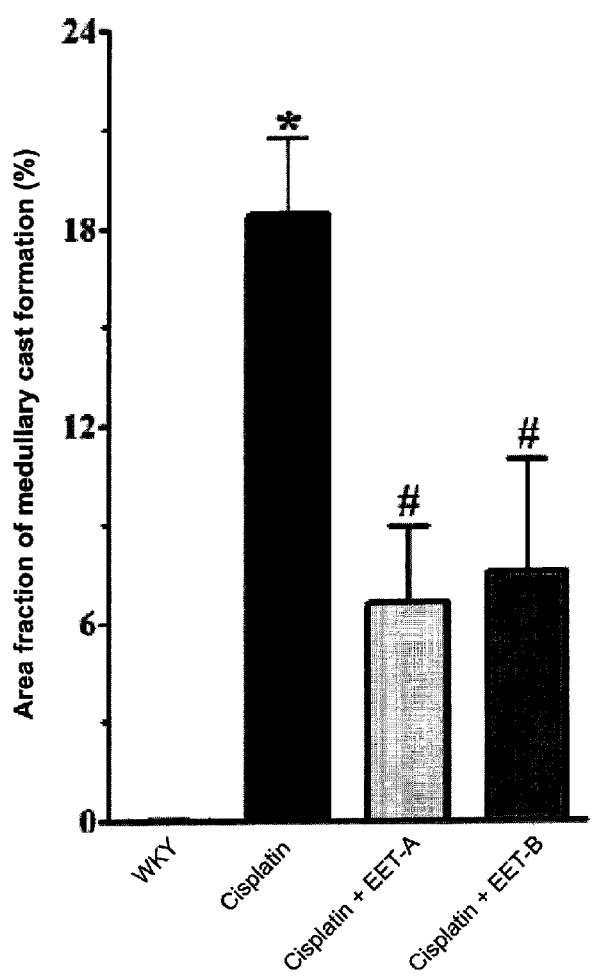
Figure 8B

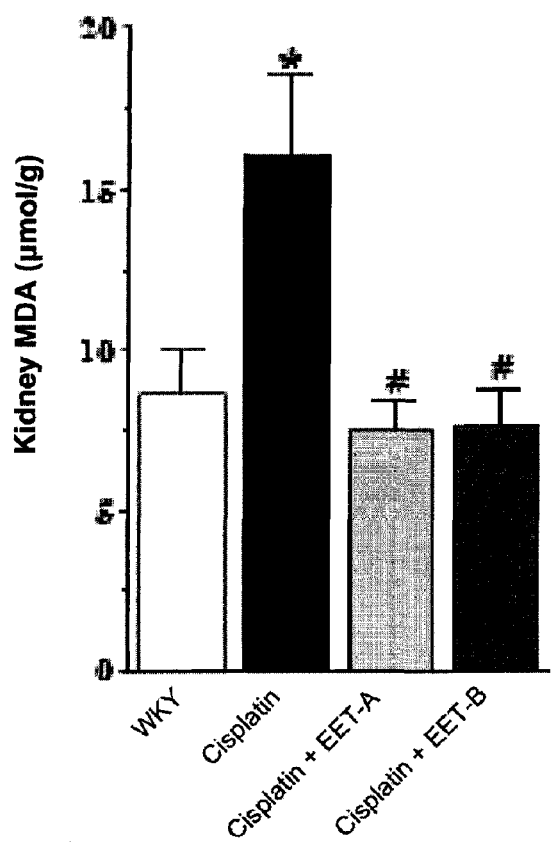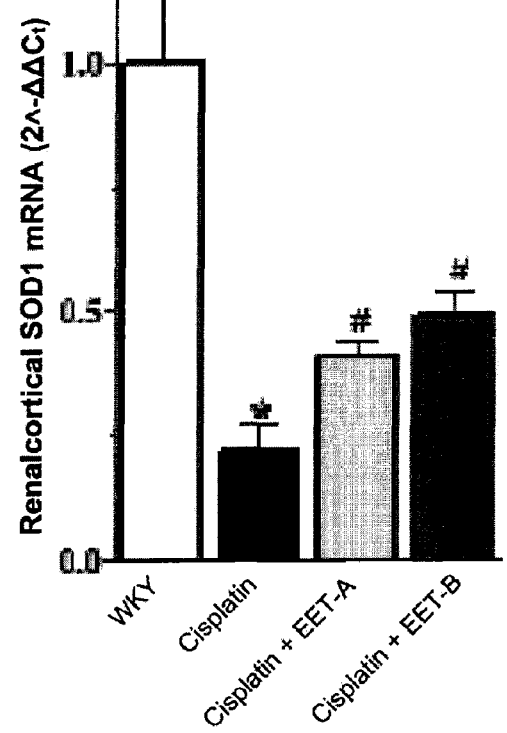
Figure 9C                    Figure 9D

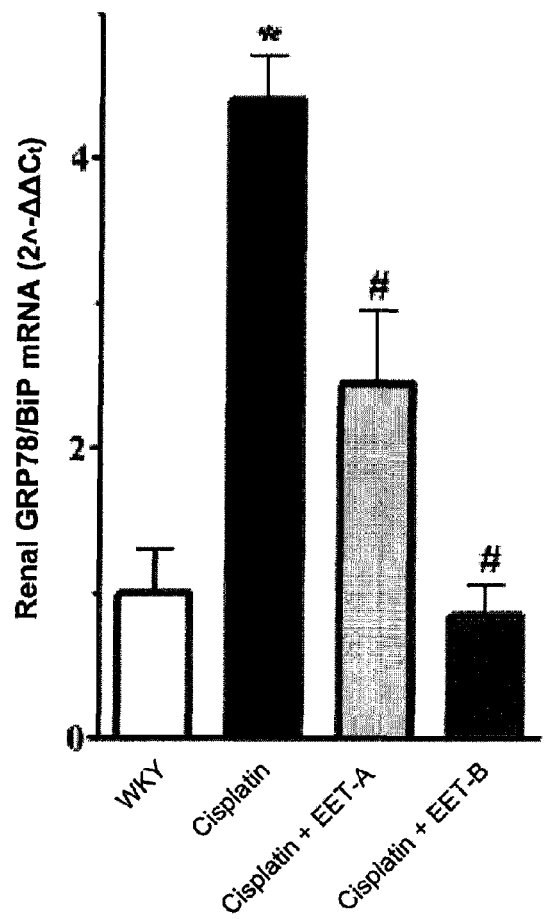 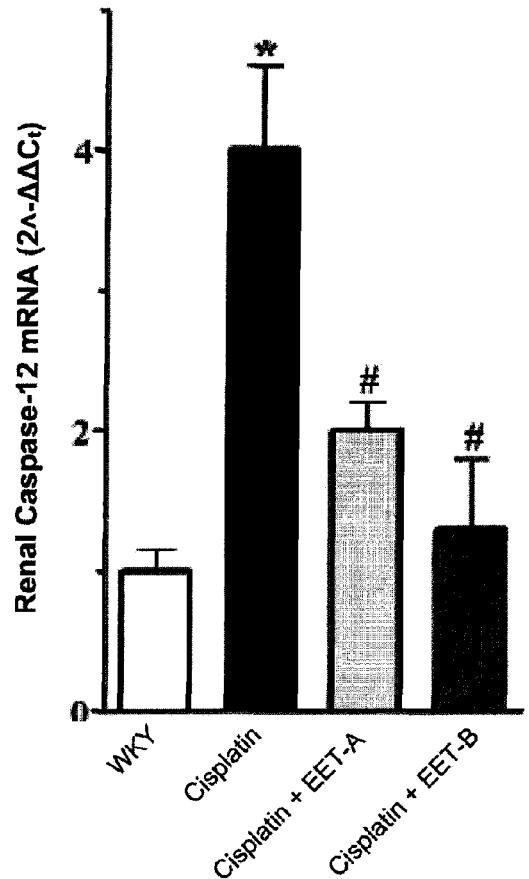
Figure 11A                                   Figure 11B

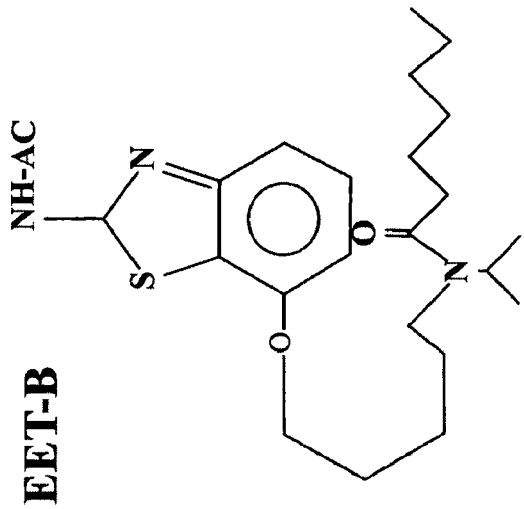
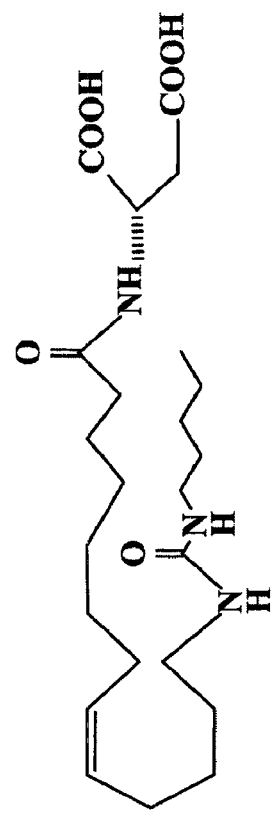
EET-B
N-(5-((2-acetamidobenzo[d]thiazol-4-yl)oxy)pentyl)-N-isopropylheptanamide
EET-A
(S)-2-(13-(3-butylureido)tridec-8(Z)-namido)succinic acid
Figure 14

N-isopropyl-N-(5-((2-pivalamidobenzo[d]thiazol-4-yl)oxy)pentyl)heptanamide
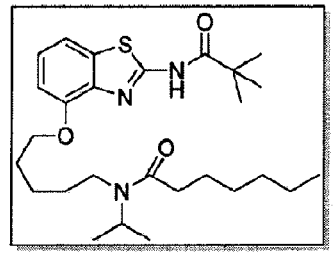
(EET-B)
Scheme
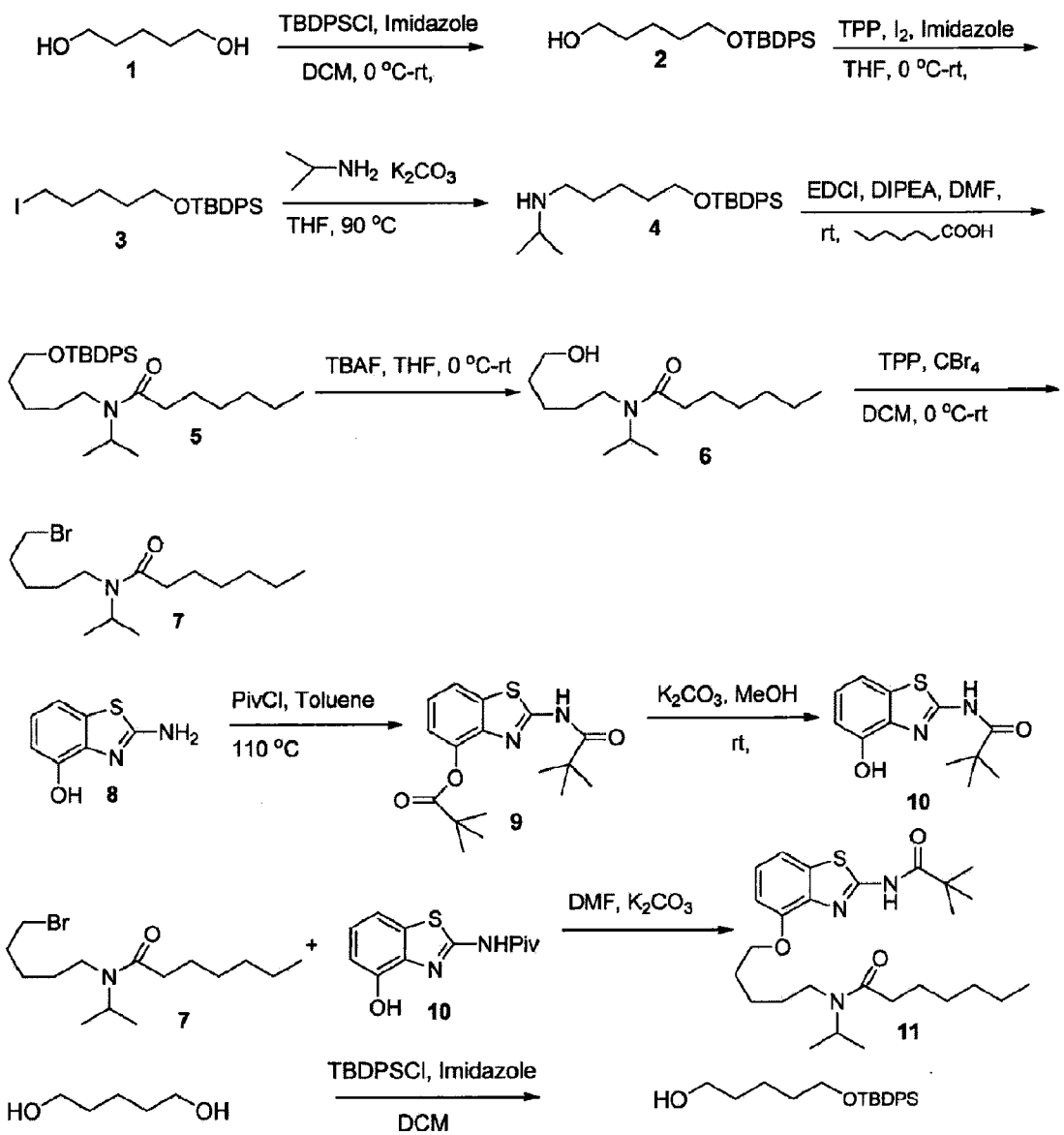
FIGURE 15

EPOXYEICOSATRIENOIC ACID ANALOGS AND METHODS OF MAKING AND USING THE SAME

CROSS-REFERENCE TO RELATED APPLICATIONS

This application is a divisional of U.S. patent application Ser. No. 14/009,658, filed Dec. 18, 2013, which represents the national stage entry of PCT International Application No. PCT/US2012/032090 filed on Apr. 4, 2012, and claims benefit of U.S. Provisional Patent Application No. 61/472,410 filed Apr. 6, 2011 and U.S. Provisional Patent Application 61/608,361 filed Mar. 8, 2012, all of which are incorporated herein by reference.

STATEMENT REGARDING FEDERALLY SPONSORED RESEARCH

This invention was made with government support under DK38226, HL59699, GM31278, and HL51055 awarded by the National Institutes of Health. The government has certain rights in the invention.

FIELD OF THE INVENTION

This invention relates generally to analogs of epoxyeicososatrienoic acid (EET). More particularly, the present invention is directed to EET analogs that act as EET agonists and are useful as medications in the treatment of drug-induced nephrotoxicity, hypertension and other related conditions.

BACKGROUND OF THE INVENTION

Epoxyeicosatrienoic acids (EETs) are signaling molecules that can act as short-range hormones, (i.e. they are autocrine and paracrine mediators) of the cardiovascular system and kidney. They produce vasorelaxation as well as anti-inflammatory and pro-fibrinolytic effects.

Hypertension and Related Conditions.

Cardiovascular disease afflicts 81 million of the 300 million people in the United States, and 75 million of these people have hypertension. CYP epoxygenase metabolites have biological actions that implicate them as important contributors to cardiovascular function and blood pressure control.

One of the first biological activities described for epoxyeicosatrienoic acids (EETs) was inhibition of renal tubular sodium reabsorption. Subsequently, EETs were determined to dilate blood vessels and were identified as endothelium-derived hyperpolarizing factors (EDHF). These biological actions are consistent with the idea that EETs would be eicosanoids that contribute to lowering of blood pressure and prevent salt-sensitive hypertension.

Altered levels of EETs may contribute to hypertension in humans. A single nucleotide polymorphism in a CYP epoxygenase gene is associated with hypertension. Experimental studies in rodents have also demonstrated hypertension in conditions where kidney CYP epoxygenase enzyme and/or EET levels were decreased. Increasing EET levels with 11,12-EET-SI, a 11,12-EET analog, improved renal afferent arteriolar function in vitro.

Currently, soluble epoxide hydrolase inhibitors (sEHI) are used in vivo to increase EET levels and this results in a generalized increase in 11,12-EET and 14,15-EET and to a lesser extent 8,9-EET. Recent in vivo studies have demonstrated that EET analogs lower blood pressure in hypertensive rats, and also ameliorate the metabolic syndrome phenotype in heme-oxygenase 2 deficient mice and prevent the adiposity-related vascular and renal damage. It does appear as if some of the EET agonists like NUDSA may also inhibit sEH and increase CYP2C epoxygenase expression. This type of combinational activity described for NUDSA could provide added beneficial effects. As a whole, these findings have generated interest in targeting the CYP epoxygenase pathway and EETs for the treatment of hypertension.

Even though EETs have actions on renal tubular transport and vascular function that are essential for blood pressure regulation it has become apparent that additional biological actions ascribed to EETs made them an excellent therapeutic target for other cardiovascular diseases. These additional activities demonstrated for EETs include inhibition of platelet aggregation and anti-inflammation. EETs also have been found to have effects on vascular migration and proliferation, including promoting angiogenesis. Thus, EETs have become a therapeutic target for end organ damage associated with cardiovascular diseases, cardiac ischemic injury, atherosclerosis, and stroke.

The therapeutic potential for EET agonists and sEHIs could extend beyond hypertension and cardiovascular diseases. Neural protection from ischemic injury has been attributed to sEHI actions on blood vessels and neurons. There is growing evidence that sEHIs provide protection from ischemic damage in the brain and heart through effects on apoptotic signaling cascades. EET agonists and sEHIs have also been demonstrated to modulate pain in various experimental animal models. Other possible therapeutic applications for EET agonists are sure to be discovered when these agents are tested in other disease models.

Accordingly, there is a need in the art for novel EET agonists that are active as therapeutic agents against hypertension and related cardiovascular and neural disease.

Drug-Induced Nephrotoxicity.

A common side-effect of many drugs used in the treatment of various conditions is nephrotoxicity. For instance, cisplatin, a platinum-based inorganic compound, is one of the most potent and widely used chemotherapy agents available to treat a variety of malignancies, including ovarian, lung, testicular and bladder cancers. Although, cisplatin is used as an important chemotherapy drug in the clinic, it has potentially lethal adverse effects. The most common of this adverse effect is nephrotoxicity (25-40% of cisplatin treated patients develop acute renal failure), which limits the safe and effective use of this widely used chemotherapeutic agent. The pathophysiology of cisplatin-induced nephrotoxicity involves enhanced oxidative stress, inflammation, increased endoplasmic reticulum (ER) stress and renal cell apoptosis.

EET is an important lipid mediator that exerts a number of biological actions including anti-inflammatory, anti-oxidative and anti-apoptotic activities. A numbers of studies demonstrated that with anti-inflammatory, anti-apoptotic and anti-oxidative activities, EET possess strong organ protective potential. For instance, increased EET bioavailability resulted from reduced conversion of EET to its less active form by soluble epoxide hydrolase (sEH) inhibitor provides kidney protection in a number of preclinical models of human diseases. These studies demonstrated that the kidney protective effect of EET was related to anti-inflammatory and anti-oxidative effects of EET. Indeed, there is strong evidence that EET have anti-inflammatory effects against acute and chronic inflammation. Apart from inflammation, EET also protect cells from apoptosis. Thus, there are strong evidences of EET's ability to protect organ by mechanisms involve its anti-inflammatory, anti-apoptotic and anti-oxidative activities.

However, it is known that endogenously produced EETs are chemically and metabolically labile. Also, rapid metabolism, low solubility and storage issue limit the therapeutic prospect of EET. As such considerable interest has arisen in developing strategies to enhance the bioavailability of EET. In this effort, attempts have been made to develop EET analogs that possess EET-mimetic activity along with several key features important for stability and bio-availability. Several of such EET analogs have demonstrated a number of biological activities including organ protection.

In the present study we have investigated the kidney protective effect of two newly developed orally active EET analogs in cisplatin-induced nephrotoxicity. We have demonstrated that EET analogs offered marked reno-protection during cisplatin administration and this effect was related to their anti-oxidative, anti-inflammatory, anti-ER stress and anti-apoptotic activities. We have further demonstrated that while protecting the kidney from the deleterious nephrotoxic effects of cisplatin, these EET analogs did not compromise cisplatin's chemotherapeutic effect.

Acordingly, there is a need in the art for novel EET analogs that are active as therapeutic agents against the deleterious nephrotoxic effects of cisplatin.

SUMMARY OF THE INVENTION

Here, the inventors demonstrate novel compositions of epoxyeicosatrienoic acids (EET) analogs and methods of use thereof for the treatment of cardiovascular disease, particularly the use of such compositions as as anti-hypertensive agents.

Accordingly, the invention encompasses in a first aspect certain compounds that are 14,15-EET analogs. In certain embodiments, the compound has the structure of any one of the following compounds.

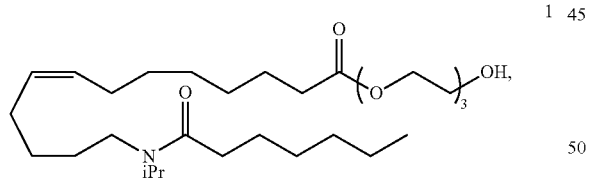

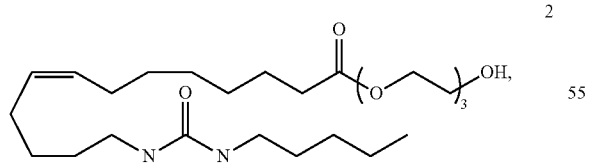

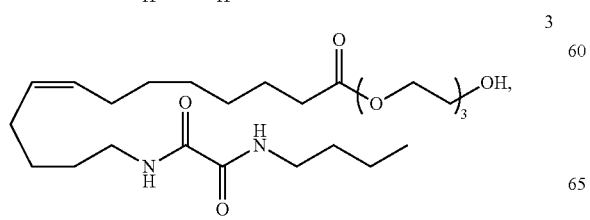

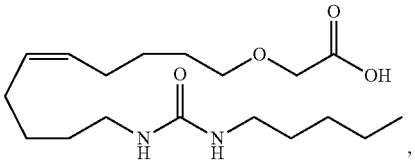

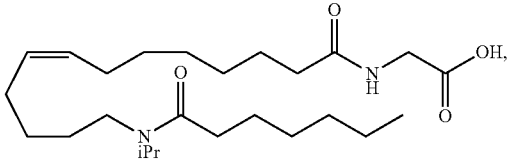

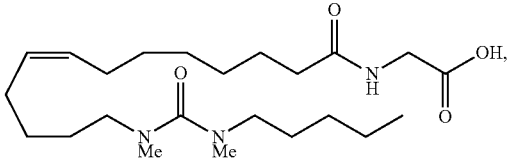

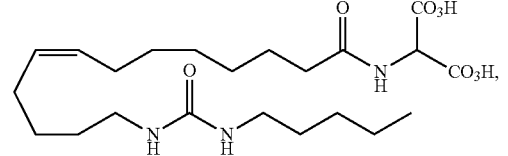

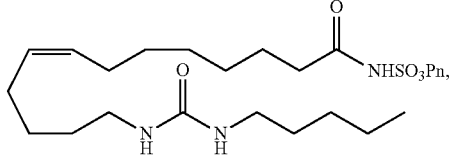

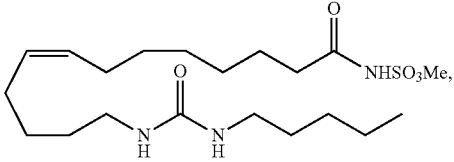

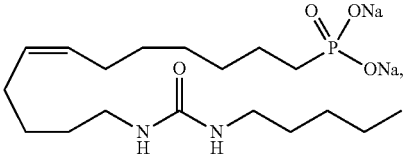

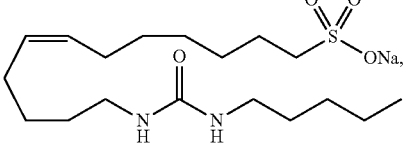

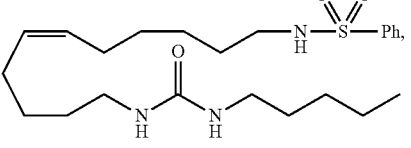

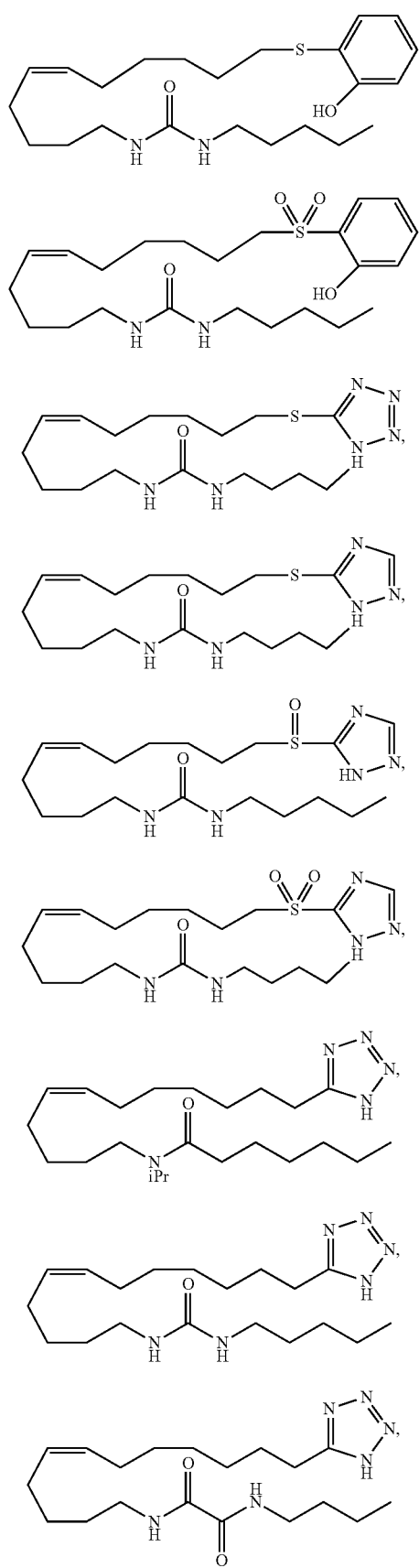
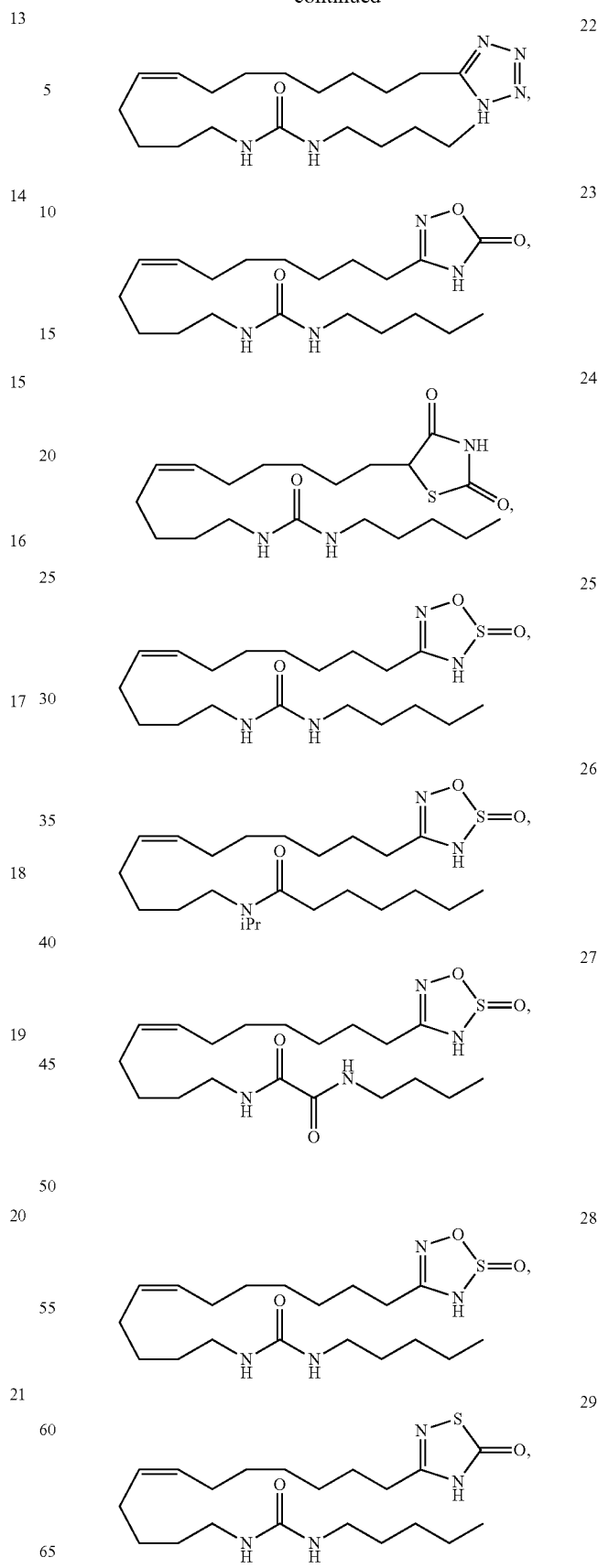

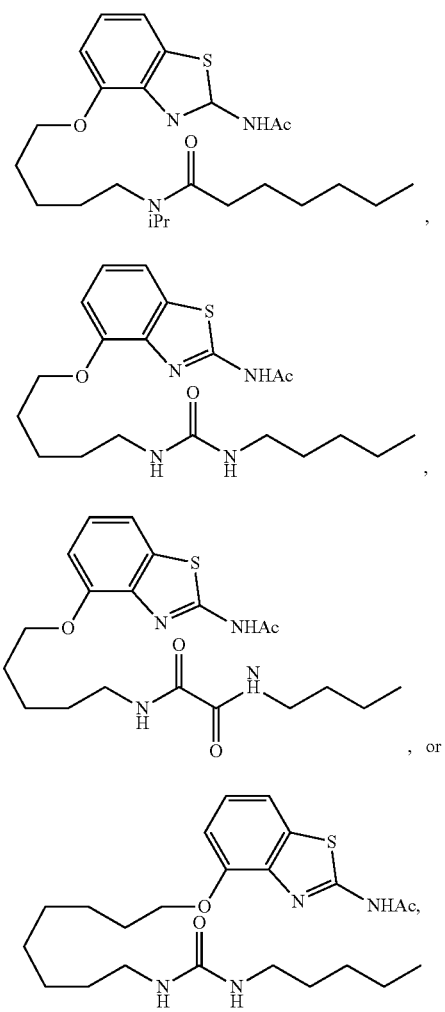

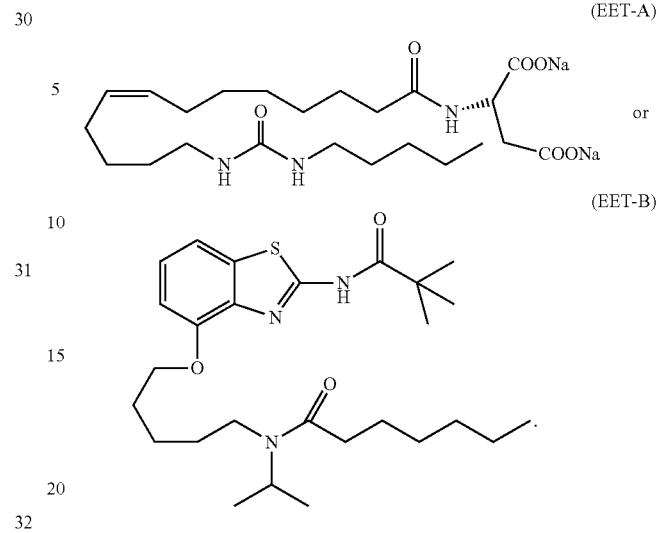

In one embodiment, the invention comprises compounds 7 and 30.

In another aspect, the invention provides a method of making any of compounds 1-33 as described and claimed herein.

Compounds according to the invention are, in certain embodiments, provided in the form of a composition comprising a compound as described and claimed herein in combination with a pharmaceutically acceptable carrier.

The present invention further encompasses methods of providing treatment of hypertension in a subject, resulting in a reduction of blood pressure in a subject. Such methods include steps of administering to a subject a therapeutically effective amount of any of compounds 1-33, alone or in combination, as described and claimed herein, whereby blood pressure in the subject is reduced. In one embodiment, the method comprises administering compound 7. In an alternate embodiment the method comprises administering compound 30.

In another embodiment, the present invention provides EET analogs having the structures selected from the group consisting of In yet another embodiment, the invention encompasses the use of any of the 14,15-EET analogs described above for the manufacture of a medicament for treating hypertension in a subject. As well, the present invention further contemplates compounds according to the invention for use in treating hypertension in a subject.

The present invention further encompasses methods of treating drug-induced nephrotoxicity in a subject. In one embodiment, the invention comprises providing treatment for the deleterious nephrotoxic effects of cisplatin in a subject. Such methods include steps of administering to a subject a therapeutically effective amount of a compound as described and claimed herein, whereby the deleterious nephrotoxic effects of the drug in the subject are reduced.

Other objects, features and advantages of the present invention will become apparent after review of the specification, claims and drawings.

BRIEF DESCRIPTION OF THE DRAWINGS

FIG. 8A represents photomicrographs of Periodicacid-Schiff (PAS) Staining (200×) depicting tubular cast formation along with the calculated cast are a fraction (%) in the renal cortical sections of different experimental groups. $*p<0.05$ vs. normal Wistar Kyotorat; $\#p<0.05$ vs. vehicle treated rat. Data expressed as mean±SEM, n=5-7.

FIG. 8B represents photomicrographs of Periodicacid-Schiff (PAS) Staining 200×) depicting tubular cast formation along with the calculated cast area fraction (%) in the renal medullary sections of different experimental groups. $*p<0.05$ vs. normal Wistar Kyoto rat; $\#p<0.05$ vs. vehicle treated rat. Data expressed as mean±SEM, n=5-7.

FIG. 9C shows measurements of kidney thiobarbituric acid-reactive substances (TBARS) in cisplatin administered rats treated with either EET analogs A, B or vehicle. $*p<0.05$ vs. normal Wistar Kyoto rat; $\# p<0.05$ vs. vehicle pretreated rat administered cisplatin. Data expressed as mean±SEM, n=5-7.

FIG. 9D shows RT-PCR analysis form RNA expressions of SOD1.

FIG. 11A shows renal expression of endoplasmic reticulum stress marker genes GRP78/BiP in cisplatin administered rats treated with either EET analogs EET-A and EET-B or vehicle. $*p<0.05$ vs. normal WistarKyoto rat; $\#p<0.05$ vs. vehicle treated rat administered. Data expressed as mean±SEM, n=5-7.

FIG. 11B shows renal expression of endoplasmic reticulum stress marker genes caspase12 in cisplatin administered rats treated with either EET analogs EET-A and EET-B or vehicle. $*p<0.05$ vs. normal WistarKyoto rat; $\#p<0.05$ vs. vehicle treated rat administered. Data expressed as mean±SEM, n=5-7.

FIG. 14 shows the structure of EET analogs EET-A and EET-B.

FIG. 15 shows the synthesis of EET-B.

DETAILED DESCRIPTION OF THE INVENTION

I. In General

Figure 1A:
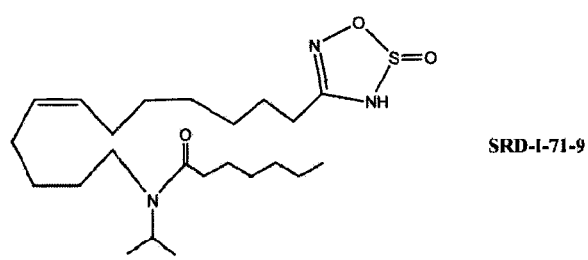
FIG. 1A depicts the chemical structure SRD-I-71-9, which corresponds to EET analog compound 26 of Table 1.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by any later-filed nonprovisional applications.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

II. The Invention

The inventors here disclose novel EET analogs, EET agonists, and other related lipid compounds, and compositions comprising such compounds, as well as methods of synthesizing such compounds and the use of such compositions in treating hypertension and related conditions in treating the deleterious effects of cisplatin nephrotoxicity and related conditions. The inventors' have shown that several of the compounds exhibit anti-hypertensive effects and are well-tolerated in relevant rat models. A number of different delivery options are possible, including intraperitoneal injections, blood injections, or oral delivery. Liposomes, mycelles, and emulsifiers can be used in to make these preparations more soluble.

As used herein, "subject" means mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

As used herein, "administering" or "administration" includes any means for introducing a compound of the present invention into the body, preferably into the systemic circulation. Examples include but are not limited to oral, buccal, sublingual, pulmonary, transdermal, transmucosal, as well as subcutaneous, intraperitoneal, intravenous, and intramuscular injection.

A "therapeutically effective amount" means an amount of a compound that, when administered to a subject for treating a disease or condition, is sufficient to effect such treatment for the disease. The "therapeutically effective amount" will vary depending on the compound, the disease state being treated, the severity or the disease treated, the age and relative health of the subject, the route and form of administration, the judgment of the attending medical or veterinary practitioner, and other factors.

For purposes of the present invention, "treating" or "treatment" describes the management and care of a patient for the purpose of combating the disease, condition, or disorder. The terms embrace both preventative, i.e., prophylactic, and palliative treatments. Treating includes the administration of a compound of present invention to prevent the onset of the symptoms or complications, alleviating the symptoms or complications, or eliminating the disease, condition, or disorder.

A compound is administered to a patient in a therapeutically effective amount. A compound can be administered alone or as part of a pharmaceutically acceptable composition. In addition, a compound or composition can be administered all at once, as for example, by a bolus injection, multiple times, such as by a series of tablets, or delivered substantially uniformly over a period of time, as for example, using transdermal delivery. Further, the dose of the compound can be varied over time. A compound can be administered using an immediate release formulation, a controlled release formulation, or combinations thereof. The term "controlled release" includes sustained release, delayed release, and combinations thereof.

A pharmaceutical composition of the invention can be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient that would be administered to a patient or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the human treated and further depending upon the route by which the composition is to be administered. By way of example, the composition can comprise between 0.1% and 100% (w/w) active ingredient. A unit dose of a pharmaceutical composition of the invention will generally comprise from about 100 milligrams to about two grams of the active ingredient, and preferably comprises from about 200 milligrams to about 1.0 gram of the active ingredient.

A preferred dosage for humans would be in the low mg/kg range administered orally once daily. Twice daily would also be acceptable.

To improve water solubility, the preferred compounds can be formulated with cyclodextrins or cyclodextrin-derived products, derivatized with substituents such as polyethylene glycols or other polar functionality, or included in liposomes. For oral delivery, the compounds may be modified with lipophilic functionality or conjugated to actively absorbed molecules. Other approaches are discussed in "Strategies to improve oral drug bioavailability", Isabel Gomez-Orellana, Expert Opinion on Drug Delivery, May 2005, Vol. 2, No. 3: Pages 419-433, which is incorporated by reference herein.

Another aspect of the invention relates to a kit comprising a pharmaceutical composition of the invention and instructional material. Instructional material includes a publication, a recording, a diagram, or any other medium of expression which is used to communicate the usefulness of the pharmaceutical composition of the invention for one of the purposes set forth herein in a human. The instructional material can also, for example, describe an appropriate dose of the pharmaceutical composition of the invention. The instructional material of the kit of the invention can, for example, be affixed to a container which contains a pharmaceutical composition of the invention or be shipped together with a container which contains the pharmaceutical composition. Alternatively, the instructional material can be shipped separately from the container with the intention that the instructional material and the pharmaceutical composition be used cooperatively by the recipient.

The invention also includes a kit comprising a pharmaceutical composition of the invention and a delivery device for delivering the composition to a human. By way of example, the delivery device can be a squeezable spray bottle, a metered-dose spray bottle, an aerosol spray device, an atomizer, a dry powder delivery device, a self-propelling solvent/powder-dispensing device, a syringe, a needle, a tampon, or a dosage-measuring container. The kit can further comprise an instructional material as described herein. The kit also comprises a container for the separate compositions, such as a divided bottle or a divided foil packet. Additional examples of containers include syringes, boxes, bags, and the like. Typically, a kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

It may be desirable to provide a memory aid on the kit, e.g., in the form of numbers next to the tablets or capsules whereby the numbers correspond with the days of the regimen that the tablets or capsules so specified should be ingested. Another example of such a memory aid is a calendar printed on the card, e.g., as follows "First Week, Monday, Tuesday, . . . etc. . . . Second Week, Monday, Tuesday," etc. Other variations of memory aids will be readily apparent. A "daily dose" can be a single tablet or capsule or several pills or capsules to be taken on a given day.

In another embodiment of the present invention, a dispenser designed to dispense the daily doses one at a time in the order of their intended use is provided. Preferably, the dispenser is equipped with a memory aid, so as to further facilitate compliance with the dosage regimen. An example of such a memory aid is a mechanical counter, which indicates the number of daily doses that have been dispensed. Another example of such a memory aid is a battery-powered micro-chip memory coupled with a liquid crystal readout, or audible reminder signal which, for example, reads out the date that the last daily dose has been taken and/or reminds one when the next dose is to be taken.

The compounds of the present invention, optionally comprising other pharmaceutically active compounds, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray. Other contemplated formulations include projected nanoparticles, liposomal preparations, resealed erythrocytes containing the active ingredient, and immunologically-based formulations.

Parenteral administration of a pharmaceutical composition includes any route of administration characterized by physical breaching of a tissue of a human and administration of the pharmaceutical composition through the breach in the tissue. Parenteral administration thus includes administration of a pharmaceutical composition by injection of the composition, by application of the composition through a surgical incision, by application of the composition through a tissue-penetrating non-surgical wound, and the like. In particular, parenteral administration includes subcutaneous, intraperitoneal, intravenous, intraarterial, intramuscular, or intrasternal injection and intravenous, intraarterial, or kidney dialytic infusion techniques. For example, the compositions of the present invention can be administered to a subject by brain (via vPAG) injections, intrathecal injections, intraperitoneal injections, or blood injections.

Compositions suitable for parenteral injection comprise the active ingredient combined with a pharmaceutically acceptable carrier such as physiologically acceptable sterile aqueous or nonaqueous solutions, dispersions, suspensions, or emulsions, or may comprise sterile powders for reconstitution into sterile injectable solutions or dispersions. Examples of suitable aqueous and nonaqueous carriers, diluents, solvents, or vehicles include water, isotonic saline, ethanol, polyols (propylene glycol, polyethylene glycol, glycerol, and the like), suitable mixtures thereof, triglycerides, including vegetable oils such as olive oil, or injectable organic esters such as ethyl oleate. Proper fluidity can be maintained, for example, by the use of a coating such as lecithin, by the maintenance of the required particle size in the case of dispersions, and/or by the use of surfactants. Such formulations can be prepared, packaged, or sold in a form suitable for bolus administration or for continuous administration. Injectable formulations can be prepared, packaged, or sold in unit dosage form, such as in ampules, in multi-dose containers containing a preservative, or in single-use devices for auto-injection or injection by a medical practitioner.

Formulations for parenteral administration include suspensions, solutions, emulsions in oily or aqueous vehicles, pastes, and implantable sustained-release or biodegradable formulations. Such formulations can further comprise one or more additional ingredients including suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions can be prepared, packaged, or sold in the form of a sterile injectable aqueous or oily suspension or solution. This suspension or solution can be formulated according to the known art, and can comprise, in addition to the active ingredient, additional ingredients such as the dispersing agents, wetting agents, or suspending agents described herein. Such sterile injectable formulations can be prepared using a non-toxic parenterally-acceptable diluent or solvent, such as water or 1,3-butanediol, for example. Other acceptable diluents and solvents include Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation can comprise pharmaceutically acceptable polymeric or hydrophobic materials such as an emulsion, an ion exchange resin, a sparingly soluble polymer, or a sparingly soluble salt.

The compounds according to the present invention may also contain adjuvants such as preserving, wetting, emulsifying, and/or dispersing agents, including, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and/or gelatin. In particular, liposomes, mysomes and emulsifiers can be used in to make the present compounds more soluble for delivery.

Dosage forms can include solid or injectable implants or depots. In preferred embodiments, the implant comprises an effective amount of an active agent and a biodegradable polymer. In preferred embodiments, a suitable biodegradable polymer can be selected from the group consisting of a polyaspartate, polyglutamate, poly(L-lactide), a poly(D,L-lactide), a poly(lactide-co-glycolide), a poly(8-caprolactone), a polyanhydride, a poly(beta-hydroxy butyrate), a poly(ortho ester) and a polyphosphazene. In other embodiments, the implant comprises an effective amount of active agent and a silastic polymer. The implant provides the release of an effective amount of active agent for an extended period of about one week to several years.

Solid dosage forms for oral administration include capsules, tablets, powders, and granules. In such solid dosage form, the active compound is admixed with at least one inert customary excipient (or carrier) such as sodium citrate or dicalcium phosphate or (a) fillers or extenders, as for example, starches, lactose, sucrose, mannitol, or silicic acid; (b) binders, as for example, carboxymethylcellulose, alginates, gelatin, polyvinylpyrrolidone, sucrose, or acacia; (c) humectants, as for example, glycerol; (d) disintegrating agents, as for example, agar-agar, calcium carbonate, potato or tapioca starch, alginic acid, certain complex silicates, or sodium carbonate; (e) solution retarders, as for example, paraffin; (f) absorption accelerators, as for example, quaternary ammonium compounds; (g) wetting agents, as for example, cetyl alcohol or glycerol monostearate; (h) adsorbents, as for example, kaolin or bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents.

A tablet comprising the active ingredient can, for example, be made by compressing or molding the active ingredient, optionally with one or more additional ingredients. Compressed tablets can be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets can be made by molding, in a suitable device, a mixture of the active ingredient, a pharmaceutically acceptable carrier, and at least sufficient liquid to moisten the mixture.

Pharmaceutically acceptable excipients used in the manufacture of tablets include inert diluents, granulating and disintegrating agents, binding agents, and lubricating agents. Known dispersing agents include potato starch and sodium starch glycolate. Known surface active agents include sodium lauryl sulfate. Known diluents include calcium carbonate, sodium carbonate, lactose, microcrystalline cellulose, calcium phosphate, calcium hydrogen phosphate, and sodium phosphate. Known granulating and disintegrating agents include corn starch and alginic acid. Known binding agents include gelatin, acacia, pre-gelatinized maize starch, polyvinylpyrrolidone, and hydroxypropyl methylcellulose. Known lubricating agents include magnesium stearate, stearic acid, silica, and talc.

Tablets can be non-coated or they can be coated using known methods to achieve delayed disintegration in the gastrointestinal tract of a human, thereby providing sustained release and absorption of the active ingredient. By way of example, a material such as glyceryl monostearate or glyceryl distearate can be used to coat tablets. Further by way of example, tablets can be coated using methods described in U.S. Pat. Nos. 4,256,108; 4,160,452; and 4,265,874 to form osmotically-controlled release tablets. Tablets can further comprise a sweetening agent, a flavoring agent, a coloring agent, a preservative, or some combination of these in order to provide pharmaceutically elegant and palatable preparation.

Solid dosage forms such as tablets, dragees, capsules, and granules can be prepared with coatings or shells, such as enteric coatings and others well known in the art. They may also contain opacifying agents, and can also be of such composition that they release the active compound or compounds in a delayed manner. Examples of embedding compositions that can be used are polymeric substances and waxes. The active compounds can also be in micro-encapsulated form, if appropriate, with one or more of the above-mentioned excipients.

Solid compositions of a similar type may also be used as fillers in soft or hard filled gelatin capsules using such excipients as lactose or milk sugar, as well as high molecular weight polyethylene glycols, and the like. Hard capsules comprising the active ingredient can be made using a physiologically degradable composition, such as gelatin. Such hard capsules comprise the active ingredient, and can further comprise additional ingredients including, for example, an inert solid diluent such as calcium carbonate, calcium phosphate, or kaolin. Soft gelatin capsules comprising the active ingredient can be made using a physiologically degradable composition, such as gelatin. Such soft capsules comprise the active ingredient, which can be mixed with water or an oil medium such as peanut oil, liquid paraffin, or olive oil.

Oral compositions can be made, using known technology, which specifically release orally-administered agents in the small or large intestines of a human patient. For example, formulations for delivery to the gastrointestinal system, including the colon, include enteric coated systems, based, e.g., on methacrylate copolymers such as poly(methacrylic acid, methyl methacrylate), which are only soluble at pH 6 and above, so that the polymer only begins to dissolve on entry into the small intestine. The site where such polymer formulations disintegrate is dependent on the rate of intestinal transit and the amount of polymer present. For example, a relatively thick polymer coating is used for delivery to the proximal colon (Hardy et al., Aliment.

Pharmacol. Therap. (1987) 1:273-280). Polymers capable of providing site-specific colonic delivery can also be used, wherein the polymer relies on the bacterial flora of the large bowel to provide enzymatic degradation of the polymer coat and hence release of the drug. For example, azopolymers (U.S. Pat. No. 4,663,308), glycosides (Friend et al., J. Med. Chem. (1984) 27:261-268) and a variety of naturally available and modified polysaccharides (see PCT application PCT/GB89/00581) can be used in such formulations.

Pulsed release technology such as that described in U.S. Pat. No. 4,777,049 can also be used to administer the active agent to a specific location within the gastrointestinal tract. Such systems permit drug delivery at a predetermined time and can be used to deliver the active agent, optionally together with other additives that my alter the local microenvironment to promote agent stability and uptake, directly to the colon, without relying on external conditions other than the presence of water to provide in vivo release.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, isotonic saline, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, almond oil, arachis oil, coconut oil, cottonseed oil, groundnut oil, corn germ oil, olive oil, castor oil, sesame seed oil, MIGLYOL™, glycerol, fractionated vegetable oils, mineral oils such as liquid paraffin, tetrahydrofurfuryl alcohol, polyethylene glycols, fatty acid esters of sorbitan, or mixtures of these substances, and the like.

Besides such inert diluents, the compounds of the present invention can also include adjuvants, such as wetting agents, emulsifying and suspending agents, demulcents, preservatives, buffers, salts, sweetening, flavoring, coloring and perfuming agents. Suspensions, in addition to the active compound, may contain suspending agents, as for example, ethoxylated isostearyl alcohols, polyoxyethylene sorbitol or sorbitan esters, microcrystalline cellulose, hydrogenated edible fats, sodium alginate, polyvinylpyrrolidone, gum tragacanth, gum acacia, agar-agar, and cellulose derivatives such as sodium carboxymethylcellulose, methylcellulose, hydroxypropylmethylcellulose, aluminum metahydroxide, bentonite, or mixtures of these substances, and the like. Liquid formulations of a pharmaceutical composition of the invention that are suitable for oral administration can be prepared, packaged, and sold either in liquid form or in the form of a dry product intended for reconstitution with water or another suitable vehicle prior to use.

Known dispersing or wetting agents include naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include lecithin and acacia. Known preservatives include methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents can be prepared in substantially the same manner as liquid suspensions, the primary difference being that the active ingredient is dissolved, rather than suspended in the solvent. Liquid solutions of the pharmaceutical composition of the invention can comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Compositions for rectal or vaginal administration can be prepared by mixing a compound of the present invention and any additional compounds with suitable non-irritating excipients or carriers such as cocoa butter, polyethylene glycol or a suppository wax, which are solid at ordinary room temperature, but liquid at body temperature, and therefore, melt in the rectum or vaginal cavity and release the active ingredient. Such a composition can be in the form of, for example, a suppository, a retention enema preparation, and a solution for rectal or colonic irrigation. Suppository formulations can further comprise various additional ingredients including antioxidants and preservatives. Retention enema preparations or solutions for rectal or colonic irrigation can be made by combining the active ingredient with a pharmaceutically acceptable liquid carrier. As is known in the art, enema preparations can be administered using, and can be packaged within, a delivery device adapted to the rectal anatomy of a human. Enema preparations can further comprise various additional ingredients including antioxidants and preservatives.

A pharmaceutical composition of the invention can be prepared, packaged, or sold in a formulation suitable for vaginal administration. Such a composition can be in the form of, for example, a suppository, an impregnated or coated vaginally-insertable material such as a tampon, a douche preparation, or a solution for vaginal irrigation.

Dosage forms for topical administration of a compound according to the present invention include ointments, powders, sprays and inhalants. The compounds are admixed under sterile conditions with a physiologically acceptable carrier, and any preservatives, buffers, and/or propellants that may be required. Formulations suitable for topical administration include liquid or semi-liquid preparations such as liniments, lotions, oil-in-water or water-in-oil emulsions such as creams, ointments or pastes, and solutions or suspensions. Topically-administrable formulations can, for example, comprise from about 0.1% to about 10% (w/w) active ingredient, although the concentration of the active ingredient can be as high as the solubility limit of the active ingredient in the solvent. Formulations for topical administration can further comprise one or more of the additional ingredients described herein.

Ophthalmic formulations, eye ointments, powders, and solutions are also contemplated as being within the scope of this invention. Such formulations can, for example, be in the form of eye drops including, for example, a 0.1-1.0% (w/w) solution or suspension of the active ingredient in an aqueous or oily liquid carrier. Such drops can further comprise buffering agents, salts, or one or more other of the additional ingredients described herein. In other embodiments, ophthalmalmically administrable formulations comprise the active ingredient in microcrystalline form or in a liposomal preparation.

Pharmaceutical compositions of the invention formulated for pulmonary delivery can provide the active ingredient in the form of droplets of a solution or suspension. Such formulations can be prepared, packaged, or sold as aqueous or dilute alcoholic solutions or suspensions, optionally sterile, comprising the active ingredient, and can conveniently be administered using any nebulization or atomization device. Such formulations can further comprise one or more additional ingredients including a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

A pharmaceutical composition of the invention can be prepared, packaged, or sold in a formulation suitable for buccal administration. Such formulations can, for example, be in the form of tablets or lozenges made using conventional methods, and can, for example, comprise 0.1 to 20% (w/w) active ingredient, the balance comprising an orally dissolvable or degradable composition and, optionally, one or more of the additional ingredients described herein. Alternately, formulations suitable for buccal administration can comprise a powder or an aerosolized or atomized solution or suspension comprising the active ingredient. Such powdered, aerosolized, or atomized formulations, when dispersed, preferably have an average particle or droplet size in the range from about 0.1 to about 200 nanometers, and can further comprise one or more of the additional ingredients described herein.

For parenteral administration in non-human animals, the compounds of the present invention may be prepared in the form of a paste or a pellet and administered as an implant, usually under the skin of the head or ear of the animal. Paste formulations can be prepared by dispersing a compound or compounds in pharmaceutically acceptable oil such as peanut oil, sesame oil, corn oil or the like. Pellets containing a therapeutically effective amount of a compound or compounds can be prepared by admixing the compound with a diluent such as a carbowax, carnauba wax, and the like, and a lubricant, such as magnesium or calcium stearate, can be added to improve the pelleting process. It is, of course, recognized that more than one pellet may be administered to an animal to achieve the desired dose level. Moreover, it has been found that such implants may also be administered periodically during the animal treatment period in order to maintain the proper active agent level in the animal's body.

The compounds of the present invention and the pharmaceutically acceptable salts of the same, can be administered to a patient at dosage levels in the range of from about 0.01 to about 1,000 mg per day. For a normal adult human having a body weight of about 70 kg, a dosage in the range of from about 0.01 to about 300 mg is typically sufficient, with 1-10 mg/kg a preferred dosage. However, some variability in the general dosage range may be required depending upon the age and weight of the subject being treated, the intended route of administration, the particular compound being administered and the like. The determination of dosage ranges and optimal dosages for a particular patient is well within the ability of one of ordinary skill in the art having the benefit of the instant disclosure. It is also noted that the compounds of the present invention can be used in sustained release, controlled release, and delayed release formulations, which forms are also well known to one of ordinary skill in the art.

It is not critical whether the compounds of the present invention are administered directly to the cell, to a tissue comprising the cell, a body fluid that contacts the cell, or a body location from which the compound can diffuse or be transported to the cell. It is sufficient that the compound is administered to the patient in an amount and by a route whereby an amount of the compound sufficient to mobilize lipids in the cell arrives, directly or indirectly at the cell. The minimum amount varies with the identity of the compounds.

The specific dosage and dosage range that can be used depends on a number of factors, including the requirements of the patient, the severity of the condition being treated, and the pharmacological activity of the compound being administered. The determination of dosage ranges and optimal dosages for a particular patient is well within the ordinary skill of one in the art in view of this disclosure. It is understood that the ordinarily skilled physician or veterinarian will readily determine and prescribe an effective amount of the compound to mobilize lipid stores, induce weight loss, or inhibit appetite in the patient. In so proceeding, the physician or veterinarian can, for example, prescribe a relatively low dose at first, subsequently increasing the dose until an appropriate response is obtained. It is further understood, however, that the specific dose level for any particular human will depend upon a variety of factors including the activity of the specific compound employed, the age, body weight, general health, gender, and diet of the human, the time of administration, the route of administration, the rate of excretion, any drug combination, and the severity of any disorder being treated.

Various exemplary embodiments of compositions and methods according to this invention are now described in the following examples. In these embodiments, specific products identified by Arabic numerals (e.g., 1, 2, 3, etc.) refer to the specific structures so identified in the following description, particularly in Table 1 below and the appended claims

III. Examples

The following examples are offered for illustrative purposes only and are not intended to limit the scope of the present invention in any way. Indeed, various modifications of the invention in addition to those shown and described herein will become apparent to those skilled in the art from the foregoing description and the following examples and fall within the scope of the appended claims.

Example 1

Synthesis of 33 EET Analogs

In this Example, the inventors report the synthesis of a library of EET analogs. The chemical structures of these compounds, designated as compounds 1-33, are shown in Table 1 below.

General Procedures.

Unless stated otherwise, yields refer to purified products and are not optimized. Final compounds were judged ≥95% pure by HPLC using a Zorbax Eclipse C18 (250×4.6 mm; Agilent) connected to an Agilent 1200 API/LC-MS with acetonitrile/water combinations as solvent. All oxygen and/or moisture sensitive reactions were performed under an argon atmosphere using oven-dried glassware and anhydrous solvents Anhydrous solvents were freshly distilled from sodium benzophenone ketyl, except for $CH_2Cl_2$, which was distilled from $CaH_2$. Extracts were dried over anhydrous $Na_2SO_4$ and filtered prior to removal of all volatiles under reduced pressure. Unless otherwise noted, commercially available materials were used without purification.

Flash chromatography (FC) was performed using E Merck silica gel 60 (240-400 mesh). Thin layer chromatography (TLC) was performed using pre-coated plates purchased from E. Merck (silica gel 60 PF254, 0.25 mm). Nuclear magnetic resonance (NMR) spectra were recorded on Varian 300, 400 or 500 spectrometers at operating frequencies of 300/400/500 MHz ($^1$H) or 75/100/125 MHz ($^{13}$C) in CDCl$_3$, unless otherwise stated. Nuclear magnetic resonance (NMR) splitting patterns are described as singlet (s), doublet (d), triplet (t), quartet (q), and broad (br); the values of chemical shifts (δ) are given in ppm relative to residual solvent (chloroform δ=7.27 for $^1$H NMR or δ=77.23 for proton decoupled $^{13}$C NMR), and coupling constants (J) are given in Hertz (Hz). Melting points were determined using an OptiMelt (Stanford Research Systems) and are uncorrected. The Notre Dame University Mass Spectroscopy Facility or Prof. Kasem Nithipatikom (Medical College of Wisconsin) kindly provided high-resolution mass spectral analyses.

TABLE 1

33 EET analogs and measured vascular relaxation and sEH inhibition activity.

| Compd | Analog | Vascular Relax. % (10 μM) | EC$_{50}$ (μM) | sEHi IC$_{50}$ (nM) |
|---|---|---|---|---|
| 1 | | 86 | 2.9 | >500 |
| 2 | | 72 | 5.1 | 255 |
| 3 | | 104 | 1.5 | >500 |
| 4 | | 49 | 0.63 | 237 |
| 5 | | 95 | 1.9 | >500 |
| 6 | | 92 | 2.75 | >500 |
| 7 | | 91 | 1.6 | 392 |

TABLE 1-continued
33 EET analogs and measured vascular relaxation and sEH inhibition activity.
| Compd | Analog | Vascular Relax. % (10 μM) | EC$_{50}$ (μM) | sEHi IC$_{50}$ (nM) |
|---|---|---|---|---|
| 8 | 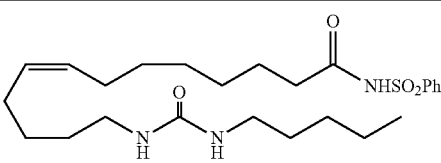 | 73 | 6.0 | 41 |
| 9 | 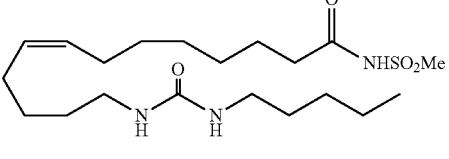 | 61 | 6.7 | 71 |
| 10 | 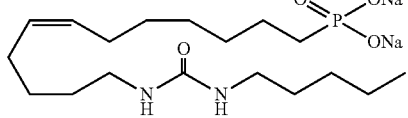 | 71 | >10 | >500 |
| 11 | 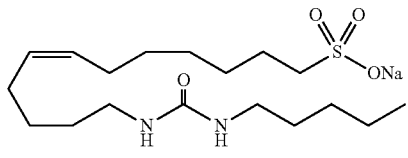 | 63 | 7.6 | 57 |
| 12 | 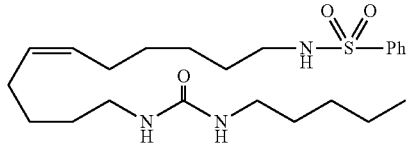 [SMILES: CCCCCNC(=O)NCCCC/C=C\CCCCCNS(=O)(=O)c1ccccc1] | 75 | 3.4 | 32 |
| 13 | 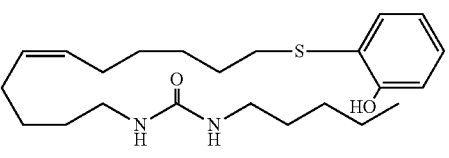 [SMILES: CCCCCNC(=O)NCCCC/C=C\CCCCCSc1ccccc1O] | 48 | >10 | 6 |
| 14 | 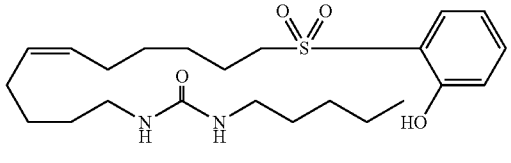 [SMILES: CCCCCNC(=O)NCCCC/C=C\CCCCCS(=O)(=O)c1ccccc1O] | 76 | 5.0 | 11 |
| 15 | 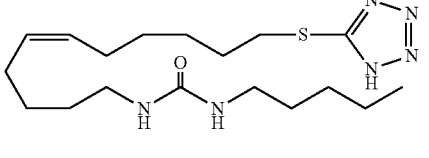 | 85 | 3.7 | 22 |
| 16 | 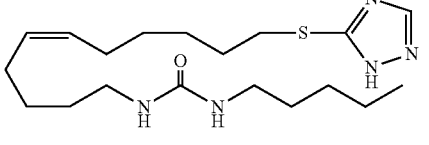 | 53 | 9.8 | 32 |

TABLE 1-continued

33 EET analogs and measured vascular relaxation and sEH inhibition activity.

| Compd | Analog | Vascular Relax. % (10 μM) | EC$_{50}$ (μM) | sEHi IC$_{50}$ (nM) |
|---|---|---|---|---|
| 17 | | 92 | 3.5 | 96 |
| 18 | | 92 | 3.1 | 23 |
| 19 | | 74 | 1.0 | >500 |
| 20 | | 119 | 0.18 | 11 |
| 21 | | 96 | 1.7 | >500 |
| 22 | | 110 | 1.1 | 32 |
| 23 | | 89 | 1.1 | 65 |
| 24 | | 47 | >10 | 57 |

TABLE 1-continued

33 EET analogs and measured vascular relaxation and sEH inhibition activity.

| Compd | Analog | Vascular Relax. % (10 μM) | EC$_{50}$ (μM) | sEHi IC$_{50}$ (nM) |
|---|---|---|---|---|
| 25 | | 109 | 0.34 | 10 |
| 26 | | 109 | 0.32 | >500 |
| 27 | | 116 | 0.36 | >500 |
| 28 | | 93 | 3.3 | 31 |
| 29 | | 54 | 2.4 | 231 |
| 30 | | 96 | 1.3 | >500 |
| 31 | | 73 | 0.9 | >500 |

TABLE 1-continued

33 EET analogs and measured vascular relaxation and sEH inhibition activity.

| Compd | Analog | Vascular Relax. % (10 μM) | EC$_{50}$ (μM) | sEHi IC$_{50}$ (nM) |
|---|---|---|---|---|
| 32 | | 96 | 2.4 | >500 |
| 33 | | 73 | 3.3 | 282 |

The synthesis of the EET-compounds of Table 1 are provided as follows:

Synthesis of Analog 25.

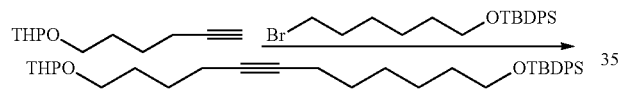

tert-Butyldiphenyl-[12-(tetrahydro-2H-pyran-2-yloxy)dodec-7-ynyloxy)]silane

N-Butyllithium (12.0 mL of 2.5 M solution in hexanes, 30.0 mmol) was added dropwise with stirring to a −78° C. solution of 2-(hex-5-ynyloxy)tetrahydro-2H-pyran (5.0 g, 27.43 mmol, G. F. Smith Chem. Co.) in THF/HMPA (4:1, 150 mL) under an argon atmosphere. After 30 min, the reaction mixture was warmed to 0° C. and maintained at this temperature for 2 h. After re-cooling to −78° C., a solution of 1-tert-butyldiphenylsilyloxy-6-bromohexane[1] (11.50 g, 27.43 mmol) in THF (55 mL) was added and the temperature was raised over 3 h to 23° C. After an additional 12 h, the reaction mixture was quenched with saturated aq. NH$_4$Cl solution (25 mL). The mixture was extracted with EtOAc (2×100 mL) and the combined extracts were washed with water (2×150 mL), brine (50 mL), dried, and concentrated under reduced pressure. The residue was purified by SiO$_2$ column chromatography to give the title compound (11.14 g, 78%), obtained as a colorless oil, whose spectral data matched literature values. TLC: 15% EtOAc/hexanes, R$_f$~0.60; $^1$H NMR (400 MHz) δ 7.64-7.68 (m, 4H), 7.34-7.42 (m, 6H), 4.57 (t, J=4.3 Hz, 1H), 3.78-3.86 (m, 2H), 3.65 (t, J=6.3 Hz, 2H), 3.32-3.54 (m, 2H), 2.10-2.22 (m, 4H), 1.24-1.84 (m, 18H), 1.04 (s, 9H); $^{13}$C NMR (100 MHz) δ 130.61, 129.17, 124.54, 122.62, 93.82, 75.48, 74.89, 72.41, 72.10, 71.78, 62.11, 58.93, 57.32, 27.51, 25.79, 24.18, 23.99, 23.68, 21.96, 21.87, 21.0, 20.55, 20.40, 14.26, 13.77, 13.67.

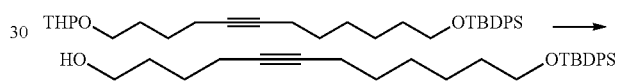

12-(tert-Butyldiphenylsilyloxy)dodec-5-yn-1-ol

A mixture of tert-butyldiphenyl-[12-(tetrahydro-2H-pyran-2-yloxy)dodec-7-ynyloxy)]silane (11.0 g, 21.14 mmol) and p-toluenesulfonic acid (165 mg) in MeOH (110 mL) was stirred at room temperature for 10 h. The reaction mixture was quenched with sat. aq. NaHCO$_3$ solution (10 mL). The methanol was evaporated, then more water (50 mL), and the mixture extracted with EtOAc (3×75 mL). The combined organic extracts were washed with water (2×50 mL), brine (40 mL), dried and concentrated under reduced pressure. The residue was purified by SiO$_2$ chromatography to give the title compound (7.93 g, 86%), obtained as a colorless oil, whose spectral data matched literature values.[1] TLC:EtOAc/hexanes (3:7), R$_f$~0.44; $^1$H NMR (300 MHz) δ 7.64-7.68 (m, 4H), 7.34-7.42 (m, 6H), 3.62 (t, J=6.3 Hz, 4H), 2.06-2.22 (m, 4H), 1.50-1.64 (m, 12H), 1.04 (s, 9H); $^{13}$C NMR (100 MHz) δ 135.81, 134.36, 129.74, 127.82, 80.89, 80.01, 64.14, 62.71, 32.71, 32.10, 29.34, 28.86, 27.11, 25.59, 25.57, 19.46, 18.93, 18.77.

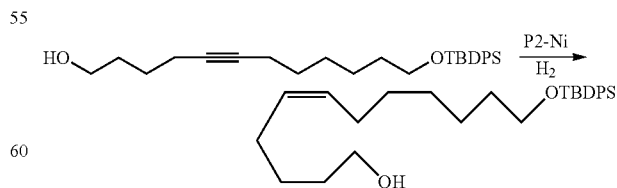

12-(tert-Butyldiphenylsilyloxy)dodec-5(Z)-en-1-ol

NaBH$_4$ (82 mg, 2.28 mmol) was added in portions with vigorously stirring to a room temperature solution of Ni(OAc)$_2$·4H$_2$O (567 mg, 2.28 mmol) in absolute ethanol (20 mL) under a hydrogen atmosphere (1 atm). After 15 min, freshly distilled ethylenediamine (0.30 mL, 4.56 mmol) was added to the black suspension, followed after a further 15 min by a solution of 12-(tert-butyldiphenylsilyloxy)dodec-5-yn-1-ol (4.0 g, 9.16 mmol) in absolute EtOH (10 mL). After 1 h, the reaction mixture was quenched with Et$_2$O (20 mL) and passed through a small bed of silica gel. The bed was rinsed with another portion of Et$_2$O (5 mL). The combined ethereal filtrates were concentrated under reduced pressure to afford the title compound (3.85 g, 96%) as a colorless oil sufficiently pure to be used directly in the next step. TLC:EtOAc/hexanes (3:7), $R_f$~0.46. $^1$H NMR (300 MHz) δ 7.64-7.68 (m, 4H), 7.34-7.42 (m, 6H), 5.42-5.28 (m, 2H), 3.65-3.60 (t, J=6.4 Hz, 4H), 2.08-1.96 (m, 4H), 1.50-1.60 (m, 4H), 1.40-1.24 (m, 10H), 1.04 (s, 9H); $^{13}$C NMR (100 MHz) δ 135.81, 134.40, 130.61, 129.71, 129.60, 127.80, 64.21, 63.14, 32.78, 32.60, 29.98, 29.27, 27.42, 27.14, 27.10, 26.08, 25.92, 19.48. HRMS calcd for C$_{28}$H$_{43}$O$_2$Si [M+1]$^+$ 439.3032, found 439.3027.

1-tert-Butyldiphenylsilyloxy-12-aminododec-7(Z)-ene

Triphenylphosphine (1.18 g, 4.50 mmol) was added to a stirring solution of azide 1-tert-butyldiphenylsilyloxy-12-azidododec-7(Z)-ene (1.90 g, 4.10 mmol) in THF (12 mL) containing 4 drops of deionized water. After 12 h, the reaction mixture was diluted with CH$_2$Cl$_2$ (10 mL), dried, and concentrated in vacuo to give the title compound (1.36 g, 76%) as a viscous, colorless oil that was used directly in the next reaction without further purification. TLC:MeOH/CH$_2$Cl$_2$ (1:4), $R_f$~0.25; $^1$H NMR (400 MHz) δ 7.62-7.68 (m, 4H), 7.32-7.40 (m, 6H), 5.30-5.40 (m, 2H), 3.63 (t, J=5.2 Hz, 2H), 2.62 (t, J=4.8 Hz, 2H), 1.92-2.06 (m, 4H), 1.40-1.58 (m, 4H), 1.20-1.40 (m, 8H), 1.03 (s, 9H); $^{13}$C NMR (100 MHz) δ 135.79, 134.37, 130.42, 129.70, 127.78, 64.19, 42.28, 33.44, 32.77, 29.93, 29.28, 27.40, 27.21, 27.10, 25.92, 19.44. HRMS calcd for C$_{28}$H$_{44}$NOSi [M+1]$^+$ 438.3192, found 438.3186.

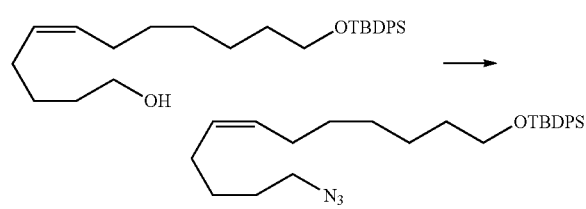

1-tert-Butyldiphenylsilyloxy-12-azidododec-7(Z)-ene

Diisopropyl azodicarboxylate (DIAD; 1.46 mL, 7.35 mmol) was added dropwise to a −20° C. solution of PPh$_3$ (2.10 g, 8.0 mmol) in dry THF (45 mL) under an argon atmosphere. After 10 min, a solution of 12-(tert-butyldiphenylsilyloxy)dodec-5(Z)-en-1-ol (3.20 g, 7.35 mmol) from above in dry THF (10 mL) was added dropwise. After 30 min, the mixture was warmed to 0° C. and diphenylphosphoryl azide (1.58 mL, 7.35 mmol) was added dropwise. After stirring 4 h at rt, the reaction mixture was quenched with water (150 mL) and extracted with EtOAc (2×100 mL). The combined organic extracts were washed with brine (100 mL), dried (Na$_2$SO$_4$), and concentrated under reduced pressure. The residue was purified by SiO$_2$ column chromatography eluting with 4% EtOAc/hexane to afford the title compound (2.45 g, 72%). TLC:EtOAc/hexanes (1:9), $R_f$~0.55; $^1$H NMR (400 MHz) δ 7.64-7.68 (m, 4H), 7.34-7.42 (m, 6H), 5.28-5.42 (m, 2H), 3.70 (t, J=5.8 Hz, 2H), 3.27 (t, J=6.3 Hz, 2H), 1.96-2.10 (m, 4H), 1.24-1.64 (m, 12H), 1.04 (s, 9H); $^{13}$C NMR (100 MHz) δ 135.84, 134.41, 130.93, 129.75, 129.12, 127.83, 64.22, 51.62, 32.81, 29.93, 29.30, 28.68, 27.46, 27.14, 27.02, 26.90, 25.96, 19.49; IR (neat) 2930, 2783, 2331, 2097, 1106 cm$^{-1}$. HRMS calcd for C$_{28}$H$_{42}$N$_3$OSi [M+1]$^+$ 464.3097, found 464.3099.

1-(12-(tert-Butyldiphenylsilyloxy)dodec-5(Z)-enyl)-3-n-pentylurea

A solution of 1-tert-butyldiphenylsilyloxy-12-aminododec-7(Z)-ene (1.32 g, 3.0 mmol) in THF (5 mL) was added dropwise to a stirring solution of n-pentyl isocyanate (0.386 mL, 3.0 mmol) in THF (10 mL). After 3 h stirring at room temperature, all volatiles were removed under reduced pressure and the residue was purified by SiO$_2$ column chromatography eluting with 20% EtOAc/hexane to afford the title compound (1.26 g, 76%) as a viscous oil. TLC:EtOAc/hexanes (2:3), $R_f$~0.40; $^1$H NMR (300 MHz) δ 7.60-7.70 (m, 4H), 7.35-7.42 (m, 6H), 5.28-5.42 (m, 2H), 5.16 (br s, —NH, 2H), 3.65 (t, J=6.5 Hz, 2H), 3.08-3.20 (m, 4H), 1.96-2.08 (m, 4H), 1.22-1.60 (m, 18H), 1.02 (s, 9H), 0.89 (t, J=7.3 Hz, 3H); $^{13}$C NMR (100 MHz) δ 159.23, 135.80, 134.24, 130.52, 129.74, 129.49, 127.82, 64.22, 40.62, 40.54, 32.80, 30.33, 29.95, 29.37, 29.32, 27.46, 27.34, 27.18, 27.11, 25.97, 22.71, 19.46, 14.29. HRMS calcd for C$_{34}$H$_{55}$N$_2$O$_2$Si [M+1]$^+$ 551.4033. found 551.4032.

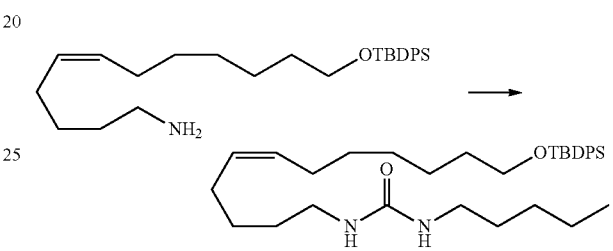

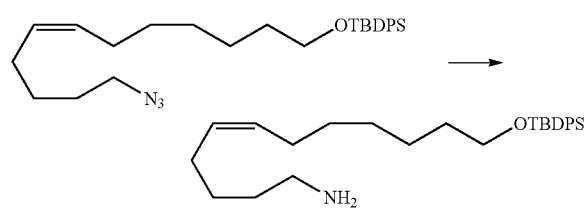

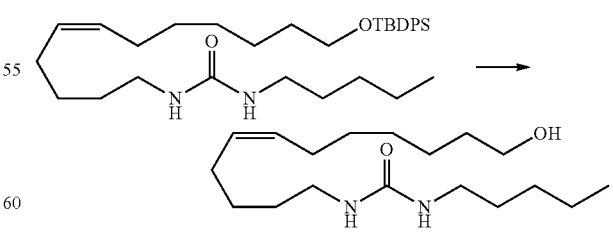

1-(12-Hydroxydodec-5(Z)-enyl)-3-n-pentylurea

A mixture of 1-(12-(tert-butyldiphenylsilyloxy)dodec-5(Z)-enyl)-3-n-pentylurea (1.12 g, 2.0 mmol) and tetra-n- butylammonium fluoride (2.20 mL of 1 M soln in THF, 2.2 mmol) in dry THF (10 mL) was stirred at room temperature under an argon atmosphere for 12 h, and then evaporated to dryness in vacuo. The residue was dissolved in EtOAc (50 mL) and washed with water (30 mL), brine (30 mL), dried and evaporated in vacuo. Purification of the residue via $SiO_2$ column chromatography gave the title compound (0.56 g, 89%) as a colorless solid, mp 63.7-63.8° C. TLC:EtOAc/hexanes (7:3), $R_f$~0.30; $^1$H NMR (300 MHz) δ 5.25-5.42 (m, 2H), 4.40-4.56 (br s, —NH, 2H), 3.60-3.68 (d, J=6.5 Hz, 2H), 3.08-3.20 (m, 4H), 1.96-2.14 (m, 4H), 1.22-1.60 (m, 18H), 0.88 (t, J=7.0 Hz, 3H); $^{13}$C NMR (125 MHz) δ 159.26, 130.23, 129.62, 63.72, 40.33, 40.29, 32.92, 30.30, 30.26, 29.74, 29.35, 29.13, 27.26, 27.20, 27.13, 25.82, 22.69, 14.27. HRMS calcd for $C_{18}H_{37}N_2O_2$ [M+1]$^+$ 313.2855, found 313.2857.

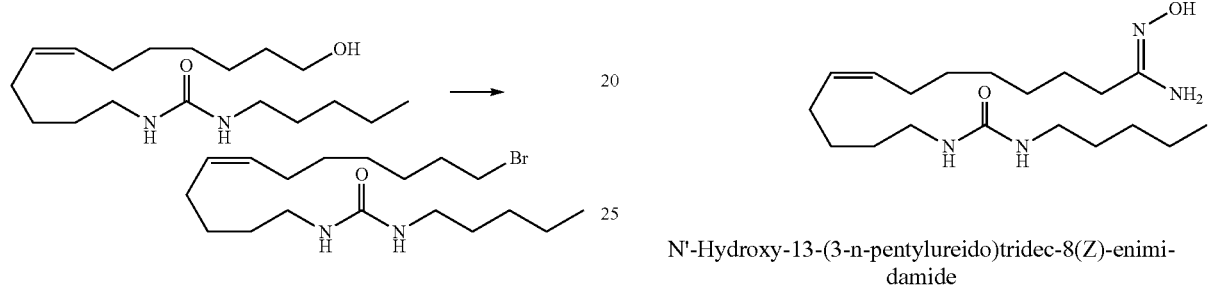

1-(12-Bromododec-5(Z)-enyl)-3-n-pentylurea $CBr_4$ (0.55 g, 1.66 mmol) and $PPh_3$ (0.43 g, 1.66 mmol) were added to a 0° C. solution of 1-(12-hydroxydodec-5(Z)-enyl)-3-n-pentylurea (0.43 g, 1.38 mmol) in $CH_2Cl_2$ (20 mL). After 2 h at room temperature, the reaction mixture was concentrated in vacuo and the residue was purified via $SiO_2$ column chromatography to give 1-(12-bromododec-5(Z)-enyl)-3-n-pentylurea (0.43 g, 83%) as a viscous oil, mp 46.7-46.8° C. TLC:EtOAc/hexanes (2:3), $R_f$~0.60; $^1$H NMR (300 MHz) δ 5.22-5.42 (m, 2H), 4.40 (br s, 2H), 3.42 (t, J=9.3 Hz, 2H), 3.10-3.20 (m, 4H), 1.98-2.10 (m, 4H), 1.80-1.90 (m, 2H), 1.25-1.55 (m, 16H), 0.92 (t, J=7.2 Hz, 3H); $^{13}$C NMR (100 MHz) δ 159.51, 130.14, 129.69, 40.48, 40.39, 34.20, 32.96, 30.34, 29.67, 29.36, 28.58, 28.25, 27.31, 27.27, 27.17, 22.68, 14.26. HRMS calcd for $C_{18}H_{36}BrN_2O$ [M+1]$^+$ 375.2011, found 375.2014.

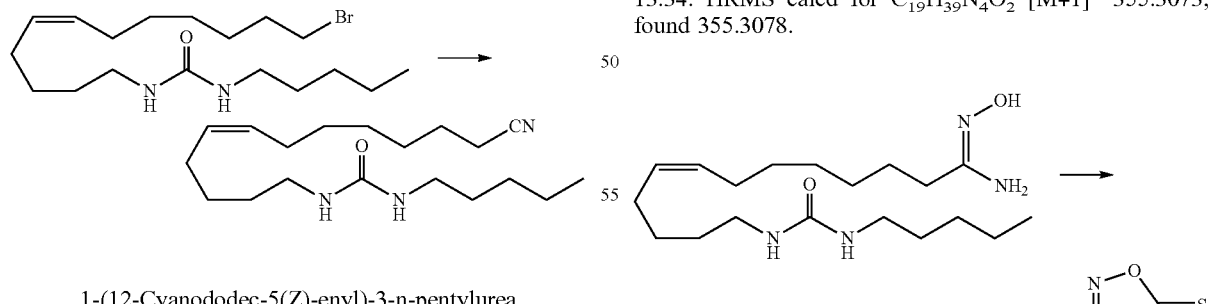

1-(12-Cyanododec-5(Z)-enyl)-3-n-pentylurea

A mixture of potassium cyanide (0.23 g, 3.54 mmol) and 1-(12-bromododec-5(Z)-enyl)-3-n-pentylurea (0.90 g, 2.40 mmol) was stirred in DMSO (5 mL) at room temperature. After 12 h, the reaction mixture was diluted with water (20 mL) and extracted with ethyl acetate (2×50 mL). The combined organic extracts were washed with water (2×25 mL), brine (25 mL), dried ($Na_2SO_4$) and was passed through a silica gel column to give the title compound (0.62 g, 81%) as a colorless solid, mp 56-57° C. TLC:EtOAc/hexanes (2:3), $R_f$~0.45. $^1$H NMR (300 MHz) δ 5.29-5.40 (m, 2H), 4.27 (br s, —NH, 2H), 3.10-3.20 (m, 4H), 2.34 (t, J=7.0 Hz, 2H), 1.98-2.08 (m, 4H) 1.24-1.70 (m, 18H), 0.89 (t, J=7.0 Hz, 3H); $^{13}$C NMR (125 MHz) δ 159.41, 129.94, 129.86, 120.14, 40.45, 40.35, 30.30, 29.50, 29.33, 28.70, 28.51, 27.26, 27.16, 25.47, 22.66, 17.28, 14.24; IR (neat) 2930, 2281, 2184, 2042, 1936, 1613, 1197, 1042 cm$^{-1}$. HRMS calcd for $C_{19}H_{36}N_3O$ [M+1]$^+$ 322.2858, found 322.2867.

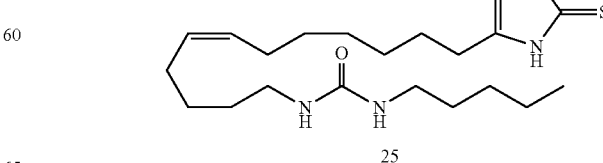

N'-Hydroxy-13-(3-n-pentylureido)tridec-8(Z)-enimidamide

To a suspension of 1-(12-cyanododec-5(Z)-enyl)-3-n-pentylurea (350 mg, 1.09 mmol) in MeOH/$H_2O$ (4:1; 12 mL) was added $H_2NOH·HCl$ (228 mg, 3.28 mmol) and $Na_2CO_3$ (344 mg, 3.25 mmol). The reaction mixture was heated at 60° C. for 18 h, then cooled to room temperature and all volatiles were removed in vacuo. The residue was diluted with water (30 mL) and extracted into ethyl acetate (2×25 mL). The combined organic extracts were washed with water (2×10 mL), brine (10 mL), dried and purified via flash silica gel column chromatography using 5% MeOH/$CH_2Cl_2$ to give the title compound (239 mg, 62%) as a colorless solid, mp 94.6-94.7° C. TLC:MeOH/$CH_2Cl_2$ (1:4), $R_f$~0.20; $^1$H NMR (CD$_3$OD, 300 MHz) δ 5.34-5.42 (m, 2H), 3.33 (s, 2H), 3.08-3.16 (m, 3H), 2.02-2.10 (m, 6H), 1.52-1.60 (m, 2H), 1.44-1.52 (m, 5H), 1.30-1.44 (m, 10H), 0.92 (t, J=7.2 Hz, 3H); $^{13}$C NMR (CD$_3$OD, 125 MHz) δ 160.14, 155.23, 129.95, 129.42, 39.86, 39.76, 30.70, 29.95, 29.89, 29.59, 29.06, 28.91, 27.18, 26.97, 26.95, 26.78, 22.39, 13.34. HRMS calcd for $C_{19}H_{39}N_4O_2$ [M+1]$^+$ 355.3073, found 355.3078.

Analog 25.

To an ice cooled solution of N'-hydroxy-13-(3-n-pentylureido)tridec-8(Z)-enimidamide (100 mg, 0.28 mmol) and pyridine (45 μL, 0.56 mmol) in THF (100 mL) was added dropwise a solution of thionyl chloride (20 μL, 0.28 mmol) in CH$_2$Cl$_2$ (2 mL). After 1 h, the reaction mixture was concentrated in vacuo, diluted with water (25 mL), and extracted with CH$_2$Cl$_2$ (2×10 mL). The combined organic extracts were washed with water and dried. The solvent was evaporated in vacuo and the residue was purified by SiO$_2$ column chromatography using 10% MeOH/CH$_2$Cl$_2$ to give 25 (80 mg, 72%) as a sticky solid. TLC:MeOH/CH$_2$Cl$_2$ (1:9), R$_f$~0.60; $^1$H NMR (CD$_3$OD, 300 MHz) δ 5.33-5.36 (m, 2H), 3.04-3.13 (m, 4H), 2.57 (t, J=7.4 Hz, 2H), 2.00-2.10 (m, 4H), 1.62-1.74 (m, 2H), 1.25-1.54 (m, 16H), 0.92 (t, J=7.2 Hz, 3H); $^{13}$C NMR (CD$_3$OD, 125 MHz) δ 160.16, 153.94, 129.83, 129.47, 39.83, 39.71, 29.89, 29.82, 29.40, 29.01, 28.59, 28.52, 26.87, 26.85, 26.71, 26.30, 23.37, 22.33, 13.25. HRMS calcd for C$_{20}$H$_{38}$N$_4$O$_2$S [M+1]$^+$ 398.2716, found 398.2720.

Synthesis of Analog 20.

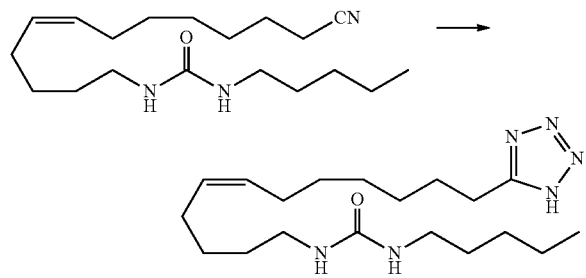

Analog 20.

A mixture of 1-(12-cyanododec-5(Z)-enyl)-3-n-pentylurea (500 mg, 1.55 mmol), sodium azide (100 mg, 1.55 mmol) and zinc bromide (335 mg, 1.48 mmol) was heated at 110° C. in isopropanol/H$_2$O (1:3, 8 mL) while stirring vigorously in a sealed tube. After 18 h, the mixture was cooled to room temperature and the pH was adjusted to 1 using aq. HCl (3 N, 4 mL). Ethyl acetate (10 mL) was added and the stirring was continued until no solid was present. The organic layer was isolated and the aqueous layer extracted with EtOAc (2×25 mL). The combined organic fractions were washed with water (3×25 mL), dried and concentrated in vacuo. The residue was purified by flash silica gel column chromatography to give the analog 20 (431 mg, 76%) as a colorless solid, mp 205.6-205.8° C. TLC: 10% MeOH/CH$_2$Cl$_2$, R$_f$~0.30; $^1$H NMR (CD$_3$OD, 300 MHz) δ 5.40-5.30 (m, 2H), 3.06-3.11 (m, 4H), 2.93 (t, J=8.0 Hz, 2H), 1.98-2.10 (m, 4H), 1.70-1.82 (m, 2H), 1.24-1.50 (m, 16H), 0.90 (t, J=7.6 Hz, 3H); $^{13}$C NMR (CD$_3$OD, 75 MHz) δ 160.16, 156.81, 129.77, 129.47, 39.81, 39.68, 29.88, 29.80, 29.35, 28.99, 28.69, 28.55, 27.48, 26.85, 26.81, 26.68, 22.96, 22.31, 13.22. HRMS calcd for C$_{19}$H$_{37}$N$_6$O [M+1]$^+$ 365.3029, found 365.3030.

Synthesis of Analog 29.

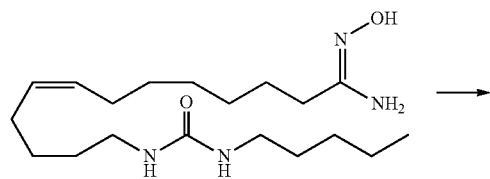

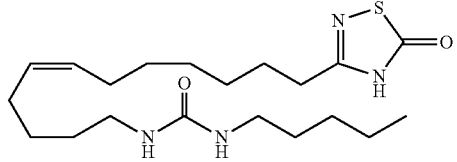

Analog 29.

A mixture of N'-hydroxy-13-(3-n-pentylureido)tridec-8(Z)-enimidamide (150 mg 0.42 mmol) and 1,1'-thiocarbonyl diimidazole (90%; 91 mg, 0.51 mmol) in THF (5 mL) was stirred at room temperature. After 45 min, the mixture was diluted with water (10 mL) and extracted with ethyl acetate (3×5 mL). The combined extracts were washed with water, dried, and concentrated in vacuo. The residue was dissolved in dry THF (5 mL) and boron trifluoride diethyl etherate (103 μL, 0.84 mmol) was added. After another 1 h, the reaction mixture was diluted with water (20 mL) and extracted with ethyl acetate (2×10 mL). The combined extracts were washed with water, dried (Na$_2$SO$_4$), and the solvent was evaporated in vacuo. The residue was purified by column chromatography to give 29 (104 mg, 63%) as a colorless solid, mp 124.2-125.1° C. TLC:MeOH/CH$_2$Cl$_2$ (1:9), R$_f$~0.60; $^1$H NMR (CD$_3$OD, 300 MHz) δ 5.30-5.40 (m, 2H), 3.02-3.12 (m, 4H), 2.54 (t, J=8.0 Hz, 2H), 1.98-2.10 (m, 4H), 1.62-1.74 (m, 2H), 1.24-1.52 (m, 16H), 0.90 (t, J=7.0 Hz, 3H); $^{13}$C NMR (CD$_3$OD, 75 MHz) δ 181.12, 160.13, 159.12, 129.48, 128.84, 39.85, 39.73, 30.90, 29.91, 29.83, 29.41, 29.03, 28.69, 28.65, 26.89, 26.86, 26.73, 26.23, 22.35, 13.29; IR (neat) 2924, 1724, 1603, 1464, 1375 cm$^{-1}$. HRMS calcd for C$_{20}$H$_{37}$N$_4$O$_2$S [M+1]$^+$ 397.2637, found 397.2638.

Synthesis of Analog 28.

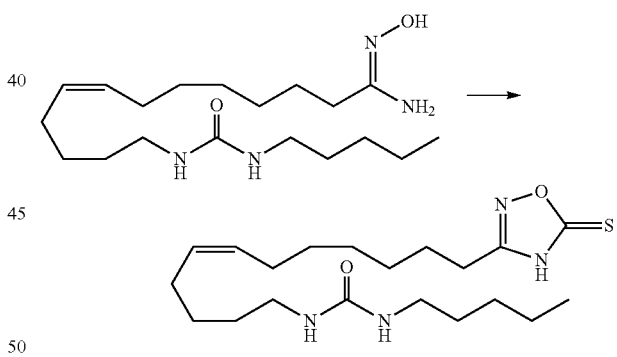

Analog 28.

A mixture of N'-hydroxy-13-(3-n-pentylureido)tridec-8(Z)-enimidamide (150 mg 0.42 mmol) and 1,1'-thiocarbonyl diimidazole (90%; 91 mg, 0.51 mmol) in THF (5 mL) was stirred at room temperature for 45 min. The mixture was diluted with water (20 mL) and extracted with ethyl acetate (3×10 mL). The combined organic extracts were washed with water, dried, and the solvent was evaporated in vacuo. The residue was dissolved in acetonitrile (5 mL) to which was then added DBU (147 mg, 0.96 mmol). After stirring at room temperature for 1 h, the mixture was diluted with water 10 mL), adjusted pH-4 with 1N HCl, and extracted with ethyl acetate (3×10 mL). The combined extracts were washed with water, dried over Na$_2$SO$_4$, and the solvent was evaporated in vacuo. The residue was purified by silica gel column chromatography to give 28 (101 mg, 61%) as a colorless syrup. TLC:MeOH/CH$_2$Cl$_2$ (1:9), R$_f$~0.55; $^1$H NMR (CD$_3$OD, 300 MHz) δ 5.30-5.40 (m, 2H), 3.04-3.14 (m, 4H), 2.62 (t, J=7.7 Hz, 2H), 2.00-2.10 (m, 4H), 1.62-1.74 (m, 2H), 1.22-1.54 (m, 16H), 0.91 (t, J=6.7 Hz, 3H); $^{13}$C NMR (CD$_3$OD, 125 MHz) δ 188.49, 161.91, 160.15, 129.82, 129.53, 39.88, 39.75, 29.92, 29.85, 29.37, 29.05, 28.63, 28.55, 26.90, 26.86, 26.75, 25.91, 23.67, 22.37, 13.31. HRMS calcd for C$_{20}$H$_{37}$N$_4$O$_2$S [M+1]$^+$ 397.2637, found 397.2645.

Synthesis of Analog 11.

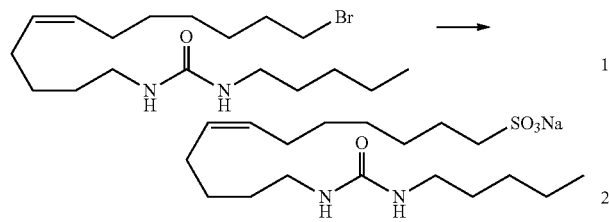

Analog 11.

A solution of 1-(12-bromododec-5(Z)-enyl)-3-n-pentylurea (300 mg, 0.79 mmol), sodium sulfite (352 mg, 2.8 mmol) and cyclohexene (649 mg, 7.9 mmol) in ethanol (5 mL) was refluxed overnight. The volatiles were removed under reduced pressure and the residue was dissolved in de-ionized water. BioRad SM-2 Bio-beads (5 g; pre-washed with 0.1 N NH$_4$OH and H$_2$O) were added, gently stirred for 30 min, and then collected on a sintered glass funnel. The beads were washed with deionized water (2×10 mL) and then EtOH (3×10 mL). Concentration of the ethanolic washes afforded 11 (235 mg, 75%) as a colorless solid, mp 133.6-133.8° C. $^1$H NMR (CD$_3$OD, 300 MHz) δ 5.30-5.40 (m, 2H), 3.02-3.14 (m, 4H), 2.78 (t, J=8.0 Hz, 2H), 1.98-2.12 (m, 4H), 1.72-1.84 (m, 2H), 1.22-1.50 (m, 16H), 0.91 (t, J=7.0 Hz, 3H); $^{13}$C NMR (CD$_3$OD, 75 MHz) δ 160.12, 129.86, 129.49, 51.46, 39.01, 38.92, 29.92, 29.32, 29.02, 28.69, 28.42, 26.93, 26.62, 25.78, 24.78, 22.34, 12.02. HRMS calcd for C$_{18}$H$_{35}$N$_2$NaO$_4$S [M]$^1$ 398.2215, found 398.2220.

Synthesis of Analog 10.

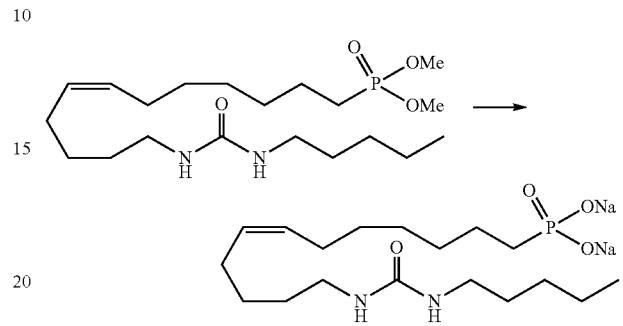

Dimethyl (12-(3-n-pentylureido)dodec-7(Z)-en-1-yl) phosphonate

A solution of 1-(12-bromododec-5(Z)-enyl)-3-n-pentylurea (250 mg, 0.67 mmol) and trimethyl phosphite (10 mL) in THF (10 mL) was heated under reflux. After for 48 h, all volatiles were removed in vacuo and the residue was purified by silica gel column chromatography using 60% EtOAc/CH$_2$Cl$_2$ to give dimethyl (12-(3-n-pentylureido)dodec-7(Z)-en-1-yl)phosphonate (160 mg, 59%) as a viscous oil. TLC:EtOAc, R$_f$~0.55; $^1$H NMR (400 MHz) δ 5.30-5.40 (m, 2H), 5.10 (br s, —NH, 1H), 5.02 (br s, —NH, 1H), 3.70 (s, 3H), 3.68 (s, 3H), 3.06-3.14 (m, 4H), 1.97-2.20 (m, 4H), 1.63-1.78 (m, 2H), 1.20-1.60 (m, 18H), 0.88 (t, J=7.2 Hz, 3H); $^{13}$C NMR (100 MHz) δ 159.11, 130.17, 129.93, 52.59, 52.56, 40.49, 30.49, 30.32, 30.28, 29.34, 29.33, 28.58, 27.21, 27.15, 27.11, 25.32, 23.93, 22.66, 22.35, 22.30, 14.24. HRMS calcd for C$_{20}$H$_{42}$N$_2$O$_4$P [M+1]$^+$ 405.2882, found 405.2883.

Analog 10.

Trimethylsilyl bromide (37 μL) was added to a solution of the above phosphonate diester (100 mg, 0.25 mmol) in dry CHCl$_3$ (4 mL). After 2 h at rt, the solution was concentrated and the residue was suspended in ethyl acetate (5 mL). The resultant precipitate was collected and dissolved in de-ionized water. BioRad SM-2 Bio-beads (5 g; pre-washed with 0.1 N NH$_4$OH and H$_2$O) were added, gently stirred for 1 h, and then collected on a sintered glass funnel. The beads were washed with deionized water (2×10 mL) and then EtOH (3×10 mL). Concentration of the ethanolic washes afforded disodium phosphonate 10 (68 mg, 65%). $^1$H NMR (CD$_3$OD, 300 MHz) δ 5.30-5.42 (m, 2H), 3.18-3.24 (m, 4H), 1.97-2.20 (m, 4H), 1.50-1.78 (m, 8H), 1.20-1.60 (m, 12H), 0.92 (t, J=7.2 Hz, 3H); $^{13}$C NMR (CD$_3$OD, 75 MHz) δ 159.48, 130.10, 129.25, 40.85, 40.76, 30.48, 30.25, 29.38, 29.13, 29.06, 28.81, 28.67, 27.62, 26.92, 26.70, 26.64, 25.80, 22.65, 22.58, 22.25, 13.02. HRMS calcd for C$_{18}$H$_{35}$N$_2$Na$_2$O$_4$P [M]$^+$ 420.2130, found 420.2122.

Synthesis of Analog 16.

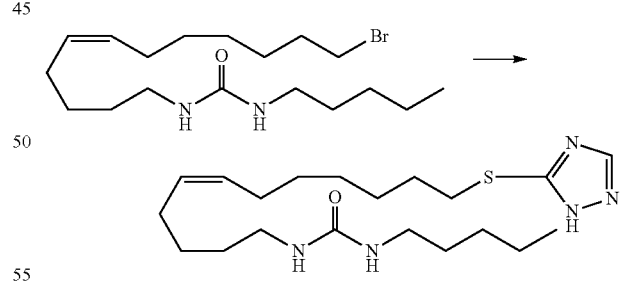

Analog 16.

Sodium methoxide (180 μL, 30% methanolic solution) was added to a solution of 1,2,4-triazole-3-thiol (101 mg, 0.99 mmol) in dry DMF (5 mL). After stirring for 10 min, 1-(12-bromododec-5(Z)-enyl)-3-n-pentylurea (250 mg, 0.66 mmol) was added. After stirring overnight, the reaction mixture was poured into ice water (100 mL) and the resultant precipitate was collected by filtration and dried in vacuo. The crude solid was suspended in dichloromethane (100 mL), stirred for 1 h and filtered to give 16 (222 mg, 85%) as a colorless solid, mp 76.1-76.2° C. TLC:EtOAc, $R_f$–0.30; $^1$H NMR (CD$_3$OD, 300 MHz) δ 8.26 (br s, 1H), 5.29-5.40 (m, 2H), 3.04-3.14 (m, 6H), 1.98-2.10 (m, 4H), 1.62-1.72 (m, 2H), 1.22-1.50 (m, 16H), 0.90 (t, J=7.2 Hz, 3H); $^{13}$C NMR (CD$_3$OD, 75 MHz) δ 160.15, 157.16, 146.90, 129.86, 129.44, 39.84, 39.73, 32.10, 29.91, 29.84, 29.65, 29.49, 29.02, 28.60, 28.30, 26.88, 26.73, 22.34, 13.28. HRMS calcd for C$_{20}$H$_{38}$N$_5$OS [M+1]$^+$ 396.2797, found 396.2805.

Synthesis of Analog 17.

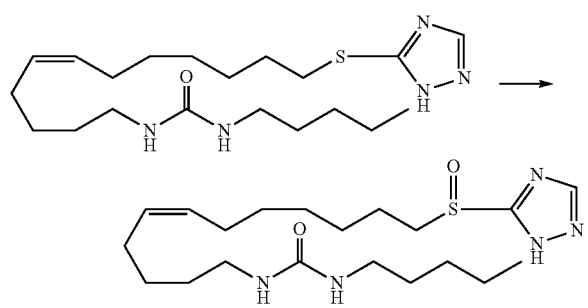

Analog 17.

Ammonium molybdate (160 mg, 0.13 mmol) and hydrogen peroxide (0.6 mL, 30% aq. soln) were combined at 0° C. and stirred for 15 min. An aliquot of the resultant bright yellow solution (0.15 mL) was added dropwise to a stirring, 0° C. solution of sulfide 16 (77 mg, 0.2 mmol) in ethanol (1.0 mL) resulting in a light yellow precipitate. Over the next 15 min, aliquots (0.15 mL) of the oxidizing solution were added every 5 min. After another 10 min, the reaction mixture was partitioned between H$_2$O and dichloromethane (10 mL). The aqueous phase was extracted with dichloromethane (10 mL) and the combined organic extracts were washed with brine and dried (Na$_2$SO$_4$). The residue was purified by flash SiO$_2$ chromatography (70% EtOAc/hexanes) to provide sulfoxide 17 (43 mg, 52%) as a colorless solid, mp 88.2-88.4° C. TLC:MeOH/EtOAc (1:9), $R_f$–0.30; $^1$H NMR (CD$_3$OD, 300 MHz) δ 8.38 (br s, 1H), 5.26-5.36 (m, 2H), 5.18 (br s, 2H), 3.04-3.26 (m, 6H), 1.92-2.08 (m, 2H), 1.70-1.84 (m, 2H), 1.20-1.50 (m, 18H), 0.86 (t, J=7.2 Hz, 3H); $^{13}$C NMR (CD$_3$OD, 75 MHz) δ 163.82, 160.15, 146.98, 129.73, 129.54, 52.62, 39.81, 39.71, 29.90, 29.84, 29.25, 29.01, 28.57, 28.22, 26.88, 26.77, 26.73, 22.33, 21.92, 13.24. HRMS calcd for C$_{20}$H$_{38}$N$_5$O$_2$S [M+1]$^+$ 412.2746, found 412.2741.

Synthesis of Analog 18.

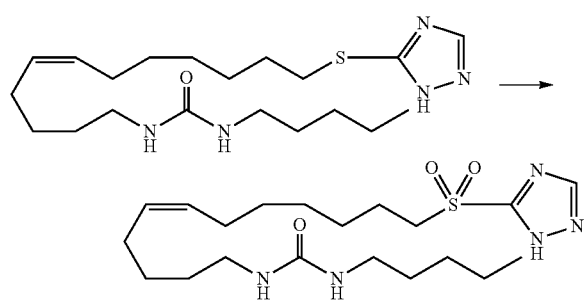

Analog 18.

Ammonium molybdate (960 mg, 0.77 mmol) and hydrogen peroxide (3.6 mL, 30% aq. soln) were combined at 0° C. and stirred for 15 min. An aliquot of the bright yellow solution (0.45 mL) was added dropwise to a 0° C. solution of sulfide 16 (154 mg, 0.39 mmol) in ethanol (3.6 mL) resulting in a light yellow precipitate. Over the next 90 min, aliquots (0.5 mL) of the oxidizing solution were added every 15 min. After another 15 min, the reaction mixture was partitioned between H$_2$O and dichloromethane (10 mL). The aqueous phase was extracted with dichloromethane (10 mL) and the combined organic phases were washed with brine and dried (Na$_2$SO$_4$). The residue was purified by flash SiO$_2$ chromatography (70% EtOAc/hexanes) to provide sulfone 18 (129 mg, 78%) as a white solid, mp 90.6-90.8° C. TLC:MeOH/EtOAc (1:9), $R_f$–0.50; $^1$H NMR (CD$_3$OD, 300 MHz) δ 8.44 (br s, 1H), 5.25-5.30 (m, 2H), 5.02 (br s, 1H), 4.90 (br s, 1H), 3.35 (t, J=7.9 Hz, 2H), 3.22-3.10 (m, 4H), 1.90-2.60 (m, 4H), 1.66-1.80 (m, 2H), 1.20-1.54 (m, 16H), 0.87 (t, J=7.3 Hz, 3H); $^{13}$C NMR (CD$_3$OD, 75 MHz) δ 161.15, 160.13, 145.87, 129.73, 129.56, 54.26, 39.85, 39.74, 29.90, 29.83, 29.21, 29.02, 28.46, 27.80, 26.89, 26.79, 26.73, 22.34, 22.19, 13.30. HRMS calcd for C$_{20}$H$_{38}$N$_5$O$_3$S [M+1]$^+$ 428.2695, found 428.2701.

Synthesis of Analog 23.

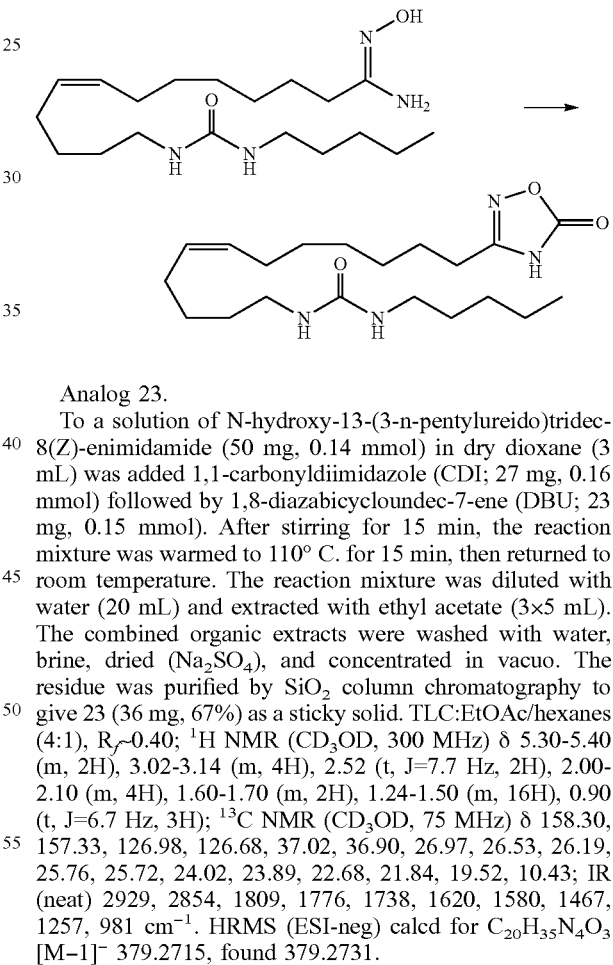

Analog 23.

To a solution of N-hydroxy-13-(3-n-pentylureido)tridec-8(Z)-enimidamide (50 mg, 0.14 mmol) in dry dioxane (3 mL) was added 1,1-carbonyldiimidazole (CDI; 27 mg, 0.16 mmol) followed by 1,8-diazabicycloundec-7-ene (DBU; 23 mg, 0.15 mmol). After stirring for 15 min, the reaction mixture was warmed to 110° C. for 15 min, then returned to room temperature. The reaction mixture was diluted with water (20 mL) and extracted with ethyl acetate (3×5 mL). The combined organic extracts were washed with water, brine, dried (Na$_2$SO$_4$), and concentrated in vacuo. The residue was purified by SiO$_2$ column chromatography to give 23 (36 mg, 67%) as a sticky solid. TLC:EtOAc/hexanes (4:1), $R_f$–0.40; $^1$H NMR (CD$_3$OD, 300 MHz) δ 5.30-5.40 (m, 2H), 3.02-3.14 (m, 4H), 2.52 (t, J=7.7 Hz, 2H), 2.00-2.10 (m, 4H), 1.60-1.70 (m, 2H), 1.24-1.50 (m, 16H), 0.90 (t, J=6.7 Hz, 3H); $^{13}$C NMR (CD$_3$OD, 75 MHz) δ 158.30, 157.33, 126.98, 126.68, 37.02, 36.90, 26.97, 26.53, 26.19, 25.76, 25.72, 24.02, 23.89, 22.68, 21.84, 19.52, 10.43; IR (neat) 2929, 2854, 1809, 1776, 1738, 1620, 1580, 1467, 1257, 981 cm$^{-1}$. HRMS (ESI-neg) calcd for C$_{20}$H$_{35}$N$_4$O$_3$ [M–1]$^-$ 379.2715, found 379.2731.

Synthesis of Analog 27.

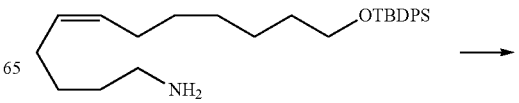

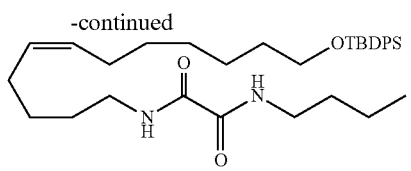

$N^1$-n-Butyl-$N^2$-(12-(tert-butyldiphenylsilyloxy)dodec-5(Z)-enyl)oxalamide A mixture of 2-(n-butylamino)-2-oxoacetic acid (0.40 g, 2.70 mmol), the above 1-tert-butyldiphenylsilyloxy-12-aminododec-7(Z)-ene (1.20 g, 2.70 mmol), 1-hydroxybenzotriazole (HOBt; 0.44 g, 3.30 mmol) and [1-(3-dimethylaminopropyl)-3-ethylcarbodiimide hydrochloride] (0.63 g, 3.30 mmol) in dry DMF (5 mL) was stirred at room temperature overnight. The reaction mixture was quenched with water (30 mL) and extracted into ethyl acetate (3×20 mL). The combined organic extracts were washed with water (2×10 mL), brine (10 mL), dried and concentrated in vacuo. The residue was purified by $SiO_2$ column chromatography to give $N^1$-n-butyl-$N^2$-(12-(tert-butyldiphenylsilyloxy)dodec-5(Z)-enyl)oxalamide (1.10 g, 73%). TLC: EtOAc/hexanes (2:3), $R_f$~0.55; $^1$H NMR (400 MHz) δ 8.05 (br s, —NH, 2H), 7.66-7.74 (m, 4H), 7.32-7.42 (m, 6H), 5.30-5.42 (m, 2H), 3.67 (t, J=3.9 Hz, 2H), 3.31 (q, J=5.2 Hz, 4H), 1.96-2.10 (m, 4H), 1.50-1.64 (m, 6H), 1.22-1.44 (m, 10H), 1.06 (s, 9H), 0.92 (t, J=7.8 Hz, 3H); $^{13}$C NMR (100 MHz) δ 160.33, 135.80, 134.35, 130.73, 129.74, 129.20, 127.83, 64.17, 39.89, 39.69, 32.79, 31.48, 29.94, 29.29, 29.07, 27.46, 27.23, 27.14, 27.0, 25.96, 20.29, 19.46, 13.96. HRMS calcd for $C_{34}H_{53}N_2O_3Si$ [M+1]$^+$ 565.3826, found 565.3824.

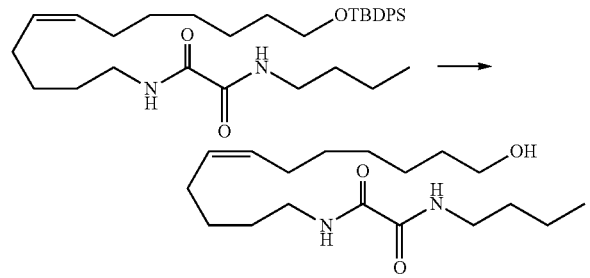

$N^1$-n-Butyl-$N^2$-(12-hydroxydodec-5(Z)-enyl)oxalamide $N^1$-n-Butyl-$N^2$-(12-(tert-butyldiphenylsilyloxy)dodec-5 (Z)-enyl)oxalamide (1.20 g, 2.12 mmol) was de-silylated as described above to give $N^1$-n-butyl-$N^2$-(12-hydroxydodec-5(Z)-enyl)oxalamide (0.568 g, 82%) as a colorless solid, mp 102.8-102.9° C. TLC:EtOAc/hexanes (7:3), $R_f$~0.55; $^1$H NMR (400 MHz) δ 7.69 (br s, 2H), 5.20-5.35 (m, 2H), 3.56 (t, J=4.2 Hz, 2H), 3.26 (q, J=5.6 Hz, 4H), 2.17 (br s, —OH), 1.95-2.02 (m, 4H), 1.44-1.56 (m, 6H), 1.20-1.40 (m, 10H), 0.87 (t, J=7.2 Hz, 3H); $^{13}$C NMR (100 MHz) δ 160.15, 130.66, 129.21, 62.98, 39.80, 39.63, 32.93, 31.39, 29.77, 29.18, 28.95, 27.26, 27.0, 26.88, 25.80, 20.18, 13.85. HRMS calcd for $C_{18}H_{35}N_2O_3$ [M+1]$^+$ 327.2648. found 327.2648.

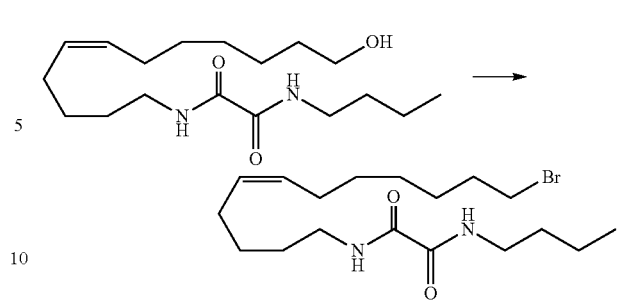

$N^1$-(12-Bromododec-5(Z)-enyl)-$N^2$-n-butyloxalamide $N^1$-n-Butyl-$N^2$-(12-hydroxydodec-5(Z)-enyl)oxalamide (330 mg, 1.0 mmol) was brominated as described above to give $N^1$-(12-bromododec-5(Z)-enyl)-$N^2$-n-butyloxalamide (330 mg, 84%) as a white solid, mp 46.0-46.3° C. TLC: EtOAc/hexanes (3:2), $R_f$~0.55; $^1$H NMR (400 MHz) δ 7.79 (br s, —NH, 1H), 7.77 (br s, —NH, 1H), 5.20-5.32 (m, 2H), 3.32 (t, J=6.4 Hz, 2H), 3.22 (q, J=7.2 Hz, 4H), 1.90-2.00 (m, 4H), 1.72-1.82 (m, 2H), 1.42-1.56 (m, 4H), 1.20-1.40 (m, 10H), 0.85 (t, J=7.3 Hz, 3H); $^{13}$C NMR (100 MHz) δ 160.17, 160.15, 130.40, 129.34, 39.77, 39.59, 34.12, 32.93, 31.40, 29.62, 29.0, 28.54, 27.25, 27.24, 27.0, 26.91, 20.18, 13.85. HRMS calcd for $C_{18}H_{34}BrN_2O_2$ [M+1]$^+$ 389.1804, found 389.1809.

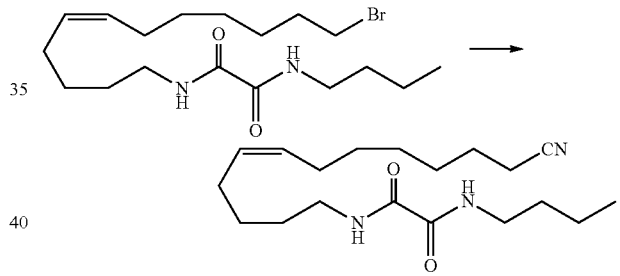

$N^1$-n-Butyl-$N^2$-(12-cyanododec-5(Z)-enyl)oxalamide $N^1$-(12-bromododec-5(Z)-enyl)-$N^2$-n-butyloxalamide (250 mg, 0.642 mmol) was treated as described above with potassium cyanide to give $N^1$-n-butyl-$N^2$-(12-cyanododec-5(Z)-enyl)oxalamide (168 mg, 78%) as a colorless solid, mp 83.0-83.3° C. TLC:EtOAc/hexanes (3:2), $R_f$~035; $^1$H NMR (400 MHz) δ 7.45 (br s, —NH, 2H), 5.30-5.40 (m, 2H), 3.34 (q, J=8.6 Hz, 4H), 2.32 (t, J=7.6 Hz, 2H), 1.98-2.08 (m, 4H), 1.30-1.68 (m, 16H), 0.92 (t, J=7.2 Hz, 3H); $^{13}$C NMR (100 MHz) δ 160.03 (2C), 130.03, 129.08, 120.10, 39.88, 39.42, 31.22, 29.40, 28.82, 28.60, 28.42, 27.07, 27.06, 26.82, 25.54, 20.06, 17.01, 13.80. HRMS calcd for $C_{19}H_{34}N_3O_2$ [M+1]$^+$ 336.2651, found 336.2650.

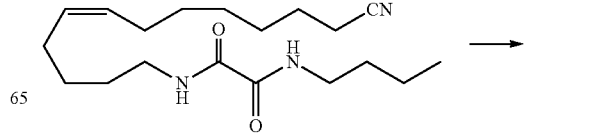

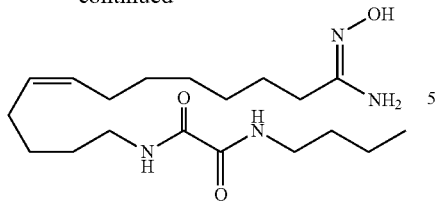

$N^1$-(13-Amino-13-(hydroxyimino)tridec-5(Z)-enyl)-$N^2$-n-butyloxalamide

Following the procedure described above, a mixture of $N^1$-n-butyl-$N^2$-(12-cyanododec-5(Z)-enyl)oxalamide, $H_2$NOH.HCl, and $Na_2CO_3$ was converted to $N^1$-(13-amino-13-(hydroxyimino)tridec-5(Z)-enyl)-$N^2$-n-butyloxalamide (102 mg, 62%) as a colorless solid, 116.3-116.4° C. TLC: MeOH/$CH_2Cl_2$ (1:4), $R_f$~0.20; $^1$H NMR ($CD_3$OD, 400 MHz) δ 5.28-5.40 (m, 2H), 3.24 (t, J=6.4 Hz, 4H), 1.98-2.00 (m, 6H), 1.50-1.60 (m, 6H), 1.26-1.40 (m, 10H), 0.92 (t, J=7.3 Hz, 3H); $^{13}$C NMR ($CD_3$OD, 100 MHz) δ 160.55 (2C), 156.31, 130.05, 129.18, 39.23, 39.09, 31.18, 30.63, 29.51, 28.83, 28.69, 27.10, 26.87, 26.59, 19.88, 12.88. HRMS calcd for $C_{19}H_{37}N_4O_3$ [M+1]$^+$ 369.2866, found 369.2864.

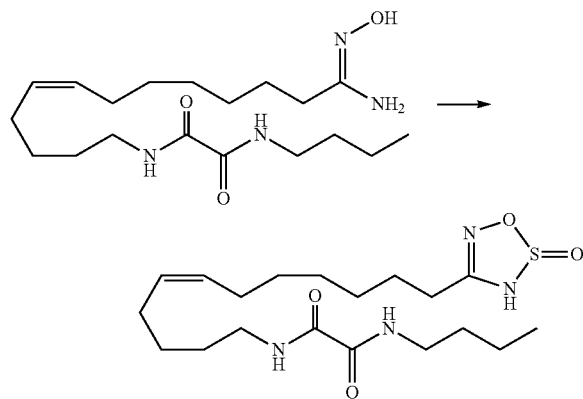

Analog 27.

Treatment of $N^1$-(13-amino-13-(hydroxyimino)tridec-5(Z)-enyl)-$N^2$-n-butyloxalamide (100 mg, 0.27 mmol) with 1,1'-thiocarbonyl diimidazole gave 27 (71 mg, 63%) as a white solid, mp 110.6-110.8° C. TLC:MeOH/$CH_2Cl_2$ (1:9), $R_f$~0.55; $^1$H NMR (400 MHz) δ 8.90 (br s, NH, 1H), 7.52 (br s, NH, 2H), 5.28-5.40 (m, 2H), 3.20-3.40 (m, 4H), 2.59 (t, J=7.5 Hz, 2H), 1.98-2.10 (m, 4H), 1.21-1.70 (m, 16H), 0.92 (t, J=7.3 Hz, 3H); $^{13}$C NMR (100 MHz) δ 160.12, 160.08, 153.31, 130.62, 129.46, 39.93, 39.85, 31.35, 29.33, 28.94, 28.89, 28.68, 27.02, 26.84, 26.69, 23.96, 20.23, 13.90. HRMS calcd for $C_{19}H_{35}N_4O_4S$ [M+1]$^+$ 415.2379, found 415.2372.

Synthesis of Analog 21.

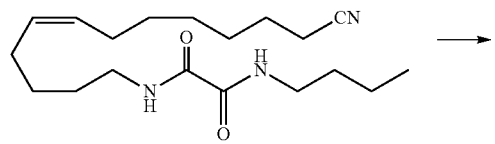

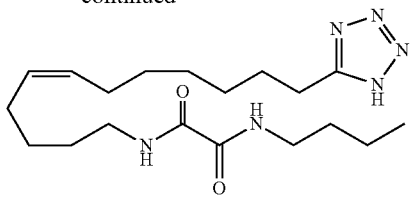

Analog 21.

Following the procedure used to prepare 22, a mixture of $N^1$-n-butyl-$N^2$-(12-cyanododec-5(Z)-enyl)oxalamide (30 mg, 0.10 mmol), sodium azide (11 mg, 0.20 mmol) and zinc bromide (40 mg, 0.20 mmol) was heated in isopropanol/methanol/$H_2$O (1:1:3, 4 mL) to give tetrazole 21 (25 mg, 74%) as a colorless solid, mp 113-114° C. TLC: 10% MeOH/$CH_2Cl_2$, $R_f$~0.26; $^1$H NMR ($CD_3$OD, 400 MHz) δ 5.40-5.35 (m, 2H), 3.26 (t, J=7.0 Hz, 4H), 2.44 (t, J=7.0 Hz, 2H), 2.05-2.15 (m, 4H), 1.65-1.60 (m, 6H), 1.40-1.30 (m, 10H), 0.94 (t, J=7.3 Hz, 3H); $^{13}$C NMR ($CD_3$OD, 100 MHz) δ 160.12, 160.05, 156.80, 130.35, 129.50, 39.20, 39.08, 31.15, 29.33, 28.66, 28.65, 28.53, 27.38, 26.83, 26.79, 26.55, 22.86, 19.85, 12.84. HRMS calcd for $C_{19}H_{35}N_6O_2$ [M+1]$^+$ 379.2822, found 379.2814.

Synthesis of Analog 26.

1-(tert-Butyldiphenylsilyloxy-12-Iodododec-7(Z)-ene

Triphenylphosphine (504 mg, 1.14 mmol) and imidazole (156 mg, 2.30 mmol) were added to a 0° C. solution of the above 12-(tert-butyldiphenylsilyloxy)dodec-5(Z)-en-1-ol (500 mg, 1.14 mmol) in dry THF (25 mL) under an argon atmosphere. After 10 min, solid iodine (252 mg, 1.2 equiv) was added in portions. After stirring at room temperature for 3 h, the reaction mixture was quenched with sat. aq. sodium bisulfite solution (10 mL). After an additional 1 h, the solution was washed with water (2×30 mL) and concentrated under reduced pressure. The residue was purified by flash $SiO_2$ column chromatography using 10% EtOAc/hexanes as eluent to give the title compound (474 mg, 76%) as a colorless oil. TLC: 20% EtOAc/hexanes, $R_f$~0.65; $^1$H NMR (300 MHz) δ 7.65-7.70 (m, 4H), 7.35-7.45 (m, 6H), 5.30-5.40 (m, 2H), 3.64 (t, J=6.4 Hz, 2H), 3.18 (t, J=5.5 Hz, 2H), 1.95-2.10 (m, 4H), 1.85-1.90 (m, 2H), 1.22-1.50 (m, 10H), 1.20 (s, 9H); $^{13}$C NMR (75 MHz) δ 135.87, 130.42, 130.22, 130.20, 129.95, 127.89, 64.15, 38.35, 36.20, 32.50, 29.90, 28.62, 28.32, 27.25, 27.20, 27.18, 26.22, 19.12. HRMS calcd for $C_{28}H_{42}$IOSi [M+1]$^+$ 549.2050. found 549.2044.

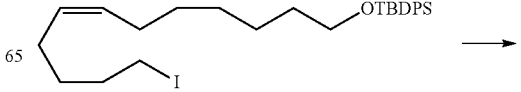

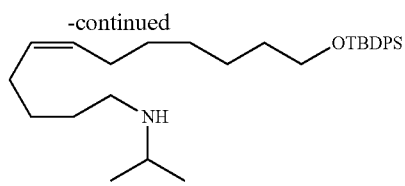

1-(tert-Butyldiphenylsilyloxy-12-N-isopropylamino-dodec-7(Z)-ene

Isopropylamine (464 μL, 5.45 mmol) and K$_2$CO$_3$ (373 mg, 2.73 mmol) were added sequentially to a room temperature solution of 1-(tert-butyldiphenylsilyloxy-12-iodododec-7(Z)-ene (500 mg, 0.91 mmol) in dry tetrahydrofuran (8 mL). The mixture was heated in a sealed tube at 90° C. for 12 h, then cooled to rt, diluted with water (5 mL), filtered and the filtrate was extracted with ethyl acetate (3×10 mL). The combined organic extracts were dried, concentrated under reduced pressure, and the residue was purified by SiO$_2$ column chromatography using a gradient from 2% to 5% MeOH/CH$_2$Cl$_2$ as eluent to give the title amine (335 mg, 77%) as a colorless oil. TLC: 5% MeOH/CH$_2$Cl$_2$, R$_f$~0.3; $^1$H NMR (300 MHz) δ 7.62-7.70 (m, 4H), 7.34-7.44 (m, 6H), 5.30-5.40 (m, 2H), 3.64 (t, J=6.4 Hz, 2H), 2.72-2.84 (m, 1H), 2.58 (t, J=7.0 Hz, 2H), 1.94-2.08 (m, 4H), 1.20-1.60 (m, 12H), 1.05 (d, J=7.2 Hz, 6H), 1.04 (s, 9H); $^{13}$C NMR (75 MHz) δ 135.81, 134.40, 132.0, 129.72, 127.81, 64.21, 48.96, 47.75, 32.80, 30.33, 29.97, 29.31, 27.85, 27.44, 27.33, 27.11, 25.95, 23.27, 19.46. HRMS calcd for C$_{31}$H$_{50}$NOSi [M+1]$^+$ 480.3662, found 480.3666.

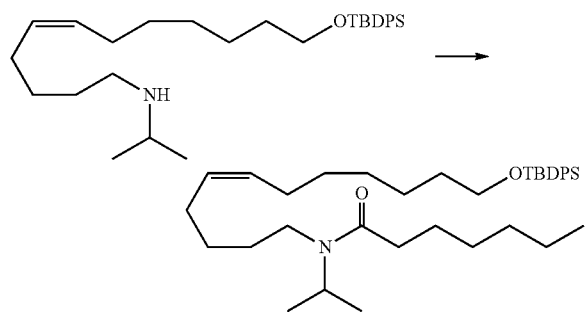

N-(12-(tert-Butyldiphenylsilyloxy)dodec-5(Z)-enyl)-N-isopropyl n-heptanamide Solid [1-(3-dimethylaminopropyl)-3-ethylcarbodiimide hydrochloride] (EDCI; 131 mg, 0.69 mmol) was added in portions to a room temperature solution of 1-(tert-butyldiphenylsilyloxy-12-N-isopropylamino-dodec-7(Z)-ene (300 mg, 0.63 mmol), DMAP (84 mg, 0.69 mmol), N-hydroxybenzotriazole (HOBt; 93 mg, 0.69 mmol), and n-heptanoic acid (90 mg, 0.68 mmol) in dry DMF (5 mL). After 12 h, the reaction mixture was diluted with water (10 mL) and extracted with ether (3×5 mL). The combined ethereal extracts were washed with brine, dried, and evaporated in vacuo. The residue was purified via SiO$_2$ column chromatography to give the title compound (281 mg, 76%) as a colorless oil. TLC:EtOAc/hexanes (1:4), R$_f$~0.65; $^1$H NMR (300 MHz, 1:1 mixture of rotamers) δ 7.62-7.70 (m, 4H), 7.34-7.44 (m, 6H), 5.30-5.40 (m, 2H), 4.60-4.70 and 4.00-4.05 (m, 1H for two rotamers), 3.05 (t, J=5.2 Hz, 2H), 3.02-3.19 (m, 2H), 2.20-2.40 (m, 2H), 1.95-2.10 (m, 4H), 1.20-1.60 (m, 20H), 1.18 and 1.08 (d, J=7.0 Hz, 6H for two rotamers), 1.02 (s, 9H), 0.88 (t, J=7.2 Hz, 3H); $^{13}$C NMR (75 MHz) δ 177.24, 173.35, 172.25, 136.16, 135.80, 135.14, 134.37, 134.34, 130.97, 130.31, 129.74, 129.73, 129.54, 129.04, 127.82, 127.75, 64.21, 64.18, 48.42, 45.68, 43.62, 41.19, 34.46, 34.02, 32.81, 32.79, 31.95, 31.94, 31.75, 31.28, 30.0, 29.92, 29.55, 29.46, 29.31, 29.09, 27.87, 27.52, 27.49, 27.45, 27.21, 27.13, 26.94, 26.88, 25.97, 25.95, 25.79, 25.15, 22.81, 22.75, 21.63, 20.77, 19.46, 19.33, 14.34, 14.30. HRMS calcd for C$_{38}$H$_{62}$NO$_2$Si [M+1]$^+$ 592.4550, found 592.4552.

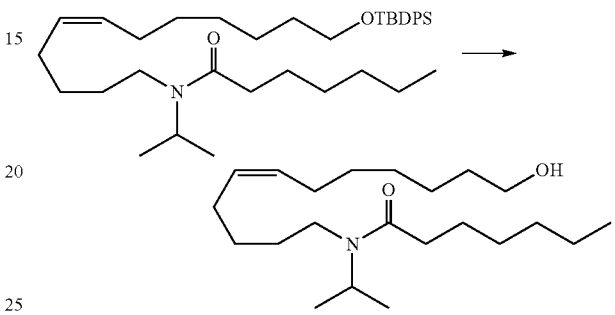

N-(12-Hydroxydodec-5(Z)-enyl)-N-isopropyl n-heptanamide

Following the desilylation procedure above, N-(12-(tert-butyldiphenylsilyloxy)dodec-5(Z)-enyl)-N-isopropyl n-heptanamide (275 mg, 0.464 mmol) was converted to the title alcohol (155 mg, 94%) as a syrup. TLC: 40% EtOAc/hexanes, R$_f$~0.45; $^1$H NMR (300 MHz, 45/55 mixture of rotamers) δ 5.30-5.46 (m, 2H), 4.62-4.72 and 4.00-4.08 (m, 1H for two rotamers), 3.63 (t, J=5.4 Hz, 2H), 3.06-3.14 (m, 2H), 2.22-2.36 (m, 2H), 1.98-2.10 (m, 4H), 1.24-1.70 (m, 20H), 1.17 and 1.10 (d, J=6.8 Hz, 6H for two rotamers), 0.88 (t, J=7.2 Hz, 3H); $^{13}$C NMR (75 MHz) δ 173.23, 172.67, 130.83, 130.12, 129.71, 128.96, 62.69, 62.64, 48.34, 45.56, 43.52, 41.07, 34.0, 33.91, 32.91, 32.88, 31.84, 31.81, 31.18, 29.82, 29.74, 29.46, 29.33, 29.11, 27.78, 27.37, 27.35, 27.16, 27.13, 26.84, 25.89, 25.81, 25.66, 22.69, 21.51, 20.65, 14.21. HRMS calcd for C$_{22}$H$_{44}$NO$_2$ [M+1]$^+$ 354.3372, found 354.3380.

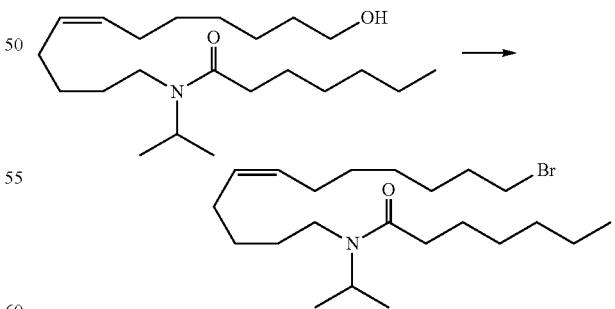

N-(12-Bromododec-5(Z)-enyl)-N-isopropyl-n-hexanamide

Following the procedure above, N-(12-hydroxydodec-5 (Z)-enyl)-N-isopropyl n-heptanamide (150 mg, 0.43 mmol)

was transformed as described above into the corresponding bromide (144 mg, 82%) as a syrup. TLC: 30% EtOAc/hexanes, $R_f$~0.65; $^1$H NMR (300 MHz, 45/55 ratio of rotamers) δ 5.30-5.42 (m, 2H), 4.60-4.70 and 4.00-4.10 (m, 1H for two rotamers), 3.42 (t, J=5.3 Hz, 2H), 3.02-3.20 (m, 2H), 2.20-2.38 (m, 2H), 1.80-2.10 (m, 4H), 1.20-1.70 (m, 20H), 1.16 and 1.12 (d, J=7.2 Hz, 6H for two rotamers), 0.87 (t, J=7.2 Hz, 3H); $^{13}$C NMR (75 MHz) δ 173.20, 172.64, 130.61, 130.46, 129.96, 129.94, 129.24, 48.34, 45.56, 43.54, 41.09, 34.20, 34.16, 34.05, 33.97, 32.98, 32.93, 32.60, 31.90, 31.88, 31.26, 29.78, 29.68, 29.62, 29.51, 29.40, 28.94, 28.55, 28.25, 28.20, 27.81, 27.69, 27.45, 27.30, 27.25, 27.18, 26.92, 25.87, 25.20, 22.75, 21.59, 20.72, 14.72. HRMS calcd for $C_{22}H_{43}BrNO$ [M+1]$^+$ 416.2528, found 416.2523.

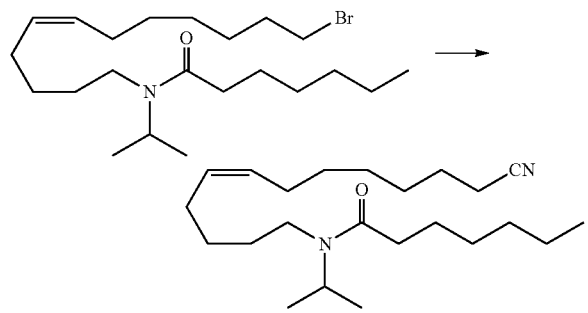

N-(12-Cyanododec-5(Z)-enyl)-N-isopropyl-n-hexanamide

Following the cyanide displacement procedure above, N-(12-bromododec-5(Z)-enyl)-N-isopropyl-n-hexanamide (500 mg, 1.20 mmol) gave the title nitrile (339 mg, 78%) as a syrup. TLC:EtOAc/hexanes (3:7), $R_f$~0.40; $^1$H NMR (500 MHz, 45/55 ratio of rotamers) δ 5.20-5.34 (m, 2H), 4.52-4.62 and 3.90-4.02 (m, 1H for two rotamers), 3.00-3.10 (m, 2H), 2.16-2.30 (m, 4H), 1.90-2.05 (m, 4H), 1.60-1.70 (m, 8H), 1.22-1.50 (m, 12H), 1.18 and 1.11, (d, J=6.8 Hz, 6H for two rotamers), 0.88 (t, J=7.2 Hz, 3H); $^{13}$C NMR (75 MHz) δ 173.22, 172.66, 130.42, 130.04, 129.78, 129.35, 120.04, 119.99, 48.34, 45.58, 43.54, 41.07, 34.02, 33.95, 31.89, 31.86, 31.22, 29.53, 29.49, 29.37, 28.73, 28.70, 28.57, 28.53, 27.78, 27.39, 27.26, 27.18, 27.17, 26.91, 25.85, 25.70, 25.52, 25.49, 22.73, 21.56, 20.70, 17.26, 14.27. HRMS calcd for $C_{23}H_{43}N_2O$ [M+1]$^+$ 363.3375, found 363.3375.

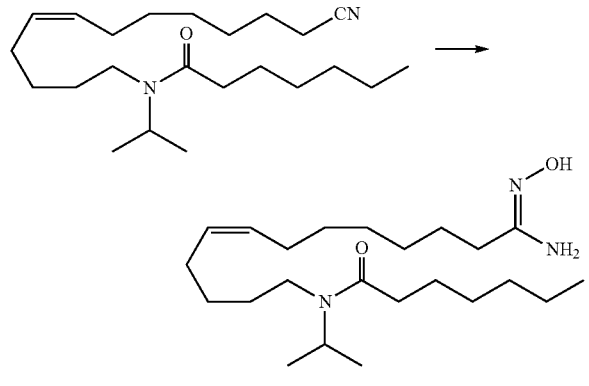

N-(13-Amino-13-(hydroxyimino)tridec-5(Z)-enyl)-N-isopropyl-n-heptanamide

Following the procedure above, a mixture of N-(12-cyanododec-5(Z)-enyl)-N-isopropyl-n-hexanamide, $H_2NOH·HCl$, and $Na_2CO_3$ was converted into the title compound (64%). TLC:MeOH/$CH_2Cl_2$ (3:7), $R_f$~0.30; $^1$H NMR (500 MHz, 1:1 ratio of rotamers) δ 5.24-5.40 (m, 2H), 4.62-4.68 (m, 0.5H), 4.50-4.60 (—NH, 2H), 3.96-4.40 (m, 0.5H), 3.02-3.14 (m, 2H), 2.18-2.28 (m, 2H), 1.90-2.16 (m, 6H), 1.46-1.64 (m, 8H), 1.20-1.36 (m, 12H), 1.15 and 1.08 (d, J=7.3 Hz, 6H for two rotamers), 0.85 (t, J=7.2 Hz, 3H); $^{13}$C NMR (75 MHz) δ 173.22, 172.58, 154.26, 154.21, 130.82, 130.13, 129.79, 129.08, 48.32, 45.50, 43.52, 41.09, 36.03, 34.05, 34.05, 33.97, 31.89, 31.86, 31.459, 31.25, 29.72, 29.67, 29.53, 29.39, 29.21, 29.19, 29.11, 29.03, 27.83, 27.41, 27.24, 27.17, 26.90, 26.84, 25.87, 25.70, 22.74, 21.58, 20.73, 14.26. HRMS calcd for $C_{23}H_{46}N_3O_2$ [M+1]$^+$ 396.3590, found 396.3698.

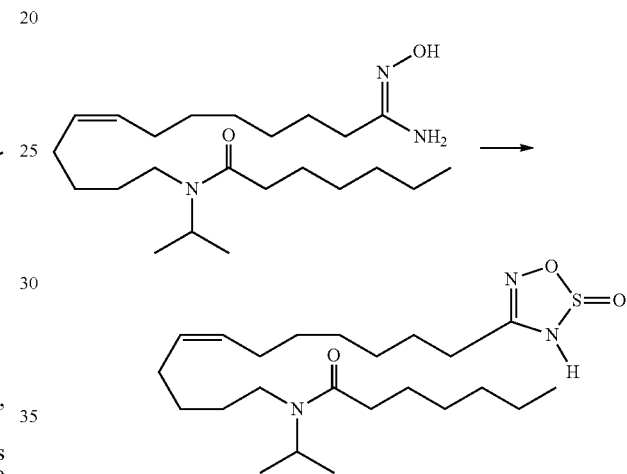

Analog 26.

N-(13-Amino-13-(hydroxyimino)tridec-5(Z)-enyl)-N-isopropyl-n-heptanamide (150 mg, 0.38 mmol) was treated with thionyl chloride at 0° C. as described above to give 26 (133 mg, 68%) as a syrup. TLC:EtOAc/hexanes (1:1), $R_f$~0.30; $^1$H NMR (400 MHz, 35/65 ratio of rotamers) δ 5.22-5.40 (m, 2H), 4.48-4.70 and 4.00-4.12 (m, 1H for two rotamers), 3.04-3.20 (m, 2H), 2.50 and 2.64 (t, J=6.9 Hz, 2H for two rotamers), 2.22, 2.38 (t, J=8.0 Hz, 2H for two rotamers), 1.90-2.10 (m, 4H), 1.50-1.78 (m, 8H), 1.20-1.40 (m, 12H), 1.22 and 1.12 (d, J=6.7 Hz 6H for two rotamers), 0.88 (t, J=7.2 Hz, 3H); $^{13}$C NMR (100 MHz) δ 173.82, 173.40, 153.39, 153.26, 131.03, 130.02, 129.97, 129.10, 48.85, 46.04, 43.82, 41.50, 34.13, 34.02, 31.85, 31.80, 31.23, 29.58, 29.32, 29.11, 29.09, 29.02, 28.80, 28.17, 27.96, 27.32, 27.24, 27.19, 26.03, 26.75, 26.64, 26.10, 24.02, 29.96, 22.75, 21.56, 21.53, 20.74, 20.72, 14.27, 14.25. HRMS calcd for $C_{24}H_{44}N_3O_3S$ [M+1]$^+$ 442.3103, found 442.3106.

Synthesis of Analog 19.

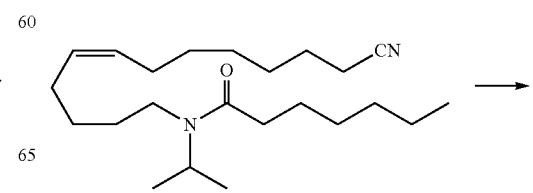

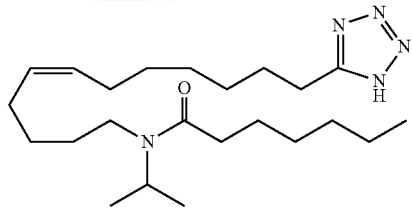

Analog 19.

N-(12-Cyanododec-5(Z)-enyl)-N-isopropyl-n-hexanamide (350 mg, 0.97 mmol) was treated with sodium azide as described above to give tetrazole 19 (250 mg, 64%) as a sticky solid. TLC:EtOAc, $R_f$~0.40; $^1$H NMR (300 MHz, 35/65 ratio of rotamers) δ 5.22-5.40 (m, 2H), 4.58-4.68 and 4.02-4.18 (m, 1H for two rotamers), 3.10-3.24 (m, 2H), 2.98 (t, J=7.6 Hz, 2H), 2.44 and 2.30 (t, J=7.3 Hz, 2H for two rotamers), 1.94-2.10 (m, 4H), 1.72-1.84 (m, 2H), 1.50-1.70 (m, 4H), 1.18-1.40 (m, 14H), 1.21 and 1.10 (d, J=7.2 Hz, 6H for two rotamers), 0.82-0.87 (m, 3H); $^{13}$C NMR (75 MHz) δ 174.06, 173.80, 130.85, 130.04, 129.79, 129.08, 48.94, 46.32, 43.97, 41.55, 34.11, 34.05, 31.79, 31.72, 31.12, 29.61, 29.61, 29.51, 29.25, 29.05, 28.85, 28.22, 27.98, 27.89, 27.32, 27.19, 26.92, 25.97, 23.70, 22.67, 21.51, 20.67, 14.02. HRMS calcd for $C_{23}H_{44}N_5O$ [M+1]$^+$ 406.3546, found 406.3547.

Synthesis of Analog 22.

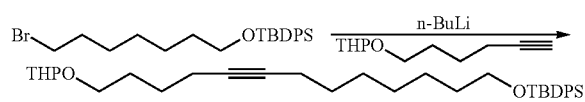

1-tert-Butyldiphenylsilyloxy-13-(tetrahydro-2H-pyran-2-yloxy)tridec-8-yne

Following the procedure applied in the synthesis of analog 25, 2-(hex-5-ynyloxy)tetrahydro-2H-pyran[1] (5.0 g, 27.40 mmol) was coupled with 1-tert-butyldiphenylsilyloxy-7-bromoheptane (11.90 g, 27.40 mmol) to give 1-tert-butyldiphenylsilyloxy-13-(tetrahydro-2H-pyran-2-yloxy)tridec-8-yne[3] (10.50 g, 72%) as a colorless syrup whose spectral data matched literature values.[3] TLC:EtOAc/hexanes (1:4), $R_f$~0.60; $^1$H NMR (400 MHz) δ 7.64-7.68 (m, 4H), 7.34-7.42 (m, 6H), 4.57 (t, J=4.3 Hz, 1H), 3.78-3.86 (m, 2H), 3.65 (t, J=6.3 Hz, 2H), 3.32-3.54 (m, 2H), 2.10-2.22 (m, 4H), 1.24-1.84 (m, 20H), 1.04 (s, 9H); $^{13}$C NMR (100 MHz) δ 135.80, 134.38, 129.72, 127.81, 99.0, 80.72, 80.10, 67.30, 64.17, 62.49, 32.77, 30.99, 29.34, 29.18, 29.13, 29.0, 27.11, 26.19, 25.91, 25.74, 19.87, 19.45, 19.0, 18.86.

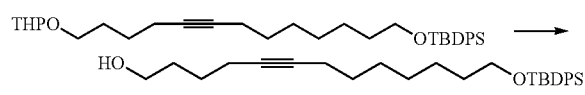

13-(tert-Butyldiphenylsilyloxy)tridec-5-yn-1-ol

Following the procedure applied in the synthesis of analog 25, 1-tert-butyldiphenylsilyloxy-13-(tetrahydro-2H-pyran-2-yloxy)tridec-8-yne (10.0 g, 18.70 mmol) was deprotected with PPTS to give 13-(tert-butyldiphenylsilyloxy)tridec-5-yn-1-ol (7.70 g, 91%) as a colorless syrup. TLC:EtOAc/hexanes (3:7), $R_f$~0.43; $^1$H NMR (300 MHz) δ 7.64-7.68 (m, 4H), 7.34-7.42 (m, 6H), 3.62 (t, J=5.6 Hz, 4H), 2.06-2.22 (m, 4H), 1.50-1.64 (m, 14H), 1.04 (s, 9H); $^{13}$C NMR (100 MHz) δ 135.82, 134.37, 129.76, 127.85, 80.93, 80.04, 64.21, 62.63, 32.77, 32.09, 29.33, 29.13, 29.10, 27.14, 25.92, 25.63, 19.47, 19.0, 18.81. HRMS calcd for $C_{29}H_{43}O_2Si$ [M+1]$^+$ 451.3032, found 451.3032.

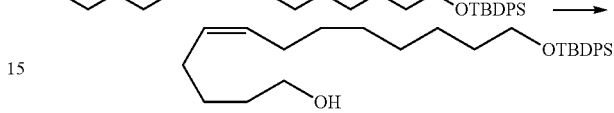

(Z)-13-(tert-Butyldiphenylsilyloxy)tridec-5-en-1-ol

Following the procedure applied in the synthesis of analog 25, 13-(tert-butyldiphenylsilyloxy)tridec-5-yn-1-ol (7.50 g, 16.60 mmol) was subjected to semi-hydrogenation to give 13-(tert-butyldiphenylsilyloxy)tridec-5(Z)-en-1-ol (6.90 g, 92%) as a syrup whose spectral values matched literature data.[2] TLC:EtOAc/hexanes (3:7), $R_f$~0.45; $^1$H NMR (400 MHz) δ 7.64-7.68 (m, 4H), 7.42-7.34 (m, 6H), 5.28-5.42 (m, 2H), 3.68-3.67 (t, J=6.4 Hz, 4H), 1.98-2.12 (m, 4H), 1.50-1.60 (m, 4H), 1.40-1.24 (m, 10H), 1.04 (s, 9H); $^{13}$C NMR (100 MHz) δ 135.83, 134.40, 130.61, 129.74, 129.60, 127.83, 64.21, 63.08, 32.83, 32.60, 29.94, 29.54, 27.50, 27.18, 27.14, 26.12, 26.01, 19.48.

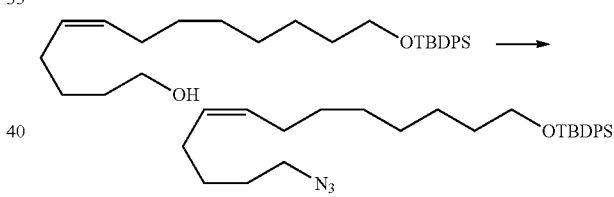

1-tert-Butyldiphenylsilyloxy-13-azidotridec-8(Z)-ene

Following the procedure applied in the synthesis of analog 25, 13-(tert-butyldiphenylsilyloxy)tridec-5(Z)-en-1-ol (7.0 g, 15.48 mmol) was converted to 1-tert-butyldiphenylsilyloxy-13-azidotridec-8(Z)-ene (5.30 g, 72%) obtained as a syrup. TLC:EtOAc/hexanes (1:9), $R_f$~0.55; $^1$H NMR (400 MHz) δ 7.68-7.64 (m, 4H), 7.42-7.34 (m, 6H), 5.28-5.42 (m, 2H), 3.64 (t, J=6.4 Hz, 2H), 3.26 (t, J=5.6 Hz, 2H), 1.96-2.10 (m, 4H), 1.64-1.24 (m, 14H), 1.04 (s, 9H); $^{13}$C NMR (100 MHz) δ 135.86, 134.44, 131.0, 129.77, 129.12, 127.85, 64.27, 51.63, 32.87, 29.95, 29.56, 28.70, 27.54, 27.17, 27.05, 26.93, 26.05, 19.51. IR (neat) 2930, 2783, 2361, 2331, 2094, 1109 cm$^{-1}$. HRMS calcd for $C_{29}H_{44}N_3OSi$ [M+1]$^+$ 478.3254, found 478.3250.

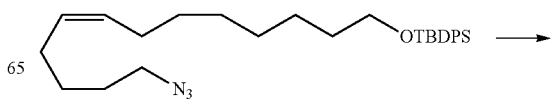

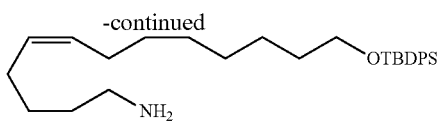

1-tert-Butyldiphenylsilyloxy-13-aminotridec-8(Z)-ene

Following the procedure applied in the synthesis of analog 25, 1-tert-butyldiphenylsilyloxy-13-azidotridec-8(Z)-ene (3.50 g, 7.32 mmol) was reduced with triphenylphosphine to give 1-tert-butyldiphenylsilyloxy-13-aminotridec-8(Z)-ene (2.44 g, 74%) as a colorless oil. TLC:MeOH/CH$_2$Cl$_2$ (1:4), R$_f$~0.25; $^1$H NMR (400 MHz) δ 7.62-7.68 (m, 4H), 7.32-7.40 (m, 6H), 5.30-5.40 (m, 2H), 3.63 (t, J=5.2 Hz, 2H), 2.62 (br s, 2H), 1.92-2.06 (m, 4H), 1.40-1.58 (m, 4H), 1.20-1.40 (m, 10H), 1.03 (s, 9H); $^{13}$C NMR (100 MHz) δ 135.79, 134.39, 130.46, 129.70, 127.78, 64.22, 42.02, 32.80, 29.92, 29.52, 27.46, 27.23, 27.10, 25.98, 19.44. HRMS calcd for C$_{29}$H$_{46}$NOSi [M+1]$^+$ 452.3349, found 452.3357.

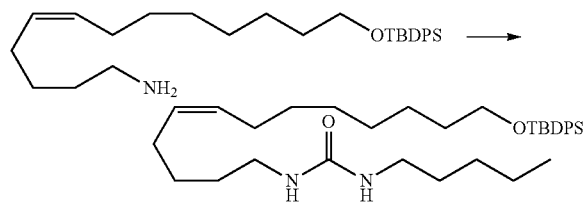

1-(13-(tert-Butyldiphenylsilyloxy)tridec-5(Z)-enyl)-3-n-pentylurea

Following the procedure applied in the synthesis of analog 25, 1-tert-butyldiphenylsilyloxy-13-aminotridec-8(Z)-ene (2.35 g, 5.20 mmol) was reacted with n-pentyl isocyanate to give 1-(13-(tert-butyldiphenylsilyloxy)tridec-5(Z)-enyl)-3-n-pentylurea (2.23 g, 76%) as a syrup. TLC:EtOAc/hexanes (1:4), R$_f$~0.65; $^1$H NMR (500 MHz) δ 7.62-7.70 (m, 4H), 7.32-7.44 (m, 6H), 5.28-5.44 (m, 2H), 4.37 (br s, 2H), 3.66 (t, J=4.2 Hz, 2H), 3.08-3.20 (m, 4H), 1.98-2.08 (m, 4H), 1.20-1.60 (m, 20H), 1.05 (s, 9H), 0.90 (t, J=7.2 Hz, 3H); $^{13}$C NMR (125 MHz) δ 159.22, 135.80, 134.12, 130.24, 129.88, 129.76, 127.81, 64.21, 40.62, 40.54, 32.82, 30.31, 29.95, 29.56, 29.39, 27.51, 27.35, 27.20, 27.13, 26.01, 22.72, 19.43, 14.30. HRMS calcd for C$_{35}$H$_{57}$N$_2$O$_2$Si [M+1]$^+$ 565.4189, found 565.4186.

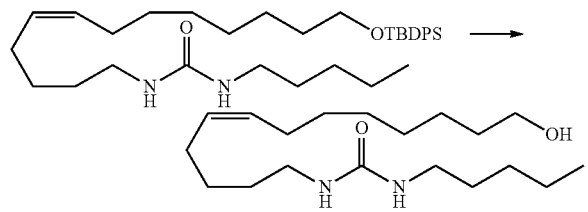

1-(13-Hydroxytridec-5(Z)-enyl)-3-n-pentylurea

Following the procedure applied in the synthesis of analog 25, 1-(13-(tert-butyldiphenylsilyloxy)tridec-5(Z)-enyl)-3-n-pentylurea (2.30 g, 4.07 mmol) was desilylated using TBAF to give 1-(13-hydroxytridec-5(Z)-enyl)-3-n-pentylurea (1.22 g, 92%) as a white solid, mp 63.1-63.3° C. TLC:EtOAc/hexanes (7:3), R$_f$~0.55; $^1$H NMR (400 MHz) δ 5.24-5.38 (m, 2H), 4.74 (br s, —NH, 2H), 3.62 (t, J=5.6 Hz, 2H), 3.06-3.18 (m, 4H), 1.98-2.06 (m, 4H), 1.20-1.60 (m, 20H), 0.86 (t, J=7.3 Hz, 3H); $^{13}$C NMR (100 MHz) δ 159.31, 130.38, 129.63, 62.90, 40.51, 40.46, 32.93, 30.30, 30.29, 29.79, 29.41, 29.34, 29.23, 27.30, 27.24, 27.15, 25.98, 22.67, 14.25. HRMS calcd for C$_{19}$H$_{39}$N$_2$O$_2$ [M+1]$^+$ 327.3012, found 327.3011.

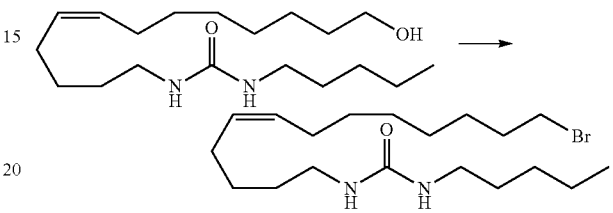

1-(13-Bromotridec-5(Z)-enyl)-3-n-pentylurea

Following the procedure applied in the synthesis of analog 25, 1-(13-hydroxytridec-5(Z)-enyl)-3-n-pentylurea (1.20 g, 3.68 mmol) was transformed into 1-(13-bromotridec-5(Z)-enyl)-3-n-pentylurea (1.17 g, 82%), obtained as a sticky solid. TLC:EtOAc/hexanes (2:3), R$_f$~0.60; $^1$H NMR (500 MHz) δ 5.28-5.40 (m, 2H), 4.71 (br s, —NH, 2H), 3.40 (t, J=4.2 Hz, 2H), 3.10-3.20 (m, 4H), 1.98-2.06 (m, 4H), 1.82-1.88 (m, 2H), 1.26-1.50 (m, 18H), 0.87 (t, J=7.2 Hz, 3H); $^{13}$C NMR (125 MHz) δ 159.38, 130.34, 129.59, 40.55, 40.46, 34.29, 33.02, 30.34, 29.81, 29.38, 29.30, 28.89, 28.35, 27.39, 27.33, 27.18, 22.71, 14.29. HRMS calcd for C$_{19}$H$_{37}$BrN$_2$O [M]$^+$ 388.2089, found 388.2090.

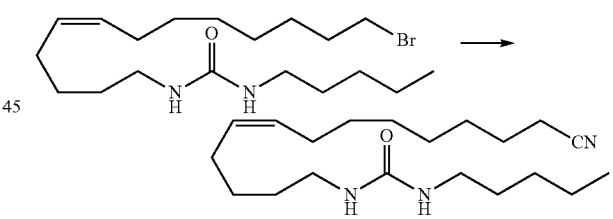

1-(13-Cyanotridec-5(Z)-enyl)-3-n-pentylurea 1-(13-Bromotridec-5(Z)-enyl)-3-n-pentylurea (1.10 g, 2.82 mmol) was reacted with potassium cyanide as described above in the synthesis of analog 25 to give 1-(13-cyanotridec-5(Z)-enyl)-3-n-pentylurea (0.69 g, 73%) as a colorless solid, mp 44.3-44.4° C. TLC:EtOAc/hexanes (1:1), R$_f$~0.32; $^1$H NMR (500 MHz) δ 5.30-5.42 (m, 2H), 4.35 (br s, 2H), 3.04-3.20 (m, 4H), 2.34 (t, J=7.6 Hz, 2H), 1.98-2.10 (m, 4H), 1.60-1.72 (m, 2H), 1.24-1.56 (m, 18H), 0.89 (t, J=7.2 Hz, 3H); $^{13}$C NMR (125 MHz) δ 159.24, 130.23, 129.68, 120.02, 40.24, 40.13, 30.27, 29.69, 29.32, 29.07, 28.82, 28.78, 27.29, 27.26, 27.13, 25.49, 22.64, 17.30, 14.24. HRMS calcd for C$_{20}$H$_{38}$N$_3$O [M+1]$^+$ 336.3015, found 336.3019.

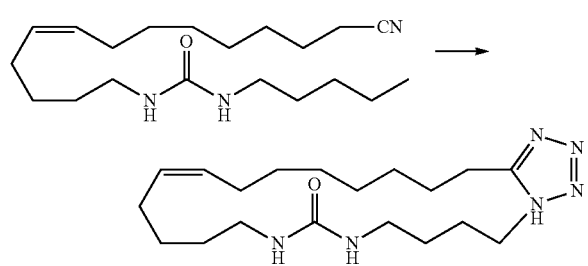

1-(13-(1H-Tetrazol-5-yl)tridec-5(Z)-enyl)-3-n-pentylurea (22)

Following the procedure described above in the synthesis of analog 20, a mixture of 1-(13-cyanotridec-5(Z)-enyl)-3-n-pentylurea, sodium azide, and zinc bromide was heated at 110° C. to give analog 22 (66%) as a colorless solid, mp 86.0-86.2° C. TLC:MeOH/CH$_2$Cl$_2$ (1:9), R$_f$~0.30; $^1$H NMR (CD$_3$OD, 300 MHz) δ 5.30-5.40 (m, 2H), 3.06-3.11 (m, 4H), 2.93 (t, J=8.0 Hz, 2H), 1.98-2.10 (m, 4H), 1.70-1.82 (m, 2H), 1.24-1.50 (m, 18H), 0.90 (t, J=7.6 Hz, 3H); $^{13}$C NMR (CD$_3$OD, 100 MHz) δ 160.15, 156.21, 129.89, 129.39, 39.84, 39.71, 29.89, 29.82, 29.53, 29.01, 29.00, 28.81, 27.45, 26.90, 26.70, 22.89, 22.33, 13.25. HRMS calcd for C$_{20}$H$_{38}$N$_6$O [M]$^+$ 378.3107, found 378.3111.

Synthesis of Analog 13.

1-(tert-Butyldiphenylsilyloxy)-11-(tetrahydro-2H-pyran-2-yloxy)undec-6-yne

Following the procedure applied in the synthesis of analog 25, 2-(hex-5-ynyloxy)tetrahydro-2H-pyran[1] was treated with n-BuLi and 1-(tert-butyldiphenylsilyloxy-5-bromopentane[4] to give the title compound (73%) as a colorless liquid. TLC:EtOAc/hexanes (1:4), R$_f$~0.60; $^1$H NMR (400 MHz) δ 7.64-7.68 (m, 4H), 7.34-7.42 (m, 6H), 4.57 (t, J=4.3 Hz, 1H), 3.78-3.86 (m, 2H), 3.65 (t, J=6.3 Hz, 2H), 3.32-3.54 (m, 2H), 2.10-2.22 (m, 4H), 1.24-1.84 (m, 16H), 1.04 (s, 9H); $^{13}$C NMR (125 MHz) δ 135.80, 134.32, 129.74, 127.84, 99.01, 80.54, 80.16, 67.30, 64.02, 62.50, 32.34, 30.98, 29.18, 29.12, 27.32, 27.10, 26.17, 25.73, 25.32, 19.87, 18.99, 18.86. HRMS calcd for C$_{31}$H$_{45}$O$_3$Si [M+1]$^+$ 493.3138, found 493.3144.

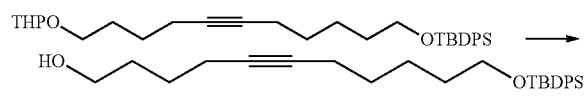

11-(tert-Butyldiphenylsilyloxy)undec-5-yn-1-ol

Following the procedure reported to prepare analog 25, 1-(tert-butyldiphenylsilyloxy)-11-(tetrahydro-2H-pyran-2-yloxy)undec-6-yne was cleaved with a catalytic amount of PPTS to give the title compound (72%) as a colorless liquid. TLC:EtOAc/hexanes (3:7), R$_f$~0.43; $^1$H NMR (300 MHz) δ 7.64-7.68 (m, 4H), 7.34-7.42 (m, 6H), 3.62 (t, J=5.6 Hz, 4H), 2.06-2.22 (m, 4H), 1.64-1.50 (m, 10H), 1.04 (s, 9H); $^{13}$C NMR (100 MHz) δ 135.82, 134.33, 129.77, 127.84, 80.77, 80.11, 64.06, 62.69, 32.35, 32.10, 29.10, 27.12, 25.60, 25.33, 18.97, 18.78. HRMS calcd for C$_{27}$H$_{39}$O$_2$Si [M+1]$^+$ 423.2719, found 423.2718.

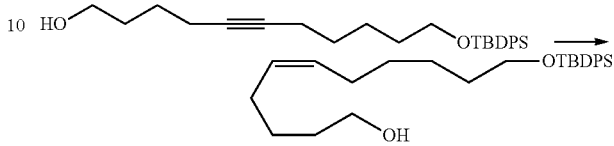

11-(tert-Butyldiphenylsilyloxy)undec-5(Z)-en-1-ol 11-(tert-Butyldiphenylsilyloxy)undec-5-yn-1-ol (6.50 g, 15.40 mmol) was subjected to semi-hydrogenation as described above to give the title olefin (6.07 g, 93%) as a colorless oil. TLC:EtOAc/hexanes (3:7), R$_f$~0.45; $^1$H NMR (300 MHz) δ 7.68-7.64 (m, 4H), 7.34-7.32 (m, 6H), 5.28-5.42 (m, 2H), 3.68-3.60 (t, J=6.4 Hz, 4H), 2.08-1.96 (m, 4H), 1.60-1.50 (m, 4H), 1.40-1.24 (m, 6H), 1.04 (s, 9H); $^{13}$C NMR (100 MHz) δ 135.79, 134.36, 130.45, 129.71, 129.63, 127.79, 64.16, 63.15, 32.69, 32.59, 29.94, 29.67, 27.43, 27.13, 27.08, 26.06, 25.68, 19.45. HRMS calcd for C$_{27}$H$_{41}$O$_2$Si [M+1]$^+$ 425.2876, found 425.2874.

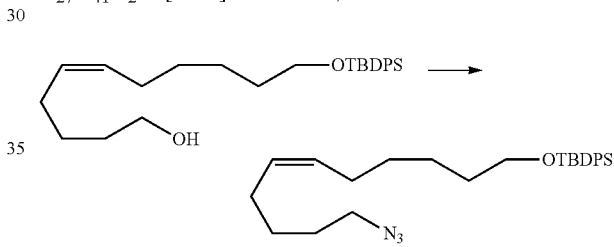

1-(tert-Butyldiphenylsilyloxy-11-azidoundec-6(Z)-ene

Following the protocol described above, 11-(tert-butyldiphenylsilyloxy)undec-5(Z)-en-1-ol (6.0 g, 14.24 mmol) was converted into the title azide (4.60 g, 72%), a colorless liquid. TLC:EtOAc/hexanes (1:9), R$_f$~0.55; $^1$H NMR (300 MHz) δ 7.64-7.68 (m, 4H), 7.34-7.42 (m, 6H), 5.28-5.42 (m, 2H), 3.65 (t, J=6.4 Hz, 2H), 3.25 (t, J=7.1 Hz, 2H), 1.96-2.10 (m, 4H), 1.24-1.64 (m, 10H), 1.04 (s, 9H); $^{13}$C NMR (100 MHz) δ 136.63, 135.85, 134.41, 130.83, 129.79, 129.22, 127.88, 64.20, 51.62, 32.77, 29.73, 28.70, 27.53, 27.18, 27.05, 26.94, 25.77, 19.52; IR (neat) 2931, 2857, 2094, 1589, 1110 cm$^{-1}$. HRMS calcd for C$_{27}$H$_{40}$N$_3$OSi [M+1]$^+$ 450.2940, found 450.2941.

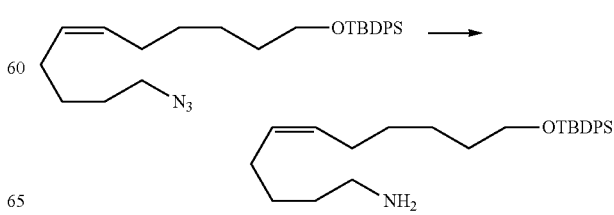

1-Amino-11-(tert-butyldiphenylsilyloxy)undec-5(Z)-ene 1-(tert-Butyldiphenylsilyloxy-11-azidoundec-6(Z)-ene (4.30 g, 9.57 mmol) was reduced with triphenylphosphine as described above to give the title amine (2.96 g, 74%) as a colorless oil. TLC:MeOH/CH$_2$Cl$_2$ (1:4), R$_f$~0.25; $^1$H NMR (300 MHz) δ 7.64-7.68 (m, 4H), 7.34-7.42 (m, 6H), 5.28-5.42 (m, 2H), 3.64 (t, J=6.4 Hz, 2H), 2.82 (t, J=4.8 Hz, 2H), 1.96-2.10 (m, 4H), 1.52-1.64 (m, 4H), 1.30-1.42 (m, 6H), 1.04 (s, 9H); $^{13}$C NMR (100 MHz) δ 135.82, 134.37, 132.37, 132.27, 130.70, 129.78, 129.21, 128.93, 128.81, 127.86, 64.19, 40.88, 32.77, 29.89, 29.73, 27.52, 27.37, 27.17, 27.12, 27.03, 25.76, 19.47. HRMS calcd for C$_{27}$H$_{42}$NOSi [M+1]$^+$ 420.3046, found 420.3050.

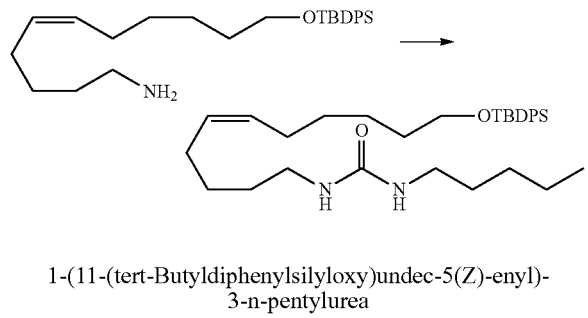

1-(11-(tert-Butyldiphenylsilyloxy)undec-5(Z)-enyl)-3-n-pentylurea

76% as a colorless oil. TLC:EtOAc/hexanes (2:3), R$_f$~0.45; $^1$H NMR (300 MHz) δ 7.64-7.68 (m, 4H), 7.34-7.42 (m, 6H), 5.28-5.42 (m, 2H), 4.13 (br s, 2H), 3.65 (t, J=6.4 Hz, 2H), 3.02-3.20 (m, 4H), 1.96-2.08 (m, 4H), 1.20-1.60 (m, 16H), 1.04 (s, 9H), 0.89 (t, J=7.2 Hz, 3H); $^{13}$C NMR (100 MHz) δ 158.02, 135.79, 134.36, 130.06, 129.74, 127.90, 127.82, 64.17, 40.42, 40.32, 32.52, 30.28, 29.71, 29.35, 27.62, 27.54, 27.16, 27.11, 25.71, 22.69, 19.45, 14.28. HRMS calcd for C$_{33}$H$_{53}$N$_2$O$_2$Si [M+1]$^+$ 537.3876, found 537.3876.

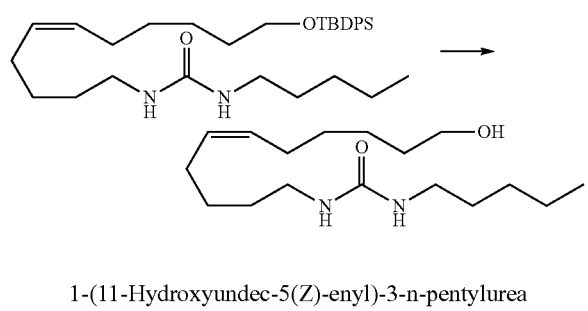

1-(11-Hydroxyundec-5(Z)-enyl)-3-n-pentylurea

94%, mp 62.2-62.5° C. TLC:EtOAc/hexanes (7:3), R$_f$~0.55; $^1$H NMR (300 MHz) δ 5.28-5.42 (m, 2H), 4.37 (br s, 2H), 3.64 (t, J=6.4 Hz, 2H), 3.02-3.20 (m, 4H), 1.96-2.10 (m, 4H), 1.20-1.60 (m, 16H), 0.89 (t, J=7.2 Hz, 3H); $^{13}$C NMR (75 MHz) δ 159.41, 130.30, 129.73, 62.77, 40.50, 40.34, 32.75, 30.27, 30.10, 29.56, 29.33, 27.23, 27.15, 27.04, 25.56, 22.66, 14.24. HRMS calcd for C$_{17}$H$_{35}$N$_2$O$_2$ [M+1]$^+$ 299.2699, found 299.2705.

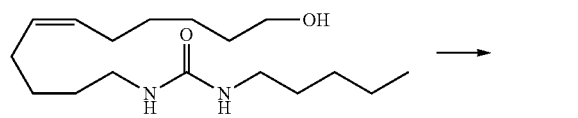

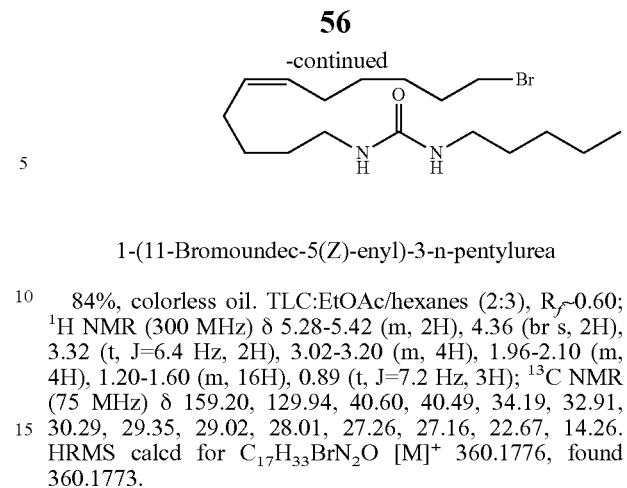

1-(11-Bromoundec-5(Z)-enyl)-3-n-pentylurea

84%, colorless oil. TLC:EtOAc/hexanes (2:3), R$_f$~0.60; $^1$H NMR (300 MHz) δ 5.28-5.42 (m, 2H), 4.36 (br s, 2H), 3.32 (t, J=6.4 Hz, 2H), 3.02-3.20 (m, 4H), 1.96-2.10 (m, 4H), 1.20-1.60 (m, 16H), 0.89 (t, J=7.2 Hz, 3H); $^{13}$C NMR (75 MHz) δ 159.20, 129.94, 40.60, 40.49, 34.19, 32.91, 30.29, 29.35, 29.02, 28.01, 27.26, 27.16, 22.67, 14.26. HRMS calcd for C$_{17}$H$_{33}$BrN$_2$O [M]$^+$ 360.1776, found 360.1773.

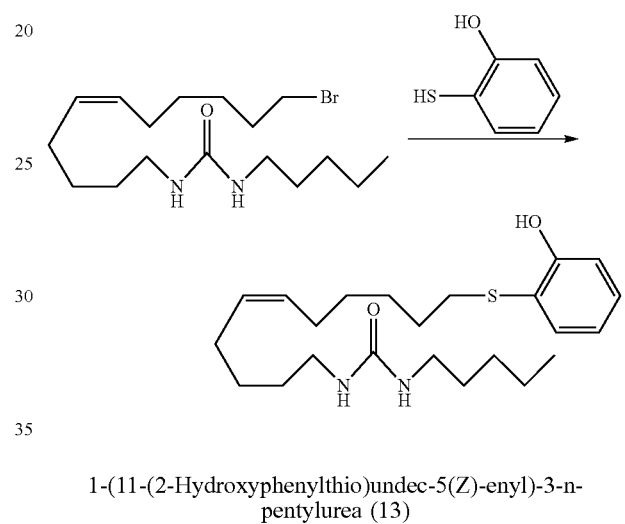

1-(11-(2-Hydroxyphenylthio)undec-5(Z)-enyl)-3-n-pentylurea (13)

To a solution of 2-mercaptophenol (100 mg, 0.79 mmol) in DMF (3 mL) was added K$_2$CO$_3$ (161 mg, 1.18 mmol) and 1-(11-bromoundec-5(Z)-enyl)-3-n-pentylurea (0.29 g, 0.79 mmol). After 12 h at rt, the solution was diluted with water (10 mL) and extracted with ethyl acetate (3×5 mL). The combined organic extracts were washed with water, brine and dried (Na$_2$SO$_4$). The residue was purified by SiO$_2$ column chromatography to give the analog 13 (230 mg, 69%) as a sticky solid. TLC:EtOAc/hexanes (1:1), R$_f$~0.32; $^1$H NMR (300 MHz) δ 7.45 (dd, J=1.9, 7.6 Hz, 1H), 7.22-7.28 (m, 1H), 6.99 (dd, J=1.2, 8.2 Hz, 1H), 6.88 (dt, J=1.2, 7.6 Hz, 1H), 5.28-5.42 (m, 2H), 4.26 (br s, 2H), 3.02-3.20 (m, 4H), 2.69 (t, J=7.7 Hz, 2H), 1.94-2.08 (m, 4H), 1.20-1.60 (m, 16H), 0.89 (t, J=7.2 Hz, 3H); $^{13}$C NMR (75 MHz) δ 159.05, 157.10, 135.60, 130.76, 130.11, 129.82, 120.78, 119.74, 115.02, 40.70, 40.60, 36.50, 30.23, 29.68, 29.32, 28.38, 27.21, 27.11, 22.66, 14.27. HRMS (ESI-neg) calcd for C$_{23}$H$_{37}$N$_2$O$_2$S [M−1]$^−$ 405.2576, found 405.2575.

Synthesis of Analog 14.

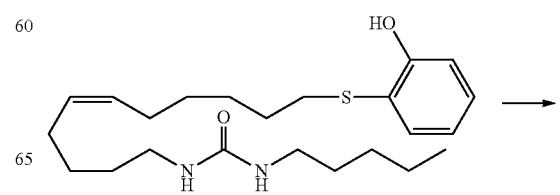

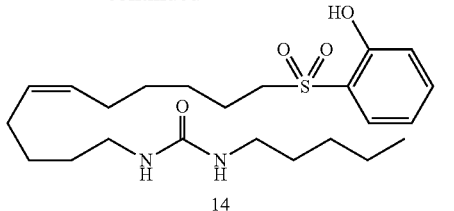

14

1-(11-(2-Hydroxyphenylsulfonyl)undec-5(Z)-enyl)-3-n-pentylurea (14)

Following the procedure utilized to prepare analog 18, analog 13 was oxidized to give 14 (60 mg, 75%) as a colorless liquid. TLC:EtOAc/hexanes (2:3), $R_f$~0.32; $^1$H NMR (300 MHz) δ 9.08 (br s, —OH), 7.72 (dd, J=1.9, 7.4 Hz, 1H), 7.44 (dt, J=1.2, 7.3 Hz, 1H), 7.10 (d, J=7.9 Hz, 1H), 7.12 (t, J=6.4 Hz, 1H), 5.28-5.42 (m, 2H), 4.70-4.85 (m, 2H), 3.40-3.60 (t, J=6.2 Hz, 2H), 3.20-3.40 (m, 4H), 1.90-2.10 (m, 4H), 1.70-1.80 (m, 2H), 1.20-1.50 (m, 14H), 0.85 (t, J=7.2 Hz, 3H); $^{13}$C NMR (75 MHz) δ 159.25, 156.66, 136.23, 130.22, 129.78, 129.52, 122.78, 120.22, 118.55, 55.97, 40.08, 40.62, 30.07, 30.02, 29.25, 28.82, 27.62, 27.15, 27.05, 26.62, 22.61, 22.20, 14.24. HRMS (ESI-neg) calcd for $C_{23}H_{37}N_2O_4S$ [M−1]$^-$ 437.2474, found 437.2454.

Synthesis of Analog 15.

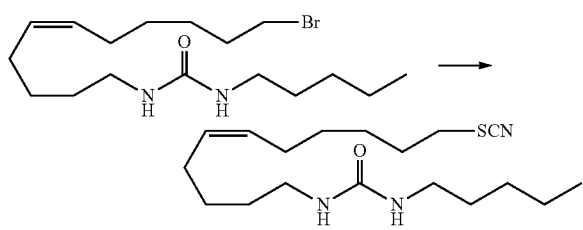

1-n-Pentyl-3-(11-thiocyanatoundec-5(Z)-enyl)urea

A mixture of 1-(11-bromoundec-5(Z)-enyl)-3-n-pentylurea (191 mg, 0.53 mmol) and potassium thiocyanate (154 mg, 1.58 mmol) in dry DMSO (4 mL) were stirred at rt. After 24 h, the reaction mixture was diluted with water (10 mL) and extracted with ethyl acetate (3×5 mL). The combined organic extracts were washed with water, brine and dried (Na$_2$SO$_4$) and concentrated in vacuo. The residue was purified by SiO$_2$ column chromatography to give the title urea (116 mg, 65%) as a colorless syrup. TLC:EtOAc/hexanes (2:3), $R_f$~0.32; $^1$H NMR (300 MHz) δ 5.28-5.42 (m, 2H), 4.42 (br s, 2H), 3.10-3.20 (m, 4H), 2.94 (t, J=7.0 Hz, 2H), 2.00-2.10 (m, 4H), 1.70-1.80 (m, 2H), 1.20-1.56 (m, 14H), 0.88 (t, J=7.2 Hz, 3H); $^{13}$C NMR (75 MHz) δ 158.92, 130.20, 129.68, 112.84, 40.67, 40.54, 34.23, 30.22, 30.03, 29.31, 29.08, 27.66, 27.19, 27.15, 27.04, 22.66, 14.27; IR (neat) 2929, 2856, 2153, 1630, 1573, 1456, 1256 cm$^{-1}$. HRMS calcd for $C_{18}H_{34}N_3OS$ [M+1]$^+$ 340.2423, found 340.2421.

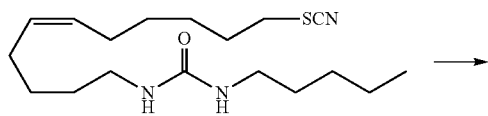

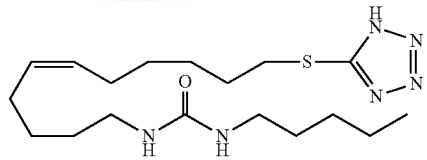

1-(11-(1H-Tetrazol-5-ylthio)undec-5(Z)-enyl)-3-pentylurea (15)

Following the procedure utilized to prepare analog 19, 1-n-pentyl-3-(11-thiocyanatoundec-5(Z)-enyl)urea (150 mg, 0.44 mmol) was treated with sodium azide to give analog 15 (104 mg, 62%) as a sticky solid. TLC: 5% MeOH/CH$_2$Cl$_2$, $R_f$~0.40; $^1$H NMR (300 MHz) δ 5.28-5.42 (m, 2H), 4.63 (br s, 2H), 3.30 (t, J=6.7 Hz, 2H), 3.17-3.23 (m, 4H), 1.95-2.04 (m, 4H), 1.44-1.80 (m, 6H), 1.24-1.42 (m, 10H), 0.89 (t, J=7.2 Hz, 3H); $^{13}$C NMR (CD$_3$OD, 75 MHz) δ 160.17, 155.38, 129.65, 129.58, 39.81, 39.69, 32.38, 29.87, 29.79, 29.36, 28.99, 28.96, 27.84, 26.84, 26.72, 26.69, 22.31, 13.21. HRMS (ESI-neg) calcd for $C_{18}H_{33}N_6OS$ [M−1]$^-$ 381.2442, found 381.2348.

Synthesis of Analog 12.

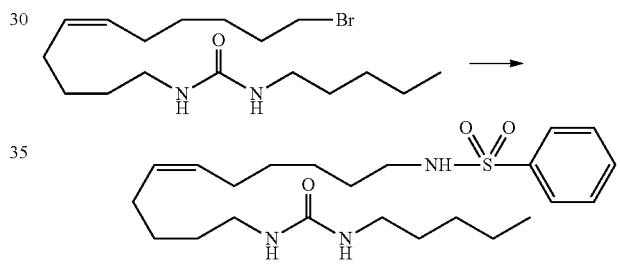

N-(11-(3-n-Pentylureido)undec-6(Z)-enyl)benzenesulfonamide (12)

To a solution of benzenesulfonamide (50 mg, 0.31 mmol) in THF/HMPA (4:1; 5 mL) was added n-butyllithium (2.5 M soln in hexane, 125 μL, 0.31 mmol) at −78° C. under an argon atmosphere. A solution of 1-(11-bromoundec-5(Z)-enyl)-3-n-pentylurea (115 mg, 0.32 mmol) in THF (2 mL) was added dropwise. After 2 h at the same temperature, the reaction was quenched with saturated aq. NH$_4$Cl (5 mL). The mixture was extracted with EtOAc (3×5 mL) and the combined extracts were washed with water, brine, dried, and concentrated under reduced pressure. The residue was purified by SiO$_2$ column chromatography to give analog 12 (44 mg, 32%) as a colorless solid, mp 73.5-73.6° C. TLC: 5% MeOH/CH$_2$Cl$_2$, $R_f$~0.40; $^1$H NMR (300 MHz) δ 7.84-7.90 (m, 2H), 7.46-7.60 (m, 3H), 5.48 (br s, —NH, 1H), 5.24-5.38 (m, 2H), 4.70 (br s, —NH, 1H), 4.60 (br s, —NH, 1H), 3.08-3.20 (m, 4H), 2.88-2.94 (q, J=6.4 Hz, 2H), 1.94-2.40 (m, 4H), 1.20-1.58 (m, 16H), 0.88 (t, J=6.8 Hz, 3H); $^{13}$C NMR (75 MHz) δ 159.90, 140.06, 132.69, 130.03, 129.98, 129.27, 127.19, 43.26, 40.80, 40.52, 30.09, 29.99, 29.61, 29.28, 29.16, 27.02, 26.99, 26.96, 26.13, 22.63, 14.25. HRMS calcd for $C_{23}H_{40}N_3O_3S$ [M+1]$^+$ 438.2790, found 438.2782.

Synthesis of Analog 24.

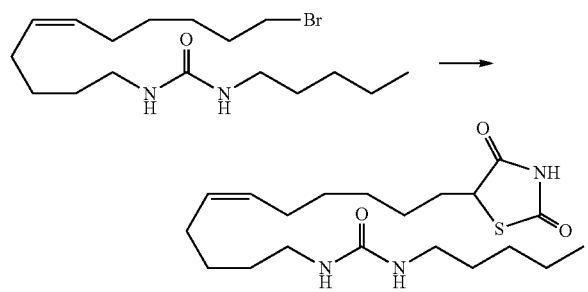

1-(11-(2,4-Dioxothiazolidin-5-yl)undec-5(Z)-enyl)-
3-n-pentylurea (24)

n-Butyllithium (1.10 mL, 2.76 mmol, 2.5 M solution in hexanes) was added dropwise to a −78° C. solution of thiazolidine-2,4-dione (0.16 g, 1.38 mmol) in dry THF/HMPA (50 mL, 4:1) under an argon atmosphere. After 30 min, the reaction mixture was warmed to 0° C. over 1 h, kept at that temperature for 2 h, and then re-cooled to −78° C. Following the addition of a solution of 1-(11-bromoundec-5(Z)-enyl)-3-n-pentylurea (0.50 g, 1.38 mmol) in THF (15 mL), the reaction temperature was slowly increased to rt over 3 h and stirred further for 12 h. The reaction mixture was quenched with sat. aq. NH$_4$Cl (5 mL), the pH was adjusted to 4 using 1 M oxalic acid, and the reaction mixture was extracted with EtOAc (3×125 mL). The combined extracts were washed with water (2×100 mL), brine (100 mL), dried (Na$_2$SO$_4$) and concentrated in vacuo. The residue was purified by SiO$_2$ column chromatography using 5% MeOH/CH$_2$Cl$_2$ to afford analog 24 (169 mg, 31%) as a colorless solid, mp 92.8-93° C. TLC: 10% MeOH/CH$_2$Cl$_2$, R$_f$~0.20; $^1$H NMR (CD$_3$OD, 300 MHz) δ 5.30-5.40 (m, 2H), 4.42 (dd, J=3.4, 4.2 Hz, 1H), 3.04-3.13 (m, 4H), 2.00-2.16 (m, 4H), 1.80-1.96 (m, 2H), 1.24-1.58 (m, 16H), 0.91 (t, J=6.7 Hz, 3H); $^{13}$C NMR (75 MHz) δ 177.09, 172.56, 160.15, 129.68, 129.60, 51.89, 39.69, 32.57, 29.90, 29.83, 29.23, 29.02, 28.43, 26.88, 26.73, 26.47, 22.35, 13.27. HRMS calcd for C$_{20}$H$_{36}$N$_3$O$_3$S [M+1]$^+$ 398.2477, found 398.2477.

Synthesis of Analog 7.

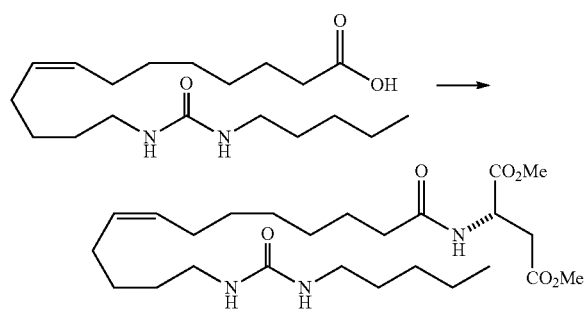

(S)-Dimethyl 2-(13-(3-n-pentylureido)tridec-8(Z)-
enamido)succinate

L-Aspartic acid dimethyl ester hydrochloride (38 mg, 0.19 mmol) and HATU (67 mg, 0.18 mmol) were added to a stirring solution of 13-(3-n-pentylureido)tridec-8(Z)-enoic acid (50 mg, 0.15 mmol) in anhydrous DMF (20 mL) under an argon atmosphere. After 5 min, 1-ethyl-3-(3-dimethylaminopropyl)carbodiimide hydrochloride (EDCI; 33 mg, 0.17 mmol) was added followed by diisopropylethylamine (33 μL, 0.19 mmol). After 12 h, the reaction mixture was diluted with EtOAc (30 mL), washed with water (30 mL), and brine (20 mL). The combined aqueous layers were back-extracted with EtOAc (3×30 mL). The combined organic extracts were dried over Na$_2$SO$_4$, concentrated under reduced pressure, and the residue was purified by SiO$_2$ column chromatography using 50% EtOAc/hexanes as eluent to give the title diester (60 mg, 84%) as a viscous oil. TLC:EtOAc/hexanes (3:2), R$_f$~0.30; $^1$H NMR (300 MHz) δ 6.62 (d, J=7.0 Hz, 1H), 5.22-5.40 (m, 2H), 4.85-5.04 (m, 1H), 4.80-4.88 (m, 2H), 3.75 (s, 3H), 3.66 (s, 3H), 3.10-3.20 (m, 4H), 3.01 (dd, J=4.3, 10 Hz, 1H), 2.82 (dd, J=4.6, 10 Hz, 1H), 2.25 (t, J=8.3 Hz, 2H), 1.98-2.07 (m, 4H), 1.60-1.68 (m, 4H), 1.20-1.50 (m, 14H), 0.88 (t, J=6.7 Hz, 3H); $^{13}$C NMR (75 MHz) δ 173.51, 171.81, 171.52, 159.02, 130.33, 129.76, 53.05, 52.30, 48.57, 40.61, 40.55, 36.61, 36.28, 30.24, 30.20, 29.51, 29.31, 29.10, 28.88, 27.20, 27.12, 25.72, 22.66, 14.26.

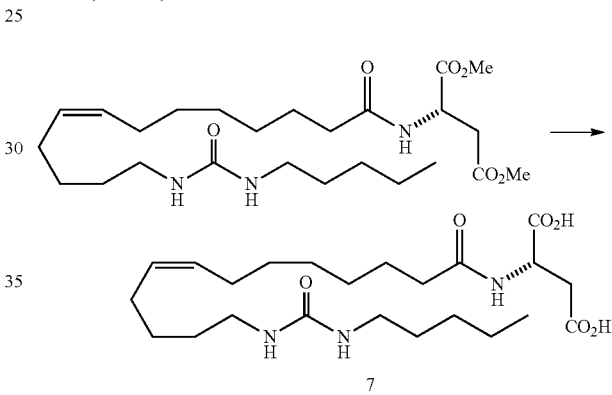

(S)-2-(13-(3-n-Pentylureido)tridec-8(Z)-enamido)
succinic acid (7)

LiOH (2 mL, 2 M aqueous solution) was added to a 0° C. solution of the above (S)-dimethyl 2-(13-(3-n-pentylureido)tridec-8(Z)-enamido)succinate (60 mg, 0.12 mmol) in THF (25 mL) and deionized H$_2$O (4 mL). After stirring at room temperature overnight, the reaction mixture was cooled to 0° C., the pH was adjusted to 4 with 1 M aq. oxalic acid, and the mixture was extracted with EtOAc (3×15 mL). The combined extracts were washed with water (30 mL), brine (25 mL), dried over anhydrous Na$_2$SO$_4$, and concentrated in vacuo. The residue was purified by SiO$_2$ column chromatography using 25% EtOAc/hexanes as eluent to give analog 7 (48 mg, 85%) as a colorless oil. TLC: 5% MeOH/EtOAc (3:2), R$_f$~0.30; $^1$H NMR (CD$_3$OD, 300 MHz) δ 5.30-5.38 (m, 2H), 4.72 (t, J=4.2 Hz, 1H), 3.26-3.32 (m, 4H), 2.86 (dd, J=4.3, 10 Hz, 1H), 2.77 (dd, J=4.6, 10 Hz, 1H), 2.22 (t, J=7.7 Hz, 2H), 1.98-2.10 (m, 4H), 1.54-1.64 (m, 4H), 1.20-1.52 (m, 14H), 0.89 (t, J=6.7 Hz, 3H); $^{13}$C NMR (CD$_3$OD, 75 MHz) δ 174.93, 173.01, 172.83, 160.17, 129.94, 129.39, 49.0, 39.81, 39.73, 35.78, 35.60, 29.90, 29.82, 29.49, 29.02, 28.87, 26.90, 26.73, 25.70, 22.35, 13.29. HRMS calcd for C$_{23}$H$_{42}$N$_3$O$_6$ [M+1]$^+$ 456.3074, found 456.3071.

Synthesis of Analog 3.

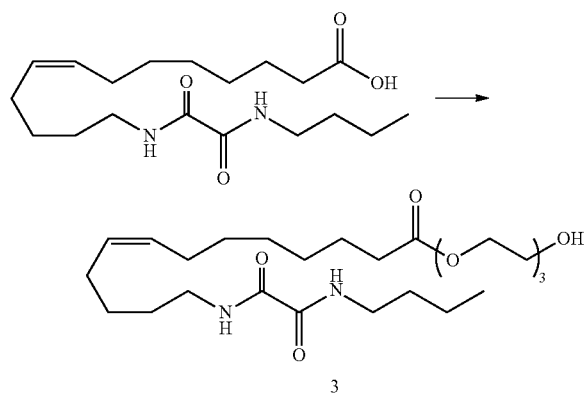

2-(2-(2-Hydroxyethoxyl)ethoxy)ethyl13-(2-(n-butylamino)-2 oxoacetamido)tridec-8(Z)-enoate (3)

Triethylene glycol (0.12 g, 0.8 mmol; dried over molecular sieves) was added to a solution of 13-(2-(n-butylamino)-2-oxoacetamido)tridec-8(Z)-enoic acid[2] (30 mg, 0.08 mmol) and N,N-dimethylaminopyridine (DMAP, 11 mg, 0.09 mmol) in anhydrous dichloromethane (10 mL) under an argon atmosphere at room temperature. After 3 min, solid EDCI (18 mg, 0.09 mmol) was added. After 12 h, the reaction mixture was diluted with EtOAc (10 mL), washed with water (5 mL), and concentrated in vacuo. The residue was purified by $SiO_2$ column chromatography using EtOAc to give analog 3 (33 mg, 82%) as a colorless solid, mp 71.7-71.9° C. TLC:EtOAc/hexanes (4:1), $R_f$~0.30; $^1$H NMR (300 MHz) δ 7.46 (br s, 2H), 5.24-5.40 (m, 2H), 4.23 (t, J=4.6 Hz, 2H), 3.58-3.78 (m, 10H), 3.27 (apparent q, J=6.7 Hz, 4H), 2.32 (t, J=7.6 Hz, 2H), 1.50-1.66 (m, 6H), 1.24-1.44 (m, 14H), 0.92 (t, J=6.7 Hz, 3H); $^{13}$C NMR (100 MHz) δ 174.10, 160.09, 130.66, 129.24, 72.70, 70.76, 70.55, 69.42, 39.80, 39.61, 34.35, 31.45, 29.69, 29.21, 29.12, 29.02, 27.36, 27.07, 26.92, 25.04, 20.21, 13.90. HRMS calcd for $C_{25}H_{47}N_2O_7$ $[M+1]^+$ 487.3383, found 487.3379.

Synthesis of Analog 2.

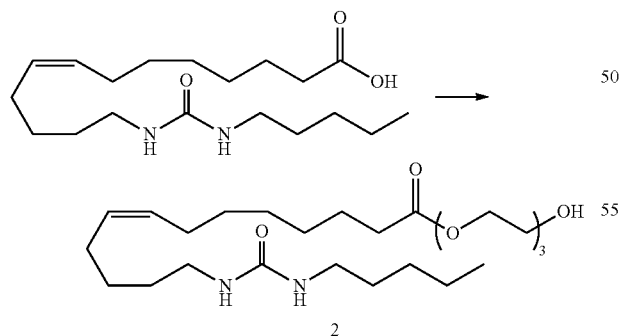

2-(2-(2-Hydroxyethoxyl)ethoxy)ethyl 13-(3-n-pentylureido)tridec-8(Z)-enoate (2)

13-(3-n-Pentylureido)tridec-8(Z)-enoic acid[2] (80 mg, 0.20 mmol) was condensed with triethylene glycol as described above to give analog 2 (86 mg, 78%) as a colorless solid, mp 42.4-42.6° C. TLC:EtOAc, $R_f$~0.20; $^1$H NMR (300 MHz) δ 5.24-5.40 (m, 2H), 4.28 (br s, 2H), 4.23 (dd, J=4.9, 1.0 Hz, 2H), 3.58-3.68 (m, 10H), 3.10-3.20 (m, 4H), 2.52 (br s, —OH, 1H), 2.33 (t, J=7.6 Hz, 2H), 1.90-2.10 (m, 4H), 1.44-1.64 (m, 4H), 1.22-1.40 (m, 14), 0.88 (t, J=7.3 Hz, 3H); $^{13}$C NMR (75 MHz) δ 174.22, 158.50, 130.41, 129.62, 72.76, 70.75, 70.51, 69.38, 63.47, 61.94, 40.78, 40.71, 34.33, 30.13, 30.08, 29.57, 29.25, 29.09, 28.94, 27.23, 27.15, 27.06, 25.03, 22.61, 14.24. HRMS calcd for $C_{25}H_{49}N_2O_6[M+1]^+$ 473.3591, found 473.3588.

Synthesis of Analog 1.

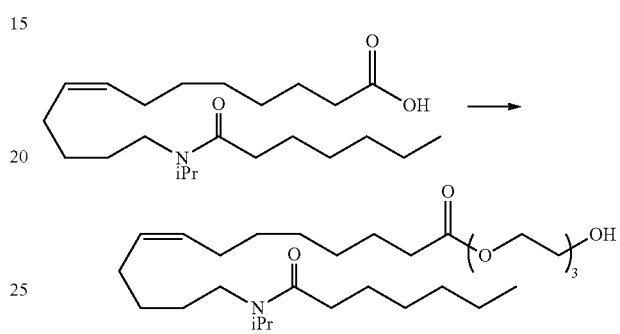

2-(2-(2-Hydroxyethoxyl)ethoxy)ethyl 13-(N-isopropylheptanamido)tridec-8(Z)-enoate (1)

13-(N-Isopropylheptanamido)tridec-8(Z)-enoic acid[2] (60 mg, 0.16 mmol) was condensed with triethylene glycol as described above to give analog 1 (58 mg, 73%) as a viscous, colorless oil. TLC:EtOAc (4:1), $R_f$~0.40; $^1$H NMR (300 MHz, 65/35 mixture of rotamers) δ 5.26-5.40 (m, 2H), 4.62-4.70 (m, 0.5H), 4.20-4.26 (m, 2H), 3.98-4.08 (m, 0.5H), 3.58-3.76 (m, 10H), 3.04-3.16 (m, 2H), 2.20-2.36 (m, 4H for the two rotamers), 1.98-2.10 (m, 4H), 1.46-1.66 (m, 6H), 1.24-1.38 (m, 14H), 1.18 and 1.10 (d, J=7.3 Hz, 6H for two rotamers), 0.87 (t, J=7.2 Hz, 3H); $^{13}$C NMR (75 MHz) δ 174.05, 174.01, 173.10, 172.55, 130.75, 130.11, 129.85, 129.15, 72.70, 70.76, 70.55, 69.40, 63.43, 61.94, 48.30, 45.52, 43.53, 41.09, 34.36, 34.32, 34.10, 34.0, 31.93, 31.89, 31.28, 29.90, 29.75, 29.69, 29.56, 29.43, 29.23, 29.12, 27.84, 27.48, 27.42, 27.35, 27.18, 26.93, 25.88, 25.70, 25.05, 25.02, 22.76, 21.60, 20.75, 14.28. HRMS calcd for $C_{29}H_{56}N\ O_6$ $[M+1]^+$ 514.4108, found 514.4111.

Synthesis of Analog 8.

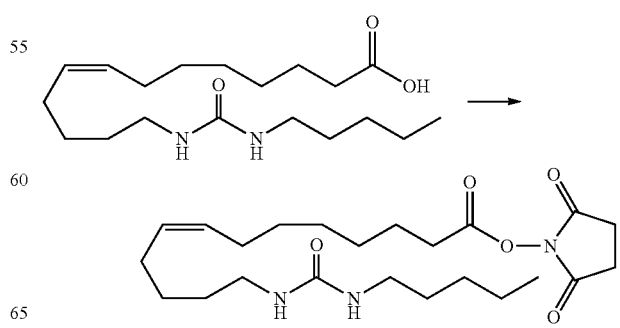

N-Hydroxysuccinimidyl 13-(3-n-pentylureido)tridec-8(Z)-enoate

A mixture of 13-(3-n-pentylureido)tridec-8(Z)-enoic acid[2] (100 mg, 0.29 mmol) and N-hydroxysuccinimide (37 mg, 0.31 mmol) were azeotropically dried using anhydrous benzene (2×5 mL), then dissolved in dry $CH_2Cl_2$ (5 mL). To this was added EDCI (67 mg, 0.35 mmol) and DMAP (38 mg, 0.31 mmol) under an argon atmosphere. After 12 h at rt, the reaction mixture was diluted with more $CH_2Cl_2$ (20 mL), washed with water, brine, dried ($Na_2SO_4$) and concentrated in vacuo. The residue was purified by $SiO_2$ column chromatography to give the title NHS ester (110 mg, 86%) as a sticky solid that was used immediately without further purification. TLC:EtOAc/hexanes (7:3), $R_f$~0.40; $^1H$ NMR (400 MHz) δ 5.27-5.36 (m, 2H), 4.48 (br s, 2H), 3.09-3.15 (m, 4H), 2.81 (br s, 4H), 2.58 (t, J=7.8 Hz, 2H), 1.94-2.06 (m, 4H), 1.68-1.74 (m, 2H), 1.20-1.50 (m, 16H), 0.86 (t, J=7.2 Hz, 3H); $^{13}C$ NMR (100 MHz) δ 169.40, 168.96, 158.62, 130.29, 129.71, 40.75, 40.68, 31.12, 30.18, 30.14, 29.51, 29.28, 28.80, 27.21, 27.19, 27.10, 25.81, 24.72, 22.62, 14.24.

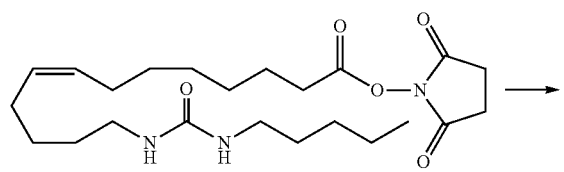

13-(3-n-Pentylureido)-N-(phenylsulfonyl)tridec-8(Z)-enamide (8)

A mixture of N-hydroxysuccinimidyl 13-(3-n-pentylureido)tridec-8(Z)-enoate (150 mg, 0.34 mmol) from above, benzenesulfonamide (78 mg, 0.49 mmol) and 4-dimethylaminopyridine (DMAP; 50 mg, 0.40 mmol) were heated in dry hexamethylphosphoramide (HMPA; 3 mL) at 80° C. for 24 h. After cooling to rt, the reaction mixture was diluted with water and extracted into EtOAc (3×10 mL). The combined extracts were washed with water, brine, dried ($Na_2SO_4$) and concentrated in vacuo. The residue was purified by $SiO_2$ column chromatography to give analog 8 (105 mg, 65%) as a colorless solid, mp 91.4-91.6° C. TLC:EtOAc/hexanes (3:2), $R_f$~0.30; $^1H$ NMR (300 MHz) δ 8.00-8.10 (dd, J=0.9, 7.3 Hz, 2H), 7.44-7.60 (m, 3H), 5.28-5.42 (m, 2H), 5.03 (br s, —NH, 1H), 4.57 (br s, —NH, 1H), 3.21 (t, J=6.8 Hz, 2H), 3.12 (t, J=6.5 Hz, 2H), 2.29 (t, J=7.9 Hz, 2H), 1.98-2.10 (m, 4H), 1.18-1.60 (m, 18H), 0.90 (t, J=7.2 Hz, 3H); $^{13}C$ NMR (75 MHz) δ 172.66, 159.28, 139.67, 133.57, 130.69, 129.65, 128.93, 128.40, 41.41, 40.53, 36.22, 29.89, 29.61, 29.24, 28.87, 28.33, 27.69, 26.91, 26.69, 26.47, 24.70, 22.588, 14.22. HRMS calcd for $C_{25}H_{42}N_3O_4S$ $[M+1]^+$ 480.2896, found 480.2899.

Synthesis of Analog 9.

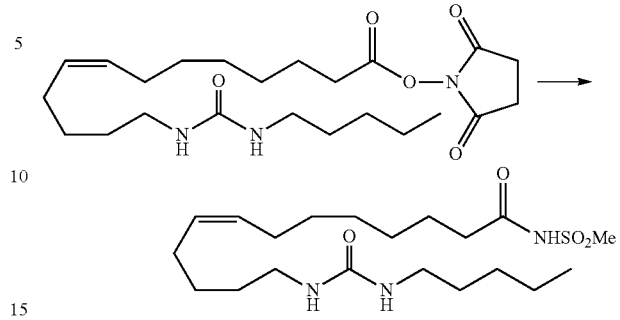

N-(Methylsulfonyl)-13-(3-n-pentylureido)tridec-8(Z)-enamide (9)

N-Hydroxysuccinimidyl 13-(3-n-pentylureido)tridec-8(Z)-enoate from above (150 mg, 0.34 mmol) was reacted with methanesulfonamide (48 mg, 0.50 mmol) as described above to give analog 8 (102 mg, 72%) as a colorless solid, mp 113.5-113.6° C. TLC:EtOAc/hexanes (1:1), $R_f$~0.30; $^1H$ NMR (300 MHz) δ 5.30-5.40 (m, 2H), 3.21 (s, 3H), 3.04-3.12 (m, 4H), 2.29 (t, J=7.3 Hz, 2H), 2.00-2.10 (m, 4H), 1.22-1.66 (m, 18H), 0.90 (t, J=7.0 Hz, 3H); $^{13}C$ NMR (75 MHz) δ 175.14, 161.50, 131.17, 130.78, 41.44, 41.10, 41.02, 37.13, 31.22, 31.15, 30.73, 30.34, 30.07, 30.05, 28.19, 28.17, 28.03, 25.80, 23.66, 14.56. HRMS calcd for $C_{20}H_{40}N_3O_4S$ $[M+1]^+$ 418.2740, found 418.2739.

Synthesis of Analog 6.

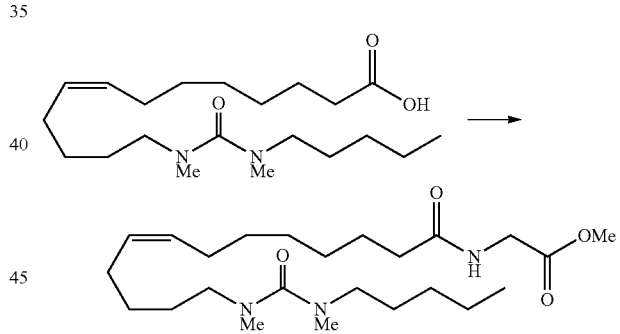

Methyl 2-(13-(1,3-dimethyl-3-n-pentylureido)tridec-8(Z)-enamido)acetate

Glycine hydrochloride (32 mg, 0.29 mmol) and 1-hydroxybenzotriazole (32 mg, 0.23 mmol; HOBt) were added to a solution of 13-(1,3-dimethyl-3-n-pentylureido)tridec-8(Z)-enoic acid[2] (70 mg, 0.19 mmol) and diisopropylethylamine (50 μL, 0.29 mmol) in anhydrous DMF (20 mL) under an argon atmosphere. After 5 min, 1-ethyl-3-(3-dimethylaminopropyl)carbodiimide hydrochloride (45 mg, 0.23 mmol; EDCI) was added as a solid. After stirring for 12 h at room temperature, the reaction mixture was diluted with water (30 mL) and extracted with EtOAc (3×30 mL). The combined organic extracts were dried over $Na_2SO_4$, concentrated under reduced pressure, and the residue was purified by $SiO_2$ column chromatography using 30% EtOAc/hexanes as eluent to give the title methyl ester (65 mg, 79%) as a viscous oil. TLC:EtOAc/hexanes (7:3), $R_f$~0.40; $^1H$ NMR (300 MHz) δ 6.18 (br s, —NH, 1H), 5.26-5.40 (m, 2H), 4.04 (d, J=5.2 Hz, 2H), 3.75 (s, 3H), 3.11 (apparent q, J=7.6 Hz, 4H), 2.77 (s, 3H), 2.76 (s, 3H), 2.24 (t, J=7.6 Hz, 2H), 1.96-2.08 (m, 4H), 1.46-1.70 (m, 6H), 1.20-1.38 (m, 12H), 0.88 (t, J=7.2 Hz, 3H); $^{13}$C NMR (100 MHz) δ 170.69, 170.07, 165.65, 130.36, 129.38, 52.45, 50.43, 50.42, 41.23, 35.86, 30.09, 29.62, 29.26, 29.22, 29.05, 27.32, 27.15, 26.67, 25.74, 25.38, 21.65, 14.48. HRMS Calcd for $C_{24}H_{46}N_3O_4$ [M+1]$^+$ 440.3488, found 440.3485.

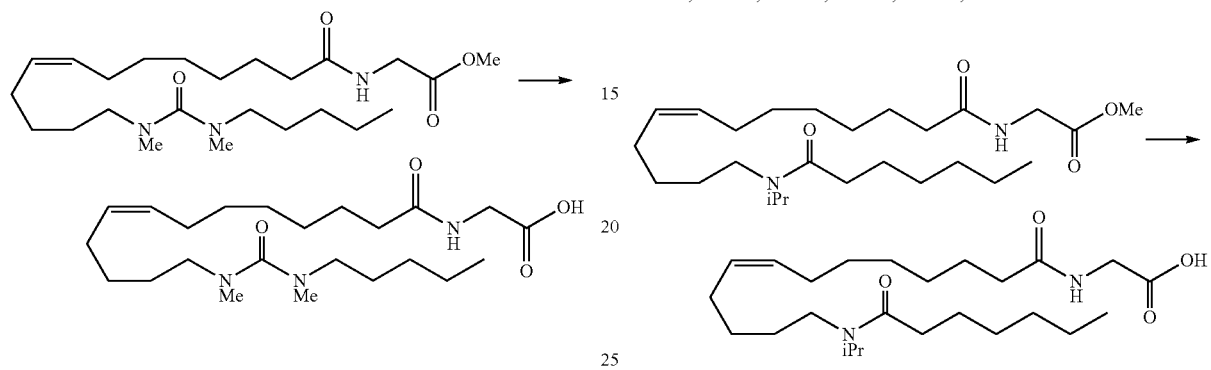

2-(13-(1,3-Dimethyl-3-n-pentylureido)tridec-8(Z)-enamido)acetic acid (6)

Following the ester hydrolysis conditions described above, methyl 2-(13-(1,3-dimethyl-3-n-pentylureido)tridec-8(Z)-enamido)acetate was converted into analog 6 (87%), obtained as a colorless liquid. TLC:EtOAc/hexanes (4:1), $R_f$-0.40; $^1$H NMR (300 MHz) δ 6.39 (br s, —NH, 1H), 5.24-5.40 (m, 2H), 4.03 (d, J=4.5 Hz, 2H), 3.16 (apparent q, J=5.8 Hz, 4H), 2.79 (s, 3H), 2.77 (s, 3H), 2.25 (t, J=7.0 Hz, 2H), 1.90-2.10 (m, 4H), 1.48-1.70 (m, 6H), 1.20-1.40 (m, 12H), 0.88 (t, J=7.2 Hz, 3H); $^{13}$C NMR (100 MHz) δ 174.31, 171.97, 166.01, 130.44, 129.51, 50.79, 50.61, 41.72, 36.86, 36.72, 36.42, 29.64, 29.18, 29.05, 27.36, 27.26, 27.09, 27.04, 25.76, 22.63, 14.24. HRMS Calcd for $C_{23}H_{44}N_3O_4$ [M+1]$^+$ 426.3332, found 426.3315.

Synthesis of Analog 5.

s, —NH, 0.5 H), 5.24-5.42 (m, 2H), 4.60-4.72 (m, 1H), 4.05 (d, J=2.4 Hz, 2H), 3.76 (s, 1.5 H), 3.75 (s, 1.5 H), 3.06-3.15 (m, 2H), 2.20-2.38 (m, 4H), 1.90-2.10 (m, 4H), 1.40-1.68 (m, 6H), 1.24-1.38 (m, 14H), 1.19 (d, J=6.7 Hz, 3H), 1.10 (d, J=6.7 Hz, 3H), 0.88 (t, J=7.1 Hz, 3H); $^{13}$C NMR (100 MHz) δ 173.60, 173.46, 173.16, 172.60, 170.82, 130.84, 130.12, 129.88, 129.16, 53.66, 52.58, 52.53, 48.35, 45.52, 43.55, 41.38, 41.15, 36.57, 34.11, 34.02, 31.95, 31.92, 31.32, 29.92, 29.72, 29.63, 29.60, 29.45, 29.40, 29.26, 29.21, 28.97, 27.94, 27.45, 27.41, 27.26, 27.16, 26.96, 25.91, 25.80, 25.75, 22.79, 21.62, 20.78, 14.31.

2-(13-(N-Isopropylheptanamido)tridec-8(Z)-enamido)acetic acid (5)

Following the ester hydrolysis conditions described above, methyl 2-(13-(N-isopropylheptanamido)tridec-8(Z)-enamido)acetate (50 mg, 0.10 mmol) was hydrolyzed to give analog 5 (44 mg, 91%) obtained as a colorless liquid. TLC:EtOAc (4:1), $R_f$-0.20; $^1$H NMR (300 MHz, 65/35 mixture of rotamers) δ 6.47 and 6.35 (br s, —NH, 1H for the two rotamers), 5.24-5.42 (m, 2H), 4.60-4.70 (m, 1H), 4.05 and 4.06 (d, J=2.8 Hz, 2H for the two rotamers), 3.06-3.18 (m, 2H), 2.20-2.38 (m, 4H), 1.90-2.10 (m, 4H), 1.50-1.68 (m, 6H), 1.24-1.38 (m, 14H), 1.20 and 1.10 (d, J=7.3 Hz, 6H for the two rotamers), 0.87 (t, J=7.2 Hz, 3H); $^{13}$C NMR (75 MHz) δ 174.35, 174.23, 174.18, 173.64, 172.0, 171.93, 130.98, 130.25, 129.75, 129.0, 48.86, 45.99, 43.77, 41.79, 41.62, 41.48, 34.05, 33.95, 31.85, 31.79, 31.13, 29.62, 29.51, 29.35, 29.31, 29.23, 28.85, 28.81, 27.83, 27.44, 27.34, 27.21, 27.02, 26.90, 26.03, 25.87, 25.80, 25.75, 22.75, 21.54, 20.70, 14.29. HRMS calcd for $C_{25}H_{47}N_2O_4$ [M+1]$^+$ 439.3536, found 439.3531.

Synthesis of Analog 31.

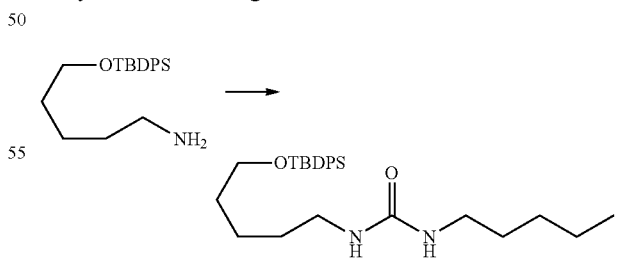

1-(5-(tert-Butyldiphenylsilyloxy)pentyl)-3-n-pentylurea 5-(tert-Butyldiphenylsilyloxy)pentan-1-amine$^5$ (3.0 g, 8.78 mmol) was reacted with n-pentyl isocyanate (995 mg, 8.78 mmol) as described above to give the title urea (85%)

Methyl 2-(13-(N-Isopropylheptanamido)tridec-8(Z)-enamido)acetate 13-(N-Isopropyl heptanamido)tridec-8(Z)-enoic acid (100 mg, 0.26 mmol) was condensed with glycine methyl ester as described above to give the corresponding amide (97 mg, 82%) as a colorless syrup that was used directly in the next step. TLC:EtOAc (2:1), $R_f$-0.45; $^{1H}$ NMR (300 MHz, 1:1 mixture of rotamers) δ 6.25 (br s, —NH, 0.5 H), 6.08 (br as a colorless oil. TLC:EtOAc/hexanes (2:3), $R_f$~0.40; $^1$H NMR (300 MHz) δ 7.60-7.70 (m, 4H), 7.30-7.40 (m, 6H), 4.24 (br s, —NH, 2H), 3.64 (t, J=7.9 Hz, 2H), 3.06-3.20 (m, 4H), 1.20-1.60 (m, 12H), 1.03 (s, 9H), 0.89 (t, J=7.2 Hz, 3H); $^{13}$C NMR (75 MHz) δ 159.7, 134.90, 132.47, 132.40, 129.70, 128.81, 128.71, 127.92, 63.2, 40.91, 40.81, 32.42, 29.60, 29.28, 27.11, 23.30, 22.35, 19.38. HRMS calcd for $C_{27}H_{43}N_2O_2Si$ [M+1]$^+$ 455.3094, found 455.3093.

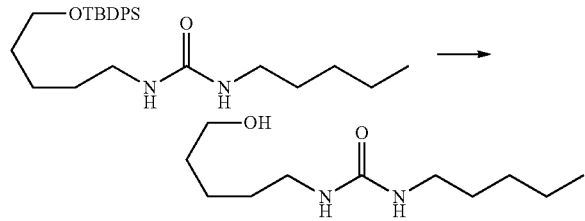

1-(5-Hydroxypentyl)-3-n-pentylurea 1-(5-(tert-Butyldiphenylsilyloxy)pentyl)-3-n-pentylurea (3.0 g, 6.60 mmol) was de-silylated as described above to give the title alcohol (1.31 g, 92%) as a colorless solid, mp 81.4-81.8° C. TLC:EtOAc/hexanes (7:3), $R_f$~0.40; $^1$H NMR (CD$_3$OD, 300 MHz) δ 3.54 (t, J=5.8 Hz, 2H), 3.06 (q, J=6.4 Hz, 4H), 1.22-1.60 (m, 12H), 0.89 (t, J=7.3 Hz, 3H); $^{13}$C NMR (CD$_3$OD, 100 MHz) δ 160.17, 61.67, 39.82, 39.77, 32.17, 30.02, 29.91, 29.03, 23.04, 22.34, 13.25. HRMS calcd for $C_{11}H_{25}N_2O_2$ [M+1]$^+$ 217.1916, found 217.1916.

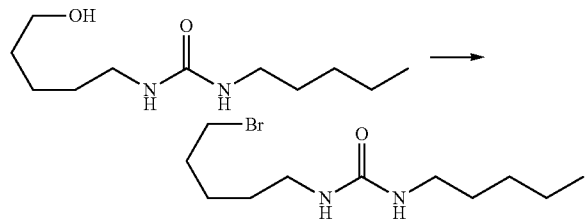

1-(5-Bromopentyl)-3-n-pentylurea

Following the protocol described above, 1-(5-hydroxypentyl)-3-n-pentylurea (1.30 g, 6.02 mmol) was converted into the corresponding bromide (1.45 g, 87%), obtained as a colorless oil. TLC:EtOAc/hexanes (2:3), $R_f$~0.40; 1H NMR (300 MHz) δ 4.44 (br s, —NH, 2H), 3.40 (t, J=6.7 Hz, 2H), 3.10-3.20 (m, 4H), 1.82-1.92 (m, 2H), 1.40-1.58 (m, 6H), 1.24-1.38 (m, 4H), 0.89 (t, J=7.3 Hz, 3H); $^{13}$C NMR (100 MHz) δ 159.46, 40.02, 33.88, 33.02, 30.29, 29.92, 29.36, 25.83, 22.12, 14.02. HRMS calcd for $C_{11}H_{24}BrN_2O$ [M+1]$^+$ 279.1072, found 279.1073.

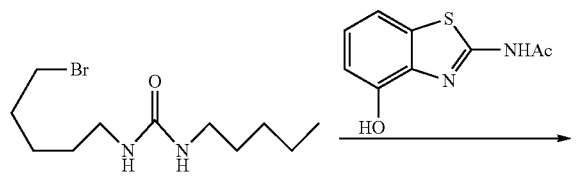

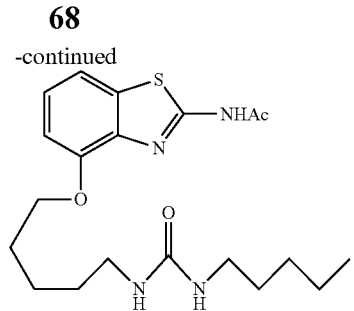

N-(4-(5-(3-n-Pentylureido)pentyloxy)benzo[d]thiazol-2-yl)acetamide (31)

A mixture of 1-(5-bromopentyl)-3-n-pentylurea (100 mg, 0.37 mmol), commercial N-(4-hydroxybenzo[d]thiazol-2-yl)acetamide (100 mg, 0.48 mmol), and $K_2CO_3$ (67 mg, 0.48 mmol) in DMF (5 mL) was heated at 60° C. After 6 h, the reaction mixture was cooled to rt, diluted with water (25 mL), and extracted into EtOAc (3×10 mL). The combined organic extracts were washed with water (2×5 mL), brine (10 mL), dried (Na$_2$SO$_4$) and concentrated in vacuo. The residue thus obtained was purified by silica gel column chromatography to give 31 (61 mg, 40%), mp 61.6-61.8° C. TLC:EtOAc/hexane (3:2), $R_f$~0.40; $^1$H NMR (300 MHz) δ 7.39 (dd, J=0.9, 7.3 Hz, 1H), 7.20 (dd, J=7.8, 7.3 Hz, 1H), 6.86 (dd, J=0.9, 7.8 Hz, 1H), 4.42 (br s, —NH, 2H), 4.17 (t, J=5.4 Hz, 2H), 3.19-3.30 (m, 4H), 2.33 (s, 3H), 1.82-1.98 (m, 2H), 1.64-1.80 (m, 4H), 1.42-1.60 (m, 2H), 1.24-1.40 (m, 4H), 0.88 (t, J=7.3 Hz, 3H); $^{13}$C NMR (75 MHz) δ 170.16, 159.91, 158.94, 151.37, 139.10, 133.67, 124.40, 113.94, 108.68, 68.21, 40.64, 39.98, 30.27, 29.30, 28.33, 26.54, 23.25, 22.64, 22.33, 14.26. HRMS (ESI-neg) calcd for $C_{20}H_{29}N_4O_3S$ [M−1]$^-$ 405.1960, found 405.1938.

Synthesis of Analog 32.

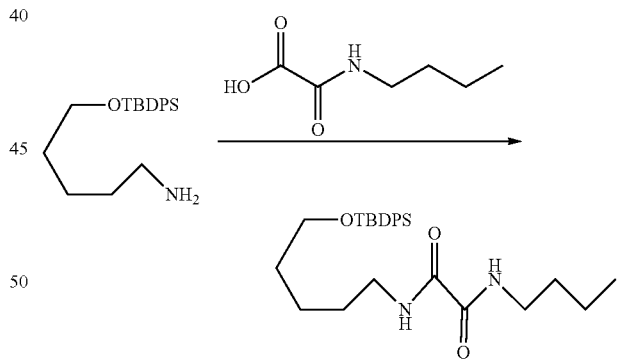

$N^1$-n-Butyl-$N^2$-(5-(tert-butyldiphenylsilyloxy)pentyl)oxalamide

A mixture of 2-(n-butylamino)-2-oxoacetic acid (22 mg, 0.15), 5-(tert-butyldiphenylsilyloxy)pentan-1-amine$^5$ (50 mg, 0.15 mmol), N,N-diisopropylethylamine (40 mg, 0.30 mmol), and 2-(1H-7-azabenzotriazol-1-yl)-1,1,3,3-tetramethyluronium hexafluorophosphate methanaminium (HATU, 72 mg, 0.19 mmol) in dry DMF (5 mL) was stirred at rt overnight under an argon atmosphere, then quenched with water (2 mL). The reaction mixture was extracted with EtOAc (3×5 mL). The combined organic extracts were washed with water, dried and concentrated in vacuo. The residue was purified by flash SiO$_2$ column chromatography using EtOAc/hexanes (1:3) as eluent to give the title oxamide (65 mg, 91%) as a colorless oil. TLC: 50% EtOAc/hexane, R$_f$~0.56; $^1$H NMR (400 MHz) δ 7.55-7.70 (m, 4H), 7.60 (br s, —NH, 2H), 7.35-7.40 (m, 6H), 3.65 (t, J=6.0 Hz, 2H), 3.35-3.25 (m, 4H), 1.55-1.35 (m, 10H), 1.05 (s, 9H), 0.92 (t, J=7.3 Hz, 3H); $^{13}$C NMR (100 MHz) δ 160.28, 160.25, 135.80, 134.20, 129.85, 127.90, 63.80, 40.0, 39.70, 32.40, 31.50, 29.20, 27.10, 27.05, 23.40, 20.30, 19.45, 14.0. HRMS calcd for C$_{27}$H$_{41}$N$_2$O$_3$Si [M+1]$^+$ 469.2886. found 469.2892.

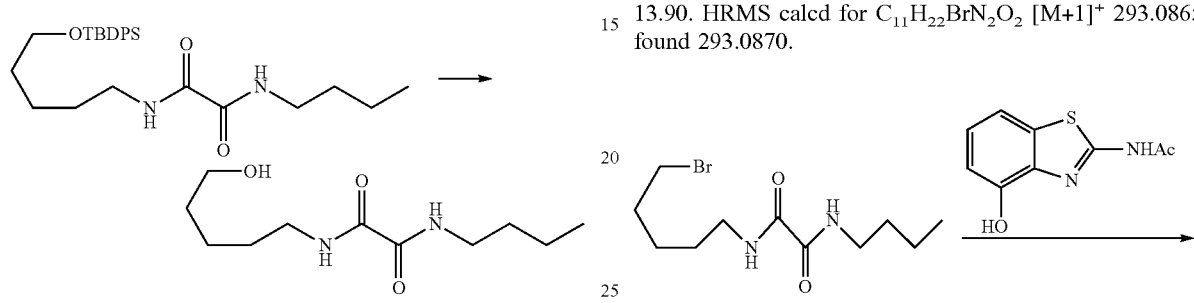

N$^1$-n-Butyl-N$^2$-(5-hydroxypentyl)oxalamide

A mixture of N$^1$-n-butyl-N$^2$-(5-(tert-butyldiphenylsilyloxy)pentyl)oxalamide (65 mg, 0.14 mmol) and n-tetrabutylammonium fluoride (0.41 mL, 1 M soln, 0.42 mmol) in dry THF solution was stirred at room temperature under an argon atmosphere for 12 h. All volatiles were evaporated in vacuo, the residue was dissolved in EtOAc (30 mL) and the organic layer was washed with water (10 mL), brine (15 mL), dried and evaporated. Purification of the residue via SiO$_2$ column chromatography using EtOAc/hexanes (1:2) as eluent gave the title compound (30 mg, 92%) as a colorless solid, mp 136-137° C. TLC: 50% EtOAc/hexane, R$_f$~0.28; $^1$H NMR (300 MHz) δ 7.65 (br s, NH, 1H), 7.60 (br s, —NH, 1H), 3.65 (t, J=6.0 Hz, 2H), 3.35-3.25 (m, 4H), 1.90 (br s —OH, 1H), 1.60-1.50 (m, 6H), 1.40-1.35 (m, 4H), 0.92 (t, J=7.3 Hz, 3H); $^{13}$C NMR (100 MHz) δ 160.25, 160.10, 62.70, 39.80, 39.65, 32.40, 31.45, 29.20, 23.25, 20.20, 13.85. HRMS calcd for C$_{11}$H$_{23}$N$_2$O$_3$ [M+1]$^+$ 231.1709, found 231.1701.

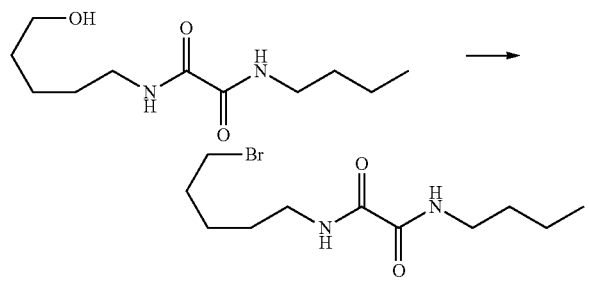

N$^1$-(5-Bromopentyl)-N$^2$-n-butyloxalamide

A solution of carbon tetrabromide (51 mg, 0.15 mmol) in CH$_2$Cl$_2$ (5 mL) was stirred into a 0° C. solution of triphenylphosphine (48 mg, 0.18 mmol) and N$^1$-n-butyl-N$^2$(5-hydroxypentyl)oxalamide (30 mg, 0.130 mmol) in dry CH$_2$Cl$_2$ (5 mL) under an argon atmosphere. After 2 h, the reaction mixture was washed with water (5 mL), brine (10 mL), dried over anhydrous Na$_2$SO$_4$, and all volatiles were removed under reduced pressure. The residue was purified by SiO$_2$ column chromatography using EtOAc/hexane (1:4) to give compound the title compound (32 mg, 84%) as a colorless solid, mp 109-110° C. TLC: 50% EtOAc/hexanes, R$_f$~0.50; $^1$H NMR (300 MHz) δ 7.55 (br s, NH, 1H), 7.50 (br s, —NH, 1H), 3.40 (t, J=6.0 Hz, 2H), 3.25-3.35 (m, 4H), 1.80-1.85 (m, 2H), 1.40-1.60 (m, 6H), 1.25-1.35 (m, 2H), 0.92 (t, J=7.3 Hz, 3H); $^{13}$C NMR (100 MHz) δ 160.30, 160.15, 39.65, 33.65, 32.45, 31.40, 28.60, 25.60, 20.20, 13.90. HRMS calcd for C$_{11}$H$_{22}$BrN$_2$O$_2$ [M+1]$^+$ 293.0865, found 293.0870.

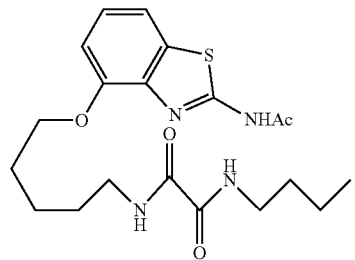

N$^1$-(5-(2-Acetamidobenzo[d]thiazol-4-yloxy)pentyl)-N$^2$-n-butyloxalamide

A mixture of N$^1$-(5-bromopentyl)-N$^2$-n-butyloxalamide (32 mg, 0.11 mmol), commercial N-(4-hydroxybenzo[d]thiazol-2-yl)acetamide (22 mg, 0.11 mmol), and K$_2$CO$_3$ (45 mg, 0.32 mmol) in DMF (3 mL) was heated at 80° C. for 3 h, then cooled to room temperature, diluted with water (15 mL) and extracted into EtOAc (3×10 mL). The combined organic extracts were washed with water (2×5 mL), brine (10 mL), dried (Na$_2$SO$_4$) and concentrated in vacuo. The residue was purified by silica gel column chromatography using EtOAc/hexanes (1:2) as eluent to give analog 32 (35 mg, 76%) as a colorless solid, mp 154-155° C. TLC: 70% EtOAc/hexanes, R$_f$~0.35; $^1$H NMR (300 MHz) δ 11.05 (br s, NH, 1H), 8.30 (br s, NH, 1H), 7.70 (br s, NH, 1H), 7.40 (d, J=7.4 Hz, 1H), 7.25 (dd, J=7.4, 7.8 Hz, 1H), 6.85 (d, J=7.8 Hz, 1H), 4.20 (t, J=6.0 Hz, 2H), 3.50 (q, J=7.2 Hz, 2H), 3.35 (q, J=7.0 Hz, 2H), 2.35 (s, 3H), 1.95-1.90 (m, 2H), 1.85-1.80 (m, 2H), 1.70-1.65 (m, 2H), 160-1.55 (m, 2H), 1.40-1.35 (m, 2H), 0.95 (t, J=7.3 Hz, 3H); $^{13}$C NMR (75 MHz) δ 169.40, 160.55, 159.90, 157.85, 151.50, 139.10, 134.00, 124.75, 113.75, 108.10, 68.90, 39.80, 39.30, 31.35, 28.20, 27.40, 23.70, 23.45, 20.25, 13.90. HRMS calcd for C$_{20}$H$_{29}$N$_4$O$_4$S [M+1]$^+$ 421.1910, found 421.1906.

Synthesis of Analog 30.

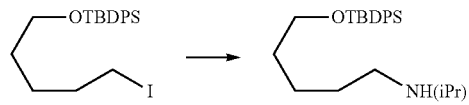

5-(tert-Butyldiphenylsilyloxy)-N-isopropylpentan-1-amine

Following literature precedent,[2] a mixture of 1-(tert-butyldiphenylsilyloxy)-5-iodopentane[6] (1.50 g, 3.32 mmol), isopropylamine (1.70 mL, 19.92 mmol) and $K_2CO_3$ (1.37 g, 10.03 mmol) was reacted to give the title amine (0.92 g, 72%) as a colorless liquid. TLC:MeOH/$CH_2Cl_2$ (1:4), $R_f$~0.30; $^1$H NMR (300 MHz) δ 7.65-7.67 (m, 4H), 7.30-7.40 (m, 6H), 3.65 (t, J=6.4 Hz, 2H), 2.70-2.82 (m, 1H), 2.55 (t, J=7.3 Hz, 2H), 1.50-1.64 (m, 2H), 1.32-1.48 (m, 4H), 1.05 (d, J=5.8 Hz, 3H), 1.04 (s, 9H); $^{13}$C NMR (100 MHz) δ 135.68, 134.21, 129.63, 127.70, 63.95, 48.81, 47.64, 32.60, 30.27, 27.0, 23.76, 23.15, 19.34. HRMS calcd for $C_{24}H_{38}NOSi$ $[M+1]^+$ 384.2723, found 384.2724.

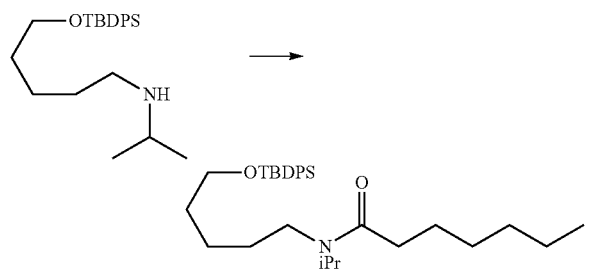

N-(5-(tert-Butyldiphenylsilyloxy)pentyl)-N-isopropylheptanamide

Following literature precedent,[2] 5-(tert-butyldiphenylsilyloxy)-N-isopropylpentan-1-amine (0.90 g, 2.30 mmol) was condensed with heptanoic acid (0.26 g, 2.0 mmol) to give the title amide (0.90 g, 79%) as a viscous oil. TLC:EtOAc/hexanes (3:8), $R_f$~0.60; $^1$H NMR (300 MHz, 1:1 mixture of rotamers) δ 7.65-7.67 (m, 4H), 7.30-7.40 (m, 6H), 4.62-4.72 (m, 0.5 H), 4.00-4.80 (m, 0.5H), 3.62 (t, J=4.8 Hz, 1H), 3.68 (t, J=4.8 Hz, 1H), 3.02 (t, J=5.2 Hz, 1H), 3.16 (t, J=5.2 Hz, 1H), 2.38 (t, J=5.3 Hz, 1H), 2.24 (t, J=5.3 Hz, 1H), 1.50-1.68 (m, 6H), 1.26-1.44 (m, 8H), 1.18 (d, J=7.3 Hz 3H), 1,12, (d, J=7.3 Hz 3H), 1.03 (s, 4.5 H), 1.04 (s, 4.5H), 0.88 (t, J=7.3 Hz, 3H); $^{13}$C NMR (125 MHz) δ 173.38, 172.76, 135.80, 135.78, 134.36, 134.12, 129.85, 129.73, 127.88, 127.82, 64.22, 63.68, 48.43, 45.62, 43.64, 41.27, 34.13, 34.05, 32.61, 32.36, 31.96, 31.93, 31.51, 29.63, 29.47, 27.10, 27.03, 25.94, 25.78, 24.03, 23.77, 22.81, 21.63, 20.78, 19.47, 14.33, 14.28. HRMS calcd for $C_{31}H_{50}NO_2Si$ $[M+1]^+$ 496.3611, found 496.3615.

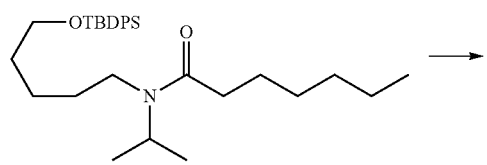

N-(5-Hydroxypentyl)-N-isopropylheptanamide

N-(5-(tert-Butyldiphenylsilyloxy)pentyl)-N-isopropylheptanamide (0.70 g, 1.37 mmol) was de-silylated as described above to give the title alcohol (0.34 g, 96%) as a colorless solid. TLC:EtOAc/hexanes (2:3), $R_f$~0.30; $^1$H NMR (300 MHz, 53/47 mixture of rotamers) δ 4.58-4.66 and 3.96-4.08 (m, 1H for the two rotamers), 3.56 and 3.70 (t, J=5.4 Hz, 2H for the two rotamers), 3.02-3.16 (m, 2H), 2.30 and 2.26 (t, J=6.3 Hz, 2H for the two rotamers), 1.50-1.64 (m, 6H), 1.22-1.40 (m, 8H), 1.13 and 1.09 (d, J=7.5 Hz, 6H for the two rotamers), 0.84 (t, J=7.3 Hz, 3H); $^{13}$C NMR (100 MHz) δ 172.81 62.66, 62.60, 48.41, 45.55, 43.56, 41.04, 34.08, 34.0, 32.46, 32.43, 31.86, 31.57, 29.40, 25.87, 25.70, 23.77, 23.73, 22.75, 21.57, 20.72, 14.26. HRMS calcd for $C_{15}H_{32}NO_2$ $[M+1]^+$ 258.2433, found 258.2436.

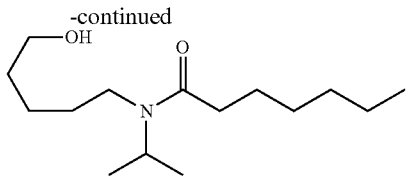

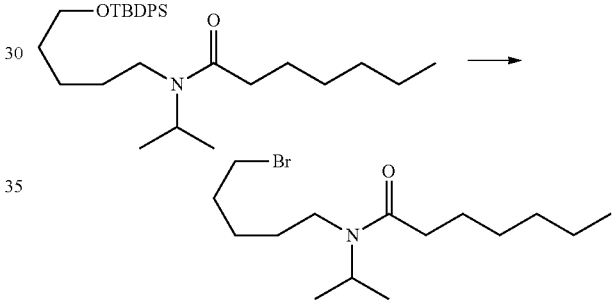

N-(5-Bromopentyl)-N-isopropylheptanamide

N-(5-Hydroxypentyl)-N-isopropylheptanamide (0.25 g, 0.97 mmol) was converted to the corresponding bromide as described above to give the title compound (0.25 g. 82%) as a colorless oil. TLC:EtOAc/hexanes (3:7), $R_f$~0.40; $^1$H NMR (300 MHz, 55/45 mixture of rotamers) δ 4.60-4.70 and 3.96-4.10 (m, 1H for two rotamers), 3.46 and 3.36 (t, J=5.8 Hz 2H for two rotamers), 3.02-3.10 (m, 2H), 2.30 and 2.22 (t, J=7.9 Hz, 2H for two rotamers), 1.80-1.97 (m, 2H), 1.40-1.70 (m, 6H), 1.20-1.40 (m, 6H), 1.16 and 1.10, (d, J=7.3 Hz, 6H for two rotamers), 0.86 (t, J=7.3 Hz, 3H); $^{13}$C NMR (75 MHz) δ 172.79, 172.39, 48.17, 45.47, 43.32, 40.70, 33.89, 33.87, 33.49, 32.48, 32.30, 31.81, 31.78, 30.78, 29.27, 28.74, 26.05, 25.84, 25.69, 25.54, 22.64, 21.47, 20.62, 14.17. HRMS calcd for $C_{15}H_{31}BrNO$ $[M+1]^+$ 320.1589, found 320.1588.

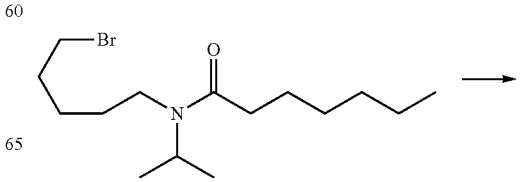

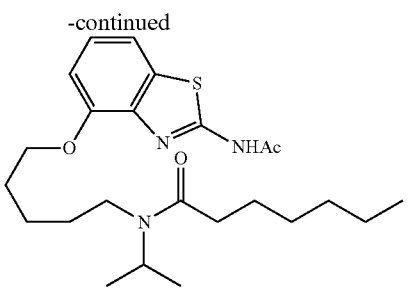

N-(5-(2-Acetamidobenzo[d]thiazol-4-yloxy)pentyl)-N-isopropylheptanamide (30)

N-(5-Bromopentyl)-N-isopropylheptanamide (75 mg, 0.23 mmol) was alkylated with commercial N-(4-hydroxybenzo[d]thiazol-2-yl)acetamide (54 mg, 0.26 mmol) as described above to give analog 30 (43 mg, 42%) as a sticky solid. TLC:EtOAc/hexanes (1:4), $R_f$~0.30; $^1$H NMR (300 MHz, 45/55 mixture of rotamers) δ 11.50 (br s, —NH, 1H), 7.37-7.42 (m, 1H), 7.18-7.26 (m, 1H), 6.84-6.88 (m, 1H), 4.58-4.78 and 4.00-4.10 (m, 1H for two rotamers), 4.02 (t, J=6.3 Hz, 2H), 3.12 (t, J=7.3 Hz, 2H), 2.22-2.45 (m, 5H), 1.82-1.92 (m, 2H), 1.44-1.70 (m, 4H), 1.20-1.40 (m, 8H), 1.11-1.19 (m, 6H), 0.82-0.95 (m, 3H); $^{13}$C NMR (75 MHz) δ 173.94, 172.78, 169.40, 169.36, 157.89, 151.62, 138.43, 138.32, 133.91, 133.87, 124.92, 124.85, 114.02, 113.87, 109.66, 108.35, 69.46, 69.08, 48.53, 48.33, 45.94, 43.61, 41.20, 34.26, 34.09, 31.91, 31.88, 31.39, 29.55, 29.45, 29.37, 29.30, 25.88, 25.77, 25.71, 24.43, 24.16, 23.55, 22.77, 21.59, 20.80, 14.28. HRMS (ESI-neg) calcd for $C_{24}H_{36}N_3O_3S$ [M-1]$^-$ 446.2477, found 446.2434.

Synthesis of Analog 33.

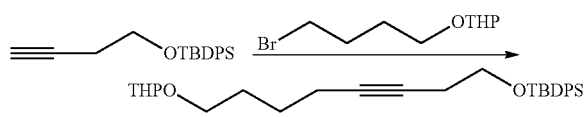

1-(tert-Butyldiphenylsilyloxy)-8-(tetrahydro-2H-pyran-2-yloxy)oct-3-yne 4-(tert-Butyldiphenylsilyloxy)-1-butyne[7] (5.0 g, 16.23 mmol) was coupled with 2-(4-bromobutoxyl)tetrahydro-2H-pyran[8] (4.59 g, 19.48 mmol) as described above to give the title acetylene (5.57 g, 74%) as a colorless oil. TLC:EtOAc/hexanes (1:9), $R_f$~0.40; $^1$H NMR (300 MHz) δ 7.66-7.69 (m, 4H), 7.34-7.42 (m, 6H), 4.57 (t, J=4.3 Hz, 1H), 3.78-3.86 (m, 2H), 3.73-3.90 (m, 3H), 3.32-3.40 (m, 3H), 2.40-2.45 (m, 2H), 2.06-2.10 (m, 2H), 1.93-2.02 (m, 2H), 1.40-1.80 (m, 6H), 1.02 (s, 9H); $^{13}$C NMR (100 MHz) δ 137.87, 133.96, 129.70, 128.0, 99.0, 81.0, 77.41, 67.32, 63.15, 62.51, 30.97, 29.20, 27.0, 26.98, 26.0, 25.74, 23.18, 19.83, 19.44, 18.88. HRMS calcd for $C_{29}H_{41}O_3Si$ [M+1]$^+$ 465.2825, found 465.2829.

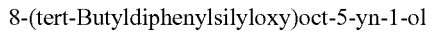

8-(tert-Butyldiphenylsilyloxy)oct-5-yn-1-ol 1-(tert-Butyldiphenylsilyloxy-8-(tetrahydro-2H-pyran-2-yloxy)oct-3-yne (5.50 g, 11.84 mmol) was de-silylated as described above to give the title compound (3.87 g, 86%) as a colorless oil. TLC:EtOAc/hexanes (2:3), $R_f$~0.40; $^1$H NMR (300 MHz) δ 7.60-7.68 (m, 4H), 7.30-7.40 (m, 6H), 3.77 (t, J=7.4 Hz, 2H), 3.60-3.72 (m, 2H), 2.40-2.48 (m, 2H), 2.22-2.40 (m, 2H), 1.50-1.70 (m, 4H), 1.03 (s, 9H); $^{13}$C NMR (100 MHz) δ 135.83, 133.96, 129.90, 127.92, 81.31, 63.16, 62.60, 32.0, 27.0, 25.43, 23.17, 19.43, 18.78. HRMS calcd for $C_{24}H_{33}O_2Si$ [M+1]$^+$ 381.2250, found 381.2256.

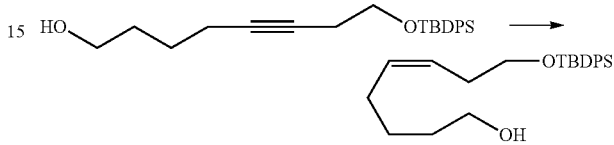

8-(tert-Butyldiphenylsilyloxy)oct-5(Z)-en-1-ol 8-(tert-Butyldiphenylsilyloxy)oct-5-yn-1-ol (5.32 g, 14.0 mmol) was semi-hydrogenated as described above to give 8-(tert-butyldiphenylsilyloxy)oct-5(Z)-en-1-ol (5.18 g, 97%) as a colorless oil whose spectral values were in agreement with literature data.[9] TLC:EtOAc/hexanes (2:3), $R_f$~0.45; $^1$H NMR (300 MHz) δ 7.60-7.70 (m, 4H), 7.30-7.40 (m, 6H), 5.34-5.44 (m, 2H), 3.65 (t, J=7.0 Hz, 2H), 3.58-3.64 (m, 2H), 2.23 (q, J=4.2 Hz, 2H), 1.98-2.20 (m, 2H), 1.30-1.60 (m, 4H), 1.03 (s, 9H); $^{13}$C NMR (100 MHz) δ 135.84, 134.21, 131.64, 129.82, 127.87, 126.28, 63.94, 63.12, 32.54, 31.12, 27.23, 27.11, 26.02.

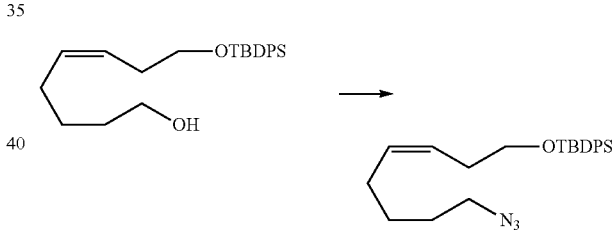

1-(tert-Butyldiphenylsilyloxy-8-azido-oct-3(Z)-en

Following the procedure described above, 8-(tert-butyldiphenylsilyloxy)-oct-5(Z)-en-1-ol (5.20 g, 13.61 mmol) was transformed into the title azide (3.98 g, 72%), obtained as a colorless oil. TLC:EtOAc/hexanes (1:9), $R_f$~0.60; $^1$H NMR (300 MHz) δ 7.60-7.70 (m, 4H), 7.30-7.40 (m, 6H), 5.34-5.44 (m, 2H), 3.63 (t, J=7.0 Hz, 2H), 3.22 (t, J=6.4 Hz, 2H), 2.31 (q, J=3.6 Hz, 2H), 1.95-2.05 (m, 2H), 1.50-1.60 (m, 2H), 1.30-1.40 (m, 2H), 1.03 (s, 9H); $^{13}$C NMR (100 MHz) δ 135.98, 135.90, 134.28, 131.24, 130.05, 129.79, 128.10, 127.87, 126.76, 63.98, 51.64, 31.24, 28.74, 27.29, 27.16, 27.07, 27.0, 19.55; IR (neat) 2931, 2858, 2095, 1111 cm$^{-1}$. HRMS calcd for $C_{24}H_{34}N_3OSi$ [M+1]$^+$ 408.2471, found 408.2470.

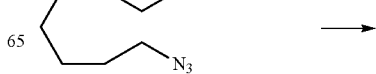

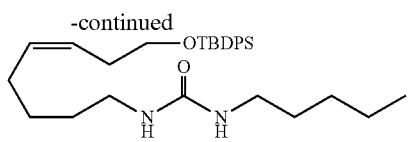

1-(8-(tert-Butyldiphenylsilyloxy)oct-5(Z)-enyl)-3-n-pentylurea 1-(tert-Butyldiphenylsilyloxy-8-azido-oct-3(Z)-en was reduced to the corresponding amine using triphenylphosphine as described above. The crude amine was reacted with n-pentyl isocyanate in THF as noted above and the product was purified by SiO$_2$ column chromatography eluting with 20% EtOAc/hexane to afford the title compound (1.94 g, 84%) as a viscous oil. TLC:EtOAc/hexanes (2:3), R$_f$~0.45; $^1$H NMR (300 MHz) δ 7.60-7.70 (m, 4H), 7.30-7.40 (m, 6H), 5.35-5.42 (m, 2H), 4.65 (br s, —NH, 2H), 3.64 (t, J=5.5 Hz, 2H), 3.06-3.18 (m, 4H), 2.24-2.34 (q, J=3.9 Hz, 2H), 1.94-2.02 (q, J=3.6 Hz, 2H), 1.20-1.50 (m, 10H), 1.03 (s, 9H), 0.83 (t, J=7.3 Hz, 3H); $^{13}$C NMR (100 MHz) δ 159.52, 135.85, 134.21, 131.53, 129.85, 127.90, 126.28, 63.93, 40.58, 40.50, 31.13, 30.43, 30.41, 29.45, 27.35, 22.77, 19.47, 14.36. HRMS calcd for C$_{30}$H$_{47}$N$_2$O$_2$Si [M+1]$^+$ 495.3407, found 495.3406.

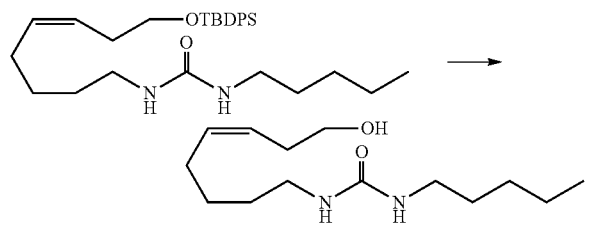

1-(8-Hydroxyoct-5(Z)-enyl)-3-n-pentylurea 1-(8-(tert-Butyldiphenylsilyloxy)oct-5(Z)-enyl)-3-n-pentylurea (3.0 g, 6.07 mmol) was de-silylated as described above to give the title alcohol (1.44 g, 93%) as a colorless solid, mp 57.8-57.9° C. TLC:EtOAc/hexanes (1:4), R$_f$~0.30; $^1$H NMR (300 MHz) δ 5.30-5.60 (m, 2H), 4.40 (br s, —NH, 2H), 3.63 (t, J=6.4 Hz, 2H), 3.08-3.22 (m, 4H), 2.29 (q, J=5.3 Hz, 2H), 2.09 (q, J=5.2 Hz, 2H), 1.20-1.58 (m, 10H), 0.88 (t, J=7.3 Hz, 3H); $^{13}$C NMR (100 MHz) δ 159.48, 132.35, 126.21, 62.28, 40.54, 40.15, 31.12, 30.28, 29.96, 29.35, 27.02, 26.98, 22.68, 14.27. HRMS calcd for C$_{14}$H$_{29}$N$_2$O$_2$ [M+1]$^+$ 257.2229, found 257.2236.

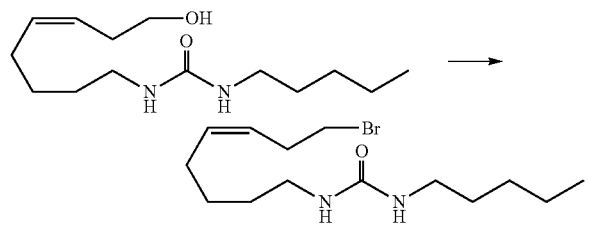

1-(8-Bromooct-5(Z)-enyl)-3-n-pentylurea

Obtained in 82% yield as a colorless oil. TLC:EtOAc/hexanes (2:3), R$_f$~0.60; $^1$H NMR (300 MHz) δ 5.30-5.58 (m, 2H), 4.70 (br s, 2H), 3.35 (t, J=6.8 Hz, 2H), 3.08-3.19 (m, 4H), 2.60 (q, J=5.6 Hz, 2H), 2.05 (q, J=5.4 Hz, 2H), 1.24-1.54 (m, 10H), 0.88 (t, J=7.3 Hz, 3H); $^{13}$C NMR (100 MHz) δ 159.54, 132.73, 126.45, 40.53, 40.33, 32.85, 30.98, 30.33, 30.30, 29.36, 27.36, 27.0, 22.69, 14.28. HRMS calcd for C$_{14}$H$_{28}$BrN$_2$O [M+1]$^+$ 319.1385, found 319.1392.

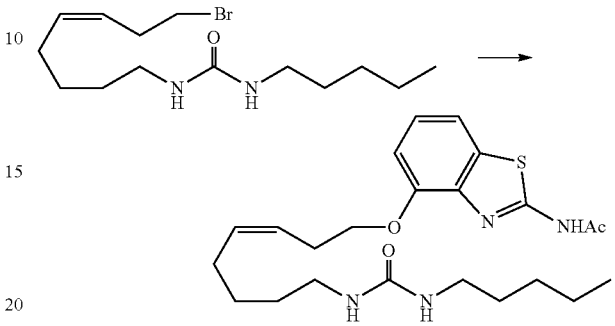

N-(4-(8-(3-n-Pentylureido)oct-3(Z)-enyloxy)benzo[d]thiazol-2-yl)acetamide (33)

Obtained in 40% yield as a colorless solid, mp 113.7-113.8° C. TLC:EtOAc/hexane (3:2), R$_f$~0.40; $^1$H NMR (300 MHz) δ 12.10 (br s, —NH, 1H), 7.40 (dd, J=0.8, 7.8 Hz, 1H), 7.22 (dt, J=0.6, 8.9 Hz, 1H), 6.90 (dd, J=0.5, 6.9 Hz, 1H), 5.40-5.50 (m, 2H), 4.60 (br s, —NH, 2H), 4.20 (t, J=5.3 Hz, 2H), 3.05-3.20 (m, 4H), 2.65 (q, J=3.9 Hz, 2H), 2.29 (s, 3H), 2.15 (q, J=3.9 Hz, 2H), 1.40-1.70 (m, 10H), 0.87 (t, J=7.3 Hz, 3H); $^{13}$C NMR (100 MHz) δ 170.07, 159.21, 158.52, 151.46, 138.41, 133.84, 132.26, 126.13, 124.81, 113.81, 108.29, 68.46, 40.75, 40.64, 30.20, 29.30, 27.78, 26.84, 26.47, 23.42, 22.62, 14.24. HRMS calcd for C$_{23}$H$_{35}$N$_4$O$_3$S [M+1]$^+$ 447.2430, found 447.2431.

Synthesis of Analog 4.

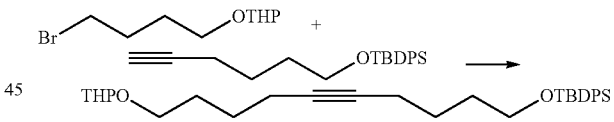

1-(Tetrahydro-2H-pyran-2-yloxy)-10-(tert-butyldiphenylsilyloxy)dec-5-yne

Obtained in 73% yield as a colorless oil. TLC: 15% EtOAc/hexanes, R$_f$~0.50; $^1$H NMR (500 MHz) δ 7.64-7.68 (m, 4H), 7.34-7.42 (m, 6H), 4.62 (t, J=4.3 Hz, 1H), 3.78-3.92 (m, 2H), 3.68 (t, J=6.3 Hz, 2H), 3.40-3.56 (m, 2H), 2.14-2.26 (m, 4H), 1.42-1.90 (m, 14H), 1.04 (s, 9H); $^{13}$C NMR (75 MHz) δ 135.83, 132.02, 129.80, 127.88, 99.0, 80.52, 80.30, 67.31, 63.74, 62.49, 32.0, 31.06, 29.21, 27.14, 26.21, 25.82, 25.78, 19.89, 18.90, 18.81. HRMS calcd for C$_{31}$H$_{45}$O$_3$Si [M+1]$^+$ 493.3138, found 493.3140.

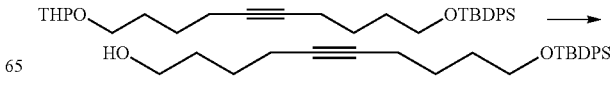

10-(tert-Butyldiphenylsilyloxy)dec-5-yn-1-ol

Obtained in 88% yield as a colorless oil whose spectral values were in agreement with literature data.[10] TLC: EtOAc/hexanes (3:7), $R_f$~0.40; $^1$H NMR (300 MHz) δ 7.64-7.68 (m, 4H), 7.34-7.42 (m, 6H), 3.67 (t, J=5.3 Hz, 4H), 2.06-2.22 (m, 4H), 1.50-1.64 (m, 8H), 1.04 (s, 9H); $^{13}$C NMR (75 MHz) δ 135.82, 135.08, 134.27, 129.80, 127.87, 80.74, 80.60, 63.67, 62.69, 32.09, 31.99, 27.12, 26.83, 25.78, 25.58, 25.48, 19.49, 18.79, 18.76.

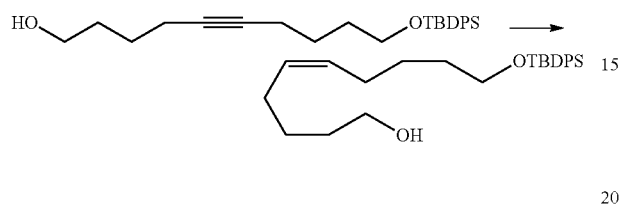

10-(tert-Butyldiphenylsilyloxy)dec-5(Z)-en-1-ol

Obtained in 92% yield as a colorless oil whose spectral values were in agreement with literature data.[10] TLC: EtOAc/hexanes (3:7), $R_f$~0.45; $^1$H NMR (300 MHz) δ 7.64-7.68 (m, 4H), 7.42-7.25 (m, 6H), 5.30-5.40 (m, 2H), 3.67 (t, J=5.3 Hz, 4H), 2.06-2.22 (m, 4H), 1.40-1.64 (m, 8H), 1.04 (s, 9H); $^{13}$C NMR (75 MHz) δ 135.90, 135.81, 134.37, 129.92, 129.87, 129.84, 127.98, 127.80, 64.09, 63.05, 32.47, 27.24, 27.22, 27.13, 26.21, 26.14, 19.51.

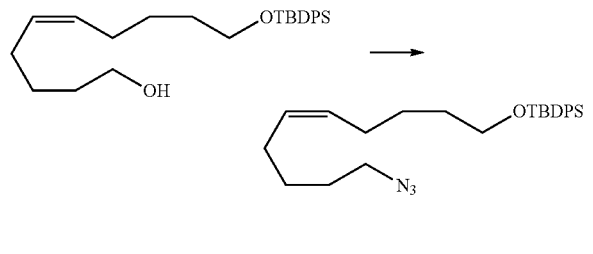

1-(10-Azidodec-5(Z)-enyloxy)(tert-butyldiphenylsilane

Obtained in 71% yield as a colorless oil. TLC:EtOAc/hexanes (1:9), $R_f$~0.60; $^1$H NMR (300 MHz) δ 7.64-7.68 (m, 4H), 7.25-7.42 (m, 6H), 5.30-5.40 (m, 2H), 3.65 (t, J=5.3 Hz, 2H), 3.24 (t, J=4.9 Hz, 2H), 2.06-2.22 (m, 4H), 1.40-1.64 (m, 8H), 1.04 (s, 9H); $^{13}$C NMR (75 MHz) δ 137.87, 134.35, 130.69, 129.74, 127.91, 64.02, 51.62, 32.44, 28.67, 27.21, 27.16, 27.08, 26.91, 26.16, 19.48; IR (neat) 2930, 2861, 2331, 2324, 2096, 1106 cm$^{-1}$. HRMS calcd for $C_{26}H_{38}N_3OSi$ [M+1]$^+$ 436.2784, found 436.2784.

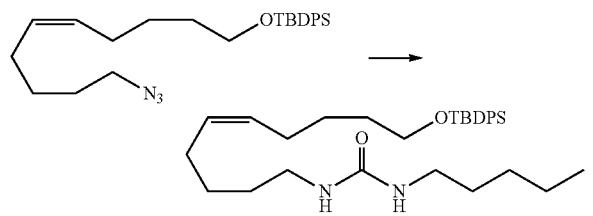

1-(10-(tert-Butyldiphenylsilyloxy)dec-5(Z)-enyl)-3-n-pentylurea

Obtained in 78% yield as a colorless oil. TLC:EtOAc/hexanes (2:3), $R_f$~0.60; $^1$H NMR (300 MHz) δ 7.64-7.68 (m, 4H), 7.34-7.42 (m, 6H), 5.22-5.43 (m, 2H), 4.50 (br s, —NH, 2H), 3.65 (t, J=6.2 Hz, 2H), 3.10-3.40 (m, 4H), 1.96-2.06 (m, 4H), 1.20-1.60 (m, 14H), 1.03 (s, 9H), 0.88 (t, J=7.3 Hz, 3H); $^{13}$C NMR (75 MHz) δ 159.08, 136.03, 134.02, 130.03, 128.26, 126.82, 63.28, 40.67, 40.47, 32.91, 30.48, 29.28, 27.26, 27.22, 26.93, 26.02, 22.64, 19.39, 14.26. HRMS calcd for $C_{32}H_{51}N_2O_2Si$ [M+1]$^+$ 523.3720, found 523.3724.

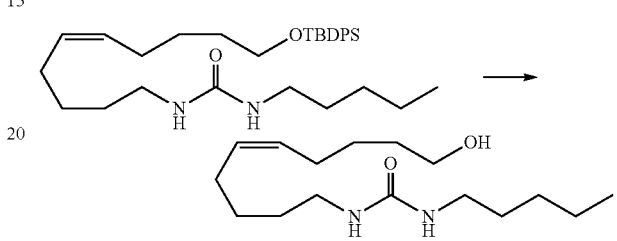

1-(10-Hydroxydec-5(Z)-enyl)-3-n-pentylurea

Obtained in 94% yield as a colorless oil. TLC:EtOAc/hexanes (7:3), $R_f$~0.30; $^1$H NMR (400 MHz) δ 5.30-5.43 (m, 2H), 4.28 (br s, 2H), 3.63 (q, J=4.6 Hz, 2H), 3.10-3.20 (m, 4H), 2.00-2.10 (m, 4H), 1.24-1.64 (m, 14H), 0.88 (t, J=7.3 Hz, 3H); $^{13}$C NMR (75 MHz) δ 158.67, 130.17, 129.88, 62.71, 40.59, 40.34, 32.52, 30.23, 30.0, 29.32, 27.09, 26.96, 25.99, 22.52, 14.25. HRMS calcd for $C_{16}H_{33}N_2O_2$ [M+1]$^+$ 285.2542. found 285.2545.

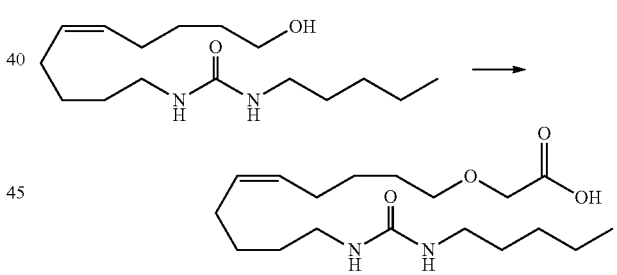

2-(10-(3-n-Pentylureido)dec-5(Z)-enyloxy)acetic acid (4)

A solution of 1-(10-hydroxydec-5(Z)-enyl)-3-n-pentylurea (66 mg, 0.23 mmol) and tetra-n-butylammonium sulfate (39 mg, 0.12 mmol) in benzene/50% aq. KOH (4 mL, 1:1) was stirred at 10° C. After 15 min, tert-butyl 2-bromoacetate (136 mg, 0.70 mmol) was added to the reaction mixture and stirred at the same temperature for an additional 1 h. The reaction mixture was then diluted with water (10 mL) and extracted into EtOAc (2×10 mL). The combined organic extracts were washed with water, brine and dried (Na$_2$SO$_4$) and concentrated in vacuo. The residue was dissolved in CH$_2$Cl$_2$ (4 mL), cooled to 0° C., and trifluoroacetic acid (1 mL) was added dropwise. The reaction mixture was diluted with more CH$_2$Cl$_2$ (5 mL), washed with water, brine and dried (Na$_2$SO$_4$). The residue was purified by SiO$_2$ column chromatography to give analog 4 (37 mg, 47%) as a sticky solid. TLC:EtOAc, $R_f$~0.30; $^1$H NMR (400 MHz) δ 5.30-5.42 (m, 2H), 4.06 (s, 2H), 3.54 (t, J=6.6 Hz, 2H), 3.07-3.15 (m, 4H), 2.00-2.12 (m, 4H), 1.21-1.66 (m, 14H), 0.88 (t, J=7.3 Hz, 3H); $^{13}$C NMR (75 MHz) δ 174.32, 160.08, 130.33, 129.71, 71.60, 68.12, 41.11, 41.02, 29.68, 29.40, 29.17, 28.96, 27.20, 27.07, 26.64, 25.96, 22.55, 14.20. HRMS calcd for $C_{18}H_{35}N_2O_4$ [M+1]$^+$ 343.2597, found 343.2594.

Example 2

Synthesis of Sodium (S)-2-(13-(3-pentylureido) tridec-8(Z)-enamido)succinate (NIH-F=EET A or JLJ)

Figure 16A:
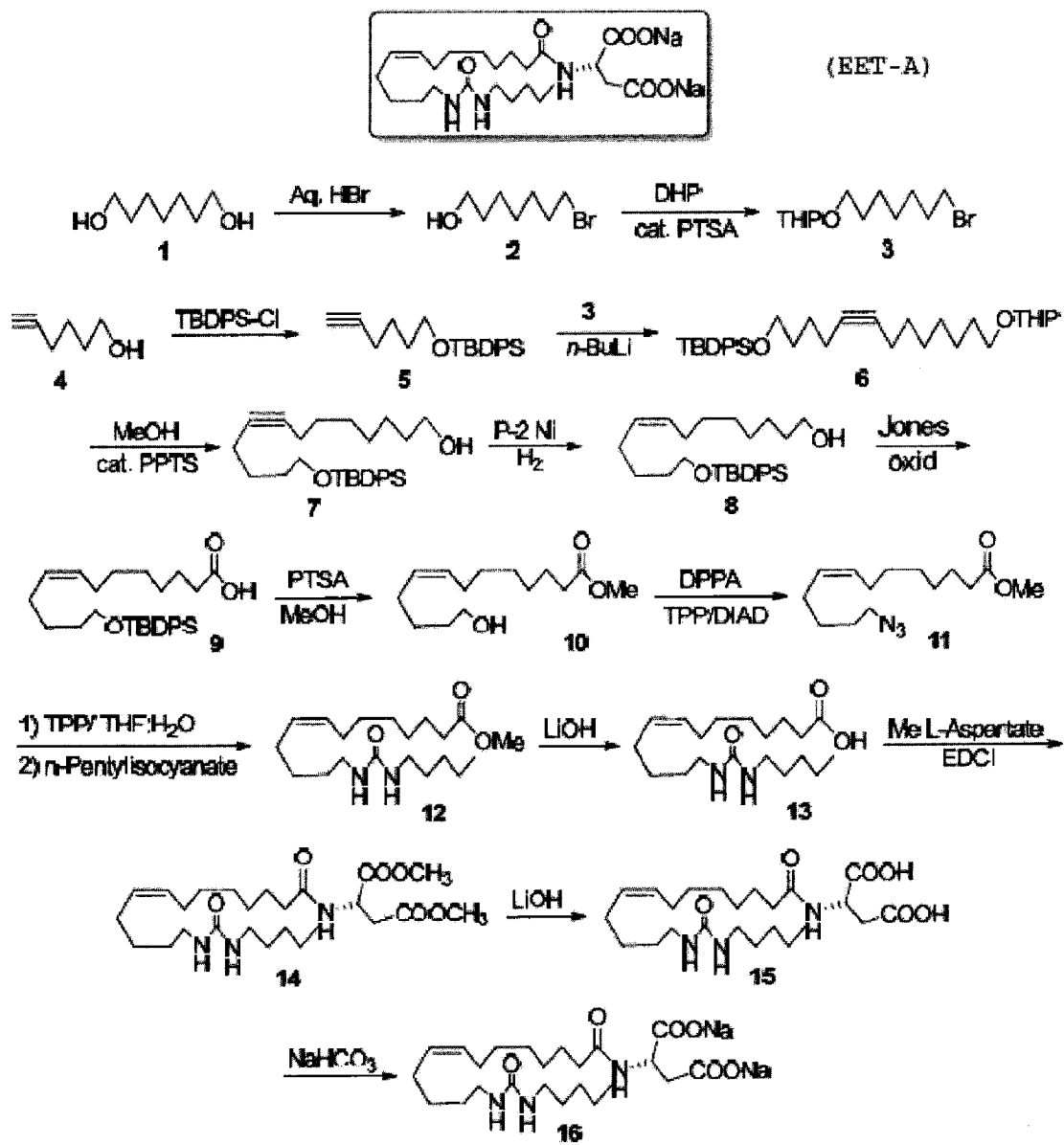
FIG. 16A shows the synthesis of EET-A.
Figure 16B:
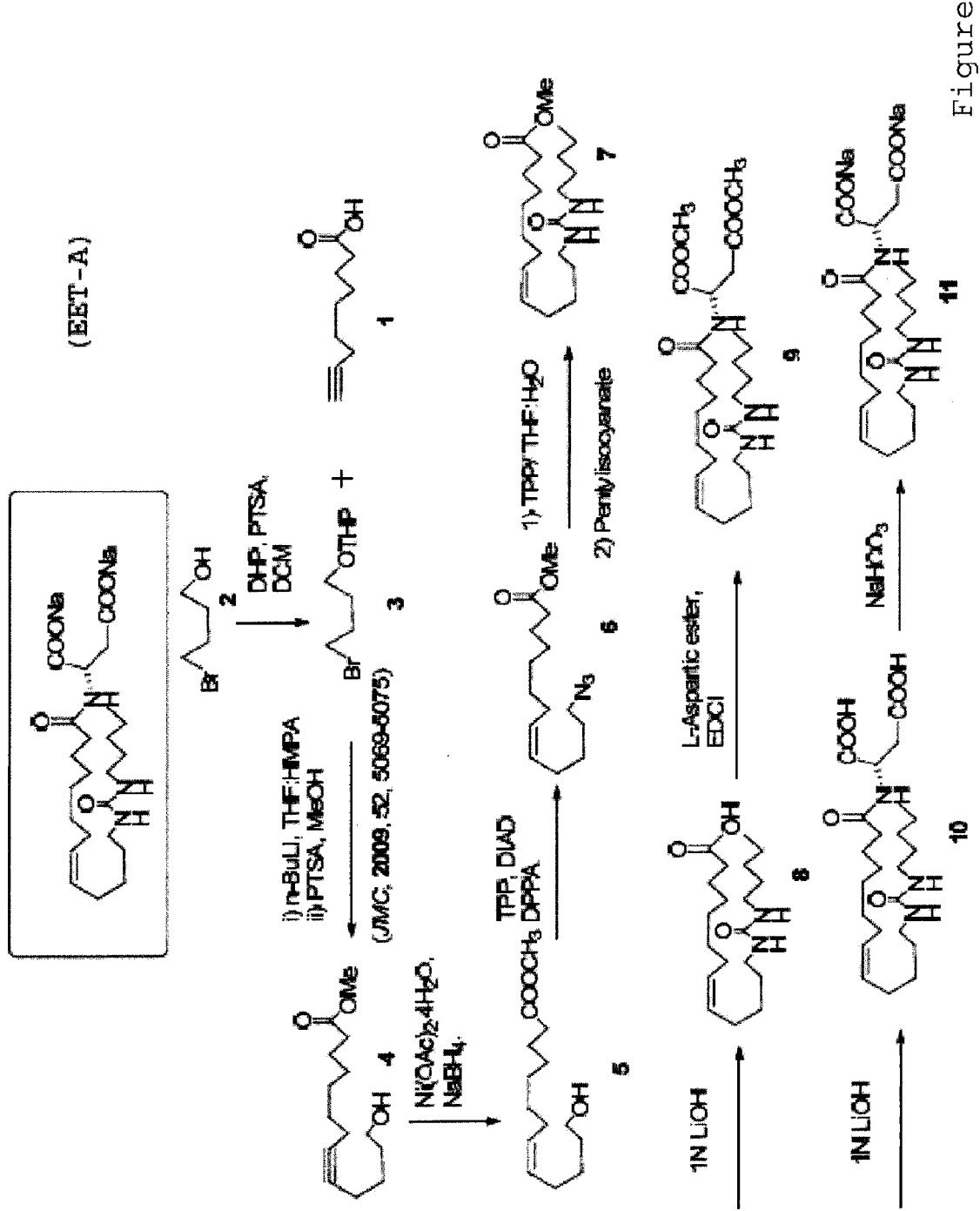
FIG. 16B shows the alternate synthesis of EET-A.

As set forth in FIGS. 16A and 16B, the synthesis of EET A is as follows:

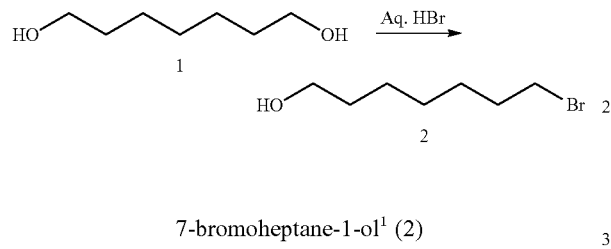

7-bromoheptane-1-ol$^1$ (2)

Heptane-1,7-diol (36.0 g, 272 mmol; Alfa Aesar) and aq. 48% HBr (38 mL, 0.9 equiv.) were heated under reflux in benzene (400 mL) with water removal using a Dean-Stark apparatus. After 16 h, all volatiles were removed in vacuo and the residue was purified by $SiO_2$ column chromatography using a gradient of 10-30% EtOAc/hexanes as eluent to give 7-bromoheptan-1-ol (26.22 g, 62%) as a colorless oil. TLC: 50% EtOAc/hexanes, $R_f$~0.40; $^1$H NMR (400 MHz, CDCl$_3$) δ 3.61 (t, 2H, J=7.1 Hz), 3.39 (t, 2H, J=6.8 Hz), 1.80-1.88 (m, 2H), 1.52-1.58 (m, 2H), 1.30-1.46 (m, 6H).

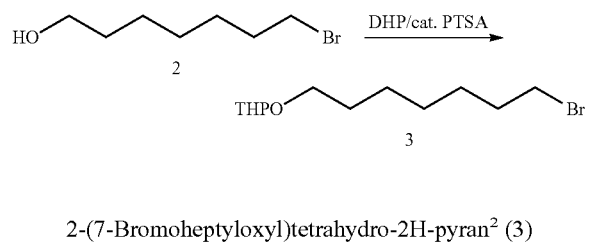

2-(7-Bromoheptyloxyl)tetrahydro-2H-pyran$^2$ (3)

Dihydropyran (5.20 g, 6.11 mmol) was added to a stirring 0° C. solution of 7-bromoheptane-1-ol (2) (11.0 g, 56.7 mmol) and a catalytic amount of PTSA in $CH_2Cl_2$. After stirring at rt for 12 h, the reaction mixture was diluted with $CH_2Cl_2$ (200 mL), washed with water (100 mL×2), brine (100 mL×3), dried over anhydrous sodium sulphate, and evaporated. The residue was purified by silica gel column chromatography using a gradient of 10-20% ethyl acetate/hexane as eluent to give 2-(7-bromoheptyloxyl)tetrahydro-2H-pyran (3) (14.50 g, 92%) as a colorless oil. TLC: 10% EtOAc/hexanes, $R_f$~0.55; $^1$H NMR (400 MHz, CDCl$_3$) δ 4.58-4.56 (m, 1H), 3.84-3.88 (m, 1H), 3.68-3.77 (m, 1H), 3.46-3.51 (m, 1H), 3.33-3.43 (m, 3H), 1.80-1.81 (m, 2H), 1.30-1.62 (m, 14H).

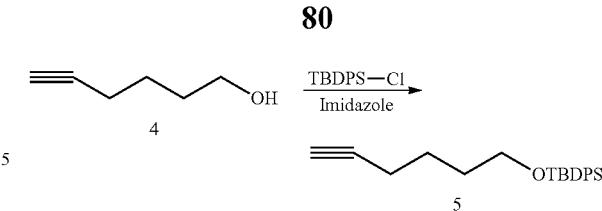

tert-Butyl(hex-5-yn-1-yloxy)diphenylsilane$^3$ (5)

tert-Butyldiphenylchlorosilane (3.2 mL, 12.4 mmol) was added dropwise to a stirring, 0° C. solution of 5-hexyn-1-ol (4, 1.07 g, 10.9 mmol) and anhydrous imidazole (1.84 g, 27.1 mmol) in anhydrous $CH_2Cl_2$ (20 mL) under an argon atmosphere. After complete addition, the reaction mixture was stirred at room temperature for 12 hours, then quenched with saturated aq. $NH_4Cl$ solution (50 mL) and extracted with $Et_2O$ (3×50 mL). The combined ethereal extracts were washed with saturated aq. NaCl solution (25 mL), dried over $NaSO_4$, and the solvent was removed in vacuo. The residue was purified by flash chromatography (5% ethyl acetate/ hexane) to yield 1-tert-butyldiphenylsilyloxy-hex-5-yne (5) (3.54 g, 10.5 mmol, 96%) as a colorless oil. TLC: 5% EtOAc/hexanes, $R_f$~0.65; $^1$H NMR (400 MHz, CDCl$_3$) δ 7.77-7.65 (m, 4H), 7.40-7.30 (m, 6H), 3.70 (t, 2H, J=5.6 Hz), 2.40-2.25 (m, 2H), 2.05 (t, 1H, J=2.8 Hz), 1.90-1.70 (m, 4H), 1.18 (s, 9H).

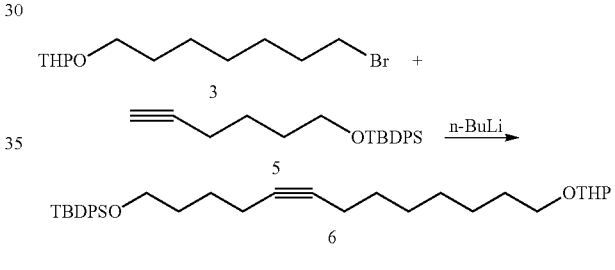

tert-Butyldiphenyl((tetrahydro-2H-pyran-2-yloxy) tridec-5-yn-1-yl)oxy)silane (6)

n-Butyllithium (14.3 mL, 35.9 mmol, 2.5 M solution in hexanes) was added dropwise to a −78° C. solution of tert-butyl(hex-5-ynyloxy)diphenylsilane (10 g, 29.76 mmol) in THF and dry HMPA (4:1, 200 mL) under an argon atmosphere. After 30 min, the reaction mixture was warmed to 0° C. over a period of 1 h and held there for 2 h. The reaction mixture was re-cooled −78° C. and a THF solution (50 mL) of bromide 3 (8.20 g, 29.3 mmol) was added. The reaction temperature was allowed to warm to rt over 3 h and was held at this temperature for 12 h before being quenched by adding saturated aq. $NH_4Cl$ solution (5 mL). The pH of the reaction mixture was adjusted to ~4 using 1 M oxalic acid and extracted with EtOAc (2×250 mL). The combined organic extracts were washed sequentially with water (2×100 mL) and brine (100 mL), the organic layer was dried using anhydrous $Na_2SO_4$ and concentrated under vacuo. Residue was purified by silica gel column chromatography using 10% EtOAc/hexanes to afford 6 (12.4 g, 78%) as a colorless thick oil. $^1$H NMR (CDCl$_3$, 400 MHz) δ 7.68-7.64 (m, 4H), 7.42-7.34 (m, 6H), 4.57 (t, J=4.3 Hz, 1H), 3.86-3.78 (m, 1H), 3.65 (t, J=6.3 Hz, 3H), 3.54-3.32 (m, 4H), 2.22-2.10 (m, 4H), 1.84-1.24 (m, 18H), 1.04 (s, 9H); $^{13}$C NMR (CDCl$_3$, 100 MHz) δ 135.82, 135.77, 134.25, 129.72, 127.85, 127.80, 127.77, 99.09, 99.05, 80.59, 80.22, 67.84, 67.74, 63.70, 62.58, 62.54, 31.00, 25.73, 19.92, 19.44, 18.97, 18.77.

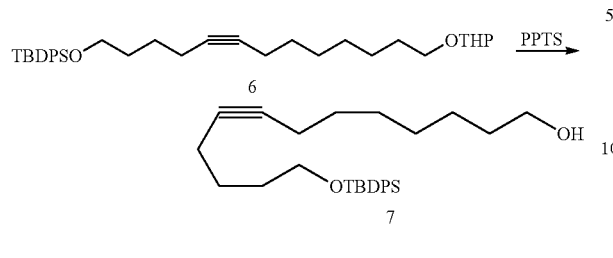

13-(tert-Butyldiphenylsilyloxy)tridec-8-yn-1-ol (7)

A solution of 6 (15.0 g, 0.59 mmol) and a catalytic amount of PPTS (10 mg) in MeOH (20 mL) was stirred at 0° C. for 10 h, then quenched with saturated aq. NaHCO$_3$ solution. Most of the methanol was evaporated in vacuo. The residue was diluted with water (100 mL) and extracted with ethyl acetate (100 mL×3). The combined organic extracts were concentrated under reduced pressure and the residue was purified by silica gel column chromatography using 20-30% ethyl acetate/hexane as eluent to afford 7 as a colorless oil (8.80 g, 78.7%). TLC: 20% EtOAc/hexanes, R$_f$~0.36; $^1$H NMR (CDCl$_3$, 400 MHz) δ 7.68-7.65 (m, 4H), 7.41-7.35 (m, 6H), 3.66-3.62 (m, 4H), 2.10-1.95 (m, 4H), 1.64-1.50 (m, 2H), 1.48-1.20 (m, 10H), 1.04 (s, 9H); $^{13}$C NMR (CDCl$_3$, 100 MHz) δ 135.79, 135.77, 134.26, 129.73, 127.84, 127.83, 127.80, 127.78, 80.56, 80.28, 63.72, 63.22, 32.96, 31.90, 29.01, 25.78, 19.45, 18.95, 18.77.

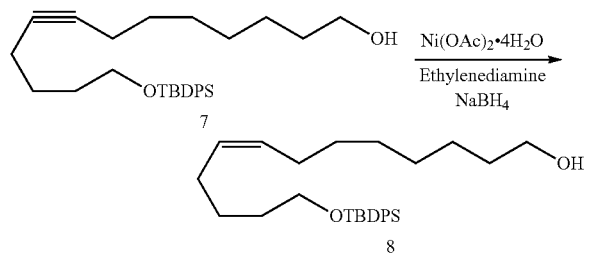

13-(tert-Butyldiphenylsilyloxy)tridec-8(Z)-en-1-ol (8)

In a two neck round bottom flask, NaBH$_4$ (176 mg, 4.65 mmol) was added in small portions to a solution of Ni(OAc)$_2$·4H$_2$O (1.16 g, 9.3 mmol) in absolute ethanol (10 mL) under a hydrogen atmosphere (1 atm). After 15 min, dry ethylenediamine (0.56 g, 9.3 mmol) was added followed after an additional 15 min by a solution of alcohol 7 (8.0 g, 18.7 mmol) in absolute ethanol (25 mL). The reduction was monitored by TLC until complete and then diluted with ether (50 mL), passed through a small pad of silica gel to remove inorganic impurities. The filtrate was concentrated under reduced pressure to afford 8 as a viscous, colorless oil (7.60 g, 95%). TLC: 50% EtOAc/hexane, R$_f$~0.42; $^1$H NMR (CDCl$_3$, 400 MHz) δ 7.68-7.65 (m, 4H), 7.41-7.35 (m, 6H), 5.40-5.30 (m, 2H), 3.58-3.65 m, 4H), 1.88-2.10 (m, 4H), 1.50-1.61 (m, 4H), 1.25-1.45 (m, 10H), 1.04 (s, 9H); $^{13}$C NMR (CDCl$_3$, 100 MHz) δ 135.83, 134.36, 130.30, 129.98, 129.77, 127.85, 64.09, 63.17, 32.48, 29.96, 29.53, 27.49, 27.37, 27.21, 27.16, 26.23, 26.01, 19.50.

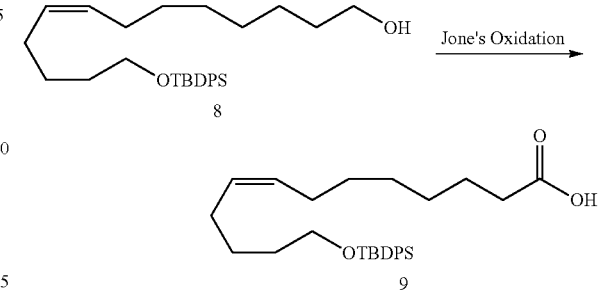

13-(tert-Butyldiphenylsilyloxy)tridec-8(Z)-enoic acid (9)

Jones reagent (5.8 mL of a 10 N solution in water) in acetone (25 mL) was added to a stirring, −40° C. solution of alcohol 8 (5.0 g, 11.8 mmol) in acetone (75 mL). After 1 h, the reaction mixture was warmed to −10° C. and maintained for another 2 h, then quenched with an excess (5.0 equiv) of isopropanol. The green chromium salts were removed by filtration and the filter cake was washed with acetone. The combined filtrates and washings were concentrated in vacuo and the resultant residue was dissolved in EtOAc (100 mL), washed with water (50 mL), dried over anhydrous sodium sulphate, and concentrated in vacuo. The residue was purified by SiO$_2$ column chromatography using 15% EtOAc/hexanes as eluent to give 9 (3.84 g, 74.20%) as a liquid. TLC: 40% EtOAc/hexanes, R$_f$~0.40. $^1$H NMR (CDCl$_3$, 400 MHz) δ 7.68-7.64 (m, 4H), 7.43-7.34 (m, 6H), 5.40-5.26 (m, 2H), 3.66 (t, J=6.6 Hz, 2H), 2.35 (t, J=7.3 Hz, 2H), 2.10-1.90 (m, 4H) 1.64-1.50 (m, 2H), 1.48-1.20 (m, 10H), 1.04 (s, 9H); $^{13}$C NMR (CDCl$_3$, 100 MHz) δ 180.62, 135.81, 134.34, 130.10, 130.07, 129.73, 127.82, 127.80, 127.79, 64.06, 32.44, 29.12, 27.38, 27.18, 27.12, 26.19, 24.87, 19.47.

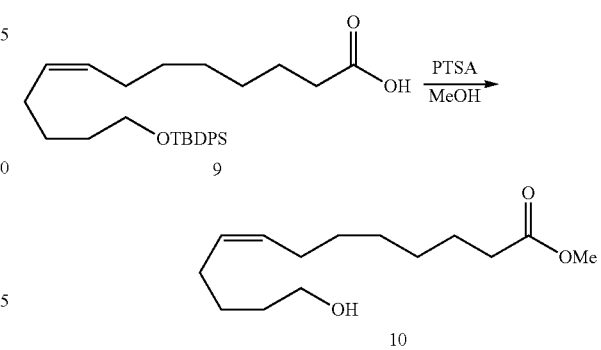

Methyl 13-hydroxytridec-8(Z)-enoate[4] (10)

A solution of 9 (7.60 g, 3.49 mmol) and p-toluenesulphonic acid (50 mg; PTSA) in MeOH (50 mL) was stirred at room temperature for 4 h, and then concentrated in vacuo. The residue was purified by SiO$_2$ column chromatography using 25% EtOAc/hexanes as eluent to give 10 (3.41 g, 87%) as a colorless oil. TLC: 40% EtOAc/hexanes, R$_f$~0.35;

¹H NMR (CDCl₃, 400 MHz) δ 5.40-5.36 (m, 2H), 3.60-3.66 (m, 5H), 2.30 (t, J=7.3 Hz, 2H), 2.10-1.90 (m, 4H) 1.64-1.50 (m, 2H), 1.48-1.20 (m, 10H).

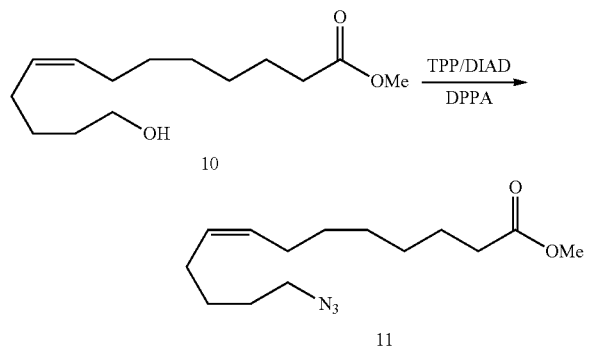

Methyl 13-azidotridec-8(Z)-enoate⁵ (11)

Diisopropyl azodicaboxylate (DIAD; 3.0 g, 14.8 mmol) was added dropwise to a −20° C. solution of triphenylphosphine (3.9 g, 14.8 mmol) in dry THF (100 mL) under an argon atmosphere. After stirring for 10 min, a solution of 10 (3.0 g, 4.75 mmol) in anhydrous THF (5 mL) was added dropwise. After 30 min at −20° C., the reaction mixture was warmed to 0° C. and diphenylphosphorylazide (DPPA, 4.0 g, 14.5 mmol) was added dropwise. After stirring at room temperature for 6 h, the reaction was quenched with water (3 mL), diluted with ether (100 mL), and washed with brine (40 mL). The aqueous layer was back-extracted with ether (2×150 mL). The combined organic extracts were dried over Na₂SO₄ and concentrated under reduced pressure. The residue was purified by SiO₂ column chromatography using 5% EtOAc/hexanes as eluent to afford 11 (2.72 g, 82%) as light yellow oil. TLC: 10% EtOAc/hexanes, R_f~0.45; ¹H NMR (CDCl₃, 400 MHz) δ 5.40-5.34 (m, 2H), 3.64 (s, 3H), 3.26 (t, J=6.7 Hz, 2H), 2.30 (t, J=7.7 Hz, 2H) 2.10-1.98 (m, 4H) 1.66-1.54 (m, 2H), 1.48-1.24 (m, 10H).

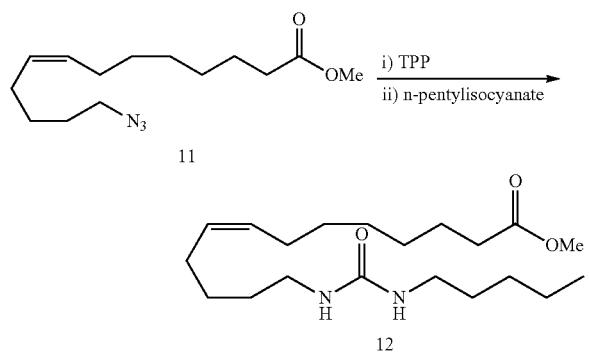

Methyl 13-(3-pentylureido)tridec-8(Z)-enoate⁶ (12)

Triphenylphosphine (2.7 g., 11.0 mmol) was added to a room temperature solution of 11 (1.4 g, 5.24 mmol) in dry THF (25 mL). After 2 h, water (200 μL) was added and the stirring was continued for another 8 h. The reaction mixture was then diluted with EtOAc (100 mL), washed with water (20 mL) and brine (25 mL). Aqueous layers were back-extracted with EtOAc (2×30 mL). The combined organic extracts were dried over Na₂SO₄, concentrated under reduced pressure and further dried under high vacuum for 4 h. The crude amine was used in the next step without additional purification. Procedure ref.: S. Chandrasekhar; S. S. Sultana; N. Kiranmai; Ch. Narsihmulu *Tetrahedron Lett.* 2007: 48, 2373.

n-Pentyl isocyanate (0.78 g, 6.9 mmol) was added to a room temperature solution of the above crude amine (1.4 g, 5.8 mmol) in dry THF (25 mL). After 6 h, reaction mixture was concentrated under reduced pressure and the residue was purified by SiO₂ column chromatography using 30% EtOAc/hexanes as eluent to give 12 (1.70 g, 85%) as a colorless, viscous oil. TLC: 50% EtOAc/hexanes, R_f~0.40; ¹H NMR (CDCl₃, 400 MHz) δ 5.40-5.26 (m, 2H), 4.46-4.32 (m, NH, 2H), 3.66 (s, 3H), 3.18-3.10 (m, 4H), 2.34 (t, J=7.7 Hz 4H), 2.06-1.94 (m, 4H), 1.66-1.56 (m, 2H), 1.54-1.42 (m, 14H), 0.88 (t, J=7.0 Hz, 3H).

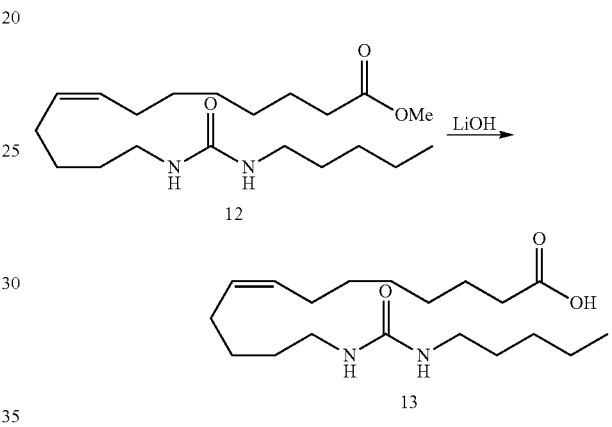

Methyl 13-(3-pentylureido)tridec-8(Z)-enoic acid (13)

LiOH (6.2 mL, 2.0 M aqueous solution, 3.0 equiv) was added to a 0° C. solution of 12 (1.80 g, 5.8 mmol) in THF (25 mL) and deionized H₂O (4 mL). After stirring at room temperature overnight, the reaction mixture was cooled to 0° C., the pH was adjusted to 4.0 with 1 M aq. oxalic acid, and extracted with ethyl acetate (2×20 mL). The combined extracts were washed with water (30 mL), brine (25 mL), dried over anhydrous Na₂SO₄, and concentrated in vacuo. The residue was purified by SiO₂ column chromatography using 25% EtOAc/hexanes as eluent to give 13 (1.48 g, 86%) as white solid, m.p.=67.1° C. TLC: 80% EtOAc/hexanes, R_f~0.30; ¹H NMR (CDCl₃, 400 MHz) δ 5.40-5.26 (m, 2H), 3.17-3.10 (m, 4H), 2.32 (t, J=6.7 Hz, 2H), 2.09-1.95 (m, 4H), 1.65-1.48 (m, 6H), 1.44-1.22 (m, 12H), 0.89 (t, J=7.1 Hz, 3H); ¹³C NMR (CDCl₃, 75 MHz) δ 178.5, 159.6, 130.5, 129.5, 40.9, 40.8, 34.4, 29.9, 29.8, 29.2, 28.7, 28.5, 27.2, 26.7, 24.9, 22.6, 14.2.

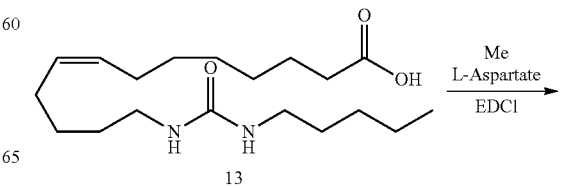

-continued

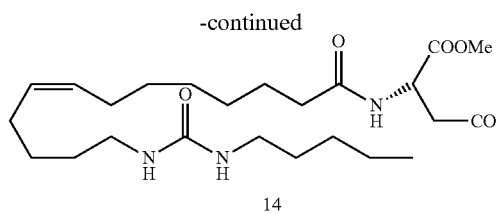

14

(S)-2-(13-(3-Pentylureido)tridec-8(Z)-enamido)succinate (14)

L-Aspartic acid dimethyl ester (38 mg, 0.191 mmol) and HATU (67 mg, 0.176 mmol) were added to a stirring solution of 13 (50 mg, 0.147 mmol) and DIPEA (74 mg, 0.573 mmol) in anhydrous DMF (2 mL) under an argon atmosphere. After 5 min, 1-ethyl-3-(3-dimethylaminopropyl)carbodiimide (33.8 mg, 0.176 mmol; EDCI) was added as a solid. After stirring for 12 h at room temperature, the reaction mixture was diluted with EtOAc (15 mL), washed with water (5 mL), and brine (10 mL). The combined aqueous layers were back-extracted with EtOAc (3×10 mL). The combined organic extracts were dried over $Na_2SO_4$, concentrated under reduced pressure, and the residue was purified by $SiO_2$ column chromatography using 50% EtOAc/hexanes as eluent to give 14 (60 mg, 84%) as viscous oil. TLC: 60% EtOAc/hexanes, $R_f$-0.35; $^1$H NMR (CDCl$_3$, 400 MHz) δ 6.64 (d, J=7.9 Hz, 1H), 5.38-5.30 (m, 2H), 4.90-4.82 (m, 1H), 4.58-4.44 (m, 2H), 3.75 (s, 3H), 3.66 (s, 3H), 3.20-3.10 (m, 4H), 3.04 (dd, $J_1$=4.3 Hz, $J_2$=13.1 Hz, 1H), 2.84 (dd, $J_1$=4.6 Hz, $J_2$=12.8 Hz, 1H), 2.22 (t, J=6.3 Hz, 2H), 2.05-1.98 (m, 4H), 1.70-1.60 (m, 2H), 1.50-1.20 (m, 16H), 0.88 (t, J=6.7 Hz, 3H).

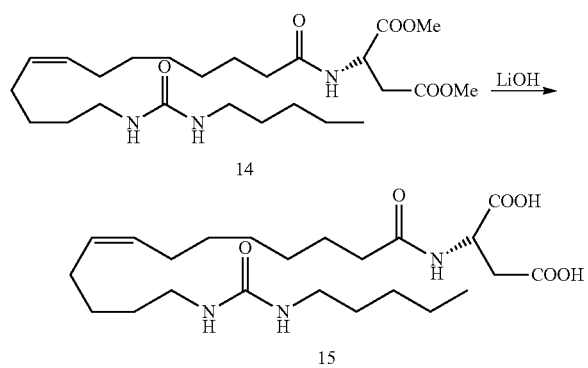

(S)-2-(13-(3-pentylureido)tridec-8(Z)-enamido)succinic acid (15)

An aqueous solution of LiOH (2 mL, 2 M solution, 6.0 equiv) was added to a 0° C. solution of 14 (60 mg, 0.124 mmol) in THF (8 mL) and deionized H$_2$O (2 mL). After stirring at room temperature overnight, the reaction mixture was cooled to 0° C., the pH was adjusted to 4.0 with 1 M aq. oxalic acid, and extracted with ethyl acetate (2×10 mL). The combined extracts were washed with water (5 mL), brine (5 mL), dried over anhydrous Na$_2$SO$_4$, and concentrated in vacuo. The residue was purified by SiO$_2$ column chromatography using 70-90% EtOAc/hexanes as eluent to give 15 (48 mg, 85%) as a viscous, colorless oil. TLC: 5% MeOH/EtOAc, $R_f$-0.20; $^1$H NMR (CD$_3$OD, 400 MHz) δ 5.38-5.30 (m, 2H), 4.72 (t, J=4.3 Hz, 1H), 3.12-3.05 (m, 4H), 2.90-2.72 (m, 2H), 2.22 (t, J=7.7 Hz, 2H), 2.10-1.98 (m, 4H), 1.60-1.22 (m, 18H), 1.20 (t, J=7.1 Hz, 3H); $^{13}$C NMR (CDCl$_3$, 75 MHz) δ 174.9, 173.0, 172.8, 160.1, 129.9, 129.3, 51.8, 49.8, 39.8, 39.7, 35.7, 35.6, 29.9, 29.8, 29.5, 29.0, 28.8, 26.9, 26.7, 25.7, 22.3, 13.2.

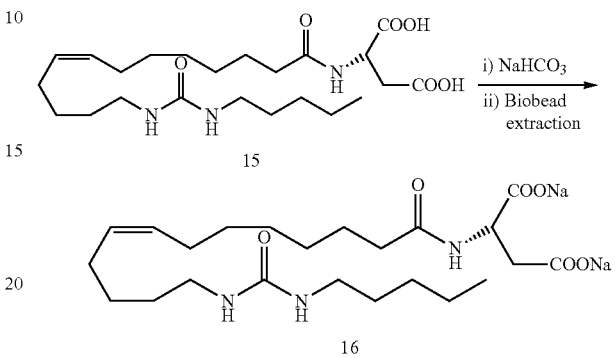

Disodium (S)-2-(13-(3-pentylureido)tridec-8(Z)-enamido)succinate (16)

Sodium bicarbonate (93 mg, 1.1 mmol) was added to a stirring solution of 15 (100 mg, 0.22 mmol) in THF/H$_2$O (4:1, 5 mL) at rt. After 2 h, the THF was removed in vacuo and the remaining aqueous phase was stirred with SM-2 Bio-Beads (Bio-Rad, 20-50 mesh; 2 g). After 1 h, the Bio-Beads were collected by filtration on a sintered-glass funnel, washed with water (5 mL×2) and finally with 95% ethanol (20 mL×3). Evaporation of the ethanol washes in vacuo gave 16 (72 mg, 84%) as a white solid, m.p.=258.5° C. TLC: 10% MeOH/CH$_2$Cl$_2$, $R_f$-0.15; $^1$H NMR (CD$_3$OD, 500 MHz) δ 5.25-5.23 (m, 2H), 4.40 (t, 1H, J=4.0), 3.01-2.97 (m, 4H), 2.58-2.56 (m, 2H), 2.13 (t, 2H, J=7.0), 1.96-1.94 (m, 4H), 1.51-1.47 (m, 2H), 1.30-1.19 (m, 16H), 0.83 (t, 3H, J=7.0); $^{13}$C NMR (75 MHz, CDCl$_3$) δ 178.52, 178.38, 173.99, 160.21, 129.93, 129.37, 52.66, 39.81, 39.74, 36.27, 29.50, 28.93, 26.76, 22.34, 13.26.

Example 3

Synthesis of N-Isopropyl-N-(5-(2-pivalamidobenzo[d]thiazol-4-yloxy)pentyl)heptanamide (MV=EET-B or SRD-2)

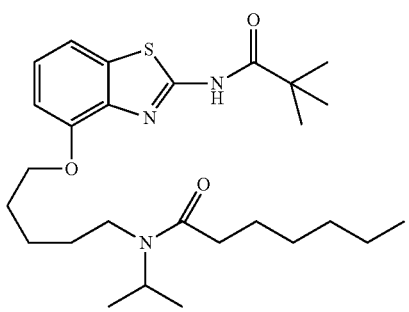

As set forth in FIG. 15, the synthesis of EET B is as follows:

5-(tert-Butyldiphenylsilyloxy)pentan-1-ol (2)

Imidazole (0.65 g, 9.60 mmol) was added to a stirring solution of pentan-1,5-diol (1.00 g, 9.60 mmol) in dry dichloromethane (10 mL) at 0° C. under an argon atmosphere followed by the dropwise addition of tert-butylchlorodiphenylsilane (3.85 mL, 9.60 mmol) in $CH_2Cl_2$ (2 mL). The reaction was allowed to slowly reach room temperature. After 12 hours, the reaction mixture was washed with water (2×30 mL), brine (20 mL), dried over $Na_2SO_4$, and concentrated under reduced pressure. The residue which was purified by $SiO_2$ flash chromatography using 30% ethyl acetate/hexane as eluent to furnish 2 (1.35 g, 46%), recovered SM and di-protected compound. TLC: 30% EtOAc/hexanes, $R_f$-0.38; $^1$H NMR ($CDCl_3$, 400 MHz) δ 7.67-7.62 (m, 4H), 7.45-7.35 (m, 6H), 3.67 (t, 2H, J=6.0 Hz), 3.52 (t, 2H, J=6.7 Hz), 2.03-1.93 (m, 2H), 1.72-1.64 (m, 4H), 1.04 (s, 9H).

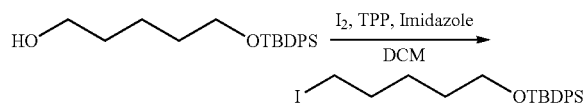

tert-Butyl(5-iodopentyloxy)diphenylsilane (3)

Imidazole (310 mg, 4.40 mmol), iodine (440 mg, 3.5 mmol), and a solution of 2 (1 g, 2.98 mmol) in $CH_2Cl_2$ (2 mL) were added sequentially to a 0° C. solution of $PPh_3$ (450 mg, 3.5 mmol) in $CH_2Cl_2$ (15 mL) and kept in the dark. After 2 h, the reaction mixture was quenched by adding 20% aq. $Na_2S_2O_3$ (5 mL). The aqueous layer was extracted with $CH_2Cl_2$ (2×50 mL). The combined organic extracts were washed with brine (30 mL), dried over anhydrous $Na_2SO_4$, and the solvent was removed in vacuo. The residue was purified by careful column chromatography using 5% EtOAC/hexane to afford iodide 3 (1.25 mg, 92%). TLC: 10% EtOAc/hexane, $R_f$-0.85; $^1$H NMR ($CDCl_3$, 400 MHz) δ 7.67-7.62 (m, 4H), 7.45-7.35 (m, 6H), 3.67 (t, 2H, J=6.0 Hz), 3.41 (t, 2H, J=6.7 Hz), 2.03-1.93 (m, 2H), 1.72-1.64 (m, 4H), 1.04 (s, 9H).

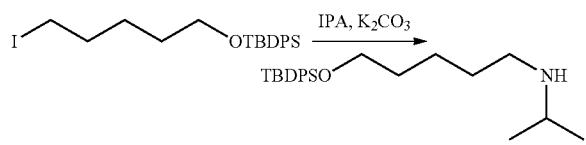

5-(tert-Butyldiphenylsilyloxy)-N-isopropylpentan-1-amine (4)

$K_2CO_3$ (1.50 g, 11.05 mmol), isopropylamine (0.65 mL, 11.05 mmol) and iodide 3 (2.50 g, 5.83 mmol) in dry THF (15 mL) were heated at 66° C. in a sealed tube under an argon atmosphere. After 12 h, water (5 mL) was added to the reaction mixture which was then extracted with EtOAc (3×50 mL). The combined organic extracts were dried over $MgSO_4$ and concentrated under reduced pressure to afford 4 as a colorless liquid (1.90 g, 92%) sufficiently pure it was used without further purification. TLC:MeOH/$CH_2Cl_2$ (1:4), $R_f$-0.30; $^1$H NMR (400 MHz) δ 7.65-7.67 (m, 4H), 7.30-7.40 (m, 6H), 3.65 (t, J=6.4 Hz, 2H), 2.70-2.82 (m, 1H), 2.55 (t, J=7.3 Hz, 2H), 1.50-1.64 (m, 2H), 1.32-1.50 (m, 4H), 1.05 (d, J=5.8 Hz, 3H), 1.04 (s, 9H); $^{13}$C NMR (100 MHz) δ 135.68, 134.21, 129.63, 127.70, 63.95, 48.81, 47.64, 32.60, 30.27, 27.0, 23.76, 23.15, 19.34.

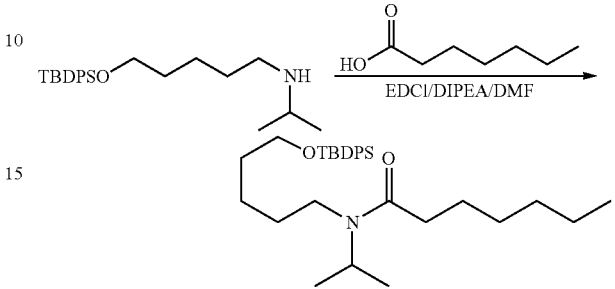

N-(5-(tert-Butyldiphenylsilyloxy)pentyl)-N-isopropylheptanamide (5)

Heptanoic acid (2.06 g, 15.86 mmol), and diisopropylethylamine (2.72 mL, 21.14 mmol; DIPEA) were added to a stirring solution of the amine 4 (4.00 g, 10.57 mmol) in anhydrous DMF (20 mL) under an argon atmosphere. After 5 min, 1-ethyl-3-(3-dimethylaminopropyl)carbodiimide (3.04 g, 15.86 mmol; EDCI) was added as a solid. After stirring for 12 h at room temperature, the reaction mixture was diluted with EtOAc (100 mL), washed with water (2×30 mL), and brine (20 mL). The combined aqueous layers were back-extracted with EtOAc (3×30 mL). The combined organic extracts were dried over $Na_2SO_4$, concentrated under reduced pressure, and the residue was purified by $SiO_2$ column chromatography using 30% EtOAc/hexanes as eluent to give amide 5 (4.75 g, 91%) as a viscous oil. TLC: EtOAc/hexanes (3:7), $R_f$-0.60; $^1$H NMR (400 MHz, 1:1 mixture of rotamers) δ 7.65-7.67 (m, 4H), 7.30-7.40 (m, 6H), 4.62-4.72 and 3.96-4.80 (m, 1H, rotamers), 3.62 and 3.68 (t, J=4.8 Hz, 2H, rotamers), 3.02 and 3.16 (t, J=5.2 Hz, 2H, rotamers), 2.38 and 2.24 (t, J=5.3 Hz, 2H, rotamers), 1.50-1.68 (m, 6H), 1.26-1.44 (m, 8H), 1.18 and 1,12, (d, J=7.3 Hz, 6H, rotamers), 1.03 and 1.04 (s, 9H, rotamers), 0.88 (t, J=7.3 Hz, 3H); $^{13}$C NMR (100 MHz, 1:1 mixture of rotamers) δ 173.38, 172.76, 135.80, 135.78, 134.36, 134.12, 129.85, 129.73, 127.88, 127.82, 64.22, 63.68, 48.43, 45.62, 43.64, 41.27, 34.13, 34.05, 32.61, 32.36, 31.96, 31.93, 31.51, 29.63, 29.47, 27.10, 27.03, 25.94, 25.78, 24.03, 23.77, 22.81, 21.63, 20.78, 19.47, 14.33, 14.28.

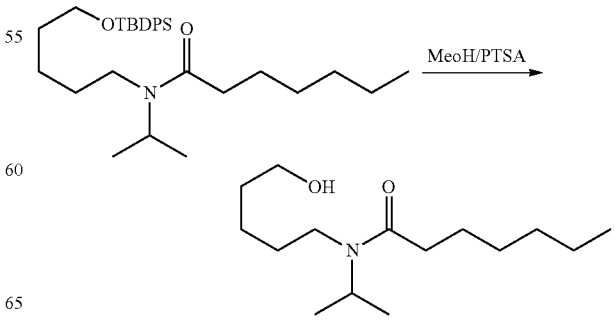

N-(5-hydroxypentyl)-N-isopropylheptanamide (6)

A solution of 5 (4.75 g, 9.02 mmol) and p-toluenesulfonic acid in MeOH (50 mL) was stirred at rt for 12 h, then quenched with solid NaHCO$_3$ and filtered. The filtrate was evaporated under vacuum and the residue was dissolved in ethyl acetate (50 mL). The ethyl acetate layer was washed with water (2×50 mL), brine (50 mL), dried over anhydrous Na$_2$SO$_4$ and concentrated under reduced pressure. The residue was purified by silica gel flash column chromatography using 50-60% ethyl acetate/hexane as eluent to afford alcohol 6 (2.35 g, 93%) as a colorless, viscous liquid. TLC: EtOAc/hexanes (1:1), R$_f$-0.30; $^1$H NMR (400 MHz, 55/45 mixture of rotamers) δ 4.58-4.66 and 3.96-4.08 (m, 1H, rotamers), 3.56 and 3.70 (t, J=5.4 Hz, 2H, rotamers), 3.02 and 3.16 (t, J=5.2 Hz, 2H, rotamers), 2.38 and 2.26 (t, J=6.3 Hz, 2H, rotamers), 1.50-1.64 (m, 6H), 1.22-1.40 (m, 8H), 1.13 and 1.09 (d, J=7.5 Hz, 6H, rotamers), 0.84 (t, J=7.3 Hz, 3H); $^{13}$C NMR (100 MHz, 55/45 mixture of rotamers) δ 172.81, 62.66, 62.60, 48.41, 45.55, 43.56, 41.04, 34.08, 34.0, 32.46, 32.43, 31.86, 31.57, 29.40, 25.87, 25.70, 23.77, 23.73, 22.75, 21.57, 20.72, 14.26.

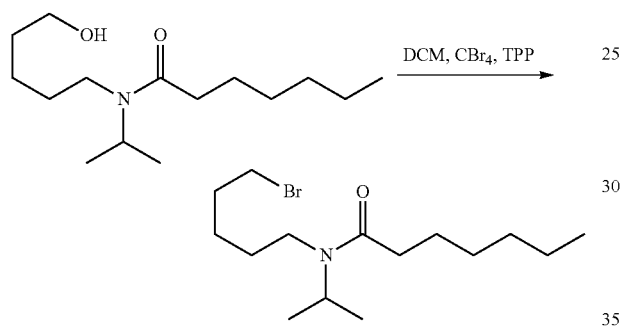

N-(5-Bromopentyl)-N-isopropylheptanamide (7)

TPP (4.45 g, 9.34 mmol) was added to a 0° C. solution of alcohol 6 (2.00 g, 7.78 mmol) in dry CH$_2$Cl$_2$ (50 mL). After 10 min, CBr$_4$ (3.10 g, 9.34 mmol) was added and the stirring was continued at 0° C. After 2 h, water (20 mL) was added and the reaction mixture was extracted with EtOAc (3×50 mL). The combined extracts were washed with water (2×20 mL), brine (20 mL), dried over Na$_2$SO$_4$, and concentrated under reduced pressure. The residue was purified by SiO$_2$ column chromatography using 30-35% ethyl acetate/hexane to afford 7 (2.20 g, 91%). TLC:EtOAc/hexanes (3:7), R$_f$-0.40; $^1$H NMR (400 MHz, 45/55 mixture of rotamers) δ 4.60-4.70 and 3.96-4.10 (m, 1H, rotamers), 3.46 and 3.36 (t, J=5.8 Hz, rotamers), 3.02-3.10 (m, 2H), 2.30 and 2.22 (t, J=7.9 Hz, 2H), 1.80-1.97 (m, 2H), 1.40-1.70 (m, 6H), 1.20-1.40 (m, 6H), 1.16 and 1.10, (d, J=7.3 Hz, 6H, rotamers), 0.86 (t, J=7.3 Hz, 3H); $^{13}$C NMR (100 MHz, rotamers) δ 172.79, 172.39, 48.17, 45.47, 43.32, 40.70, 33.89, 33.87, 33.49, 32.48, 32.30, 31.81, 31.78, 30.78, 29.27, 28.74, 26.05, 25.84, 25.69, 25.54, 22.64, 21.47, 20.62, 14.17.

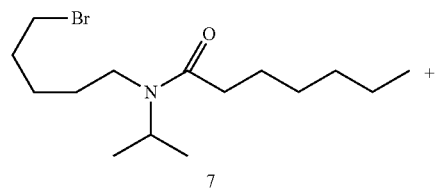

7

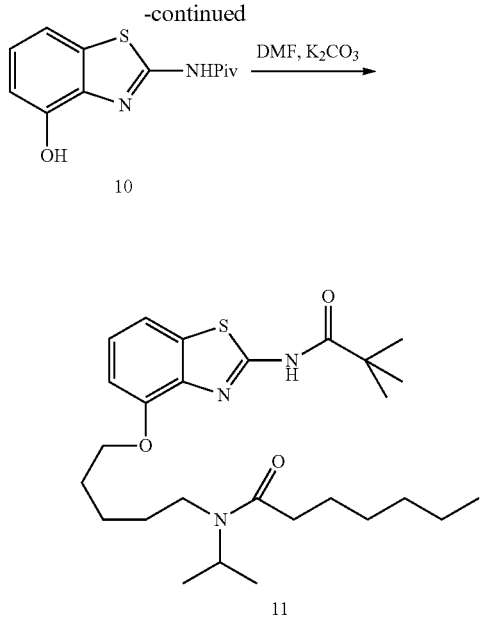

Isopropyl-N-(5-(2-pivalamidobenzo[d]thiazol-4-yloxy)pentyl)heptanamide (11)

A solution of bromide 7 (0.35 g, 1.09 mmol), N-(4-hydroxybenzo[d]thiazol-2-yl)pivalamide (10) (0.27 g, 1.09 mmol), and K$_2$CO$_3$ (0.30 g, 2.18 mmol) in DMF (10 mL) was heated at 80° C. After 4 h, the reaction mixture was cooled to rt, water (5 mL) was added and the mixture was extracted using ethyl acetate (3×30 mL). The combined organic extracts were washed with H$_2$O (2×20 mL), brine (20 mL), dried over Na$_2$SO$_4$, and filtered. The filtrate was evaporated under reduced pressure and the residue was purified by silica gel column chromatography (50-70% EtOAc/hexanes) to give 11 (0.39 g, 72%) as a viscous liquid. TLC:EtOAc/hexanes (7:3), R$_f$0.26; $^1$H NMR (400 MHz, 45/55 mixture of rotamers) δ 7.24 and 7.20 (d, J=7.4 Hz, 1H, rotamers), 7.16 and 7.14 (dd, J=7.4 Hz, J=7.4 Hz, 1H, rotamers), 6.90 and 6.80 (d, J=7.4 Hz, 1H, rotamers), 4.58-4.78 and 3.96-4.10 (m, 1H, rotamers), 4.02 (t, J=6.3 Hz, 2H), 3.12 (t, J=7.3 Hz, 2H), 2.30 and 2.27 (t, J=5.6 Hz, 2H, rotamers), 1.82-1.92 (m, 2H), 1.44-1.70 (m, 4H), 1.38-1.32 (m, 8H), 1.20 (d, J=6.4 Hz, 3H), 1.13 (d, J=6.4 Hz, 3H), 1.11 (d, J=6.4 Hz, 3H), 0.88-085 (m, 6H); $^{13}$C NMR (100 MHz, 45/55 mixture of rotamers) δ 189.64, 189.62, 173.04, 172.57, 172.55, 167.16, 167.09, 167.06, 146.85, 146.77, 146.67, 128.90, 128.87, 125.90, 125.79, 124.24, 124.13, 115.32, 115.06, 111.00, 110.09, 110.05, 68.97, 68.74, 58.50, 48.34, 45.62, 41.24, 41.10, 40.95, 34.10, 29.52, 29.15, 25.72, 24.28, 21.66, 20.76, 14.30.

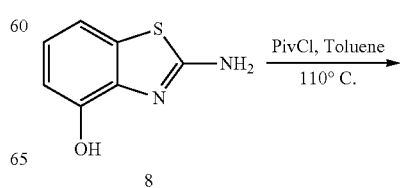

8

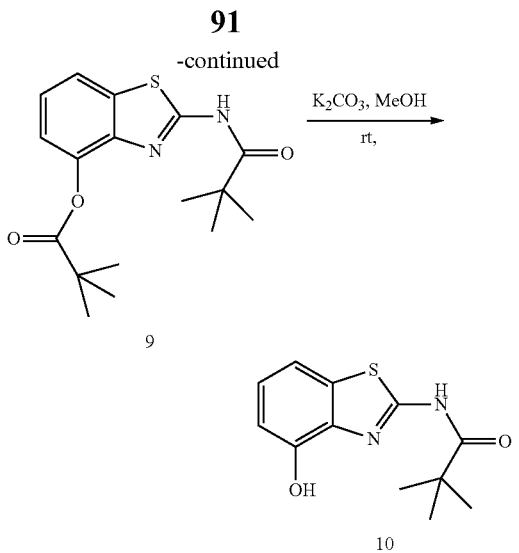

N-(4-hydroxybenzo[d]thiazol-2-yl)pivalamide (10)

To a suspension of 2-aminobenzo[d]thiazol-4-ol (0.50 g, 3.01 mmol) in toluene (10 mL) was added trimethyacetyl chloride (3.60 mL, 30.10 mmol) at room temperature. The reaction mixture was stirred at 115° C. for 22 h. The solvents were evaporated and the residue was azeotroped with EtOAc to give 9 (0.78 g, 78%) as a tan solid. The suspension of the above solid (0.78 g) in MeOH (15 mL) was treated with $K_2CO_3$ (0.20 g, 3.50 mmol) and stirred at room temperature for 6 h. MeOH was evaporated and the residue was diluted with $H_2O$. The resulting mixture was neutralized with concd HCl to pH=7 and extracted with EtOAc (3×30 mL). The combined organic phases were dried over sodium sulfate, filtered, and concentrated in vacuo to provide 10 (0.48 g, 82%) s a tan solid. TLC:EtOAc/hexanes (7:3), $R_f$~0.32; $^1$H NMR (400 MHz, $CDCl_3$) δ 10.25 (br s, 1H), 9.66 (br s, 1H), 7.33 (d, J=7.4 Hz, 1H), 7.09 (dd, J=7.4, 7.4, Hz, 1H), 6.82 (d, J=7.4 Hz, 1H), 1.45 (s, 9H). $^{13}$C NMR (100 MHz, $CDCl_3$) δ 177.15, 159.12, 148.10, 136.55, 133.00, 125.55, 113.40, 111.50, 39.70, 27.38.

Example 4

In Vitro Screening of EET Analog Library

In this Example, the inventors performed both vascular relaxation assays and a soluble epoxide hydrolase inhibition assay using the newly synthesized compounds. The results of these assays are recorded in the last three columns of Table 1 above and FIG. 14. As a result of these assays, four compounds, compounds 26, 20, 7 and 30 were selected for further in vivo testing, as outlined in later Examples.

Soluble Epoxide Hydrolase Inhibition.

Compounds were tested for their ability to inhibit recombinant soluble epoxide hydrolase (sEH) protein. The assay utilizes (3-Phhenyl-oxiranyl)-acetic acid cyano-(6-methoxy-naphthalen-2-yl)-methyl ester (PHOME), a sensitive substrate for sEH that can be used to monitor the activity of both human and murine enzymes. Hydrolysis of the substrate epoxide yields a highly fluorescent product, 6-methoxy-2-Naphthaldehyde, which can be monitored at excitation and emission wavelengths of 330 and 465 nm, respectively. See Wolf et al., *Anal Biochem* 355:71-80, 2006 PMID: 16729954. Human recombinant sEH was incubated with substrate and compounds ranging in concentration from 0.1 to 1000 nM. The percent activity remaining at each concentration was plotted and an IC50 (concentration at which there is 50% inhibition) determined utilizing statistical software.

Vasodilator Activity.

Vasorelaxant activity was measured in bovine coronary artery. Bovine hearts were obtained and the left anterior descending coronary artery was dissected and cleaned of connective tissue. Vessels of 1 mm diameter were cut into rings of 3 mm width as previously described (3, 27, 39). Vessels were stored in Krebs buffer consisting of (in mM) 119 NaCl, 4.8 KCl, 24 $NaHCO_3$, 1.2 $KH_2PO_4$, 1.2 $MgSO_4$, 11 glucose, 0.02 EDTA, and 3.2 $CaCl_2$. The vessels were suspended from a pair of stainless steel hooks in a 6-ml water jacketed organ chamber. The organ chamber was filled with Krebs buffer and bubbled with 95% $O_2$-5% $CO_2$ at 37° C. One hook was anchored to a steel rod and the other hook to a force transducer (model FT-03C; Grass Instruments, West Warwick, R.I.). Tension of the vessel was measured by an ETH-400 bridge amplifier, and the data were acquired with a MacLab 8e analog-to-digital converter and MacLab software version 3.5.6 (AD Instruments, Milford, Mass.) and stored on a Macintosh computer for subsequent data analysis.

Basal tension was set at the length-tension maximum of 3.5 g and equilibrated for 1.5 h. KCl (40 mM) was added to the chamber until reproducible maximal contractions were maintained. U-46619 (10-20 nM), a thromboxane receptor agonist, was used to precontract the vessels from basal tension to between 50% and 90% of the maximal KCl contraction. Cumulative additions of compounds were added to the chamber. Between concentration-response curves, the chambers were rinsed with fresh Krebs buffer, 40 mM KCl was administered to determine the maximum contraction, and the vessels were rinsed. Consecutive concentration-response curves were performed with 14,15-EET followed by a concentration-response curve to a compound. The experiment was always repeated with the order of the agonists reversed. In control experiments with consecutive concentration-response curves to 14,15-EET, the second concentration-response curve with compound was identical to the first. Tension was represented as percent relaxation where 100% relaxation was basal pre-U-46619 tension. The relaxation was plotted versus compound concentration and the EC50 determined utilizing statistical software.

Results of Vasodilator and sEH Inhibitory Activity Assays.

The results of vasorelaxant and sEH inhibitory activities of the 33 synthesized compounds are summarized in Table 1. Using the pharmacophoric moiety of EET, a number of EET analogs were designed with improved solubility and resistance to auto-oxidation, etherification and metabolism by soluble epoxide hydrolase (sEH). It is observed that these compounds possess activity analogous to EET as evident from their vasorelaxant activity in bovine coronary artery and sEH inhibitory (sEHi) activity. Among these, four compounds among those that were designed by replacing COOH group of the EET pharmacophore with isosteric replacement or a heterocyclic surrogate were studied for potential antihypertensive effect. The results of vasorelaxant and sEH inhibitory activities of these compounds are summarized in Table 2 below.

TABLE 2

Characteristics of the compounds selected for testing in the in vivo models.

| Compound | Structure | Vascular relaxation | | SEHi activity |
| --- | --- | --- | --- | --- |
| | | % relaxation (10 µM) | EC$_{50}$ (µM) | IC$_{50}$ (nM) |
| SRD-I-71-9 | | 109 | .32 | >500 |
| LGK-I-119-15 | | 119 | 0.18 | 11 |
| JLJ-I-94-6 | | 91 | 1.6 | 392 |
| MV-IV-110-20 | | 96 | 1.3 | >500 |

Example 5

In Vitro Testing of Four Compounds Using Rat Models of Hypertension

Telemetry Blood Pressure Measurement.

To accurately detect changes in blood pressure and heart rate, telemetry transmitters (Data Sciences Inc., St. Paul, Minn.) were implanted in rats one week prior to the experimental period according to manufacturer's specifications while under pentobarbital anesthesia. In brief, an incision was made to expose the femoral artery that was occluded to allow insertion of the transmitter catheter. The catheter was secured in place with tissue glue and the transmitter body was sutured in place and the incision line was closed. Rats were allowed to recover from surgery and were returned to individual housing. A baseline arterial pressure was recorded for prior to the experimental period. Mean arterial pressure was continuously recorded throughout the experimental period.

Angiotensin Hypertension.

Telemetry transmitters were implanted into male Sprague-Dawley rats (225-275 g) as described. After recording basal blood pressure, osmotic pumps were implanted (s.c.) to deliver angiotensin at a dose of 60 ng/min. EET analogs were administered by an osmotic pump (2 mg/d, i.p.) and blood pressure was continuously monitored.

Spontaneously Hypertensive Rats (SHR).

Telemetry transmitters were implanted into male SHR as described. After the surgical recovery period, baseline mean arterial pressure was recorded. In this series of experiments, EET analogs were administered by osmotic pump (2 mg/d, i.p.) and blood pressure was continuously monitored.

Protein Excretion Measurements.

Animals were placed in a metabolic cage and urine was collected in a conical tube. Samples were stored at −80'C until assayed. Urinary protein excretion was assessed as an index for renal injury. Protein was determined by the Bradford colorimetric method and creatinine was determined by the picric acid colorimetric method.

Telemetry and urinary analysis methods are further outlined in the following publications: Imig J D, Zhao X, Zaharis C Z, Olearczyk J J, Pollock D M, Newman J W, Kim I H, Hammock B D. An orally active epoxide hydrolase inhibitor lowers blood pressure and provides renal protection in salt-sensitive hypertension. *Hypertension* 46:975-981, 2005. PMID: 1615779; Elmarakby A A, Quigley J E, Olearczyk J J, Srindhar A, Cook A K, Inscho E W, Pollock D M, Imig J D. Chemokine receptor 2b blockade inhibition provides renal protection in angiotensin II-salt hypertension. *Hypertension* 50:1069-1076, 2007. PMID: 17938380; and Olearczyk J J, Quigley J E, Mitchell B, Yamamoto T, Kim I H, Newman J W, Lauria A, Hammock B D, Imig J D. Inhibition of the soluble epoxide hydrolase protects the kidney from damage in hypertensive Goto-Kakizaki rats. *Clinical Science* 116:61-70, 2009. PMID: 18459944. These publications are incorporated by reference herein.

Statistical Analysis.

All data are presented as mean±SEM. Mean arterial blood pressure data were analyzed using analysis of variance (ANOVA) for repeated measurements. Differences were considered statistically significant with p<0.05 compared to the control. Analyses were performed using GraphPad Prism Version 4.0 software (GraphPad Software Inc, La Jolla, Calif.).

Results-Effects on Blood Pressure and Heart Rate.

Spontaneously Hypertensive Rat (SHR).

Figure 1B:
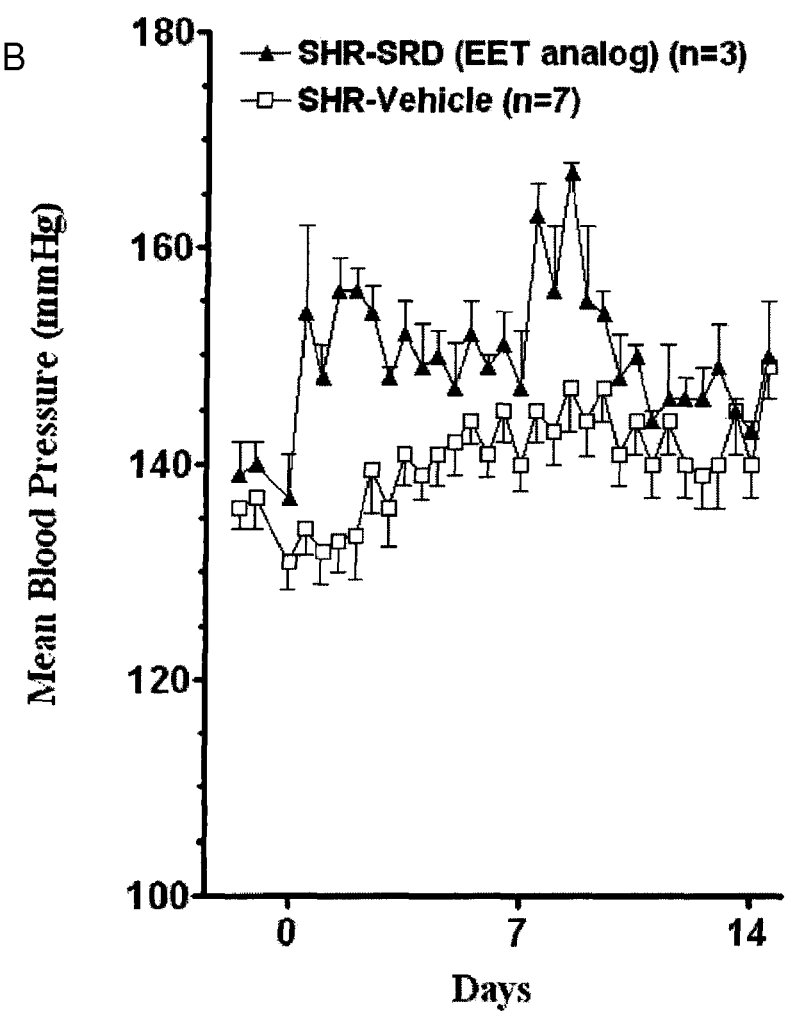
FIG. 1B shows mean measured blood pressure as a function of days of treatment in spontaneously hypertensive rats administered a composition containing vehicle or compound 26.
Figure 1C:
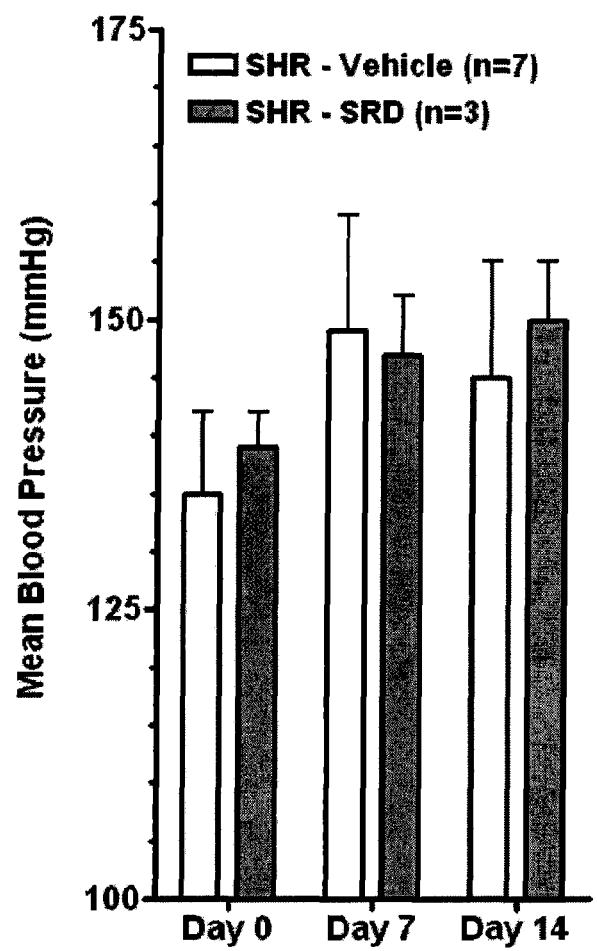
FIG. 1C shows mean measured blood pressure at day 0, day 7, and day 14 in spontaneously hypertensive rats administered a composition containing vehicle or compound 26.
Figure 2A:
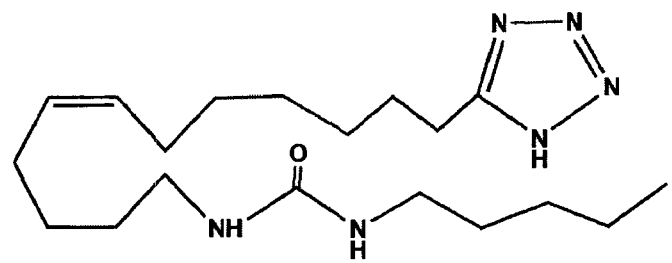
FIG. 2A depicts the chemical structure LGK-I-119-15, which corresponds to EET analog compound 20 of Table 1.
Figure 2B:
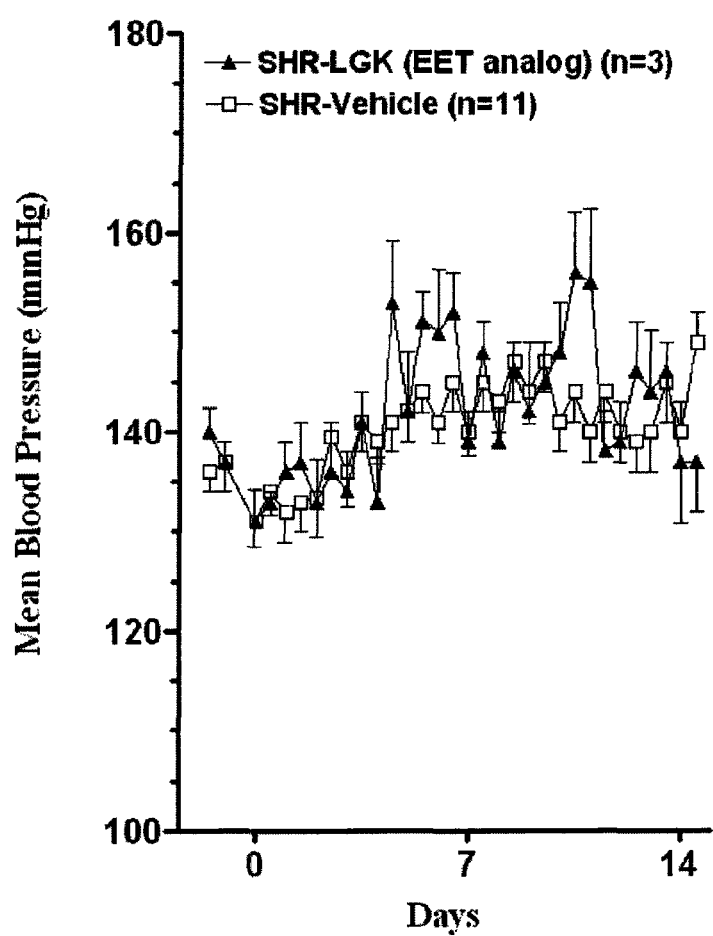
FIG. 2B shows mean measured blood pressure as a function of days of treatment in spontaneously hypertensive rats administered a composition containing vehicle or compound 20.
Figure 2C:
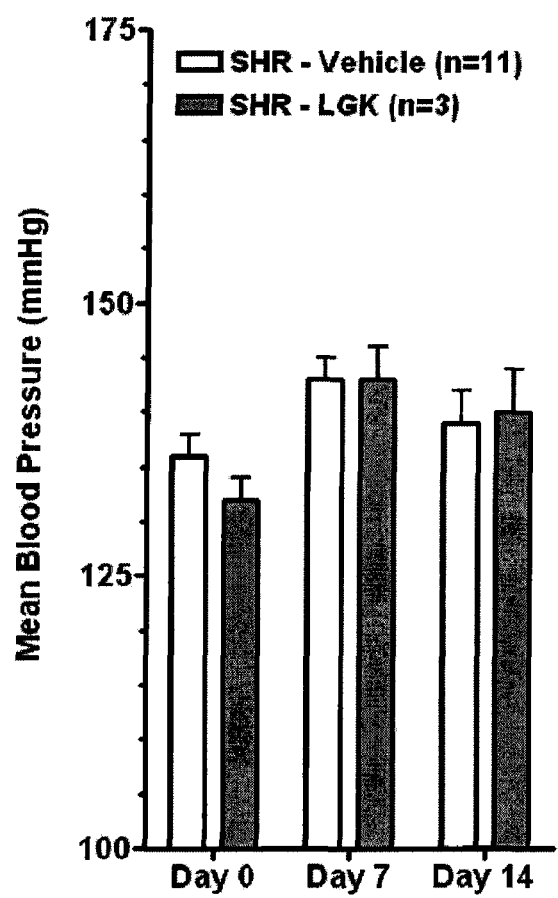
FIG. 2C shows mean measured blood pressure at day 0, day 7, and day 14 in spontaneously hypertensive rats administered a composition containing vehicle or compound 20.

In this model of hypertension, blood pressure lowering abilities of four selected compounds were studied. It is observed that two of these four compounds had blood pressure lowering effects. SRD (chemical structure shown in FIG. 1A) and LGK (chemical structure shown in FIG. 2A) lacked blood pressure lowering actions in SHR. In the SRD treated SHR group, after two weeks of treatment the blood pressure was similar to the vehicle treated SHR group (150±5.0 vs. 141±3.0 mmHg) (see FIG. 1B-C) After two weeks of treatment, LGK did not change the blood pressure (137±1.0 vs. 141±3.0 mmHg) compared to the vehicle in SHR (FIG. 2 C-D). Similar to their effects on blood pressure, neither SRD nor LGK affected the heart rate (SRD, 344±23.0 vs. 331±17.0 BPM; LGK, 325±11.0 vs. 331±17.0 BPM) compared to vehicle SHR.

Figure 3A:
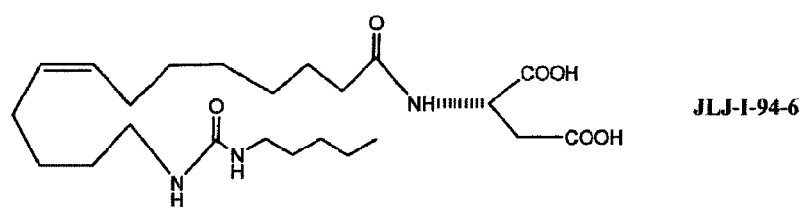
FIG. 3A depicts the chemical structure JLJ-I-94-6, which corresponds to EET analog compound 7 of Table 1.
Figure 3B:
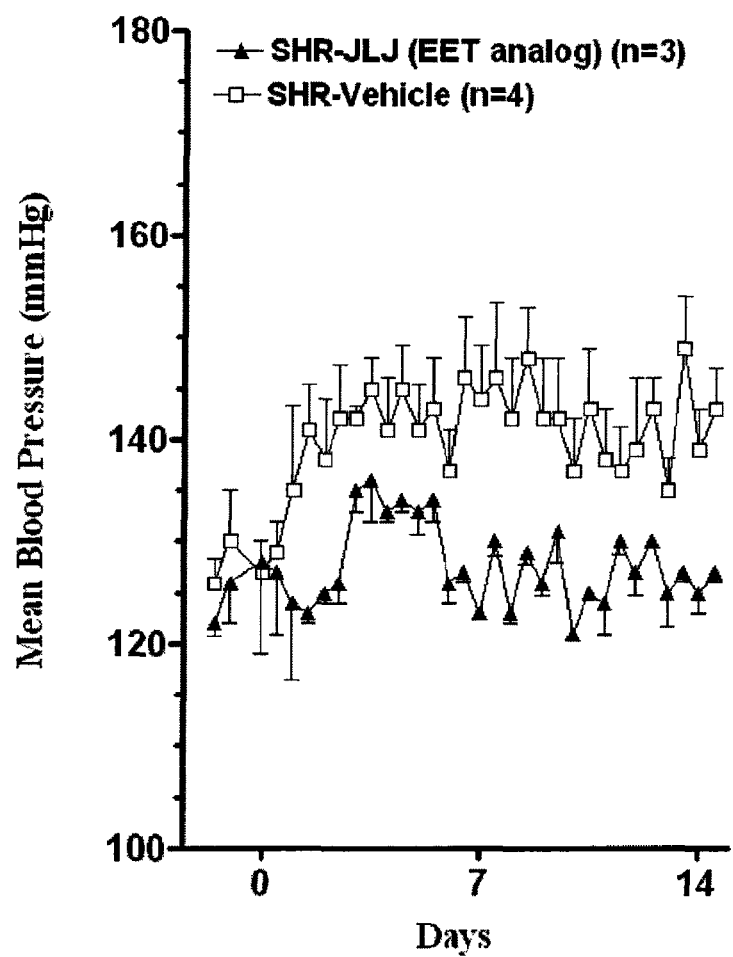
FIG. 3B shows mean measured blood pressure as a function of days of treatment in spontaneously hypertensive rats administered a composition containing vehicle or compound 7. The data is graphed as 12 hour averages. Compounds were delivered i.p. for 14 days.
Figure 3C:
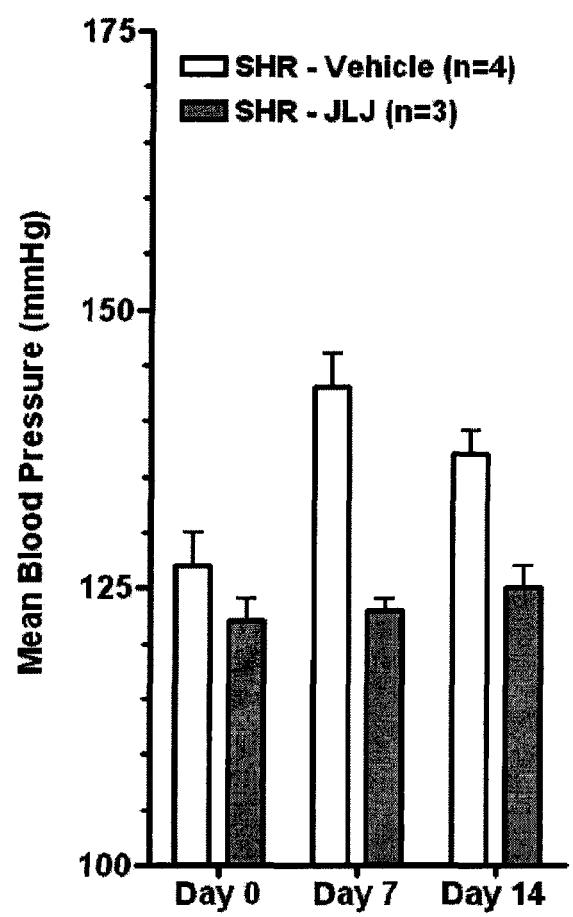
FIG. 3C shows mean measured blood pressure at day 0, day 7, and day 14 relative to initial treatment in spontaneously hypertensive rats administered a composition containing vehicle or compound 7.
Figure 4A:
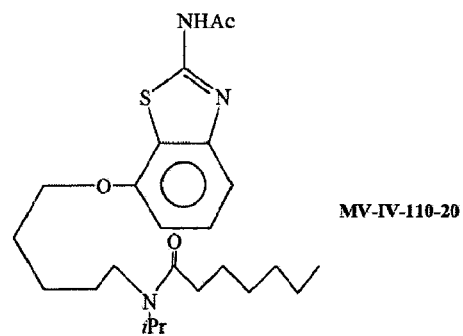
FIG. 4A depicts the chemical structure MV-IV-110-20, which corresponds to EET analog compound 30 of Table 1.
Figure 4B:
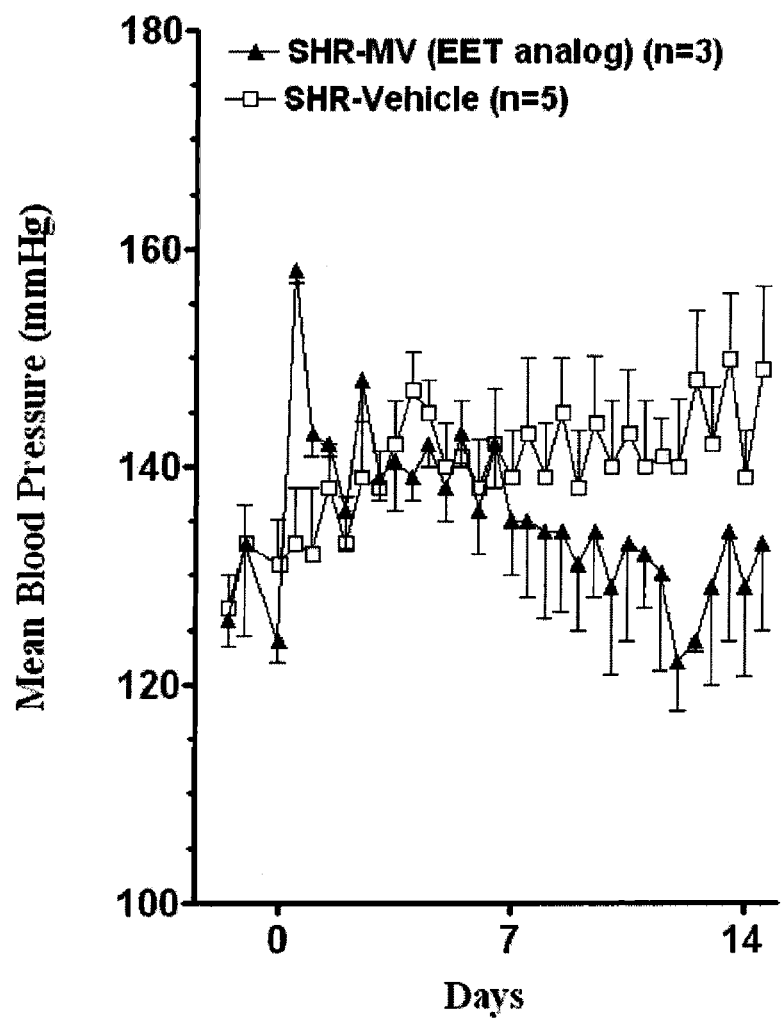
FIG. 4B shows mean measured blood pressure as a function of days of treatment in spontaneously hypertensive rats administered a composition containing vehicle or compound 30. The data is graphed as 12 hour averages.
Figure 4C:
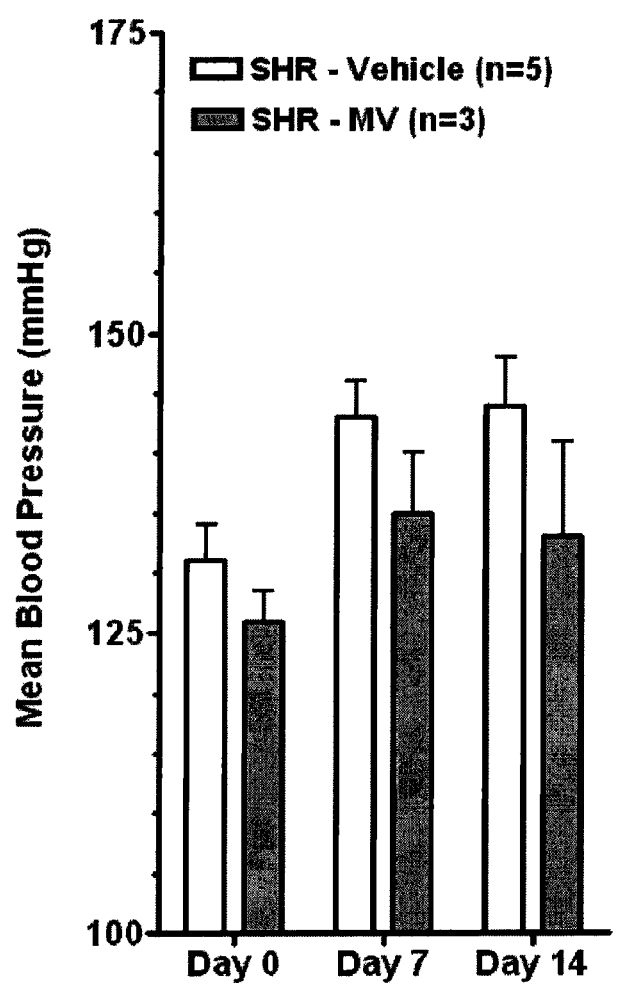
FIG. 4C shows mean measured blood pressure at day 0, day 7, and day 14 in spontaneously hypertensive rats administered a composition containing vehicle or compound 30.

Two weeks treatment with JLJ (chemical structure shown in FIG. 3A) caused a moderate decrease in blood pressure in SHR compared to vehicle treated group (131±2.0 vs. 141±3.0 mmHg) and its blood pressure lowering effect has been seen from the first week of the treatment (FIG. 3 B-C). The compound MV (chemical structure shown in FIG. 4A) also demonstrates a similar blood pressure lowering effect in SHR and caused a 12 mmHg decrease in blood pressure compared to vehicle (129±2.0 vs. 141±3.0 mmHg). Moreover, similar to JLJ, it was observed that MV started to lower blood pressure within four days of the treatment in SHR and maintained this effect until the end of the two-week treatment period (see FIG. 4 B-C). In contrast to their blood pressure lowering effect it was further observed that, neither JLJ nor MV had any affect on the heart rate (JLJ, 316±23.0 vs. 331±17.0 BPM; MV, 318±24.0 vs. 331±17.0 BPM) compared to vehicle SHR. Considering promising blood pressure lowering effects of JLJ and MV in SHR model, we have further tested these compounds in another model of hypertension, angiotensin II (Ang II) hypertension.

Ang II Hypertensive Rats.

Figure 5A:
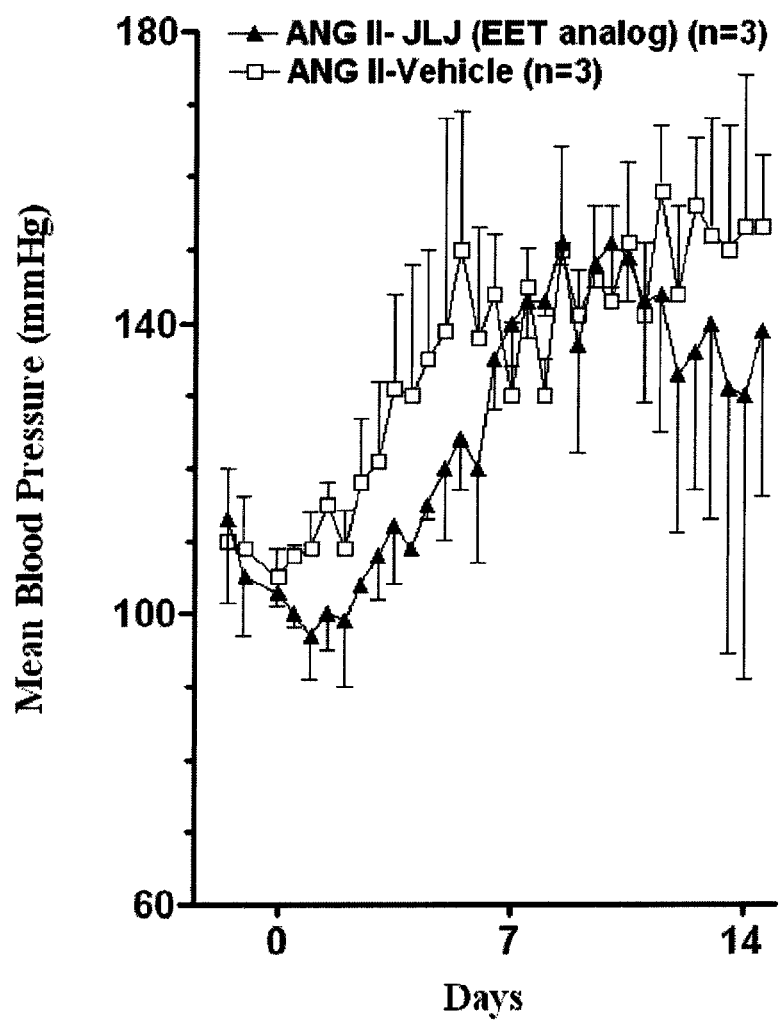
FIG. 5A shows mean measured blood pressure as a function of days of treatment inangiotensin II induced hypertensive rats administered a composition containing vehicle or compound 7. The data is graphed as 12 hour averages.
Figure 5B:
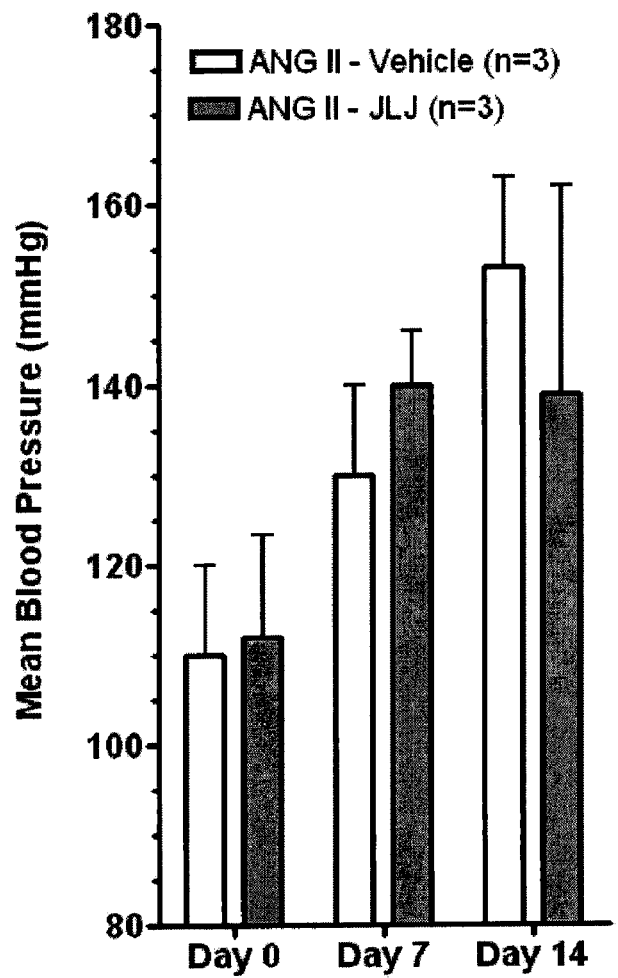
FIG. 5B shows mean measured blood pressure at day 0, day 7, and day 14 in angiotensin II induced hypertensive rats administered a composition containing vehicle or compound 7.
Figure 6A:
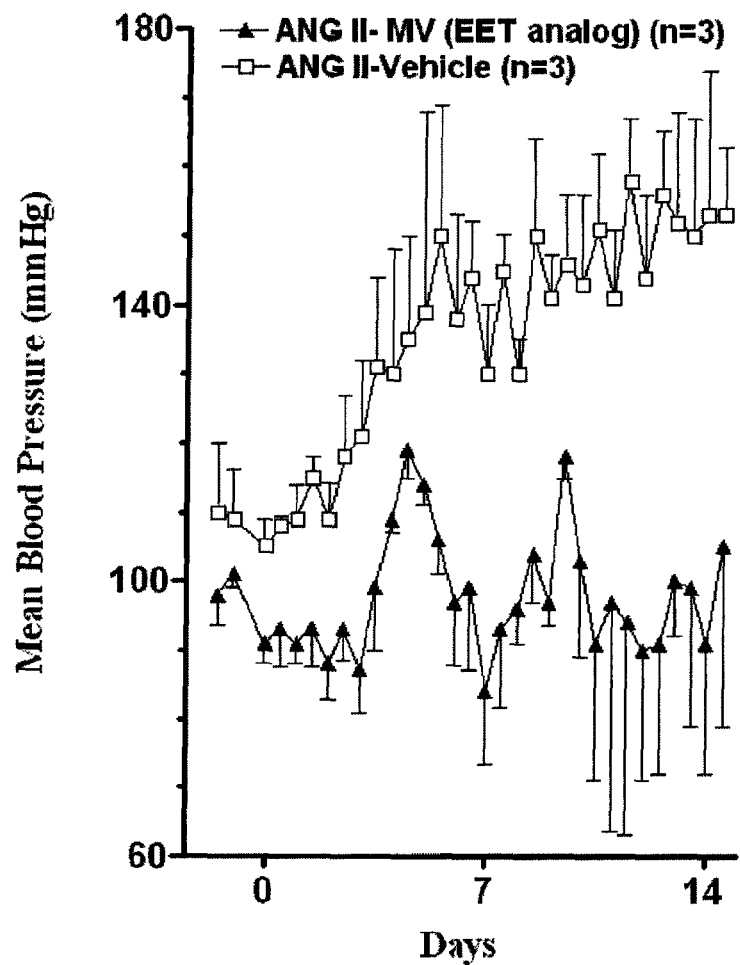
FIG. 6A shows mean measured blood pressure as a function of days of treatment in angiotensin II induced hypertensive rats administered a composition containing vehicle or compound 30. The data is graphed as 12 hour averages.
Figure 6B:
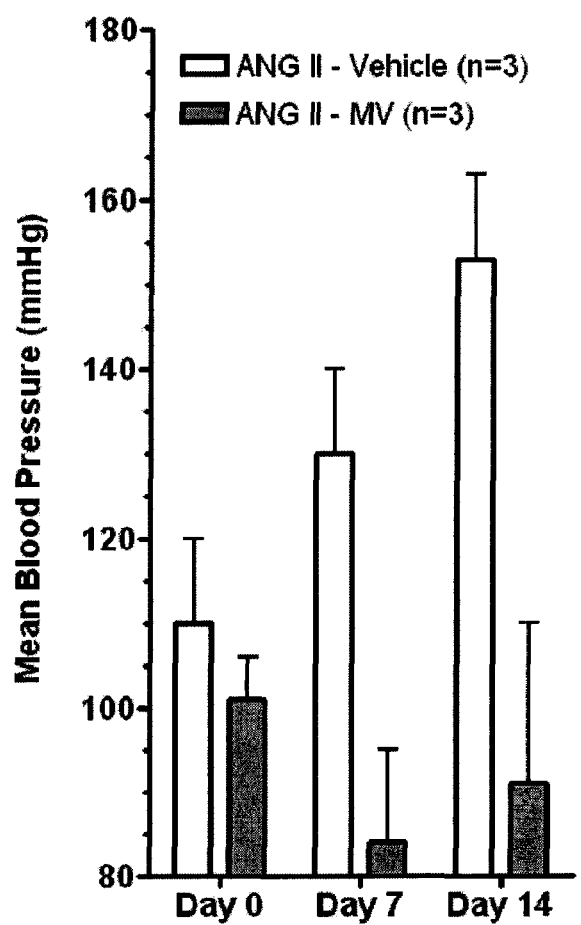
FIG. 6B shows mean measured blood pressure at day 0, day 7, and day 14 in angiotensin II induced hypertensive rats administered a composition containing vehicle or compound 30.

The compound JLJ demonstrates an attenuating effect on the Ang II induced elevation in blood pressure from the beginning of the treatment and this was maintained throughout the treatment period. It is observed that at the end of two-week of treatment period JLJ markedly attenuated the Ang II induced hypertension compared to vehicle (135±5.0 vs. 150±3.2 mmHg) (FIG. 5 A-B). Similar to JLJ, the compound MV also demonstrates marked attenuating effect on the Ang II hypertension (107±2.0 vs. 150±3.2 mmHg) and this attenuating effect was observed throughout the treatment period (FIG. 6 A-B). Similar to the SHR, in ANG II hypertension neither JLJ (410±25.0 vs. 396±25.0 BPM) nor MV (385±16.0 vs. 396±25.0 BPM) demonstrates any effect on the heart rate compared to vehicle after two weeks of treatment.

Effects of MV on Sodium Excretion and Protein Excretion in Ang II Hypertension.

In the present study we have observed that the two weeks treatment with compound MV (chemical structure shown in FIG. 4A) caused natriuresis compared to vehicle (2.7±0.3 vs. 1.9±0.7 mmol/d) in Ang II hypertension. It is also observed that the compound MV decreased the urinary protein to creatinine ratio (1.5±0.2 vs. 2.8±0.7), an indicator of renal injury, in Ang II hypertension.

Example 6

Effect of EET Analogs in Treating Cisplatin Nephrotoxicity

In this Example, the inventors investigated the kidney protective effect of two newly developed orally active EET analogs in cisplatin-induced nephrotoxicity. It was demonstrated that EET analogs offered marked reno-protection during cisplatin administration and this effect was related to their anti-oxidative, anti-inflammatory, anti-ER stress and anti-apoptotic activities. We have further demonstrated that while protecting the kidney from the deleterious nephrotoxic effect of cisplatin, these EET analogs did not compromise cisplatin's chemotherapeutic effect.

Nephrotoxicity severely limits the use of the anti-cancer drug cisplatin. Oxidative stress, inflammation and endoplasmic reticulum (ER) stress contribute to cisplatin-induced nephrotoxicity. We developed orally active EET analogs (including without limitation compounds EET-A & EET-B) by modifying the carboxylate, olefins, and epoxide moieties of EET pharmacophore. We determined if administering the claimed EET analogs would decrease nephrotoxicity, including cisplatin-induced nephrotoxicity. Cisplatin was administered (7 mg/kg i.p.) in rats pretreated for 7 days with EET analogs (10 mg/kg/d p.o., n=5) or vehicle (n=7). On day 5 following cisplatin injection, urine, plasma, and kidneys were collected. Cisplatin-induced nephrotoxicity was manifest by a 3-5-fold increase in BUN, plasma creatinine (PCr), urinary N-acetyl-(D)-glucosaminidase activity (NAG), kidney injury molecule-1 (KIM-1), and renal tubular cast formation. EET analogs attenuated cisplatin-induced increases in BUN (vehicle: 241±51 vs. EET-A: 108±30 & EET-B: 120±33 mg/dL), PCr (3.1±0.2 vs. 2.0±0.2 & 1.4±0.2 mg/dL), KIM-1 (296±94 vs. 85±29 & 57±13 ng/d), and NAG (3.0±0.6 vs. 0.5±0.1 & 0.6±0.2 U/d) (P<0.05). Cisplatin-induced renal tubular cast formation was reduced 50% by EET analog treatment. EET analogs attenuated cisplatin-induced kidney TBARS formation (vehicle: 16±2 vs. EET-A: 7±1; EET-B: 8±1 µmol/g) and cause 2-3-folds decrease in kidney expression of NOX1 and gp91phox mRNAs (P<0.05). Cisplatin-induced nephrotoxicity was accompanied by elevated renal inflammation and ER stress resulting in increased kidney mRNA expression of inflammatory (TNF-α, IL-6, IL-1β) and ER stress (caspase 12, GRP78) genes. EET analogs caused 30-70% reductions in the expression of these inflammatory and ER stress genes (P<0.05). Cisplatin caused apoptotic signalling in the kidney with elevated Bak/Bcl2 and Bax/Bcl2 mRNA expression ratios and renal cortical caspase 3 activity. EET analogs caused 2-14-folds reduction in kidney Bak/Bcl2 and Bax/Bcl2 mRNA expression ratios as well as a 50% reduction in renal caspase 3 activity (P<0.05). In an in vitro study with several cancer cell-lines, we also demonstrate that EET analog's kidney protective effects dose not compromise cisplatin's anti-cancer property. Collectively, these data demonstrate that orally active EET analogs protect from nephrotoxcity, including cisplatin-induced nephrotoxicity, by reducing oxidative stress, inflammation, and ER stress without affecting cisplatin's chemotherapeutic effects. In addition, the EET analogs will also protect against other common cisplatin side effects, including loss of hearing.

In Vivo Animal Experiments.

Experiments were approved and carried out according to the guidelines of the Institutional Animal Care and Use Committee, Medical College of Wisconsin, Milwaukee, USA. Male Wistar-Kyoto (WKY) rats weighing 180-200 g (Charles River, Mass., USA). All animals were kept in a temperature-controlled environment with a 12-h light/dark cycle and were allowed free access to food and water at all times. An acclimatization period of 6 days was allowed for the rats before experimentation. The rats were assigned into four groups. Group 1 (WKY, n=5-7): Rats received drinking water ad libitum for seven days and on day 7 DMSO (Sigma Aldrich, St. Louis, Mo., USA) was administered (300-500 µl i.p.). DMSO was used to prepare the cisplatin (CP) (Sigma Aldrich, St. Louis, Mo., USA) solution used in this study, and the maximum volume of the injection set at 500 µl. Group 2 (CP+Vehicle, n=5-7): Rats were pretreated with vehicle (0.05% ethanol and 0.1% PEG-400 v/v) in drinking water for seven days and then on day 7 CP was administered (7 mg/kg i.p.) followed by another five days treatment with vehicle. Group 3 (CP+EET-A, n=5-7): These rats are pretreated with the EET analog EET-A (10 mg/kg/day p.o.) for seven days in drinking water and then on day 7 administered CP as a single injection (7 mg/kg i.p.) followed by another five days treatment with EET-A. Group 4 (CP+EET-B, n=5-7): Rats of this group are pretreated with another EET analog EET-B (10 mg/kg/day) for 7 days in drinking water and then on day 7 CP was administered as a single injection (7 mg/kg i.p.) followed by another five days treatment with EET-B. Rats of groups 2, 3 and 4 had free access to vehicle, EET-A and -B in drinking water, respectively. One day before the rats were sacrificed, urine of each rat was collected over a 24-h period, and the volume was measured. Five days after CP or DMSO administration, rats were anesthetized for blood sample collection followed by euthanasia and tissue collection. Urine and plasma samples were kept frozen at −80° C. until analyzed. The kidneys were removed, washed with physiological saline and stored at −80° C. until used for RT-PCR analysis, thiobarbituric acid reactive substance (TBARS) measurement and caspase 3 activity assay. A part of the kidney also preserved in 10% buffered formalin for histological examination.

Biochemical Analysis.

The levels of blood urea nitrogen (BUN) (BioAssay Systems, Hayward, Calif., USA) and serum creatinine (Cayman Chemical Company, Ann Arbor, Mich., USA) were measured spectrophotometrically using commercial kits. Urinary content of creatinine and protein were measured using commercial kits (Cayman Chemical Company, Ann Arbor, Mich., USA), and the activity of urinary N-acetyl-b-glucosaminidase (NAG) in the urine was measured by a kit from Diazyme (Diazyme Laboratories, Poway, Calif., USA). While urine content of kidney injury molecule-1 (KIM-1) was measured using ELISA (R&D Systems, Inc. Minneapolis, Minn., USA).

Determination of Malondialdehyde in the Kidney.

Malondialdehyde (MDA) is a thiobarbituric acid reactive substance (TBARS) that is formed as an end-product of lipid peroxidation and serves as an important index of oxidative stress. To determine the kidney MDA level, the rat kidney was homogenized with buffer containing 1.5% potassium chloride to obtain a 1:10 (w/v) whole kidney homogenate. Using a commercially available kit (Cayman Chemical Company, Ann Arbor, Mich., USA), MDA was measured spectrophotometrically after reaction with thiobarbituric acid.

Determination of Caspase 3 Activity.

Caspase 3 activity in the kidney homogenate was determined using a commercial fluorimetric assay kit (Sigma Aldrich, St. Louis, Mo., USA). Kidney homogenate was prepared with a lysis Buffer (50 mM HEPES, pH 7.4, with 5 mM CHAPS and 5 mM DTT). Kidney homogenate was centrifuged at 10,000 g for 10 min and the resulting supernatant was used for the assay. The caspase 3 fluorimetric assay is based on the hydrolysis of the peptide substrate acetyl-Asp-Glu-ValAsp-7-amido-4-methylcoumarin (Ac-DEVD-AMC) by caspase 3, resulting in the release of the fluorescent 7-amino-4-methylcoumarin (AMC) moiety. The caspase 3 activity is expressed as nmol of AMC/min/µL.

Real-Time PCR Analyses.

Real-Time analysis was carried out to assess the expression of oxidative (gp91phox, NOX1, SOD1, SOD2, SOD3), inflammatory (TNF-α, IL-6, apoptotic (Bax, Bak, Bcl-2) and endoplasmic reticulum stress (GRP78, caspase 12) related genes in the kidney. Total RNA was isolated from kidney homogenate using TRIzol LS reagents (Invitrogen Life Technologies, Carlsbad, Calif., USA) according to the manufacturer's instructions. The isolated RNA was treated with RNase-free DNase (Invitrogen, Carlsbad, Calif., USA) to remove traces of genomic DNA contamination. The mRNA samples were quantified by spectrophotometry at 260 nm and 1 µg of total RNA was reverse-transcribed to cDNA using iScript™ Select cDNA Synthesis Kit (Bio-Rad, Hercules, Calif., USA).

The target gene expression was quantified by iScript One-Step RT-PCR Kit with SYBR green using MyiQ™ Single Color Real-Time PCR Detection System (Bio-Rad Laboratories, Hercules, Calif., USA). Each amplified sample in all wells was analyzed for homogeneity using dissociation curve analysis using iQ5 Optical System Software, Version 2.1 (Bio-Rad Laboratories, Hercules, Calif., USA). After denaturation at 95° C. for 2 min, 40 cycles were performed at 95° C. for 10 s and at 60° C. for 30 s. Each sample was run in triplicate, and the comparative threshold cycle ($C_t$) method was used to quantify fold increase ($2^{-\Delta\Delta C_t}$) in the expression of the target genes compared to controls. In analyzing the relative expression of the target genes, the $C_t$ values were normalized to a housekeeping gene (pgk1). Statistical analyses were carried out for at least 5-7 experimental samples in each experimental group. Primers used in this study were designed based on several earlier reports. HAfter fixation of the kidneys with 10% buffered formalin, renal tissues were sectioned and stained with periodic acid-Schiff (PAS) reagents for histological examination. The numbers of tubules that contain proteinaceous casts were determined at magnification of ×200 to assess tubular damage using an image analyzing software NIS Elements AR version 3.0 (Nikon instruments inc., Melville, N.Y., USA). The percentage area positive for cast was calculated from the mean of eight cortical and five medullary fields (×200) for each kidney sample. To minimize observer bias, the cast area calculation was performed in a blinded fashion without knowledge of the treatment group from which the tissues are originated.

In Vitro Anti-Tumor Activity of Cisplatin in the Presence and Absence of EET Analog.

In this study, HEK293, U87MG, Hela cell-lines were obtained from the ATCC (Manassas, Va., USA) (HEK293, U87MG, Hela), and NCCIT was collected from Department of Pediatrics, UT Southwestern Medical Center at Dallas, Tex., USA. All cell lines were maintained in DMEM or RPIM with 10% fetal bovine serum and penicillin/streptomycin purchased from Life Technologies (Grand Island, N.Y., USA). Cisplatin was purchased from either Sigma (St. Louis, Mo., USA) or CalBiochem/EMD Biosciences (Billerica, Mass., USA). Cells were seeded in 96-well plates at 500 to 4,000 cells per well depends on cell type. Twenty-four hours later, the cells were treated with cisplatin or vehicle and/or the EET analogue EET-A at various concentrations for 72 h. Cell viability was measured by alamar blue assay using resazurin (Sigma Aldrich) according to the manufacturer's guidelines. Viability results were measured by fluorescence/absorbance in a 96-well plate reader from BMG Labtech (Cary, N.C., USA) and the $IC_{50}$ was calculated by GraphPad Prism5 software (GraphPad Software Inc, La Jolla, Calif., USA).

Statistical Analysis.

Results are reported as mean±S.E.M. Statistical significance between two measurements was determined by the two-tailed unpaired Student's t test (and among groups it was determined by repeated measure one-way analysis of variance followed by Tukey's post-hoc test) by using Graph-Pad Prism® Version 4.0 software (GraphPad Software Inc, La Jolla, Calif., USA). Probability values of $P<0.05$ were considered significant where the critical value of P was two-sided.

Results.

EET Analog Treatment Attenuates Renal Dysfunction and Injury in Cisplatin Administered Rats.

Figure 7A:
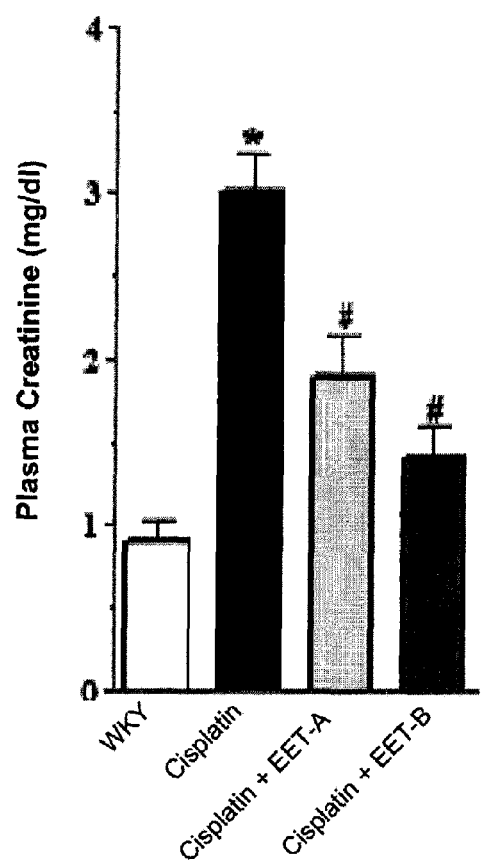
FIG. 7A shows plasma creatinine administered rats pretreated with either EET analogs, EET-A and EET-B or vehicle. $*p<0.05$ vs. normal Wistar Kyotorat; $\#p<0.05$ vs. vehicle treated rat administered cisplatin. Data expressed as mean±SEM, n=5-7.
Figure 7B:
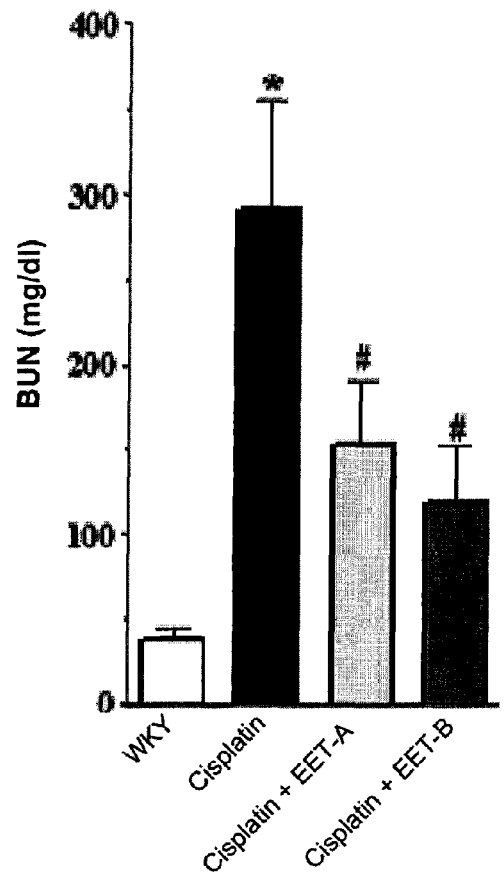
FIG. 7B shows blood urea nitrogen (BUN) administered rats pretreated with either EET analogs, EET-A and EET-B or vehicle. $*p<0.05$ vs. normal Wistar Kyotorat; $\#p<0.05$ vs. vehicle treated rat administered cisplatin. Data expressed as mean±SEM, n=5-7.
Figure 7C:
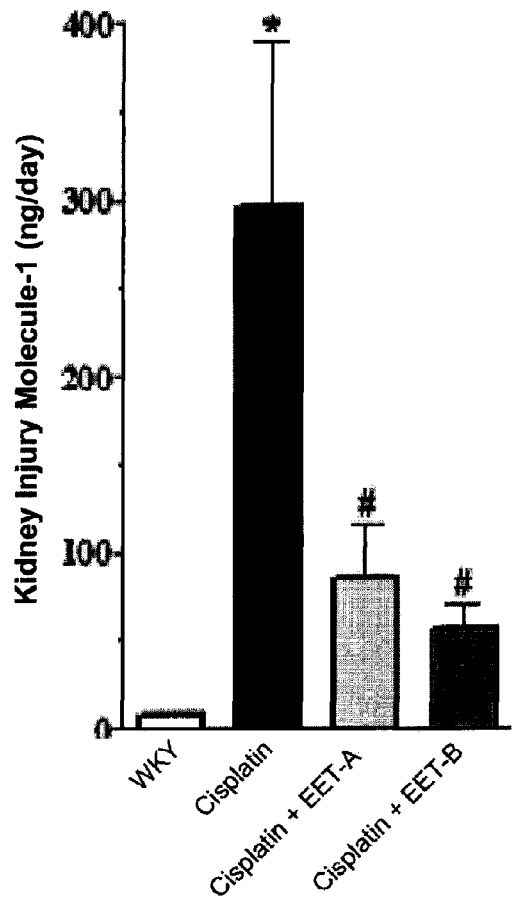
FIG. 7C shows kidney injury molecule-1 administered rats pretreated with either EET analogs, EET-A and EET-B or vehicle. $*p<0.05$ vs. normal Wistar Kyotorat; $\#p<0.05$ vs. vehicle treated rat administered cisplatin. Data expressed as mean±SEM, n=5-7.
Figure 7D:
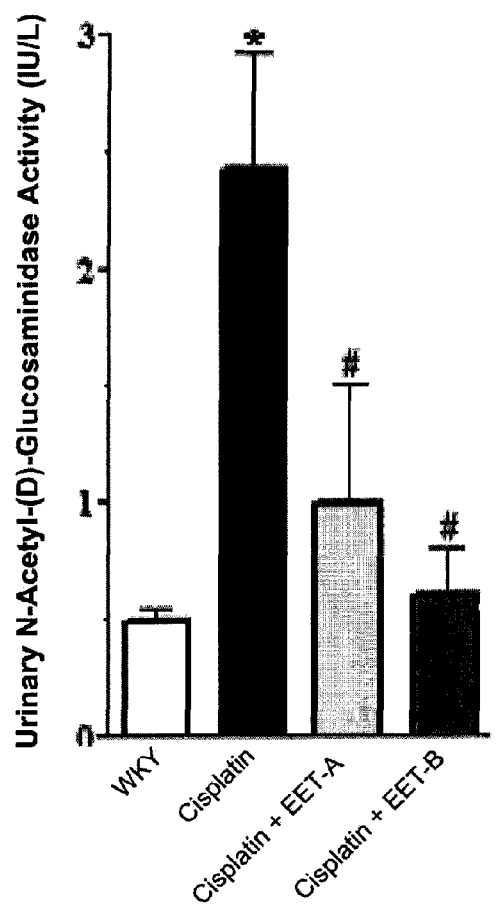
FIG. 7D shows urinary NAGin cisplatin administered rats pretreated with either EET analogs, EET-A and EET-B or vehicle. $*p<0.05$ vs. normal Wistar Kyotorat; $\#p<0.05$ vs. vehicle treated rat administered cisplatin. Data expressed as mean±SEM, n=5-7.

To investigate the effects of EET analogs in cisplatin (CP)-induced renal dysfunction, levels of urea (blood urea nitrogen or BUN) and creatinine were measured in the serum of both EET analog-treated and -untreated rats after five days of the CP administration. As shown in the FIG. 8, CP administration caused 3 and 9-fold increase in the serum creatinine and BUN levels (FIGS. 7a and 7b), respectively ($P<0.05$). Treatment with EET analogs (EET-A and -B) resulted in 30-50% reductions in the elevated levels of serum creatinine and BUN in rats administered with CP compared to those given vehicle (DMSO) ($P<0.05$). To determine the effects of EET analogs in CP-induced renal dysfunction, we further studied urinary excretion of KIM-1, NAG and protein after five days of CP administration (FIGS. 7c and 7d). There were 5 and 10-fold increases in urinary excretion of NAG and KIM-1 in the CP-administered rats compared to vehicle-administered controls ($P<0.05$). Moreover, we also demonstrated that cisplatin-administration caused marked proteinuria compare to vehicle administration (vehicle vs. cisplatin, 25.7±1 vs. 53±5.1 mg/d, $P<0.05$). Both EET analogs, EET-A and EET-B resulted 30-50% reduction in the urinary excretion of NAG and KIM-1 compared to CP-administered rats treated with vehicle ($P<0.05$) (FIGS. 7c-d).

We have also observed at least a 40% reduction of cisplatin-induced proteinuria by both EET analogs (Vehicle vs. EET-A and -B; 53±5 vs. 33±8 and 32±3 mg/d, $P<0.05$). In the present study the CP-induced kidney dysfunction was further assessed using histological examination of the kidney. Administration of CP resulted in tubular injury as manifested by a vacuolation and desquamation of the renal epithelial cells along with severe intra-tubular proteinaceous cast formation in both the cortical and medullary regions of the kidney compared to vehicle-administered rats. Both EET analogs protected the kidney in CP-administered rats with >50% reduction of the tubular cast area in cortex and medulla compared to CP-administered rats treated with vehicle ($P<0.05$) (FIGS. 8a-b).

EET Analog Treatment Attenuates Cisplatin-Induced Renal Oxidative Stress, Inflammatory Response and Endoplasmic Reticulum Stress.

Figure 9A:
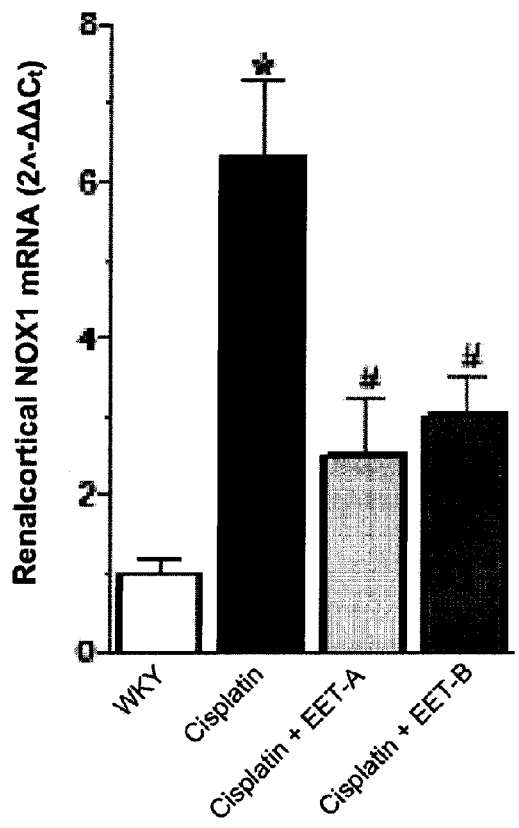
FIG. 9A shows RT-PCR analysis form RNA expressions of NOX1.
Figure 9B:
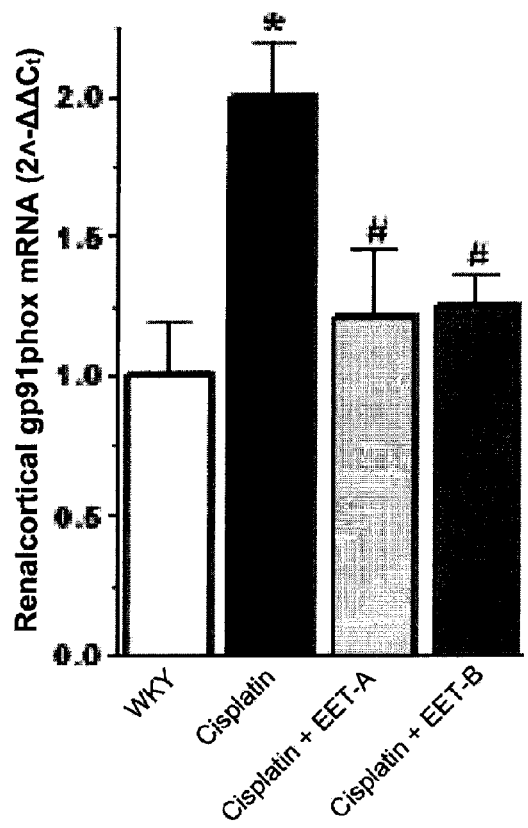
FIG. 9B shows RT-PCR analysis form RNA expressions of gp91Phox.
Figure 9E:
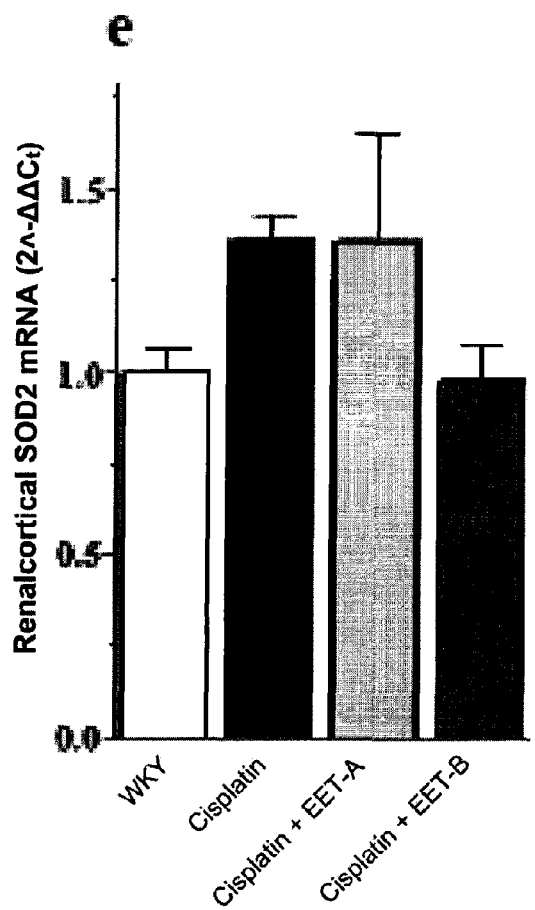
FIG. 9E shows RT-PCR analysis form RNA expressions of SOD2.
Figure 9F:
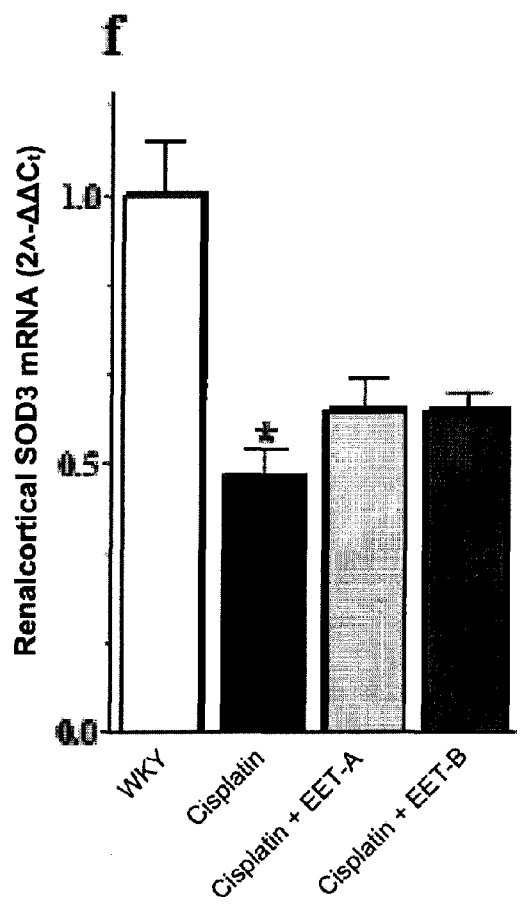
FIG. 9F shows RT-PCR analysis form RNA expressions of SOD3.

Real-Time PCR analysis of the mRNA expressions of NADPH oxidase subunits NOX1 and gp91phox (FIG. 9) demonstrated increased expression of these oxidative marker genes in cisplatin (CP) administered rats ($P<0.05$). There was 2-3-folds attenuation in the cisplatin-induced increase in the renal expression of NOX1 and gp91phox mRNA were reduced by EET analogs A and B ($P<0.05$) (FIG. 9a-b). CP-administration also resulted in a marked elevation in the kidney content of melondialdehyde (MDA), which is one of the important indicators of oxidative stress. Treatment with EET analogs caused 50% reduction of MDA level in the kidney of CP-administered rats ($P<0.05$) (FIG. 9c). It was further observed that administration of CP resulted in 2-5-folds reductions in the mRNA expression of superoxide dismutase (SOD) 1 and SOD3 ($P<0.05$) while expression of SOD2 was unchanged. Treatment with EET analogs caused 2-3-folds increase in the expression of SOD1 in the CP-administered rats ($P<0.05$) while the expression of SOD3 remained unaltered across the experimental groups (FIGS. 9d-f).

Figures 10A, 10B, 10C:
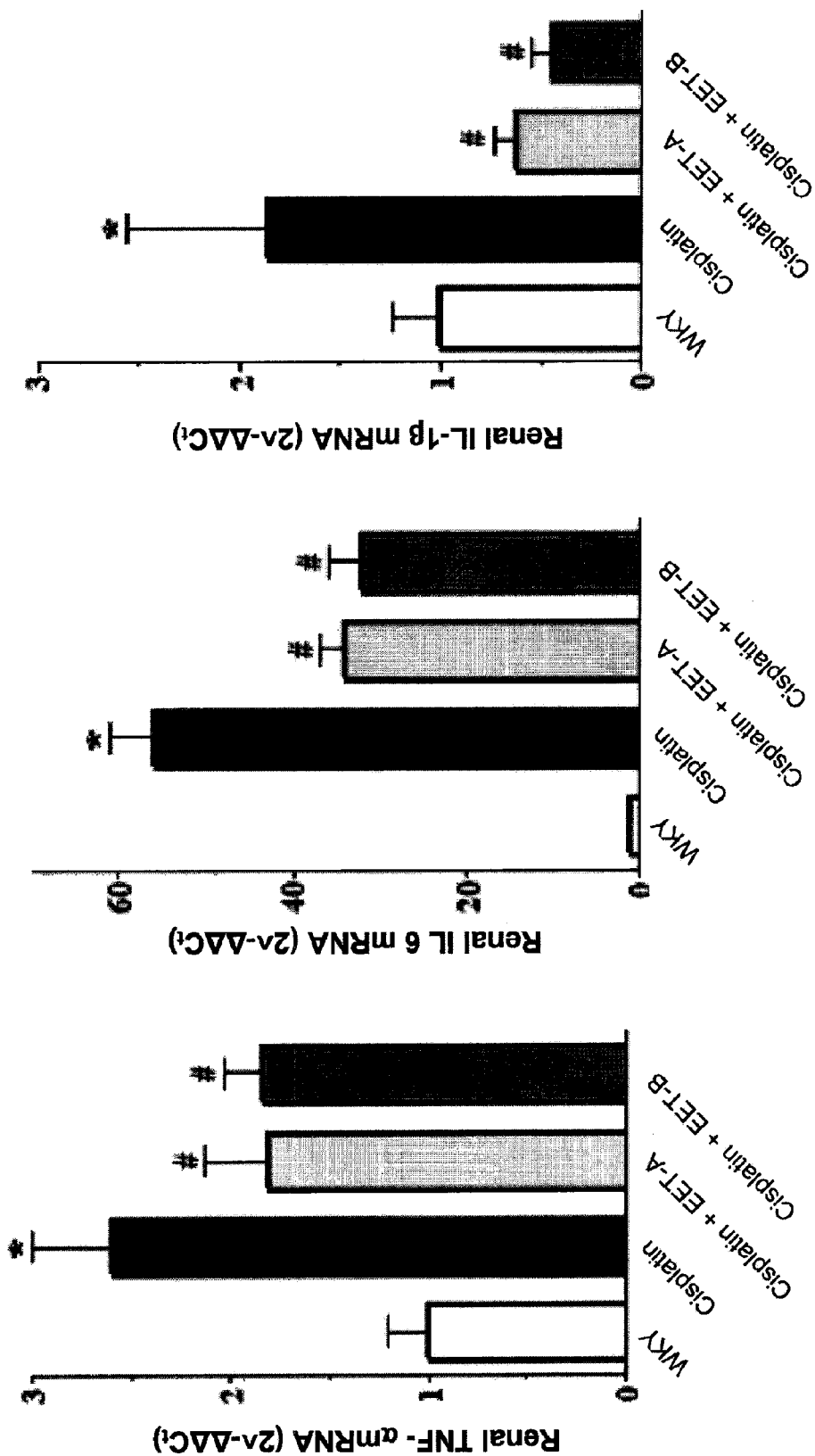
FIG. 10A shows renal expression of inflammatory marker genes TNF-α in cisplatinadministered rats pretreated with either EET analogs EET-A and EET-B or vehicle. $*p<0.05$ vs. normal Wistar Kyoto rat; $\#p<0.05$ vs. vehicle pretreated rat administered cisplatin. Data expressed as mean±SEM, n=5-7.
FIG. 10B shows renal expression of inflammatory marker genes IL-6 in cisplatinadministered rats pretreated with either EET analogs EET-A and EET-B or vehicle. $*p<0.05$ vs. normal Wistar Kyoto rat; $\#p<0.05$ vs. vehicle pretreated rat administered cisplatin. Data expressed as mean±SEM, n=5-7.
FIG. 10C shows renal expression of inflammatory marker genes IL-10 in cisplatinadministered rats pretreated with either EET analogs EET-A and EET-B or vehicle. $*p<0.05$ vs. normal Wistar Kyoto rat; $\#p<0.05$ vs. vehicle pretreated rat administered cisplatin. Data expressed as mean±SEM, n=5-7.

To investigate the effect of EET analogs on the CP-induced inflammation that is associated with renal dysfunction, we studied the renal expression of mRNAs that code for tumour necrosis factor-α (TNF-α), interleukin-6 (IL-6) and interleukin-1β. These variables demonstrated a 2-50-fold increase in their expression in the vehicle treated CP-administered rats compared to the rats administered vehicle ($P<0.05$) (FIGS. 10a-c). Treatment with both EET analogs (EET-A and B) resulted in 40-60% reductions in the renal mRNA expressions of all the inflammatory markers in CP-administered rats (all $P<0.05$).

We have also observed 4-fold increase in the mRNA expressions of ER stress markers GRP78/BiP and caspase 12 in the vehicle treated CP-administered rats compared to vehicle-administered rats ($P<0.05$) (FIGS. 11a-b). In CP-administered rats, treatment with both EET analogs (EET-A and B) caused 2-4-fold reduction in the elevated renal expressions of GRP78 and caspase 12 mRNAs compared to vehicle treatment ($P<0.05$) (FIGS. 11a-b).

EET Analog Treatment Attenuates Cisplatin-Induced Renal Apoptosis.

Figure 12A:
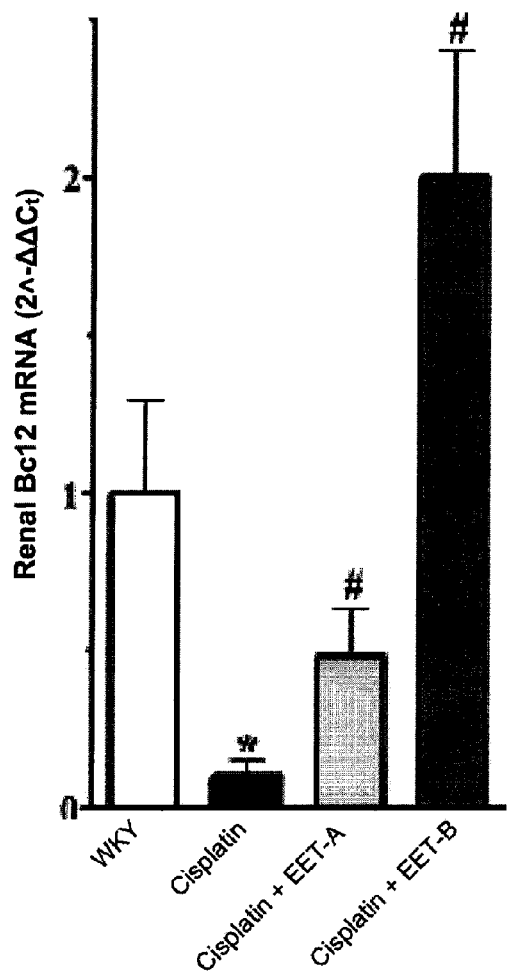
FIG. 12A shows renal cortical caspase 3 activity andrenal expression of anti-apoptotic gene Bcl2.
Figure 12B:
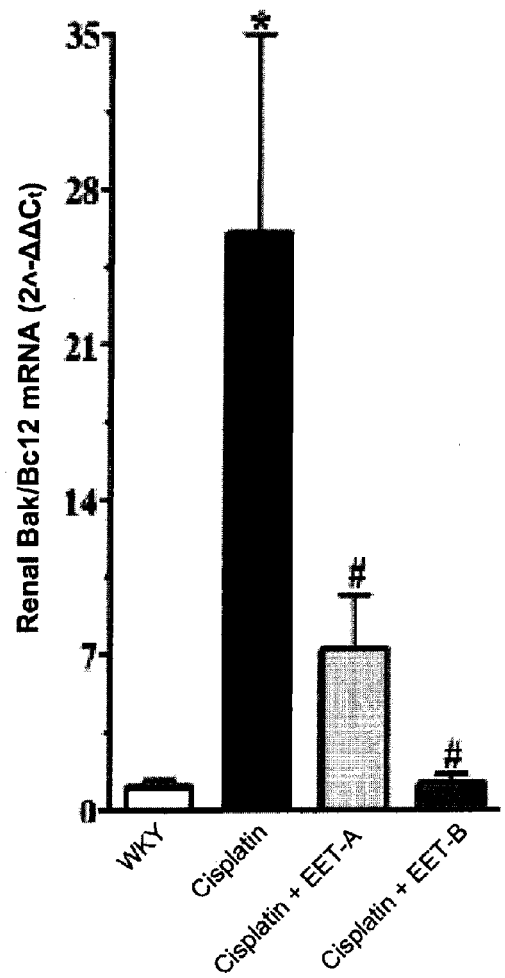
FIG. 12B shows renal cortical caspase 3 activity in different experimental groups.
Figure 12C:
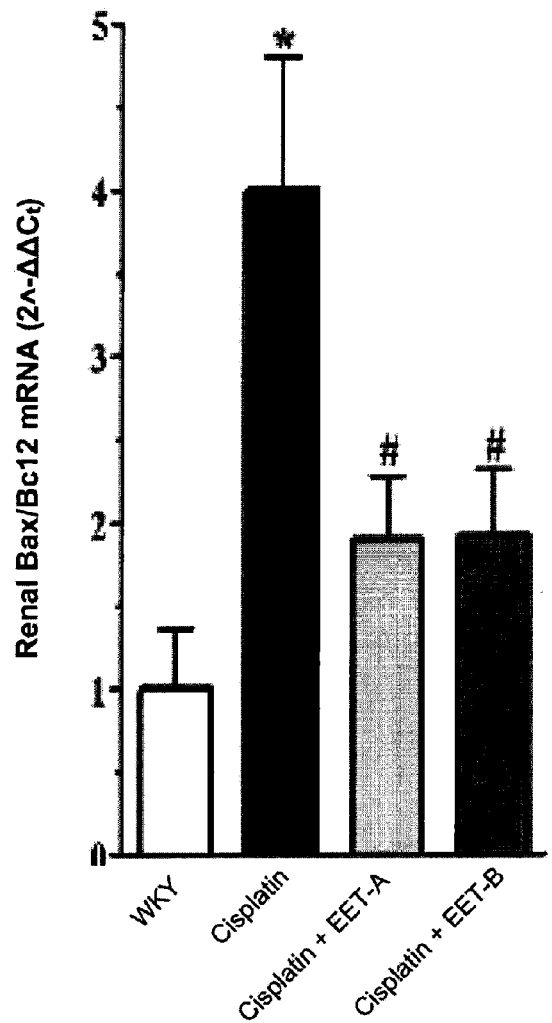
FIG. 12C shows the ratios between the renal expression of anti-apoptotic gene Bcl2 and the apoptotic genes Bak in different experimental groups. $*p<0.05$ vs. normal Wistar Kyoto rat; $\#p<0.05$ vs. vehicle treated rat administered cisplatin. Data expressed as mean±SEM, n=5-7.
Figure 12D:
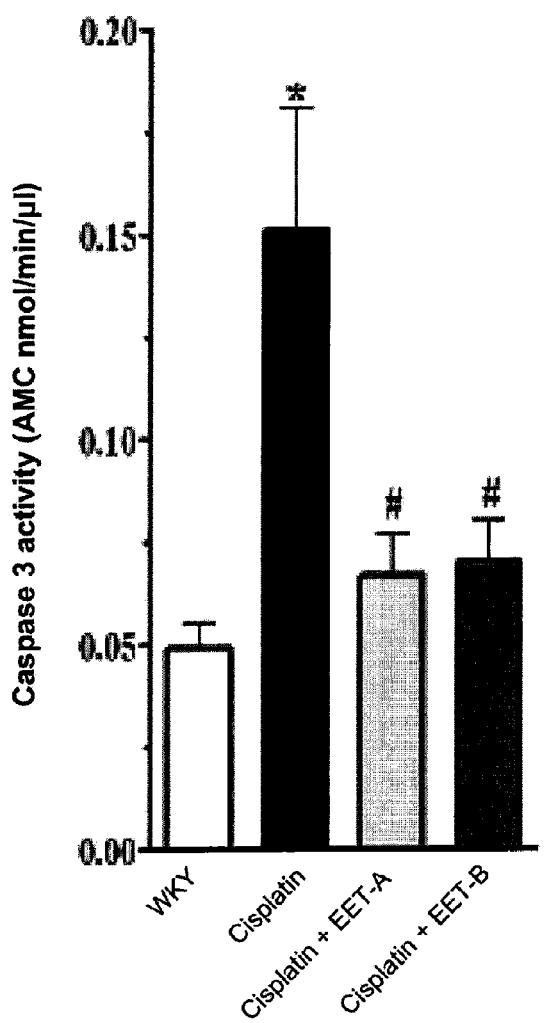
FIG. 12D shows the ratios between the renal expression of anti-apoptotic gene Bcl2 and the apoptotic genes Bax in different experimental groups. $*p<0.05$ vs. normal Wistar Kyoto rat; $\#p<0.05$ vs. vehicle treated rat administered cisplatin. Data expressed as mean±SEM, n=5-7.

There was a 70% reduction in the renal expression of Bcl-2 mRNA in the vehicle treated CP-administered rats compared to rats administered vehicle ($P<0.05$) (FIG. 12a). EET analog treatment caused 2-10-fold increase in the expression of the anti-apoptotic Bcl-2 in the CP-administered rats compared to vehicle treated CP-administered rats ($P<0.05$) (FIG. 12a). Moreover, CP administration resulted in 4-20-fold raise in the Bax/Bcl-2 and Bak/Bcl-2 ratios, and therefore indicated elevated apoptotic signalling in the CP-administered rats (FIGS. 12b-c) ($P<0.05$). EET analogs treatment caused 2-3-fold reduction in Bax/Bcl-2 and Bak/Bcl-2 ratios compared to CP-administered rats treated with vehicle ($P<0.05$) (FIGS. 12c-d). The CP-induced elevated apoptotic signalling was further characterized with higher caspase 3 activity (FIG. 12d) in CP-administered rats compared to the rats administered vehicle ($P<0.05$). Treatment with EET analogs attenuated such CP-induced caspase 3 activity by 50% compared to the CP-administered rats treated with vehicle ($P<0.05$) (FIG. 12d). These results clearly demonstrated attenuation of CP-induced apoptotic signaling in the presence of EET analog treatment.

EET Analog Treatment Dose not Compromise the Chemotherapeutic Effect of Cisplatin.

Figure 13A:
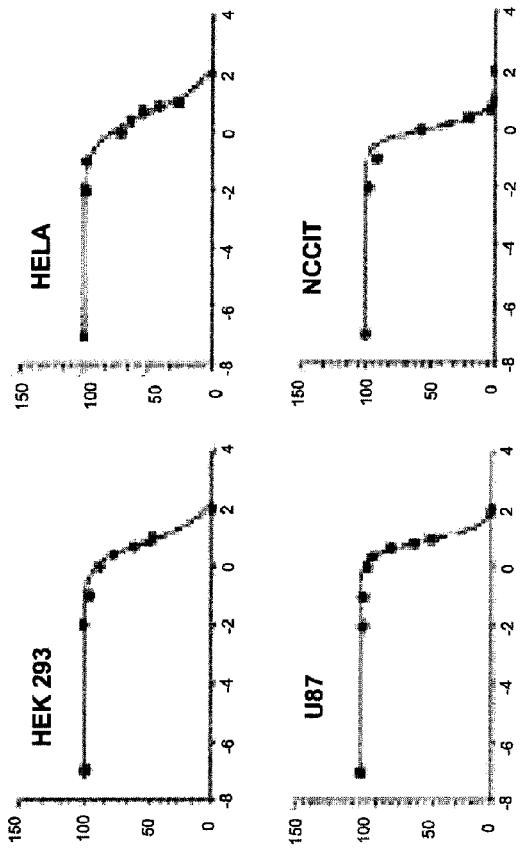
FIG. 13A depicts cytotoxic effect of cisplatin in normal kidney cell (HEK293) and cancer cells (Hela, U87, NCCIT).
Figure 13B:
FIG. 13B depicts the effect of EET analog EET-A on the cell growth of HEK293, Hela, U87, and NCCIT. EET-A does not effect the chemotherapeutic effect of cisplatin in NCCIT cancer cells. Data expressed as mean±SEM, n=5-7.
Figure 13C:
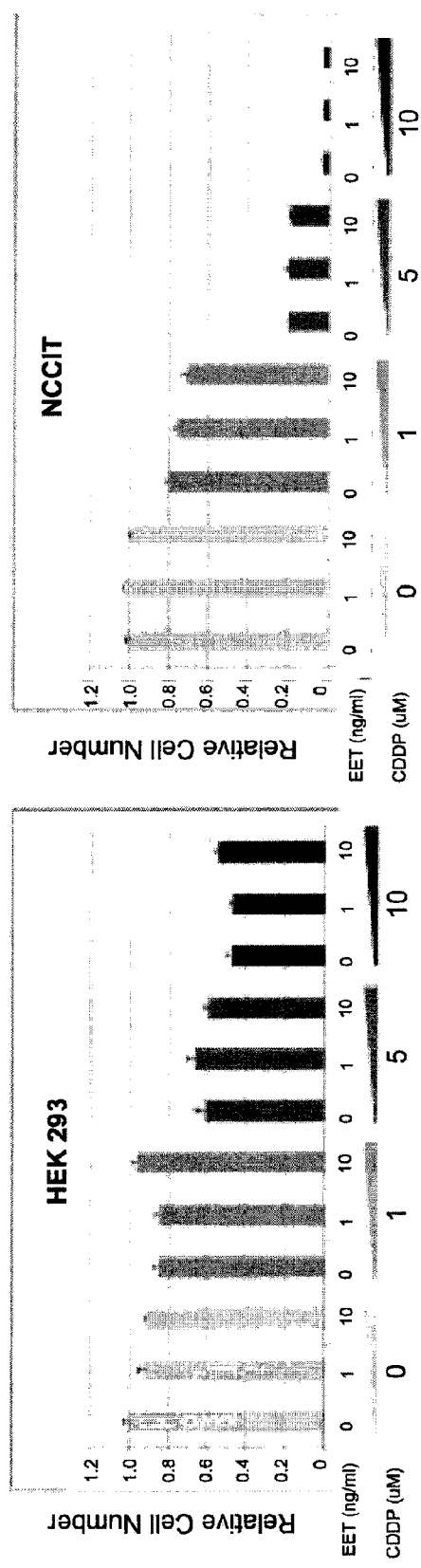
FIG. 13C shows the concurrent application of EET-A and cisplatin did not influence the cisplatin's chemotherapeutic effect neither on the normal kidney cells nor on the NCCIT cancer cell line.

We demonstrate that in three different cancer cell lines, Hela, NCCIT and U87 cisplatin markedly inhibit the cell growth with $IC_{50}$ ranged from 1.1-9.24 µM (FIG. 13a). In a similar approach with these cell lines, EET-A had no observable effects on cell number (FIG. 13b). Moreover, concurrent application of EET-A and cisplatin did not influence the cisplatin's chemotherapeutic effect neither on the normal kidney cells (data not shown) nor on the NCCIT cancer cell line (FIG. 13C). It is demonstrated that when cisplatin and EET-A were used concurrently, the $IC_{50}$ for cisplatin was 2.60, 2.55, and 2.44 µM with 0, 1, and 10 ng/ml EET in NCCIT cells.

Discussion.

A critical limitation of cisplatin chemotherapy is the induction of tubulointestinal inflammation, renal oxidative stress, ER stress and tubular cell apoptosis that lead to acute kidney injury. It is reported that 40% cancer patients who treated with cisplatin develops acute renal injury. Unfortunately, efficient pharmacotherapies to attenuate this debilitating complication of a widely used chemotherapy like cisplatin are not available. In an attempt to contribute to this area, current study investigated the kidney protective effect of chronic treatment of epoxyeicosatrienoic acid (EET) analogs on cisplatin-induced nephrotoxicity.

There is strong evidence that EET analogs have ability to protect organ by mechanisms involving its anti-inflammatory, anti-apoptotic and anti-oxidative activities. With this background, in the present study we hypothesized that with its strong organ protective ability, EET will protect the kidney from cisplatin nephrotoxicity. In our attempt, we have synthesized two novel EET analogs and investigated their kidney protective effects in cisplatin-induced nephrotoxicity using a clinically relevant approach with chronic administration of EET analogs in drinking water to the rat. We demonstrate that a single administration of cisplatin caused marked renal injury evident from increased PCr, BUN, urinary excretion of renal tubular injury markers like NAG and KIM-1 along with marked proteinuria and tubular cast formation. Our results supports several earlier studies reported cisplatin-induced nephrotoxicity in pre-clinical animal models. Interestingly, we also demonstrate that the chronic treatment with EET analogs in drinking water markedly protected the kidney from cisplatin-induced nephrotoxic injury with reductions in all renal injury markers studied in this study. In relation to our approach in the present study, a recent study demonstrated that acute administration of sEH inhibitor could reduce cisplatin-induced renal dysfunction in mice. However, it is known that current sEH inhibitors are limited in effects as they undergo metabolism and incorporation into the membrane,[36] thus indicates a limitation of this finding in clinical translational implication. Moreover, the study carried out by Parrish et al.[35] did not provide evidence on the possible mechanism by which EET or sEH inhibitor reduces renal dysfunction in cisplatin-induced nephrotoxicity.

Currently, we demonstrate marked over-expression of mRNAs for the major components of NADPH oxidase (NOX1 and gp91phox) in cisplatin-induced nephrotoxicty. Over-expression of these oxidative marker genes further accompanied by increased ROS generation evident from the elevated kidney lipid per-oxidation in the cisplatin-administered rat. We also demonstrate reduced renal SOD1 and SOD3 expressions, and suggest that such reduction contributes to the oxidative stress in cisplatin administered rat. Similar observations are reported in earlier studies where cisplatin-induced nephropathy is accompanied by increased MDA level and elevated expression and activity of NADPH oxidase. Interestingly, our study also demonstrate that EET analogs markedly reduced the renal oxidative stress by reducing the renal lipid per-oxidation, marked reductions in the expression of the major NADPH oxidase subunits, and also by increased expression of SOD1. Indeed, in a recent study it is reported that EET up-regulates the expression and activity of SOD during toxic insult, thus enhance ROS scavenging and reduce oxidative stress. Similar to our findings, in another pathological model characterized with renal injury, EET mediated reduction in oxidative stress and renal injury has been reported. Apart from oxidative stress, we also demonstrate that cisplatin-induced nephrotoxicity is further accompanied by elevated renal inflammatory response and supports earlier evidences on important role for inflammatory mechanisms in the pathogenesis of cisplatin-induced nephrotoxicity. Indeed, cisplatin induces increased renal expression of a variety of inflammatory chemokines and cytokines, such as TNF-α and IL-1β.

We further demonstrate that EET analog treatment reduced renal expression of these inflammatory markers in cisplatin-induced nephrotoxicity. Our data support earlier reports of anti-inflammatory activity of EET that has been implicated in EET mediated organ protection in a number of pathologies characterized with organ injury. For instance, increased bioavailability of EET by sEH inhibition provides kidney protection in streptozotocin-induced diabetes. Moreover, over-expression of the EET producing enzyme CYP2J2 markedly protected kidney in a chronic renal failure model of 5/6 nephrectomy. Thus, our data clearly indicate that along with marked reduction in oxidative stress, attenuation of cisplatin-induced renal inflammatory responses is another mechanism by which EET analog protected kidney from cisplatin-induced nephrotoxicity.

We have further investigated EET analog's effect on cisplatin-induced endoplasmic reticulum (ER) stress. There is evidence that ER is one of the sub-cellular targets of toxins and play important role in xenobiotic-induced nephrotoxicity. In the present study we examined the renal expression of caspase 12 and GRP78 (glucose-regulated protein 78) mRNAs to investigate the involvement of the ER stress in cisplatin-induced nephrotoxicity. GRP78 is considered one of the hallmarks of ER stress, while caspase 12 is an ER-specific caspase that is activated by ER stress and specifically participates in ER stress-induced apoptosis. We observe marked up-regulation in the renal expression of these ER stress markers that is attenuated by EET analog treatment. Our study supports earlier observations that cisplatin-induced nephrotoxicity is associated with ER stress. Most importantly, the present study also provided an interesting and novel finding regarding the biological actions of EET, and demonstrates an important aspect on the therapeutic potential of this lipid mediator in treating cisplatin-induced nephrotoxicity.

Cisplatin and other drug-related nephrotoxicity is associated with apoptosis[10] that is caused by elevated oxidative stress, inflammation and ER stress. It is reported that during cisplatin-induced nephrotoxicity, the cellular stress caused by oxidative stress, inflammation and ER stress leads to a reduction of anti-apoptotic Bcl2 and activation of the pro-apoptotic Bcl2 family proteins like the Bcl-2 associated X protein (Bax) and Bcl-2 antagonist/killer protein (Bak) in the kidney. This enhanced pro-apoptotic signaling leads to the activation of caspase 3 followed by apoptosis of the renal cells. Here, we demonstrate that EET analog treatment protect the kidney from cisplatin-induced cell death by increasing the expression of anti-apoptotic Bcl2 and reducing the pro-apoptotic Bak/Bcl2 and Bax/Bcl2 ratios along with a marked reduction in caspase 3 activity.

We also demonstrate an EET analog mediated attenuation in the renal expression of caspase 12 that plays an essential role in ER stress mediated apoptosis. Indeed, it is earlier reported that EET attenuates several major apoptotic events including elevated Bcl2 protein mediated pro-apoptotic signaling and caspase 3 activity. These observations support our view on EET analog's ability to reduce renal cell death in cisplatin-induced nephrotoxicity through its effect on the Bcl2 proteins, ER stress specific caspase 12 and on the apoptosis executioner caspase, caspase 3.

We have clearly demonstrated that EET analog treatment provides protection from cisplatin-induced nephrotoxicity through multiple mechanisms, and strongly indicate a possible therapeutic promise. However, it is important that before the clinical use of new cytoprotective agents, not only protection from toxicity, but also the absence of an interference of the agent with the anti-cancer activity of the cytotoxic agents used is demonstrated. To this end, in an in vitro approach we have investigated whether in vitro exposure of normal kidney cells (HEK293) or several human cancer cell-lines (Hela, NCCIT, U87) to various concentrations of an EET analog (EET-A) influence cell growth or the cytotoxic effect of cisplatin. Considering the comparable kidney protective effects of the two EET analogs used in this study, we have chosen one EET analog for this particular experiment. We demonstrated that in the presence and absence of EET analog (EET-A) cisplatin is equally potent in exerting its chemotherapeutic effect. Moreover, we have also investigated if EET-A influence the growth of any of the cancer lines used in this study, and clearly demonstrated that EET-A had no effect on the growth of any of these cancer cell lines.

In conclusion, we have provided strong evidence that the kidney protective effect of the above-identified EET analogs in drug-induced nephrotoxicitn, including cisplatin-induced nephrotoxicity. We have demonstrated that these EET analogs offered kidney protection by the inhibition of multiple signaling pathways that critically involve in the pathophysiology of cisplatin-induced nephrotoxicity. This study highlighted several important biological actions of novel EET analogs in terms of their anti-oxidative, anti-inflammatory, anti-ER stress and anti-apoptotic activities. The results of the current study strengthen our view on the therapeutic promise of these novel EET analogs in treating cisplatin-induced nephrotoxicity without compromising cisplatin's chemotherapeutic potential.

While this invention has been described in conjunction with the various exemplary embodiments outlined above, various alternatives, modifications, variations, improvements and/or substantial equivalents, whether known or that are or may be presently unforeseen, may become apparent to those having at least ordinary skill in the art. Accordingly, the exemplary embodiments according to this invention, as set forth above, are intended to be illustrative, not limiting. Various changes may be made without departing from the spirit and scope of the invention. Therefore, the invention is intended to embrace all known or later-developed alternatives, modifications, variations, improvements, and/or substantial equivalents of these exemplary embodiments. All technical publications, patents and published patent applications cited herein are hereby incorporated by reference in their entirety for all purposes.

REFERENCES

1. American Heart Association. High blood pressure statistica. Available at: http://www.americanheart.org/presenter.jhtml?identifier=4621. Accessed November 2010.
2. Jacobson et al. Prostaglandins, and Membrane Ion Transport. New York: Raven Press, 1985:311-318.
3. Sakairi et al. Am J Physiol 1995; 268:F931-939.
4. Campbell et al. Circ Res 1996; 78:415-423.
5. Archer S et al. Circulation 2003; 107:769-776.
6. Fisslthaler et al. Nature 1999; 401:493-497.
7. King et al. Pharmacogenet Genomics 2005; 15:7-13.
8. Capdevila et al. Kidney Int 2007; 72:683-689.
9. Imig J D. Am J Physiol Renal Physiol 2005; 289:F496-503.
10. Imig et al. Hypertension 2005; 46:975-981.
11. Imig et al. J Hypertens 2001; 19:983-992.
12. Imig et al. Nat Rev Drug Discov 2009; 8:794-805.
13. Sodhi et al. J Pharmacol Exp Ther 2009; 331:906-916.
14. Imig et al. U.S. Pat. No. 7,550,617, Issued Jun. 23, 2009
15. Imig et al. U.S. Pat. No. 7,732,470, Issued Jun. 8, 2010
16. Heizer et al. Stroke 1991; 22:1389-1393.
17. Krotz et al. Arterioscler Thromb Vasc Biol 2004; 24:595-600.
18. Node et al. Science 1999; 285:1276-1279.
19. Davis et al. Proc Natl Acad Sci USA 2002; 99:2222-2227.
20. Fleming I. Prostaglandins Other Lipid Mediat 2007; 82:60-67.
21. Yang et al. Arch. Biochem Biophys 2009; 489:82-91.
22. Potente et al. J Biol Chem 2003; 278:29619-29625.
23. Sun et al. Circ Res 2002; 90:1020-1027.
24. Simpkins et al. Am J Pathol 2009; 174:2086-2095.
25. Zhang et al. Stroke 2008; 39:2073-2078.
26. Terashvili et al. J Pharmacol Exp Ther 2008; 326:614-622.
27. Inceoglu et al. Life Sci 2006; 79:2311-2319.
28. Bongers et al. Pharmacoeconomics. 2012; 30(1):17-34.
29. Costantini et al. Scientific World Journal. 2011; 11:1981-94.
30. Levy et al. Curr Med Res Opin. 2011; 27(12):2253-9.
31. Wang et al. Nat Rev Drug Discov; 4(4):307-20.
32. Lameire et al. Acta Clin Belg. 2011; 66(5):337-45.
33. Miller et al. Toxins (Basel). 2010; 2(11):2490-518.
34. Yao et al. Am J Med Sci. 2007 August; 334(2):115-24.
35. Lieberthal et al. Am J Physiol. 1996 April; 270(4 Pt 2):F700-8.
36. Ma et al. Clin Exp Pharmacol Physiol. 2010; 37(4):460-5.
37. Pabla N and Dong Z (2008) Kidney Int 73:994-1007.
38. Imig J D. Physiol Rev. 2012 January; 92(1):101-30.
39. Imig J D. J Cardiovasc Pharmacol. 2010; 56(4):329-35.
40. Imig J D. Am J Physiol Renal Physiol. 2005; 289(3):F496-503.
41. Pfister et al. Adv Pharmacol. 2010; 60:27-59.
42. Gauthier et al. J Cardiovasc Pharmacol. 2007 December; 50(6):601-8.
43. Olearczyk et al. Clin Sci (Lond). 2009; 116(1):61-70.
44. Elmarakby et al. Am J Physiol Regul Integr Comp Physiol. 2011; 301(5):R1307-17.
45. Imig J D, Hammock B D. Nat Rev Drug Discov. 2009 October; 8(10):794-805.
46. Yang et al. Mol Pharmacol 60: 310-320, 2001.

47. Yang et al. Am J Physiol Heart Circ Physiol. 2007; 293(1):H142-51.
48. Morisseau C, Hammock B D (2005). Annu Rev Pharmacol Toxicol 45: 311-333.
49. Falck J Med Chem 2009, 52: 5069-5075.
50. Batchu et al. Br J Pharmacol. 2011; 162(4):897-907.
51. Simpkins et al. Am J Pathol. 2009; 174(6):2086-95.
52. Zhao et al. Am J Physiol Heart Circ Physiol. 2006; 290(6):H2187-95.
53. Jia Z et al. Kidney Int. 2011; 79(1):77-88.
54. Liu et al. Eye (Lond). 2010; 24(1):137-44.
55. Xu et al. Nephrol Dial Transplant. 2010; 25(12):3859-67.
56. Akcali et al. World J Gastroenterol. 2004; 10(2):279-83.
57. Chabrashvili et al. Am J Physiol Regul Integr Comp Physiol. 2003; 285(1):R117-24.
58. Inagi R. Nephron Exp Nephrol. 2009; 112(1):e1-9.
59. Mukhopadhyay et al. Free Radic Biol Med. 2012; 52(2):497-506.
60. Aleisa et al. Clin Exp Pharmacol Physiol. 2007; 34(12):1252-9.
61. Sahu et al. Food Chem Toxicol. 2011 December; 49(12):3090-7.
62. Parrish et al. Cell Biol Toxicol. 2009; 25(3):217-25.
63. Spector et al. Prog Lipid Res. 2004; 43(1):55-90.
64. Suddek G M. 2011 Oct. 11. doi: 10.1111/j.1472-8206.2011.00996.x.
65. El-Beshbishy et al. Eur J Pharmacol. 2011; 668(1-2):278-84.
66. Liu et al. J Pharmacol Exp Ther. 2011; 339(2):451-63.
67. Ramesh G and Reeves W B (2002) J Clin Invest 110:835-842.
68. Yamate et al. Vet Pathol 39:322-333.
69. Faubel et al. J Pharmacol Exp Ther 322:8-15.
70. Zhang et al. (2007) Kidney Int 72:37-44.
71. Zhao et al. Hum Gene Ther. 2012 Jan. 19.
72. Cribb et al. Drug Metab Rev. 2005; 37(3):405-42.
73. Mandic et al. J Biol Chem. 2003; 278(11):9100-6.
74. Peyrou et al. Toxicol Sci. 2007 September; 99(1):346-53. Epub 2007 Jun. 12. PubMed PMID: 17567590.
75. Breckenridge et al. Oncogene. 2003; 22(53):8608-18.
76. Park et al. (2002) et al. J Am Soc Nephrol 13:858-865.
77. Wei et al. (2007) Kidney Int 72:53-62.
78. Lorz et al. J Am Soc Nephrol. 2004; 15(2):380-9.

What is claimed is:

1. A compound selected from the group consisting of

15
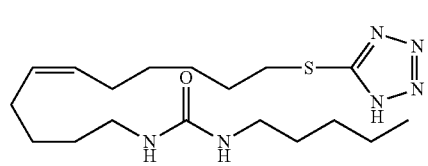 [SMILES: CCCCCNC(=O)NCCCC/C=C\CCCCCSc1nnn[nH]1]

16
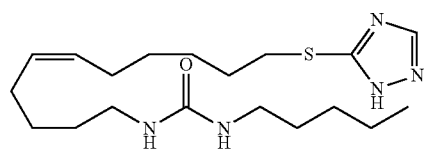 [SMILES: CCCCCNC(=O)NCCCC/C=C\CCCCCSc1ncn[nH]1]

17
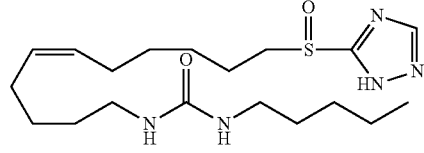 [SMILES: CCCCCNC(=O)NCCCC/C=C\CCCCCS(=O)c1ncn[nH]1]

18
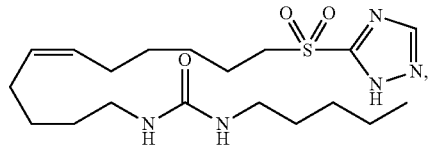

19
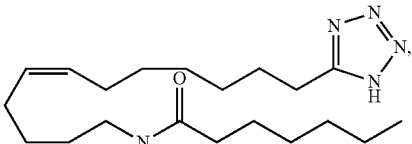

20
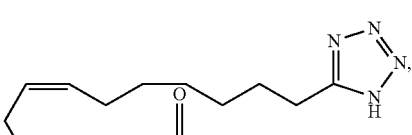

21
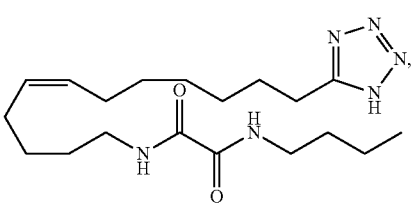

22
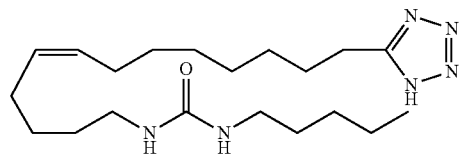

23
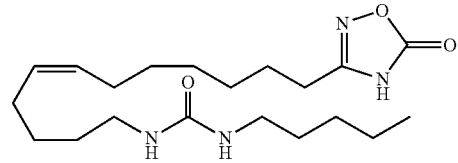 [SMILES: CCCCCNC(=O)NCCCC/C=C\CCCCCCc1noc(=O)[nH]1]

24
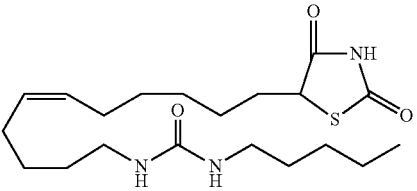

25
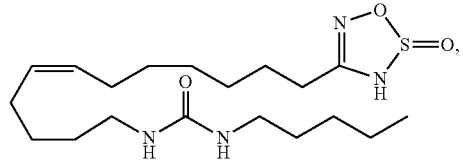

26
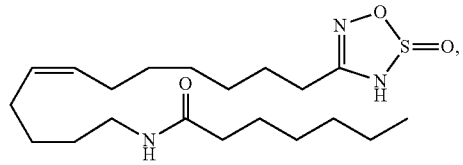

-continued

27 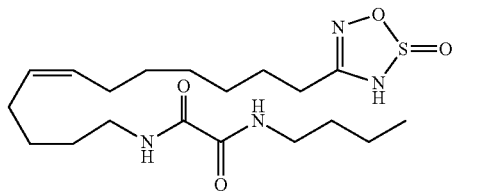 [SMILES: CCCCNC(=O)C(=O)NCCCC/C=C\CCCCCCC1=NOS(=O)N1]

28 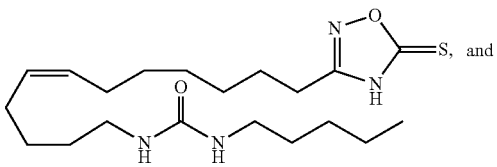

29 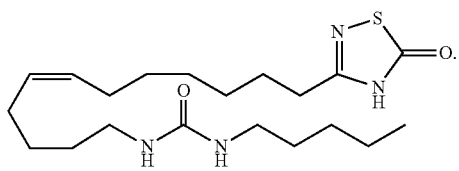

2. A composition comprising a compound of claim 1 and a pharmaceutically acceptable carrier.

3. A method of reducing hypertension in a subject, comprising administering to a subject a therapeutically effective amount of a compound according to claim 1, wherein hypertension in said subject is reduced.

4. A method of reducing nephrotoxicity in a subject, comprising administering to a subject a therapeutically effective amount of a compound according to claim 1, wherein nephrotoxicity in said subject is reduced.

5. The method of claim 4, wherein the nephrotoxicity is drug-induced.

6. The method of claim 4, wherein the nephrotoxicity is cisplatin-induced.

7. A method of reducing cisplatin nephrotoxicity in a subject, comprising administering to a subject a therapeutically effective amount of a compound according to claim 1, wherein cisplatin nephrotoxicity in said subject is reduced.

\* \* \* \* \*